(12) United States Patent
Hoogeveen et al.

(10) Patent No.: US 6,635,623 B1
(45) Date of Patent: Oct. 21, 2003

(54) LIPOPROTEINS AS NUCLEIC ACID VECTORS

(75) Inventors: Ron C. Hoogeveen, Houston, TX (US); J. Paul Moore, Stafford, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 09/079,030

(22) Filed: May 14, 1998

Related U.S. Application Data

(63) Continuation-in-part of application No. 08/874,807, filed on Jun. 13, 1997, now abandoned.

(51) Int. Cl.$^7$ ............................................. A61K 48/00
(52) U.S. Cl. ...................... 514/44; 435/320.1; 435/455; 435/458; 424/93.2
(58) Field of Search .......................... 514/44; 424/93.2; 435/320.1, 455, 458, 69.1, 91.4

(56) References Cited

U.S. PATENT DOCUMENTS

| | | |
|---|---|---|
| 4,396,601 A | 8/1983 | Salser et al. |
| 4,403,035 A | 9/1983 | Anderson et al. |
| 4,497,796 A | 2/1985 | Salser et al. |
| 4,663,292 A | 5/1987 | Wong et al. |
| 4,868,116 A | 9/1989 | Morgan et al. |
| 4,885,248 A | 12/1989 | Ahlquist |
| 4,904,582 A | 2/1990 | Tullis |
| 5,023,243 A | 6/1991 | Tullis |
| 5,096,815 A | 3/1992 | Ladner et al. |
| 5,149,782 A | 9/1992 | Chang et al. |
| 5,168,062 A | 12/1992 | Stinski |
| 5,198,346 A | 3/1993 | Ladner et al. |
| 5,219,740 A | 6/1993 | Miller et al. |
| 5,252,479 A | 10/1993 | Srivastava |
| 5,283,185 A | 2/1994 | Epand et al. |
| 5,298,422 A | 3/1994 | Schwartz et al. |
| 5,385,839 A | 1/1995 | Stinski |
| 5,482,853 A | 1/1996 | Sandmeyer |
| 5,518,913 A | 5/1996 | Massie et al. |
| 5,521,291 A | 5/1996 | Curiel et al. |
| 5,523,222 A | 6/1996 | Page et al. |
| 5,547,932 A | 8/1996 | Curiel et al. |
| 5,574,142 A | 11/1996 | Meyer, Jr. et al. |
| 5,578,475 A | 11/1996 | Jessee |
| 5,580,558 A | 12/1996 | Kitamura |
| 5,580,859 A | 12/1996 | Felgner et al. |
| 5,585,254 A | 12/1996 | Maxwell et al. |
| 5,585,362 A | 12/1996 | Wilson et al. |
| 5,591,601 A | 1/1997 | Wagner et al. |
| 5,747,469 A * | 5/1998 | Roth et al. ..................... 514/44 |
| 6,143,290 A * | 11/2000 | Zhang et al. ............... 424/93.2 |
| 6,156,567 A * | 12/2000 | Fischer ....................... 435/325 |
| 6,344,436 B1 * | 2/2002 | Smith et al. |

FOREIGN PATENT DOCUMENTS

| | | | |
|---|---|---|---|
| WO | WO 87/02061 | | 4/1987 |
| WO | WO 93/04701 | | 3/1993 |
| WO | 93/18759 | * | 9/1993 |
| WO | WO 95/28494 | | 10/1995 |
| WO | WO 95/31557 | | 11/1995 |
| WO | WO 98/00556 | | 1/1998 |

OTHER PUBLICATIONS

Sipehia et al. High–Efficiency transformation of human endothelial cells byt apoe–mediated transfection with plasmid DNA vol. 214 No. 1, 1995 pp. 206–211.*

Kim et al. In vitro gene expression on smooth muscle cells using a terplex delivery system 1997 pp. 51–59.*

AN: 2000400575, Medline, Journal of Protein Chemistry, Nov. 1999, vol. 18, No. 8, pp. 845–857.*

Tait et al., Ovarian Cancer BRCA1 Gene Therapy: Phase I and II Trial Differences in Immune Response and Vector Stability, Jul. 1999, Clinical Cancer Research, vol. 5, pp. 1708–1714.*

Branch, A good antisense molecule is hard to find, Feb. 1998, TIBS, pp. 45–50.*

Ngo et al., Computational Complexity, Protein Structure Prediction, and the Levinthal Parasox, 1994 pp. 491–495.*

Chiu et al., Optimizing energy protetoals of succuess in protein tertiary structure prediction, May 7, 1998, Folding & Design, vol. 3, pp. 223–228.*

Plenat, Animal models of antisense oligonucleotides: lessons for use in humans, Jun. 1996, Molecular Medicine Today, pp. 250–257.*

Meng et al., Tumor Suppressor Genes as Targets for Cancer Gene Therapy, 1999, Gene Therapy of Cancer, Chapter 1, pp. 3–20.*

Verma et al., Gene therpy–promises, problems and propects, Sep. 18, 1997, Nature, vol. 389, pp. 239–242.*

Anderson, Human gene therapy, Apr. 30, 1998, Nature, vol. 392, pp. 25–30.*

Mastrangelo et al., Gene therapy for Human Cancer: An Essay of Clinicians, Feb. 1996, Seminars in Oncology, vol. 23 No. 1, pp. 4–21.*

Guevara Jr., et al., "Src signal sequences in apoprotein B–100: Does LDL or Lp[a] a role in signal transduction," In: *Multiple Risk Factors in Cardiovascular Disease,* Yamamoto, ed., Churchill Livingston Japan, ICIC, 1994.

Baleja and Sykes, "Comparison of the structures of operator DNA free and in complex with λ repressor," *Biochem. Cell Biol.,* 69(2–3):202–205, 1991.

Banner et al., "Structure of the ColE1 Rop protein at 1•7 Å resolution." *J. Mol. Biol.,* 196(3):657–675, 1987.

(List continued on next page.)

*Primary Examiner*—Dave T. Nguyen
(74) *Attorney, Agent, or Firm*—Fulbright & Jaworski

(57) ABSTRACT

The present invention relates to materials and methods for the in vivo transport and deliver of nucleic acids. More particularly, it concerns the use of lipoproteins, including but not limited to, low density lipoproteins ("LDL"), and/or apolipoproteins for the binding and in vivo transport of nucleic acids. In addition, the present invention relates to the use of lipoproteins in the early detection of cancer and/or metastatic cancer and/or arteriosclerosis.

33 Claims, 54 Drawing Sheets

OTHER PUBLICATIONS

Benvensty and Reshef, "Direct introduction of genes into rats and expression of the genes," *Proc. Natl. Acad. Sci. USA*, 83:9551–9555, 1986.

Biou et al., "The 2.9 Å crystal structure of *T. thermophilus* seryl–tRNA synthetase complexed with tRNA$^{Ser}$," *Science*, 263(5152):1404–1410, 1994.

Blackhart et al., "An expression system for human apolipoprotein B100 in a rat hepatoma cell line," *J. Biol. Chem.*, 265(15):8358–8360, 1990.

Blanco–Vaca et al., "Identification and quantification of apolipoproteins in addition to apo[a] and apo B–100 in human lipoprotein[a]," *Chem. Physics, Lipids*, 67/68:35–42, 1994.

Blanco–Vaca et al., "Characteriztion of disulfide–linked heterodimers containing apolipoprotein D in human plasma lipoproteins," *J. Lipid Res.*, 33:1785–17986, 1992.

Briggs et al., "Nuclear protein that binds sterol regulatory element of low density lipoprotein receptor promoter," *J. Biol. Chem.*, 268:14490–14496, 1993.

Brown and Goldstein, "A receptor–mediated pathway for cholesterol homeostasis," *Science*, 232:34–47, 1986.

Bullough et al., "Structure of influenza haemagglutinin at the pH of membrane fusion," *Nature*, 371(6492):37–43, 1994b.

Bullough et al., "Crystals of a fragment of influenza haemagglutinin in the low pH induced conformation," *J. Mol. Biol.*, 236(4):1262–1265, 1994a.

Cardin et al., "Physical–chemical interaction of heparin and human plasma low–density lipoproteins," *Biochem.*, 26:5513–5518, 1987.

Carpenter, "Receptor tyrosine kinase substrates: src homology domains and signal transduction," *FASEB J.*, 6:3283–3289, 1992.

Cicchetti et al., "Identification of a protein that binds to the SH3 region of Abl and is similar to Bcr and GAP–rho," *Science*, 257:803–806, 1992.

Cohen and Parry, "β–helical coiled coils—a widespread motif in proteins," *TIBS*, 11:245–248, 1986.

Coleman et al., "Determination of cysteine on low–density lipoproteins using the fluorescent probe, 5–iodoacetamidofluoresceine," *Biochim. Biophys. Acta*, 1037:129–132, 1990.

Connelly et al., "Identification of disulfide–linked apolipoprotein species in human lipoproteins," *J. Lipid Res.*, 34:1717–1727, 1993.

Cusack et al., "A second class of synthetase structure revealed by X–ray analysis of *Escherichia coli* seryl–tRNA synthetase at 2.5 Å," *Nature*, 347(6290):249–255, 1990.

Ellenberger et al., "The GCN4 basic region leucine zipper binds DNA as a dimer of uninterrupted α helices: crystal structure of the protein–DNA complex," *Cell*, 71(7):1223–37, 1992.

Escobedo et al., "A phosphatidylinositol–3 kinase binds to platelet–derived growth factor receptors through a specific receptor sequence containing phosphotyrosine," *Mol. Cell Biol.*, 11: 1125–1132, 1991.

Felgner et al., "Lipofection: a hifhly efficient, lipid–mediated DNA–transfection procedure," *Proc. Natl. Acad. Sci. USA*, 84:7413–7417, 1987.

Glover and Harrison, "Crystal structure of the heterodimeric bZIP transcription factor c–Fos–c–Jun bound to DNA," *Nature*, 373(6511):257–261, 1995.

Guevara Jr., et al., "A structural assessment of the apo[a] protein of human lipoprotein[a]," *Proteins*, 12(2):188–199, 1992.

Guevara Jr., et al., "Comparison of ligand–binding sites of modeled apo[a] kringle–like sequences in human lipoprotein [a]," *Arterioscler.*, 13(5):758–770, 1993.

Guevara Jr., et al., "Proposed mechanism for binding of apo[a] kringle type 9 to apo B–100 in human lipoprotein[a]," *J. Biophys.*, 64(3):686–700, 1993.

Guevara Jr., et al., "Evidence that apoB–100 of low–density lipoproteins is a novel Src–related protein kinase," *J. Protein Chem.*, 14(7):627–631, 1995.

Guevara Jr., et al., "Interaction of apolipoprotein[a] with apolipoprotein B–100 Cys3734 region in lipoprotein[a] is confirmed immunochemically," *J. Protein Chem.*, 15(1):17–25, 1996.

Innerarity et al., "Functional domains of apolipoprotein E and apolipoprotein B," *Acta Med. Scand Suppl.*, 715:51–59, 1986.

International Search Report dated Oct. 13, 1998 (PCT/US98/11927)(ARAG:003P).

Kaneda et al., "Increased expression of DNA cointroduced with nuclear protein in adult rat liver," *Science*, 24:375–378, 1989.

Kim et al., "Terplex system of lipoprotein, cationic polymer and DNA for gene delivery," *Pharm. Res.*, 12(9):S80, 1995.

Kinoshita et al., "Modification of the core lipids of low density lipoproteins produces selective alterations in the expression of apoB–100 epitopes," *J. Lipid Res.*, 31:701–708, 1990.

Knott et al., "Complete protein sequence and identification of structural domains of human apolipoprotein B," *Nature*, 323:734–738, 1986.

Koch et al., "SH2 and SH3 domains: elements that control interactions of cytoplasmic signaling proteins," *Science*, 252:668–674, 1991.

Kostner and Grillhofer, "Lipoprotein(a) mediates high affinity low density lipoprotein association to receptor negative fibroblasts," *J. Biol. Chem.*, 266:21287–21292, 1991.

Kraulis et al., "Structure of the DNA–binding domain of zinc GAL4," *Nature*, 356(6368):448–450, 1992.

Lee et al., "Detailed analysis of structures and formulations of cationic lipids for efficient gene transfer to the lung," *Human Gene Therapy*, 7:1701–1717, 1996.

Lowenstein et al., "The SH2 and SH3 domain–containing protein GRB2 links receptor tyrosine kinases to ras signaling," *Cell*, 70:431–442, 1992.

Lupas et al., "Predicting coiled coils from protein sequences," *Science*, 252(5010):1162–1164, 1991.

MacArthur and Thornton, "Influence of proline residues on protein conformation," *J. Mol. Biol.*, 218:397–412, 1991.

Mahley, "Apolipoprotein E: cholesterol transport protein with expanding role in cell biology," *Science*, 240:622–630, 1988.

Marcel et al., "Expression of Apolipoprotein B epitopes in lipoproteins. Relationship to conformation and function," *Arterioscl.*, 8:832, 1988.

Margolis, "Proteins with SH2 domains: transducers in the tyrosine kinase signaling pathway," *Cell, Growth and Differentiation*, 3:73–80, 1992.

Marmorstein et al., "DNA recognition by GAL4: structure of a protein–DNA complex," *Nature*, 356(6368):408–414, 1992.

McLean et al., "cDNA sequence of human apolipoprotein(a) is homologous to plasminogen," *Nature*, 330:132–137, 1987.

Milne et al., "The use of monoclonal antibodies to localize the low density lipoprotein receptor–binding domain of apolipoprotein B," *J. Biol. Chem.*, 264(33):19754–19760, 1989.

Musacchio et al., "Crystal structure of a Src–homology 3 (SH3) domain," *Nature*, 359:851–855, 1992.

Myant, LDL: Physical and Chemical Characteristics, Chapter 5, In: Cholesterol Metabolism, LDL, and the LDL Receptor, San Diego, Academic Press, pp. 99–111, 1990.

Neumann et al., "Gene transfer into mouse lyoma cells by electroporation in high electric fields," *EMBO J.*, 7:841–845, 1982.

O'Shea et al., "X–ray structure of the GCN4 leucine zipper, a two–stranded, parallel coiled coil," *Science*, 254(5031):539–544, 1991.

Pawson, "SH2 and SH3 domain," *Current Opinion in Structural Biology*, 2:432–437, 1992.

Pleiman et al., "Activation of phosphatidylinositol-3' kinase by Src–family kinase SH3 binding to the p85 subunit," *Science*, 263:1609–1612, 1994.

Ren et al., "Identification of a ten–amino acid proline–rich SH3 binding site," *Science*, 259:1157–1161, 1993.

Rudd et al., "src–related protein tyrosine kinases and their surface receptors," *Biochim. Biophys. Acta.*, 1155:239–266, 1993.

Schimotohono and Temin, "Formation of infectious progeny virus after insertion of herpes simplex thymidine kinase gene into DNA of an avian retrovirus," *Cell*, 26:67–77, 1981.

Schumaker and Puppione, "Sequential flotation ultracentrifugation," *Methods in Enzymology*, 128:155–170, 1986.

Smith et al., "Identification of nucleotides responsible for enhancer activity of sterol regulatory element in low density lipoprotein receptor gene," *J. Biol. Chem.*, 265:2306–2310, 1990.

Sompayrac and Danna, "Efficient infection of monkey cells with DNA of simian virus 40," *Proc. Natl. Acad. Sci. USA*, 78:7575–7578, 1981.

Songyang et al., "SH2 domains recognize specific phosphopeptide sequences," *Cell*, 72:767–778, 1993.

Stribling et al., "Aerosol gene delivery in vivo," *Proc. Natl. Acad. Sci USA*, 89:11277–11281, 1992.

Teng et al., "Modulation of apolipoprotein B antigenic determinants in human low density lipoprotein subclasses," *J. Biol. Chem.*, 260:5067–5072, 1985.

Trieu and McConathy, "Lipoprotein(a) binding to other apolipoprotein B containing lipoproteins," *Biochem.*, 29(25):5919–5924, 1990.

Trieu et al., "Interaction of apolipoprotein(a) with apolipoprotein B–containing lipoproteins," *J. Biol. Chem.*, 266(9):5480–5485, 1991.

Ugi et al., "Src homology 2 domains of protein tyrosine phosphatase are associated in vitro with both the insulin receptor and insulin receptor substrate–1 via phosphotyrosine motifs," *FEBS Lett.*, 340:216–220, 1994.

Veals et al., "Subunit of an alpha–interferon–responsive transcription factor is related to interferon regulatory factor and Myb families of DNA–binding proteins," *Mol. Cell. Biol.*, 12:3315–3324, 1992.

Waksman et al., "Binding of a high affinity phosphotyrosyl peptide to the Src SH2 domain: crystal structures of the complexed and peptide–free forms," *Cell*, 72:779–790, 1993.

Wang et al., "Nuclear protein that binds sterol regulatory element of low density lipoprotein receptor promoter," *J. Biol. Chem.*, 268:11497–14504, 1993.

Weisgraber and Rall Jr., "Human apolipoprotein B–100 heparin–binding sites," *J. Biol. Chem.*, 262:11097–11103, 1987.

Wigler et al., "DNA–mediated transfer of the adenine phosphoribosyltransferase locus into mammalian cells," *Proc. Natl. Acad. Sci. USA*, 76:1373–1376, 1979.

Wolff et al., "Direct gene transfer into mouse muscle in vivo," *Science*, 247:1465–1468, 1990.

Yang et al., "Structure of polipoprotein B–100 of human low density lipoproteins," *Arteriosclerosis*, 9(1):96–108, 1989.

Yang et al., "Sequence, structure, receptor–binding domains and internal repeats of human apolipoprotein B–100," *Nature*, 323:738–742, 1986.

Yang et al., "Isolation and characterization of sulfhydryl and disulfide peptides of human apolipoprotein B–100," *Proc. Natl. Acad. Sci. USA*, 87:5523–5527, 1990.

Ye et al., "Interactions of low density lipoprotein$_2$ and other apolipoprotein B–containing lipoproteins with lipoprotein(a)," *J. Biol. Chem.*, 263(13):6337–6343, 1988.

Young et al., "Conservation of the low density lipoprotein receptor–binding domain of apoprotein B," *Arterioscl.*, 6:178–188, 1986.

Curiel et al., "High efficiency gene transfer mediated by adenovirus coupled to DNA–polylysine complexes," *Human Gene Therapy*, 3:147–154, 1992.

Schlessinger, "SH2/SH3 signaling proteins," *Current Opinions in Genetics and Development*, 4:25–30, 1994.

Carlsson, J. et al. Biochem. J. 173:723–737 (1978).

Ghislain J. J., and Fish, E.N., J. Biochem. 271(21):12408–12413 (1996).

Hunter T. and Cooper, J.A. Ann. Rev Biochem 54:897–930 (1985).

Innerarity, T. L. et al., Acta Med. Scand. Suppl. 715:51–59 (1986).

Krishna, P. et al. Proc. Natl. Acad. Sci USA 87:1292–1295 (1990).

Koch, C.A. Science 252:668–674 (1991).

Lee, E.R., et al., Human Gene Therapy 7:1701–1717 (1996).

Mahley, R.W. et al J. Lipid Research 25:1277–1284 (1984).

McLean, J.W. et al., Nature 330:132–137 (1987).

Neumann, E. et al., EMBO J. 7:841–845 (1982).

Noble, M.E.M. et al., EMBO J. 12:2617–2624 (1993).

Nureki, O. et al. Science 267:1958–1965 (1995).

Schumaker, V.N., and Puppione, D.L., Methods in Enzymology 128:155–179(1986).

Smeenk, R. et al., J. Immunol. Methods 55:361–373 (1982).

Winfield, J.B., J. Immunology 126(4):1596–1602 (1981).

Wu, C.H. et al., J. Biol. Chem. 264:16985–16987 (1989).

Wu, G.Y. et al., J. Biol. Chem. 263:14621–14624 (1988).

Xu, X–X et al. J. Biol. Chem. 266(26):17040–17048 (1991).

Yoo, J.S.H. et al. Lipid Research 159:83–89 (1986).

Yu, H. et al., Cell 76:933–945 (1994).

Zhou, Y.F., et al., The Journal of Clinical Investigation 98(9);2129–2138 (1996).

* cited by examiner

1: The Amino Acid Sequence of Apo B-100

```
         10         20         30         40         50         60         70         80         90
EEEMLENVSLVCPKDATRFKHLRKYTYNYEAESSSGVPGTADSRSATRINCKVELEVPQLCSFILKTSQCTLKEVYGFNPEGKALLKKTKNSEEFAAAMS   100
RYELKLAIPEGKQVFLYPEKDEPTYILNIKRGIISALLVPPETEEAKQVLFLDTVYGNCSTHFTVKTRKGNVATEISTERDLGQCDRFKPIRTGISPLAL   200
IKGMTRPLSTLISSSQSCQYTLDAKRKHVAEAICKEQHLFLPFSYNNKYGMVAQVTQTLKLEDTPKINSRFFGEGTKKMGLAFESTKSTSPPKQAEAVLK   300
TLQELKKLTISEQNIQRANLFNKLVTELRGLSDEAVTSLLPQLIEVSSPITLQALVQCGQPQCSTHILQWLKRVHANPLLIDVTYLVALIPEPSAQQLR   400
EIFNMARDQRSRATLYALSHAVNNYHKTNPTGTQELLDIANYLMEQIQDDCTGDEDYTYLILRVIGNMGQTMEQLTPELKSSILKCVQSTKPSLMIQKAA   500
IQALRKMEPKDKDQEVLLQTFLDDASPGDKRLAAYLMLMRSPSQADINKIVQILPWEQNEQVKNFVASHIANILNSEELDIQDLKKLVKEALKESQLPTV   600
MDFRKFSRNYQLYKSVSLPSLDPASAKIEGNLIFDPNNYLPKESMLKTTLTAFGFASADLIEIGLEGKGFEPTLEALFGKQGFFPDSVNKALYWNGQVP   700
DGVSKVLVDHFGYTKDDKHEQDMVNGIMLSVEKLIKDLKSKEVPEARAYLRILGEELGFASLHDLQLLGKLLLMGARTLQGIPQMIGEVIRKGSKNDFFL   800
HYIFMENAFELPTGAGLQLQISSSGVIAPGAKAGVKLEVANMQAELVAKPSVSVEFVTMGIIIPDFARSGVQMNTNFFHESGLEAHVALKAGKLKFIIP   900
SPKRPVKLLSGGNTLHLVSTTKTEVIPPLIENRQSWSVCKQVFPGLNYCTSGAYSNASSTDSASYYPLTGDTRLELELRPTGEIEQYSVSATYELQREDR  1000
         10         20         30         40         50         60         70         80         90
ALVDTLKFVTQAEGAKQTEATMTFKYNRQSMTLSSEVQIPDFDVDLGTILRVNDESTEGKTSYRLTLDIQNKKITEVALMGHLSCDTKEERKIKGVISIP  1100
RLQAEARSEILAHWSPAKLLLQMDSSATAYGSTVSKRVAWHYDEEKIEFEWNTGTNVDTKKMTSNFPVDLSDYPKSLHMYANRLLDHRVPETDMTFRHVG  1200
SKLIVAMSSWLQKASGSLPYTQTLQDHLNSLKEFNLQNMGLPDFHIPENLFLKSDGRVKYTLNKNSLKIEIPLPFGGKSSRDLKMLETVRTPALHFKSVG  1300
FHLPSREFQVPTFTIPKLYQLQVPLLGVLDLSTNVYSNLYNWSASYSGGNTSTDHFSLRARYHMKADSVVDLLSYNVQGSGETTYDHKNTFTLSCDGSLR  1400
HKFLDSNIKFSHVEKLGNNPVSKGLLIFDASSSWGPQMSASVHLDSKKQHLFVKEVKIDGQFRVSSFYAKGTYGLSCQRDPNTGRLNGESNLRFNSSYL  1500
QGTNQITGRYEDGTLSLTSTSDLQSGIIKNTASLKYENYELTLKSDTNGKYKNFATSNKMDMTFSKQNALLRSEYQADYESLRFFSLLSGSLNSHGLELN  1600
ADILGTDKINSGAHKATLRIGQDGISTSATTNLKCSLLVLENELNAELGLSGASMKLTTNGRFREHNAKFSLDGKAALTELSLGSAYQAMILGVDSKNIF  1700
NFKVSQEGLKLSNDMMGSYAEMKFDHTNSLNIAGLSLDFSSKLDNIYSSDKFYKQTVNLQLQPYSLVTTLNSDLKYNADLTNNGKLRLREPLKLHVAGNL  1800
KGAYQNNEIKHIYAISSAALSASYKADTVAKVQGVEFSHRLNTDIAGLASAIDMSTNYNSDSLHFSNVFRSVMAPFTMTIDAHTNGNGKLALWGEHTGQL  1900
YSKFLLKAEPLAFTFSHDYKGSTSHHLVSRKSISAALEHKVSALLTPAEQTGTWKLKTQFNNNEYSQDLDAYNTKDKIGVELTGRTLADLTLLDSPIKVP  2000
```

FIG. 1A

```
                10                    20                    30                    40                    50                    60                    70                    80                    90
LLLSEPINIIDALEMRDAVEKPQEFTIVAFVKYDKNQDVHSINLPFFETLQEYFERNRQTIIVVVENVQRNLKHINIDQFVRKYRAALGKLPQQANDYLN    2100
SFNWERQVSHAKEKLTALTKKYRITENDIQIALDDAKINFNEKLSQLQTYMIQFDQYIKDSYDLHDLKIAIANIIDEIIEKLKSLDEHYHIRVNLVKTIH    2200
DLHLFIENIDFNKSGSTASWIQNVDTKYQIRIQIQEKLQQLKRHIQNIDIQHLAGKLKQHIEAIDVRVLLDQLGTTISFERINDVLEHVKHFVINLIGD    2300
FEVAEKINAFRAKVHELIERYEVDQQIQVLMDKLVELTHQYKLKETIQKLSNVLQQVKIDYFEKLVGFIDDAVKKLNELSFKTFIEDVNKFLDMLIKKL    2400
KSFDYHQFVDETNDKIREVTQRLNGEIQALELPQKAEALKLFLEETKATVAVYLESLQDTKITLIJNWLQEALSSASLAHMKAKFRETLEDTRDRMYDMD    2500
IQQELQRYLSLVGQVYSTLVTYISDWWTLAAKNLTDFAEQYSIQDWAKRMKALVEQGFTVPEIKTILGTMPAFEVSLQALQKATFQTPDFIVPLTDLRIP    2600
SVQINFKDLKNIKIPSRFSTPEFTILNTFHIPSFTIDFVEMKVKIIRTIDQMQNSELQWPVPDIYLRDLKVEDIPLARITLPDFRLPEIAIPEFIIPTLN    2700
LNDFQVPDLHIPEFQLPHISHTIEVPTFGKLYSILKIQSPLFTLDANADIGNGTTSANEAGIAASITAKGESKLEVLNFDFQANAQLSNPKINPLALKES    2800
VKFSSKYLRTEHGSEMLFFGNAIEGKSNTVASLHTEKNTLELSNGVIVKINNQLTLDSNTKYFHKLNIPKLDFSSQADLRNEIKTLLKAGHIAWTSSGKG    2900
SWKWACPRFSDEGTHESQISFTIEGPLTSFGLSNKINSKHLRVNQNLVYESGSLNFSKLEIQSQVDSQHVGHSVLTAKGMALFGEGKAEFTGRHDAHLNG    3000

10                    20                    30                    40                    50                    60                    70                    80                    90
KVIGTLKNSLFFSAQPFEITASTNNEGNLKVRFPLRLTGKIDFLNNYALFLSPSAQQASWQVSARFNQYKYNQNFSAGNNENIMEAHVGINGEANLDFLN    3100
IPLTIPEMRLPYTIITTPPLKDFSLWEKTGLKEFLKTTKQSFDLSVKAQYKKNKRHSITNPLAVLCEFISQSIKSFDRHFEKNRNALDFVTKSYNETK    3200
IKFDKYKAEKSHDELPRTFQIPGYTVPVVNEVSPFTIEMSAFGYVFPKAVSMPSFSILGSDVRVPSYTLILPSLELPVLHVPRNLKLSLPHFKELCTIS    3300
HIFIPAMGNITYDFSFKSSVITLNTNAELFNQSDIVAHLLSSSSVIDALQYKLEGTTRLTRKRGLKLATALSLSNKFVEGSHNSTVSLTTKNMEVSVAK    3400
TTKAEIPILRMNFKQELNGNTKSKPTVSSSMEFKYDFNSSMLYSTAKGAVDHKLSLESLTSYFSIESSTKGDVKGSVLSREYSGTIASEANTYLNSKSTR    3500
SSVKLQGTSKIDDIWNLEVKENFAGEATLQRIYSLWEHSTKNHLQEGLFFTNGEHTSKATLELSPWQMSALVQVHASQPSSFHDFPDLGQEVALNANTK    3600
NQKIRWKNEVRIHSGSFQSQVELSNDQEKAHLDIAGSLEGHLRFLKNIILPVYDKSLWDFLKLDVTTSIGRRQHLRVSTAFVYTKNPNGYSFSIPVKVLA    3700
DKFITPGLKLNDLNSVLVMPTFHVPFTDLQVPSCKLDFREIQIYKLRTSSFALNLPTLPEVKFPEVDVLTKYSQPEDSLIPFEITVPESQLTVSQFTL    3800
PKSVSDGIAALDLNAVANKIADFELPTIIVPEQTIEIPSIKFSVPAGIVIPSFQALTARFEVDSPVYNATWSASLKNKADYVETVLDSTCSSTVQFLEYE    3900
LNVLGTHKIEDGTLASKTKGTLAHRDFSAEYEEEDGKFEGLQEWEGKAHLNIKSPAFTDLHLRYQKOKKGISTSAASPAVGTVGMDMDEDDDFSKWNFYYS    4000
```

FIG. 1B

```
          10        20        30        40        50        60        70        80        90
PQSSPDKKLTIFKTELRVRESDEETQIKVNMEEEAASGLLTSLKDNVPKATGVLYDYVNKYHWEHTGLTLREVSSKLRRNLQNNAEWVYQGAIRQIDDID    4100
VRFQKAASGTTGTYQEWKDKAQNLYQELLTQEGQASFQGLKDNVFDGLVRVTQKFHMKVKHLIDSLIDFLNFPRFQFPGKPGIYTREELCTMFIREVGTV    4200
LSQVYSKVHNGSEILFSYFQDLVITLPFELRKHKLIDVISMYRELLKDLSKEAQEVFKAIQSLKTTEVLRNLQDLLQFIFQLIEDNIKQLKEMKFTYLIN    4300
YIQDEINTIFNDYIPYVFKLLKENLCLNLHKFNEFIQNELQEASQELQQIHQYIMALREEYFDPSIVGWTVKYYELEEKIVSLIKNLLVALKDFHSEYIV    4400
SASNFTSQLSSQVEQFLHRNIQEYLSILTDPDGKGKEKIAELSATAQEIIKSQAIATKKIISDYHQQFRYKLQDFSDQLSDYYEKFIAESKRLIDLSIQN    4500
YHTFLIYITELLKKLQSTTVMNPYMKLAPGELTIIL
```

FIG. 1C

Comparison of SH3-like Regions in Apo B-100 to Known SH3 Domains of Signal Transduction Proteins. Percent similarities are indicated at Right margin.

```
              10         20         30         40         50         60
B1    KYTYNYEA--ESSSGVPGTADSR-SATRINCKVELEVPQLCSFILKTSQ              (SEQ ID NO:3)
R9    AYDFNYPIKDSSSQLL-SVQQGETIYILN-KNSSGWWDG--LVIDDSN               (SEQ ID NO:4)   55%
       Y**NY * *SSS ** *** ** *N K      ***   S*

B2    VYGFNPEGKALLKTKNSEEFAAAMSRYELKLAIPEGKQV--FLYPE                 (SEQ ID NO:5)
R33   LYDFVASGDNTLSITKGEKLRVLGYNHYNGEWCEAQTKNGQGWVPSN                (SEQ ID NO:6)   51%
       *Y F * G   L  TK    **** *Y*  *  ** K*    ** *

B3-1  FLPFSYNNKYGMVAQVTQTLKLEDTPKINSRFF-GE-GTKKMGLAF                 (SEQ ID NO:7)
R35   LFDYKAQREDELT--FTKSAIIQNVEKQEGGWARGDYGGKKQ-LWF                 (SEQ ID NO:8)   54%
       ** * **   *   *T ** *** K  *  ** G* G KK  L*F

B3-2  FLPFSYNN-KYG-MVAQVTQTLKL-EDTPKINSRFF-GEGTKKM---GLA-FE          (SEQ ID NO:9)
R18   LH--SYEPSHDGDLGFEKGEQLRILEQSGE----WWKAQ-SLTTGQEGFIPFN          (SEQ ID NO:10)  51%
       *    SY*  * G ****  * L** E**          G** F*
```

FIG. 2A

Comparison of SH3-like Regions in Apo B-100 to Known SH3 Domains of Signal
Transduction Proteins. Percent similarities are indicated at Right margin.

```
B4    YTYLILRVIGNMGQTMEQLTPEL-KSSILKCVQSTKPSLMIQKAAIQALRKMEPKDKD---QEVLL  (SEQ ID NO:11)
R52   VVALFD-YAA-VNDR-DL--QVLKGE--K-LQVLRSTG--DWWLARSLVTG--REGYVPSNFVAP   (SEQ ID NO:12)
      * *L* * * *L  K **K  K*Q * *  ***** *L            V**                        50%

B5    AFGFASADLIEIGLEGKGFEPTLEALFGKQGFFPDS-VN--KALYWVNGQVPD              (SEQ ID NO:13)
R34   LYDFAAENPDELTFNEGAVVTVINKSNP-Q-WW-EGELNGQRGVFPAS--YVE              (SEQ ID NO:14)
      ***FA* ** E* **  **   * **      * *** * *N ******  ***                              59%

B8    FGYTKDDKHEQ-DMVNGIMLSVEK--LIKDLKSK--EV-PEARAYLRILGEE               (SEQ ID NO:15)
R25   YDYKKEE--EDIDLHLGDILTVNKGSLVALGFSDGQEAKPEEIGWLNGY-NE               (SEQ ID NO:16)
      * Y K** E* D* G ***V*K  L**    S    E* PE  **L * *E                                 56%

B8    FDYHQFVDETNDK-IREVTQRLNGEIQ-ALELPQKAEALKLFLEETKAT-V-AVYL           (SEQ ID NO:17)
R32   YDY------QEKSPREVTMKK-GDILTLLNSTNK-DWWKVEVND-RQGFVPAAYV            (SEQ ID NO:18)
      *DY       **K *REVT *  G*I  *L*  *K  ****K ****  * V A*Y*                           52%
```

FIG. 2B

| | | | |
|---|---|---|---|
| B9-1 | YDM--DIQQELQRYLSLVGQVYSTLVTYISDWWT--LAAK-NLTDFAEQYSIQDWA | (SEQ ID NO:19) | |
| R35-2 | FDYKAQREDELTFTKSAIIQNVEKQDGG---WWRGDYGGKKQLW-FPSNY-VEEMI | (SEQ ID NO:20) | 54% |
| | *** * EL    S Q *           WW  ***K *L  F* *Y ***** | | |
| B9-2 | YDMDIQ----QELQRYLSLVGQVYSTLVTYISDWWTLAAKNLTDFAEQ-YSIQDWAKRMK | (SEQ ID NO:21) | |
| R43 | IQ-DYEPRLTDEI-RI-SL-GEKVK-ILATHTDGWCLVEKCNTRKGTIHVSDD--KRYL | (SEQ ID NO:22) | 57% |
| | *Q D**   *E* R* SL G* * *** *D W L* K T  *   *S**D  KR* | | |
| B9-1 | YQMDI--QQELQ--RYLSLVGQVYSTLVTYIS-DWW---TLAA-KNLTDFAEQYSIQDWA | (SEQ ID NO:23) | |
| R49 | YDYEARTEDDLTFTK-----GEKF-HILNNTEGDWWEARSLSSGK--T--G-CIPSNYVA | | 51% |
| | Y**** ***L  *   .G* * **    DWW  *L ** K T *  *  * *A | | |
| B10 | TYDFSFK---SS-VITLNTNAE-LFNQSDIVAHLLSSSSSVIDALQY-----KLE | (SEQ ID NO:24) | |
| R9-2 | DFNYPIKKDSSSQQLLSVQ-QGETIY----ILNK--NSS-GWWDGLVIDDSNGKVN | (SEQ ID NO:25) | 56% |
| | DF ** K  SS ***** **E **   I* *  SS **D*L *     K** | | |
| B11 | KYDFNSSMLYSTAKGAVDHKLSLESLTS------YFSIESSTKGDVKGSVLSREY | (SEQ ID NO:26) | |
| R47 | EPYVAIK-AYTAVEGDEVSLLEGEAVEVIHKLLDGWMVIR---KDDVTGYFPSMYL | (SEQ ID NO:27) | 50% |
| | * *   *Y**** G   L  E**      **  I    K DV G  **S    * | | |

FIG. 2C

Comparison of SH3-like Regions in Apo B-100 to Known SH3 Domains of Signal Transduction Proteins. Percent similarities are indicated at Right margin.

```
B12     LWDFLKLD----VTTSIGRRQHLRVSTA------FVYTKNPNGYSFSIPVKVLADKFITPGLKL    (SEQ ID NO:28)
R3      LYDF-KAEKADELTTYVG---ENL-FICAHHNCEWFIAK-PIGRLGGPGL-VPVG-FVSI-IDI    (SEQ ID NO:29)
        L*DF K**   *T *G  *L * A    ****K P G   * *V** F*** *            54%

B13     VLYDYVNKY-HWEHTGLT-LR-EVSSK-LRRNLQNNAEWVYQGAIRQIDDI                  (SEQ ID NO:30)
R3-2    VLYDF--KAEKADE--LTTYVGENLFICAHHN----CEWFI---AKPIGRL                  (SEQ ID NO:31)
        VLYD* K* ***   LT * E     ***N    EW**  ** I *                     51%

B14     KPGIY--TREELCTMFIREVGTVL--------SQVYSKVHNGSE--ILF-SYFQ--DL           (SEQ ID NO:32)
R36     LFGFVPETKEELQ-VMPGNIVFVLKKGNDNWATVM--F-NG-QKGLVPCNYLEPVEL            (SEQ ID NO:33)
        **G* *T*EEL *** ** VL         * V*  * *** *Y** *L                  56%

B15     GKPGIYTREELCTMFIREVGTVLSQ------VYSKVHNGS-E---ILFS-YFQ--D             (SEQ ID NO:34)
R59     AKFDYVAQQEQE LDIKKNERLWLLDDSKSWW-RVRN-SMNKTGFVPSNYVERKN              (SEQ ID NO:35)
        *K* **** *E   *I*   **       ** *V*N S *   ***S Y** *              53%
```

FIG. 2D

Identification of the regions of apo B-100 and the proteins compared in Figures 2A-2D.

| Reference Protein Name: | SEQ ID NO. |
|---|---|
| Apo B-100 region B1 (aa 24-69) | SEQ ID NO:3 |
| r9 (aa 66-114). cell division control protein 25 gim\|4857 | SEQ ID NO:4 |
| Apo B-100 region B2 (aa 75-119) | SEQ ID NO:5 |
| r33 (aa 69-114). Abl proto-oncogene tyrosine kinase (P150) gim\|13887 | SEQ ID NO:6 |
| Apo B-100 region B3-1 (aa 240-283) | SEQ ID NO:7 |
| r35 (aa 799-841). 1-Phosphatidylinositol-4,5-bisphosphate phosphodiesterase gamma (PLC-gamma. PLC-II) gim\|18895 | SEQ ID NO:8 |
| Apo B-100 region B3-2 (aa 240-284) | SEQ ID NO:9 |
| r18 (aa 69-114). Lck proto-oncogene tyrosine kinase (P56-LCK) gim\|14213 | SEQ ID NO:10 |
| Apo B-100 region B4 (aa 457-518) | SEQ ID NO:11 |
| r52 (aa 57-109). BLK protein tyrosine kinase (B lmphocyte kinase) (P55-BLK) gim\|13991. | SEQ ID NO:12 |
| Apo B-100 region B5 (aa 652-700) | SEQ ID NO:13 |
| r34 (aa 984-1031). Myosin IC heavy chain gim\|16466 | SEQ ID NO:14 |
| Apo B-100 region B6 (aa 711-756) | SEQ ID NO:15 |
| r25 (aa 12-61). Phosphatidylinositol 3-OH gim\|18072 | SEQ ID NO:16 |

FIG. 2E

Identification of the regions of apo B-100 and the proteins compared in Figures 2A-2D.

| | |
|---|---|
| Apo B-100 region B9-1 (aa 2497-2547) | SEQ ID NO.19 |
| r35-2 (aa 800-850). 1-Phosphatidylinositol-4.5-bisphosphate phosphodiesterase gamma. (PLC-gamma. PLC-II) gim\|18895 | SEQ ID NO:20 |
| Apo B-100 region B9-2 (aa 2497-2551) | SEQ ID NO:21 |
| r43 (aa 444-496). nuclear fusion protein FUS1 gim\|9498 | SEQ ID NO:22 |
| r49 (aa 86-134). Fgr Proto-oncogene Tyrosine gim\|14097 | SEQ ID NO:23 |
| Apo B-100 region B10 (aa 3311-3355) | SEQ ID NO:24 |
| r9-2 (aa 66-114). Cell division control protein 25 gim\|4857 | SEQ ID NO:25 |
| Apo B-100 region B11 (aa 3434-3482) | SEQ ID NO:26 |
| r47 (aa 229-280). Neutrophil Cytosol Factor 1 (NCF-47K) gim\|16659 | SEQ ID NO:27 |
| APO B-100 region B12 (aa 3657-3710) | SEQ ID NO:28 |
| r3 (aa 162-201)Bem-1 protein gim\|3905 | SEQ ID NO:29 |
| Apo B-100 region B13 (aa 4053-4099) | SEQ ID NO:30 |
| r3-2 (aa 163-214)Bem-1 protein gim\|3905 | SEQ ID NO:31 |
| Apo B-100 region B14 (aa 4180-4222) | SEQ ID NO:32 |
| r36 (aa 248-299). Neutrophil NADPH oxidase factor (P67-PHOX) gim\|16660 | SEQ ID NO:33 |
| Apo B-100 region B15 (aa 4179-422) | SEQ ID NO:34 |
| r59. Cytoplasmic protein gim\|16669 | SEQ ID NO:35 |

FIG. 2F

Comparison of SH2-like Regions in Apo B-100 to Known SH2 Domains of Sign Transduction Proteins.

```
 9.  WYHASLTRAQAEHMLMRV--------PRDGA-FLVRKRNEPNSYAISFR-AEGKIKH
10.  FFGEG-IK----KMGLAFESTKSTSPPKQ-AEAVLKTLQELKKLTISEQNIQ-RANL
     **  T* *M * *              P** A ****  *E* ***S  **        (SEQ ID NO:36)

9.  C-RVQQEGTVMLGNSEFDSLV-DLISYYEKHPL------------------YRKMKLK
10.  FNKLVTELRGLSDEAVT-SLLPQLIEVSSPITLQALVQCGQPCSTHILQWLKRVHAN    (SEQ ID NO:37) 4
     ** E * ** SL* *LI *  L                            *******

5.  WFHG--KISKQEAYNLLMTVGQACSFLVRPS-DNTPGDY-SLYFRTSENIQRFKICP
11.  IMLSVEKLIKDLKSKE---VPEAR-AYLRILGEEL-G-FASLHDLQLLGKLLLMGAR
     **  K* K*            V *A ****R* **  G * SL             *

5.  T----PNNQFMMGGRYYN-SSIGDIIDHYRK-EQIVEGYY--LKEP               (SEQ ID NO:38)
11.  TLQGIPQ---MIGE-VIRKGSKNDFFLHYIFMENAFELPTGAGLQL               (SEQ ID NO:39) 4
     T  P*  M*G ** S D** HY E***E *
```

FIG. 3A

Comparison of SH2-like Regions in Apo B-100 to Known SH2 Domains of Sign Transduction Proteins.

5.  WFHGKIS--KQEAYNLLMTVGQACSFLVRPSDNTPGDYSLYFRTSENIQ----R--F
16. YFH-KLNIPK---LD--FSS-QAD---LR--NEIK---TLL--KAGHIAWTSSGKGSW
    *FH K*   K        QA     *R  **    *L*          *    *     (SEQ ID NO:40)
5.  KI-CPTPNNQFMMGGRYYNSSIGDLIDHYRKEQIVEGYYLK
16. KWACPRFSDE---GTH--ESQISFTIEGPLTSFGLSNKINS
    K*  CP *  **   G  *  *S I    I**   *       *                   (SEQ ID NO:41)

6.  WYWGDISR---EEVNE---KLRDTPDGTFLVRDASSKIQG--DYTLTLRKGGNNKL
17. EFSAQPFEITASTNNEGNLKVR------FPLR-LTGKIDFLNNYALFLSPSAQQAS
      *           NE   K*R           FR  KI*  *Y*L  L  ***  (SEQ ID NO:42)
6.  IKVFHR--DGKYG--FSEPLTFCSVVDLITHYRHESLAQYNAKLDTRLLYPVSKY
17. WQVSARFNQYKYNQNFSAGNNEN--IMEA--HVGINGEANLDF-LNIPLTIPEMRL
    * V  R  * KY   FS        **E*  H*  *  A** L L  *P  **     (SEQ ID NO:43)

FIG. 3B

Comparison of SH2-like Regions in Apo B-100 to Known SH2 Domains of Sign Transduction Proteins.

```
8.    WFHGKLGAG-RDGRHIAERLLTEYCIETGAPDGSFLVRESETFVGD-YTLSFWRNGK
21.   EP-GKPGIYTRE---------ELC---------TMEIREVGTVLSQVYSK--VHNGS    (SEQ ID NO:44)
      ** GK*G*   R*                    ****RE   T** * Y*  **NG    (SEQ ID NO:45)

8.    VQHCRIHSRQDAGTPKFFLTDNL-VFD--SLY-DLITH-----YQQVPLRCNEFEMRLSE
21.   -EILFSYF-QDLVITLPFELRKHKLIDVISMYRELL-KDLSKEAQEV-FKAIQS-LKTTE
         QD*    *F     **D S*Y *L* *       Q*V ** *  ** *E
```

Structurally important motifs are indicated by double underline. Percent similarity is a right.

FIG. 3C

Comparison of the Apo B-100 SH1-like Region to SH1 Kinase Domains Known Signal Transduction Proteins.

```
              10        20         N*        VA K*      P T* VPE   *E*  *K *      *V    *
           V G  ***                                                   *
     APOB  VSDGIAALDL------NA------VANK-IADFELP-TIIVPEQTI-EIPSIK-FSVPAGIVIPSF
     SRC   LGQGCFG-EVWMG-TWNG-T--TRVAIKTLK----PGTMS-PEAFLQEAQVMKKLRH-EKLV----
     cFYN  LGNGQFG-EVWMG-TWNGNT---KVAIKTLK----PGTMS-PESFLEEAQIMKKLKH-DKLV----
     HCK   LGAGQFGE-VWMA-TYN----KHTKVAVKTMK----PGSMSV-EAFLAEANVMKTLQH-DKLVKLH-
     LYN   LGAGQFG-EVWMGY-YN-NS---TKVAVKTLK----PGTMSV-QAFLEEANLMKTLQH-DKLVRL-Y
     LCK   LGAGQFG-EVWMGY-YNG---HTKVAVKSLKQ----GSMS-PDAFLAEANLMKQLQH-QRLVRL-Y 70       80        90        100         K       *L    *   ***    I *G
           * ***       * P*Y *T *  * * K                                  110       120         130
     APOB  QAL-TARFEVDSPVYNAT-WSASLKNKADYVETVL--DSTCSSTVQFL---EYELNVLGTHKIEDG
     SRC   Q-LY-A-VVSEEPIYIVTEY-MS-KG-S-LLD-FLKGET-G-K---YLRLPQL-VDMAAQ--IASG
     cFYN  Q-LY-A-VVSEEPIYIVTEY-MN-KG-S-LLD-FLK-DGEG-RAL---KLPNL-VDMAAQ--VAAG
     HCK   -AVVT-K---E-PIYIITEF-MA-KG-S-LLD-FLKSDE-GSKQP-LPKL----IDFSAQ--IAEG
     LYN   -AVVT-R---EEPIYIITEY-MA-KG-S-LLD-FLKSDEGG-KVL-LPKL----IDFSAQ--IAEG
     LCK   -AVVT----QEPIYIITEY-MEN-G-S-LVD-FLKTPSGI-K-LTINKL----LDMAAQ--IAEG
```

FIG. 4A

Identification of the Apo B-100 SH1-like Region and the SH1 Kinase Domains of Known Signal Tranduction Proteins and Their Corresponding Sequence Identification Numbers

| Reference Protein | Sequence ID No. |
|---|---|
| ApoB (aa 3804-4006) | SEQ ID NO:46 |
| SRC (aa 275-488) | SEQ ID NO:47 |
| FYN (275-488) | SEQ ID NO:48 |
| HCK (268-480) | SEQ ID NO:49 |
| LYN (252-469) | SEQ ID NO:50 |
| LCK (250-462) | SEQ ID NO:51 |

FIG. 4B

The Inter-Kringle Proline-Rich Regions of Apo[a] are Compared to
Proline-Rich Region of SH3-Binding Protein 1 (3BP1).

```
3BP1   TS-LRAPT-MPPP-LPPVPP-Q-PARRQSRR--LPA---SPVIS              (SEQ ID NO:57)
ikr2   -SDAEG-TAVAPPTVTPVPSLEAPSE-QA------PTEQR-PGVQE            (SEQ ID NO:58)

3BP1   TS-LRAPT-MPPP-LPPVPP-Q-PARRQSRR--LPA---SPVIS              (SEQ ID NO:57)
ikr3   -SDAEG-TAVAPPTITPIPSLEAPSE-QA------PTEQR-PGVQE            (SEQ ID NO:59)

3BP1   TS-LRAPT-MPPP-LPPVPP-Q-PARRQSRR--LPA---SPVIS              (SEQ ID NO:57)
ikr4   -SDAEW-TAFVPPNVILAPSLEAFFE-QA----L-TEE-TPGVQD             (SEQ ID NO:60)

3BP1   TS-LRAPT-MPPP-LPP--VPPQPARRQSRR--LPA---SPVIS              (SEQ ID NO:57)
ikr5   ---L-V-TE--SSVLATLTVVPDPST-EASSEEAPTEQ-SPGVQD             (SEQ ID NO:61)

3BP1   TS-LRAPT-MPPP-LPPVPP-Q-PARRQSRR--LPA---SPVIS              (SEQ ID NO:57)
ikr7   P--VMESTLLTTPTVVPVPSTELPSE-EA------PTEN-STGVQD            (SEQ ID NO:62)

3BP1   TS-LRAPT-MPPP-LPPVPP-Q-PARRQSRR--LPA---SPVIS              (SEQ ID NO:57)
ikr8   P--VTESSVLTTPTVAPVPSTEAPSE-QA------PP-E-KSPVVQD           (SEQ ID NO:63)

3BP1   TS-LRAPT-MPPP-LPPVPP-Q-PARRQSRR--LPA---SPVIS              (SEQ ID NO:57)
ikr9   -SETE--SGVLET--PTVVP-E-PSM-EAHSEAAPTEQ-TPVVRQ             (SEQ ID NO:64)

3BP1   TS-LRAPT-MPPP-LPPVPP-Q-PARRQSRR--LPASPVIS                 (SEQ ID NO:57)
ikr10  -SDTESGTVVAPPTV--I---QVPSL--------GPPSEQD-                (SEQ ID NO:65)
```

FIG. 5A

Identification of the Inter-Kringle Proline-Rich Regions of Apo[a] and the Proline-Rich Region of SH3-Binding Protein 1 (3BP1) compared in FIG. 5A.

| Reference Protein | Sequence ID No. |
|---|---|
| 3BP1 Proline-Rich Region of Sh3-Binding protein 1 | SEQ ID NO:57 |
| ikr2 amino acids (106-141) | SEQ ID NO:58 |
| ikr3 amino acids (3322-3357) | SEQ ID NO:59 |
| ikr4 amino acids (3436-3471) | SEQ ID NO:60 |
| ikr5 amino acids (3550-3585) | SEQ ID NO:61 |
| ikr7 amino acids (3770-3805) | SEQ ID NO:62 |
| ikr8 amino acids (3884-3919) | SEQ ID NO:63 |
| ikr9 amino acids (3998-4033) | SEQ ID NO:64 |
| ikr10 amino acids (4112-4137) | SEQ ID NO:65 |

FIG. 5B

Proteins Are Compared to the Analogous Regions in Apo B-100.

```
              *K*A***   R* ****  ** **G*    G***  * * ***
B100(13-49)   PKDATRFKHLRKYTYNYEAESSSGV-PGTAD--SRSATRI    (SEQ ID NO:66)
SRC(7-40)     PKDAS----QRRRSLEP-AENVHGA-GGGAFPASQTPSKP    (SEQ ID NO:67)
FYN(7-38)     DKEATKLTEERDGSLN---Q-SSGYRYGT-DP---TPQHY    (SEQ ID NO:68)

*** * TF  Y*  *L   *  **T  *P Y    PGE L
apoB-100 (4448-4536) IQNYH-TFLIYITELLKKLQSTTVMNP-YMKLAPGE-LTIIL   (SEQ ID NO:69)
SRC(505-535)         PEE-RPTF-EYLQAFLEDYFTST--EPQYQ---PGENL----   (SEQ ID NO:70)
FYN(506-536)         PEE-RPTF-EYLQSFLEDYFTAT--EPQYQ---PGENL----   (SEQ ID NO:71)
HCK(498-526)         PEE-RPTF-EYIQSVLDDFYTAT--ESQYQQQ-P--------   (SEQ ID NO:72)
LYN(483-511)         AEE-RPTF-DYLQSVLDDFYTAT--EGQYQQQ-P--------   (SEQ ID NO:73)
LCK(480-508)         PED-RPTF-DYLRSVLEDFFTAT--EGQYQPQ-P--------   (SEQ ID NO:74)
```

*indicates conserved amino acids

FIG. 6

Examples of Proline Pipe Helix Structures in ApoB-100

| SEQ ID NO: | Sequence | Sequence Source |
|---|---|---|
| 77 | PQNAKLKIKRPVKVQPIARVWY | Tus proline pipe (223-243) |
| 78 | PDFRLPEIAIPEFIIPTLNLND | ApoB-100 (2682-2702) |
| 79 | NDFQVPDLHIPEFQLPHISHTI | ApoB-100 (2702-2723) |
| 80 | PSLELPVLHVPRNLKLSLPHFK | ApoB-100 (3273-3294) |

FIG. 7

Sequence Comparison of DNA-Binding Protein ISGF3γ SEQ ID NO:81, and a Similar Region of Apo B-100 SEQ ID NO:82, Located Between Residues 0008 and 0393.

```
MAS--GRARCT--RKLRNWVVEQVESGQ----FPGVCWDDTA-KTMFRI           ISGF3γ
VSLVCPKDA-TRFKHLRKYTYN-YEAESSSGVPGTADSRSATRINCKV            apoB100
**    *    T  **LR  *  ** *E*          *PG    *A  *    **
      -                                         -

PW--KHAGKQDFRESQDAAFFKAWAIF-----KGKYK---EGDKEVPER           ISGF3γ
ELEVPQLCSFILKTSQCTL--KEVYGFNPEGKALLKKTKNSEEFAAAM            apoB100
 *    **  SQ **  K  *  F   K*  *K   *
              -         -     -

GRMDVAEPYKVYQLLPPG-IVSGQPGTQKV-PS-----KRQHSSVSSE            ISGF3γ
SRYE----LKL--AIPEGKQVFLYP--EKDEPTYILNIKRGIISALLV            apoB100
R**   *KV  **P G V   P  *K* P*        KR    S*
-              -                      -

RKE-EDAMQNCTLSPSVLQDSLNNEEGASGGAVHSDIGSSSSSSPEP             ISGF3γ
PPETEEAKQVL-FLDTVYGNCSTHFTVKTRKGNVATEISTERDLGQCD            apoB100
 E E*A Q   *   *    *v* *          *  *    S*
                                                -

QEVTDTTEAPFQGQDQRSLEFLLPPEPDYSLLLTFIYNGRVVGEAQVQS           ISGF3γ
RFKPIRTGISPLALIKGMTRPLSTLISSSQSCQYTLDAKRKHVAEAIC            apoB100
        T * * * * *L *  S   * **** A**
         -
```

FIG. 8A

Sequence Comparison of DNA-Binding Protein ISGF3γ SEQ ID
NO:81, and a Similar Region of Apo B-100 SEQ ID NO:82,
Located Between Residues 0008 and 0393.

```
LDCRLVAEPSGSESS-ME-QVLF-PKPGPEPTQRLLSQLERGILVASN         ISGF3γ
KEQRLFLPFSYKNKYGMVAQVTQTLKL--EDTPKINSRFFGEGTKKMG         apoB100
 *  *L** *S  *  M  QV  *R*    E T  S *

PRGLFVQ--RLCPIPISWNAPQAPPGPHLLPSNECVELFRTAYFCR           ISGF3γ
---LAFESTKSTSPPKQAEAVLKTLQELKRLTISEQNIQ--RANLFNK         apoB100
   L***  *     *  *A*  *     *L *S** **  R* *F *

DLVRYFQGLGPPPKFQVTLNFWEESHGSSHTPQNLITVKMEQAFARYL         ISGF3γ
-LVTELRGLSDEAVTSLLPQLIEVSSPIT-LQALVQCGDPQCSTHTL          apoB100
 LV *GL  *    * ****E S   *   *Q L*    Q   *** L KMEQAFARYLLEQ-TPEQQAAILSLV                               ISGF3γ
KRVHANP-LLIDVVTY---LVALIPE                               apoB100
K  A * L** T*  *** L *
```

* indicates conserved amino acids
bold type indicates positively charged, basic amino acids

FIG. 8B

Sequence Comparison of DNA-Binding Protein ISGF3γ SEQ ID
NO:81, and a Similar Region of Apo B-100 Located Between
Residues 2930 and 3324, SED ID NO:83.

```
MA-SGRARCTRKLRNWVEQVESGQFPGVCWDD------------        ISGF3γ
FGLSNKIN-SKHLRVNQNLVYESGSLNFSKLEIQSQVDSQHVGHSVL      apoB100
** S  **  ****LR         *ESG  *        -**

TAKTM-----FRIPW--KHAGKQDFRESQDAAFFKAWAIFKGKYKEG      ISGF3γ
TAKGMALFGEGKAEFTGRHDAFLNGKVIG-TL--KNSLFFSAQPFEI      apoB100
TAK M          **  *  H   * K  **F ---DKEVPE-RGRMDVAEPYKVYQLLPPGIVSGQPGTQKVPSKRQHS      ISGF3γ
TASTNNEGNLKVRFPLRLTGKI-DFLNNYALFLSPSAQQA-SWQVSA      apoB100
         *   R* *       R* *  *L   **  P *Q * S KRQHSSVSSE---RKEEDAMQNCTLSPSVLQDSLNNEEGASGGAVHS      ISGF3γ
RFNQYKYNQNFSAGNNENIMEAHVGINGEANLDFLNI-PLTIPEMR-      apoB100
 *       *     *E**M*         * N    **  *    *

DIGSSSSSSPEPQEVTDTTEAPFQGDQRSLEFLLPPEPDYSLLLTF       ISGF3γ
-LPYTITTPPLKDFSLWEKTGLKEFL-KTTKQSFDLSVKAQYKKNK       apoB100
  * ** P  *   V  *  *    ***   * *   * *  *
```

FIG. 8C

Sequence Comparison of DNA-Binding Protein ISGF3γ SEQ ID
NO:81, and a Similar Region of Apo B-100 Located Between
Residues 2930 and 3324, SED ID NO:83.

```
IYNGRVVGEAQVQSLDCRLVAEPSGSESSMEQVLFPKPGPEPTQRLL     ISGF3γ
HRHSTNPLAVLCEFISQSIKSFDRHFEKNRNNALDFVTKSYNETKIK     apoB100
 *  *  ****  *              E  ****  *     ***

SQLERGILVASN-PRGLFVQRLCPIPISWNAPQAPPGPHLLPSNE       ISGF3γ
FDKYRAEKSHDELPRT-FQIPGYTVPV-VNVEVSPFTIEMSAFGYVF     apoB100
 *  *  **       * PR  F∇/   **P* *N*  P*  *   **

CVELFRTAYF---CRDLVRYFQGLGPPPKFQVTLNFWEESHGSSHTP     ISGF3γ
-PKAVSMPSFSILGSD-VRVPSYTLILPSLELPVLHVPRNCKLSCPH     apoB100
  *  **  *  F     D  VR     P  *** *  *   S -QNLITVKMEQAFARYLLEQTPEQQAAILSLV                    ISGF3γ
FKELCTISHIFIPAMGNITYDFSFKSSVITLN                    apoB100
 &L T*    **A  *  *  *****L
```

* indicates conserved amino acids
bold type indicates positively charged, basic amino acids
ISGF3γ = sequence ID No:81. Apo B-100 amino acids (aa
2930-3324) = sequence ID NO:83.

FIG. 8D

Various regions of apoB-100 having similarity of ISGF3γ (1-51)

| Sequence | Region | SEQ ID NO: |
|---|---|---|
| MASGRARCTRKLRNWVVEQVESGQFPGVCWDDTAKTMFRIPWKHAGKQDFR | ISGF3γ(1-51) | 84 |
| --PKDATRFKHLRKYTYNYEAESSSGVPGTAD-SRSATRINCKVELEVLPQ | APOB(13-59) | 85 |
| --PEGKALLKKTKNSEEFAAM----------SRYELKLAIP-EGKQVFL | APOB(80-116) | 86 |
| --CSTHFTVKTRKGNVATEIST----------ERDLGQCDRFKPIRTGIS | APOB(159-196) | 87 |
| CSTHILQWLKRVHANPLLIDVVTYLVALIPEPSAQQLREIFNMARDQRSRA | APOB(363-413) | 88 |
| HLSCDTKEERKIKGVISI----------PRLQAEARSEILAHWSPAKL | APOB(1082-1119) | 89 |
| --SVHLDSKKQHLFVKEVKIDGQFRVSSFY--AKGTYGLSCQRDPNTGRL | APOB(1441-1487) | 90 |
| KHINIDQFVRKYRAALGKLPQQANDYLSFNWERQVSHAKE---------- | APOB(2073-2113) | 91 |
| ---KLTALTKKYRITENDIQIA----------LDDAKINFNEKLSQLQTYMIQ | APOB(2114-2153) | 92 |
| -ERINDVLEHVKHFVINLIGDFEVAEKINAFRAKVHELIERYEVDQQIQVL | APOB(2281-2330) | 93 |
| -NKFLDMLIKKLKSFDYHQFVDETNDKIREVTQRLNGEIQALELPQKAEAL | APOB(2390-2439) | 94 |
| ---SNKINSKHLRVNQNLVYESGSLN------------------- | APOB(2933-2955) | 95 |
| ----FSKLEIQSQVDSQHVGHSVLTAKGMALFGEGGKAEFTGRHDAHLNGK | APOB(2956-3001) | 96 |

FIG. 9A

Various regions of apoB-100 having similarity of ISGF3γ (1-51)

| | | |
|---|---|---|
| KLDVTTSIGRRQHLRVSTAFVYTKNPNGYSFSIPVKVLADKFITPGLKLND | APOB(3662-3712) | 99 |
| --FREIQIYKKLRTSSFALNLPTLPEVKFPEVDVLTKYSQPEDSLIPFFEI | APOB(3738-3786) | 100 |
| ---LHLRYQKDKKGISTSAASPAVGTVGMDMDEDDDFSKWNFYYSPQSSPD | APOB(3959-4006) | 101 |
| ---LREVSSKLRRNLQNNAEWVYQGAIRQIDDIDVRFQKAASGTTGTYQEW | APOB(4070-4117) | 102 |
| -RVTQKFHMKVKHLIDSLIDFLNFPRFQFPGKPGIYTREELCTMFIREVGT | APOB(4150-4199) | 103 |

FIG. 9B

Various regions of apoB-100 having similarity of ISGF3γ (42-69)

| | | SEQ ID NO: |
|---|---|---|
| WKHAGKQDFRESQDAAFF-------KAWAIFKGKYKEG-DKEVPERGRMDVAEPYK | iSGF3γ(42-69) | 104 |
| EHVKHFVINLIGD-------FEVAEKINA-FRAKVHELIERYEVDQQIQVLMDKLV | APOB(2288-2335) | 105 |
| VRKYRAALGKLPQQANDYLNSFNWERQVS--HAKEKLTALTKKYRITENDIQIA | APOB(2081-2132) | 106 |
| YIKDSYDLHDLKIAIANIIDEIIEKLKSLDEHYHIRVNLVKTIHDLHLFIENIDFNK | APOB(2157-2213) | 107 |
| -----------KITLIINWLQEALSSASLAHMKAKFRETLEDTR------------ | APOB(2461-2493) | 108 |
| -------------------------TDHFSLRARYHMKADSVVDLSYNVQGSGETTY | APOB(1353-1385) | 109 |
| -------------------------KLTTNGRFREHNAKFSLDGK------------ | APOB(1656-1675) | 110 |
| DTKYQIRIQIQEKLQQLKRHIQNIDIQHLAGKLKQHIEAIDVRVLLDQLGTT----- | APOB(2226-2277) | 111 |
| -----------FHDFPDLGQEVALNANTKNQKIRWKNEVRIHSGSFQSQVELSNDQ- | APOB(3583-3627) | 112 |
| ------------------KDNVFDGLVRVTQKFHMKVKHLIDSLIDFLNFPR----- | APOB(4141-4174) | 113 |
| --------------HRNIQEYLSILTDPDGKGKEKIAELSATAQEIIKS-------- | APOB(4418-4452) | 114 |

FIG. 9C

Sequence Comparison of DNA-Binding Domains of SREBP 1 (aa 279-452) SEQ ID NO:116, SREBP 2 (aa 287-568) SEQ ID NO:117 and ADD1 (aa 250-421) SEQ ID NO:118 to a Similar Region of Apo B-100 (aa 2024-2234) SEQ ID NO:115.

```
EFTIVAFVKYKYDKNQDVHSINLPFFETLQEYFERNRQTIIVVLENVQ         APOB100
GPLPTLVSGGTILATVPLVVDAEKLPINRLAAGSKAPASAQSR-GE           SREBP1
QVPTLVGSSSGTILTTMPVMMGQEKVPIKQVPGGVKQ-LEPPKE-GE          SREBP2
GPLQTLVSGGTILATVPLVVDTDKLPIHRLAAGGKALGSAQSR-GE           ADD1
*******     V * * ***** *Q * ** E *

RKLKHINIDQFVRKYRAAL-GKLPQQANDYLNSFNWERQVSHAKEK           APOB100
KRTAH-NAIE--KRYRSSINDKIIELK-DLVVGTEAKLNKSAVLRK           SREBP1
RRTTH-NIIE--KRYRSSINDKIIELK-DLVMGTDAKMHKSGVLRK           SREBP2
KRTAH-NAIE--KRYRSSINDKIVELK-DLVVGTEAKLNKSAVLRK           ADD1
R* H NI *  YR* K* D  K*  *  *S * K

LTALTKYRITEND-IQIALDDAKINFNEKLS-----QLQTYMIQF            APOB100
AIDYIR-FLQHSNQKLKQENLSLRTAV-HKSKSLK--DLVSAC---           SREBP1
AIDYIK-YLQQVNHKLRQENMVLKLA-NQKNKLLGIDLGSLV---            SREBP2
AIDYIR-FLQHSNQKLKQENLTLRSA--HKSKSLK--DLVSAC---           ADD1
 *  * K Y   N* *   *K*  *N*K             *L ***
```

FIG. 10A

Sequence Comparison of DNA-Binding Domains of SREBP 1 (aa 279-452) SEQ ID NO:116, SREBP 2 (aa 287-568) SEQ ID NO:117 and ADD1 (aa 250-421) SEQ ID NO:118 to a Similar Region of Apo B-100 (aa 2024-2234) SEQ ID NO:115.

```
EFTIVAFVKYDKNQDVHSINLPFFETLQEYFERNRQTIIVVLENVQ        APOB100
GPLPTLVSGGTILATVPLVVDAEKLPINRLAAGSKAPASAQSR-GE        SREBP1
QVPTLVGSSGTILTTMPVMMGQEKVPIKQVPGGVKQ-LEPPKE-GE        SREBP2
GPLQTLVSGGTILATVPLVVDTDKLPIHRLAAGGKALGSAOSR-GE        ADD1
 ******      V *   *    *****  *Q * ** E   *

RKLKHINIDQFVRKYRAAL-GKLPQOANDYLNSFNWERQVSHAKEK        APOB100
KRTAH-NAIE--KRYRSSINDKIIELK-DLVVGTEAKLNKSAVLRK        SREBP1
RRTTH-NIIE--KRYRSSINDKIIELK-DLVMGTDAKMHKSGVLRK        SREBP2
KRTAH-NAIE--KRYRSSINDKIVELK-DLVVGTEAKLNKSAVLRK        ADD1
 R*  H NI *  YR* K*  D  *  *  S *   K

LTALTKKYRITEND-IQIALDDAKINFNEKLS-----QLQTYMIQF        APOB100
AIDYIR-FLQHSNQKLKQENLSRTAV-HKSKSLK--DLVSAC---         SREBP1
AIDYIK-YLQQVNHKLRQENMVLKLA-NQKNKLLKGIDLGSLV---        SREBP2
AIDYIR-FLQHSNQKLKQENLTLRSA-HKSKSLK--DLVSAC---        ADD1
 *  *  K  Y    N*    *     *K*  *N*K       *L ***
```

FIG. 10B

Sequence Comparison of SREBP1 to Apolipoprotein apo A1
apoA1 (1-243) SEQ ID NO: 119 and SREBP1 (aa 233-500) SEQ ID NO:120

```
DEPPQSPWDRVKDLATVYVDVLKDSGRDYVSQFEGSALGKQLNLKLLDNWDSVTSTFSKLREQLGPVTQEFWDN    apoA1
QQVPVLLQQPHFTKADSLLLTAMKTDGATVK----AAGLSPLVSGTTVQTG-PLPTLVSGG--TILATVPLVVD-   SREBP
 ***P * ** * **** **K/G     ***L *     **    * * *S    * **  *

LEKETEGLRQEMSKDLEEVKAKVQPYLDDFQKKWQEEMELYRQKVEPLRAELQEGARQKLHELQ-EKLSPLGEE    apoA1
AEKLPINRLAAGSKAPASAQSRG------EKRTAHNAIEKRYRSSINDKIIELKDLVVGTEAKLNKSAVL---    SREBP
 *EK   SR  * **           *K*  */  R  * */ R * **    E*  *R ***

MRDRAR--AHVDALRTHLAPYSDELRQRLAARLEA-LKEN------GGARLAEY-HAKATE---------         apoA1
-R-KATDYIRF-LQHSNQKLKQENLSLRTAVHKSKSLKDLVSACGSGGNTDVLMEGVK-TEVEDTLTPPPSDAG    SREBP
 R*A   ***  *  ** * _*  **L  R  ***    LK*

-------------HLSTLSEKAKPALEDLRQGLLPVLESFKVSFLSALEEYTKK--                       apoA1
SPFQSSPLSLGSRGSGSGSGSGSDSEPDSPVF----EDSKAKP--EQ-RPSLHSRGMLDR-SRL-ALCTLVFLC-   SREBP
                          *KAKP    E* R  L  *  ST AL *

LNTQ    apoA1
LSCN    SREBP
L *
```

FIG. 10C

Sequence Comparison of apoAII (1-77) SEQ ID NO:121 and SREBP1 (aa 353-423) SEQ ID NO:122

```
QAKEPCVESLVSQYFQTVTDYGKDLM---EKVKSPELQAEAKSYFEKSKEQLTPLIKKAGTELVNFLSYFVEL-    apoA-II
EAKLNK--SAVLRKAI---DYIRFLQHSNQKLKQENLSL--RTAVHKSKS-LKDLVSACGSG-GNTD-VLMEGV    SREBP1
 *AK\/⎺   S*V         DY*L       *K*K  *L L  *R**KSR   L⎺L*   G*    N   ***E GTQPATQ    apoA-II
KTEVEDT    SREBP1
 T** \/
```

FIG. 10D

Sequence Comparison of apoAIV (30-376) SEQ ID NO:123 and SREBP1 (aa 330-1146) SEQ NO:124

```
QKSELTQQLNALFQDKLGEVNTYAGDLQKLVPFATELHERLAKDSEKLKEEIGKELE---ELRA-R-LLPH          apoAIV
EKLPI-NRLAAGS--KAPASAQSRGE--KRTAHNAIEKRYRSSIN-DKITE-L-KDLVGTEAKLNKSAVLR          SREBP1
 *K    *  *L A  R*         *  G*  R*   *  * *R*  *  *K* E *** E****

-ANEVSQKIGDNLRELQQRLEPYADQLRTQVNTQAEQLRRQLDPLAQ--RMERVLRENADS-LQASLRPH--         apoAIV
KAIDY-IRFLQHS---NQKLQENLSLRTAVHKSKS-LK-DLVSACGSGGNTDVLMEGVKTEVEDTLTPPPR          SREBP1
 A     *    *Q*L      LRT V     L* *L  *              VL E  * ** *L P ADELKAKIDQNVEELKGRLTPYADEFKVKIDQ-TVEELR      apoAIV
DAGSPFQSSPLSLGSRGSGSGGSGSDSEPDSPVFEDSKAKPEQRP-SLHSR----GMLDRSRLALCTLVFLC         SREBP1
                                     KAKQ *  L*R       T* L RSLAPYAQDTQEKLNHQLEGLTFQMKKNAEELKARISASAEID-QTVEELRRSLAPYAQDTQEKLNHQLEGL         apoAIV
ESCNPLASLLGARGLPSPSDTTSVYHSPGRNVEGTESRDGPGWAQAVQLFCDLLLVVRTSLWRQQ-QPPAP          SREBP1
 S   P*A           T     **  * *       S  *   Q*V*   L****   *   Q*  **

TFQMKKNAEELKARISASAEELR--QR---LAPLAEDVRGNLKGNT--EGLQKSLAELGGHLDQQVEE--F         apoAIV
APAAQGASSRP----QASALEIRGFQRDLSSLRRLAQSFRPAMRRVFLHEATARLMAGASPTRTHQLLDRSL         SREBP1
 *        *     ASA  E R  QR    L   LA *R     *R   HA      E* *A   Q*    F RRRVEPYGENFNKALVQQMEQLRQKLGPHAGDVEGHLS-FLEKD----LRDKVNSFFSTFKEKESQ-DKTLS         apoAIV
RRRAGPGGKGG--AVAE-LE-PRPTRREHA-EALLLASCYLPPGFLSAPGQRVGMLAEAARTEKLGDRRL-         SREBP1
RRR*  P G    A***  *E    *R      HA **      *S  *L      *  *V  *  *E  D*  L
```

FIG. 10E

Sequence Comparison of apoAIV (30-376) SEQ ID NO:123 and SREBP1 (aa 330-1146) SEQ ID NO:124        apoA
                                                                                                  SREB1

```
LPELEQQQEQQQEQVQMLAPLES
LHDCQQ------MLMRLGGGTTVTSS
 L-*   *Q           **   S
```

FIG. 10F

Sequence Comparison of acat (fragment 1) SEQ ID NO:125 and SREBP1        acat
                        (aa 300-486) SEQ ID NO:126                       SREBP1

```
EKMSLRNRLS-KSRENPEEDED-QRNPAKESLETPSNGRIDIKQLIA          acat
ERLPI-NRLAAGSKAPASAQSRGEKRTAHNAIE---------              SREBP1
 E R* *  NRL *   S*  *  *     *      A*****E KKIKLTANGRI-DIKQLIAKK-IKLTAENGRIDIKQLIAKKIKLTAE          acat
KRYRSSINDKIIELKDLVGTEARLNKSYIRFLQHS--NQKLKQENL          SREBP1
 K* N *I ***K*L**   *KL     R*\/*     K*K AEELKPFFMKEVGSHFDDFVT-------NLI-EKSAS-LDNKAHSF          acat
S--LRTAVHKSKSLR--DLVSACGSGGNTDVLMEGVKTEVEDKAKPE         SREBP1
 *  L****R    D*V*          ***  E  *  ***KA*

VRENV-PR-VLNSAKEK                                        acat
QRPSLHSRGMLD--RSR                                        SREPB1
 *R    *R  *L*  **
```

FIG. 10G

Sequence Comparison of acat (fragment 2) SEQ ID NO:127 with
SREBP1 (aa 1061-1085) SEQ ID NO:128

```
RRHC-PLKNPTFLDYVRPRSWTCRYVF         acat
RRRAGPGGKGGAVAELEPRPTRREH           SREBP1
RR*  P   ** * PR
```

FIG. 10H

Sequence Comparison of apoE (aa 124-181) SEQ ID NO:129 and SREBP1 (aa 302-360) SEQ ID NO:130

```
AMLGQSTEE-LRVRLA--SHL-RKLKRLLRDADDLQKRL-AVYQAGAREGAERGLSAIRE-RL    apoE
KLPINRLAAGSKAPASAQSRGEKRT----AHNA--IEKRYRSSIN--DKIIELKDLVVGTEAKL  SREBP1
   ** S*  **   *        KR* * **  *  \/* L *  E *L --GPLVEQGRVRAATVGSLAGQPLQERAQAWGERLRARMEEMGSRT-RDRLDEVKEQVA        apoE
NKSAVL---R-RAIDYIRFLQHSNQKCKQENLS-LRTAVHK--SKSLKD-LVSACGSGG       SREBP1
  ***     R RA* *  ** *  Q  Q         LR*      S** *D 1  *
```

FIG. 10I

Sequence Comparison of apoC-II (aa 1-42) SEQ ID NO:131 with
SREBP1 (aa 231-275) SEQ ID NO:132

```
TQQPQQDEMPSPTFLTQVK----ES--LSSYWE---SAKTAAQNLYEKTYL    apoC-II
SQ-IQQ----VPVLLQPHFIKADSLLLTAMKTDGATVKAAGLSPLVSGTT     SREBP1
*Q *QQ      * *L Q**    *S  L***  _   **K*A* **
```

FIG. 10J

Sequence Comparison of apoC-III (aa 7-51) SEQ ID NO:133 with
SREBP1 (aa 314-360) SEQ ID NO:134

```
SLLSFMQGYMKHATKTAKDAL--SSVQESQVAQQARGWVTDGFSSLK--     apoC-I
APASAQSRGEKRTAHNATEKRYRSSIND-KIIE-LKDLVVGTEAKLNKS     SREBP1
*S    _K**_A *  _*SS* *        *L
```

FIG. 10K

Sequence Comparison of APO C-III (aa 52-79) SEQ ID NO:135 with
SREBP1 (aa 717-748) SEQ ID NO:136

DYWST--VKDKFSEFWDLDPEVRP--TSAVAA      apoC-III
EIYVAAALRVKTSLPRALHFLTRFFLSSARQA      SREBP1
*** *  *** R S * L * R*  *SA  A

FIG. 10L

Sequence Comparison of apo D (aa 30-34) SEQ ID NO:137 with SREBP1
(aa 301-305) SEQ ID NO:138

EKIPT       apoD
ERLPI       SREBP1
EK*P

FIG. 10M

Sequence Comparison of apo D (aa 36-65) SEQ ID NO:139 with SREBP1 (aa 361-391) SEQ ID NO:140

ENGRCIQANYS-LME-NGKIKVLNQELRADG    apoD
AVLRKA-IDYIRFLQHSNQKEKQENLSERTAV   SREBP1

FIG. 10N

Comparison of the Primary Structures of Known Coiled-Coil Regions of DNA-Binding Proteins and Analogous Regions in Apo B-100

| Sequence | Name | SEQ ID NO |
|---|---|---|
| MKQLEDKVEELLSKNYHLENEVARLKKLVGER | GCN4-p1 | (SEQ ID NO:141) |
| KHEIQEMFDQLRAKEKELRTWEEELTRAALQQ | hMLK1(286-317) | (SEQ ID NO:142) |
| EELLRRREQELAEREIDILERELNIIIHQLCQ | hMLK1(321-352) | (SEQ ID NO:143) |
| RIQIQEKLQQLKRHIQNIDIQHLAGKLKQHIE | apoB(2232-2264) | (SEQ ID NO:144) |
| VLQQVKIKDYFEKLVGFIDDAVKKLNELSFKTFIE | apoB(2353-2387) | (SEQ ID NO:145) |
| ELSFKTFIEDVNKFLDMLIKKLKSFDYHQFV | apoB(2379-2409) | (SEQ ID NO:146) |
| HQFVDETNDKIREVTQRLNGEIQALELP | apoB(2406-2433) | (SEQ ID NO:147) |
| AAKNLTDFAEQYSIQDWAKRMKALVEQGFTV | apoB(2530-2560) | (SEQ ID NO:148) |
| SASLAHMKAKFRETLEDTRDRMYDMDIQQELQRYL | apoB(2475-2509) | (SEQ ID NO:149) |
| CLNLHKFNEFIQNELQEASQELQQIHQYIMALREE | apoB(4326-4360) | (SEQ ID NO:150) |
| FLIYITELLKKLQSTTVMNPYMKLAPGELTIIL | apoB(4504-4536) | (SEQ ID NO:151) |

FIG. 11

Comparison of Known ATP-Binding loop Motifs to Similar Regions in Apo B-100. The critical amino acid H is indicated by (#)

A: THE HIGH LOOP

| Sequence | Source | SEQ ID |
|---|---|---|
| RLLDHRVPETDMTFRHVGSKLIVAMSSWLQ | apoB(1183-1212) | (SEQ ID NO:152) |
| LNFSKLEIQSQVDSQHVGHSVLTAKGMALF | apoB(2954-2983) | (SEQ ID NO:153) |
| NQNFSAGNNENIMEAHVGINGEANLDFLNI | apoB(3072-3101) | (SEQ ID NO:154) |
| MVVTRIAPSPT-GDPHVGTAYIALFNYAWA | TTETS(1-29) | (SEQ ID NO:155) |
| TTVHTRFPPEPNGYLHIGHAKSICLNFGIA | ECQTS(25-54) | (SEQ ID NO:156) |
| KIKLYCGVDPTAQSLHLGNLVPMVLLHFYV | YSCMSY1(85-114) | (SEQ ID NO:157) |
| PIALYCGFDPTADSLHLGHLVPLLCLKRGQ | ECOTYRS(33-62) | (SEQ ID NO:158) |
| RVTLYCGFDPTADSLHIGNLAAILTLRRFQ | BACTYRSA(30-59) | (SEQ ID NO:159) |
| RIGAYVGIDPTAPSLHVGHLLPLMPLFWMY | NEUTYRSM(95-124) | (SEQ ID NO:160) |
| PIALYCGFDPTADSLHLGHLVPLLCLKRFQ | SYY ECOLI(31-61) | (SEQ ID NO:161) |
| PLKVKLGADPTAPDIHLGHTVVLNKLRQFQ | HEAHI1610(31-60) | (SEQ ID NO:162) |
|                             # |   |   |

FIG. 12A

Comparison of Known ATP-Binding loop Motifs to Similar Regions in Apo B-100. The critical amino acid K is indicated by (#)

B: THE KMSK LOOP

| Sequence | Source | SEQ ID |
|---|---|---|
| VSKGLLIFDASSSMGPQMSASVHLDSKKQHLFVKEVKIDGQF | apoB(1421-1463) | SEQ ID NO. 163 |
| TIITTPPLKDFSLWEKTGLKEFLKTTKQSFDLSVKAQYKKNKH | apoB(3113-3155) | SEQ ID NO. 164 |
| KNRNNALDFVTKSYNETK----IKFDKYKAEKSQDELPRTFQI | apoB(3183-3221) | SEQ ID NO. 165 |
| DALQYKLEGTTRL---TR----KRGLKLATALSLSNKFVEGSH | apoB(3348-3390) | SEQ ID NO. 166 |
| RAFGWEAPREYHMPLLRNPDK-TKISKRKSHTSLDWYKAEGFL | ttets(221-262) | SEQ ID NO. 167 |
| DNITIPVHPRQYEFSRLNLEY-TVMSKRKLNLLVTDKHVEGWD | ecqts(245-287) | SEQ ID NO. 168 |
| KNKGL--PFGITVPLLTTATGE-KFGKSAGNAVFIDPSINTAY | YSCMSY1(282-320) | SEQ ID NO. 169 |
| RLHQNQ-VFGLTVPLITKADG-TKFGKTEGGAVWLDPKKTSPY | ECOTYRS(215-254) | SEQ ID NO. 170 |
| KTKGEARAFGLTIPLVTKADG-TKFGKTESGTIWLDKEKTSPY | BACTYRSA(210-249) | SEQ ID NO. 171 |
| KTALDE-CVGFTVPLLTDSSG-AKFGKSAGNAIWLDPYQTSVF | NEUTYRSM(303-343) | SEQ ID NO. 172 |
| RLHQNQ-VFGLTVPLITKADG-TKFGKTEGGAVWLDPKKTSPY | SYY ECOLI(213-253) | SEQ ID NO. 173 |
| SAGKK-PQVAITLPLLVGLDGEKKMSKSLGNYIGVTEAPSDMF | HEAHI1610(202-243) | SEQ ID NO. 174 |

FIG. 12B

Examples of Nuclear Localization Signal Sequences in the ApoB-100 Amino Acid Sequence Compared to Known NLS Sequences.

Human apoB-100 sequences with 10 amino acids in the spacer region between the bipartite NLS element

| SEQ ID NO. | Sequence | Source of Sequence |
|---|---|---|
| 178 | HKNTSTLSCDGSLRHKF | human apoB-100 (1387-1403) |
| 179 | RKLKHINIDQFVRKYRA | human apoB-100 (2070-2086) |
| 180 | RHIQNIDIQHLAGKLKQH | human apoB-100 (2244-2261) |
| 181 | KKGFYKKQCRPSKGRK | human IGFBP-3 |
| 182 | KKPLDGEYFTLQIRGRER | human p53 fragment 1 |
| 183 | KRALPNNTSSSPQPKKK | human p53 fragment 2 |
| 184 | KKTNLFSALIKKKKKTA | human Ab1 |
| 185 | RKTLLNSLEEAKKKKED | human apoJ fragment 1 |
| 186 | RRELDESLQVAERLTRK | human apoJ fragment 2 |

FIG. 13A

Human apoB-100 sequences with 10 amino acids in the spacer region between the bipartite NLS element

| SEQ ID NO. | Sequence | Source of Sequence |
|---|---|---|
| 187 | RRSYALVSLSFFRKLRL | human ir fragment 1 |
| 188 | RRYGDEELHLCVSRKHF | human ir fragment 2 |
| 189 | KRVAKRKLIEQNRERRR | human thyroid receptor fragment 1 |
| 190 | HRSTNAQGSHWKQRRKF | human thyroid receptor fragment 2 |
| 191 | KRPPISDSEELSAKKRK | human af9 |
| 192 | KKGKKPKTEKEDKVKHI | human irf2 |
| 193 | RKRMRNRIAASKCRKRK | human apl |
| IGFBP-3 = interferon growth factor binding protein 3; apoʃ = apolipoprotein ʃ; ir-insulin receptor; af9-activation factor 9; irf-insulin response factor 2; apl = activation protein 1 | | |

FIG. 13B

Human apoB-100 sequences with more or less than 10 amino acids in the spacer region between the bipartite NLS element

| SEQ ID NO. | Sequence | Source of Sequence |
|---|---|---|
| 194 | RHIQNIDIQHLAGKLKQH | human apoB-100 (2244-2261) |
| 195 | KKITEVALMGHLSCDTKEERK | human apoB-100 (1072-1094) |
| 196 | KHINIDQFVRKYRA | human apoB-100 (2073-2086) |
| 197 | HRNIQEYLSILTDPDGKGKEK | human apoB-100 (4418-4438) |

FIG. 13C

Human apoB-100 sequences with more or less than 10 amino acids in the spacer region between an imperfect bipartite NLS element

| SEQ ID NO. | Sequence | Source of Sequence |
|---|---|---|
| 198 | KEVYGFNPEGKALLKKTK | human APOB100 73-90 |
| 199 | KVLVDHFGYTKDDKHEDM | human APOB100 705-723 |
| 200 | KAGKLKFIIPSPKRPVKL | human APOB100 891-908 |
| 201 | RQVSHAKEKLTALTKKYR | human APOB100 2106-2123 |
| 202 | KYQIRIQIQEKLQQLKRH | human APOB100 2228-2245 |
| 203 | KGMALFGEGKAEFTGRHDAH | human APOB100 2978-2997 |
| 204 | KQSFDLSVKAQYKKNKHR | human APOB100 3139-3156 |
| 205 | KLEGTTRLTRKRGLK | human APOB100 3353-3367 |
| 206 | KLDVTTSIGRRQHLR | human APOB100 3662-3676 |
| 207 | KLDFREIQIYKKLR | human APOB100 3735-3748 |

FIG. 13D

Human apoB-100 sequences with more or less than 10 amino acids in the spacer region between an imperfect bipartite NLS element

| SEQ ID

Alignment of Human 2701-3540 SEQ ID NO:214 with Hamster SEQ ID NO:215 and Mouse SEQ
ID NO:216 apoB-100 Sequences

```
LNDFQVPDLHIPEFQLPHISHTIEVPTFGKLYSILKIQSPLFTLDANADIGNGTTSANEA-           Human   (2701-2760)
          EFQLPRLSHTIEIPAFGRLHGILKIQSPLFILDANANIQNVTTLENKAE              Hamster (frag 1)
          EFQLPHLSHTIEIPAFGKLHSILKIQSPLFILDANANIQNVTTSGNKAE              Mouse   (frag 1)

GIAASITAKGESKLEVLNFDFQANAQLSNPKINPLALKESVKFSSKYLRTEHGSEMLFFG           Human   (2761-2820)
IVASIAAT-GESEIEALNFDFQAQAQFLELNPNPLILKESMNFSSKHARMEHEGEILFSG           Hamster (frag 1)
IVAS-VTAKGESQFEALNFDFQAQAQFLELNPHPPVLKESMNFSSKHVRMEHEGEIVFDG           Mouse   (frag 1)

NAIEGKSNTVASLHTEKNTLELSNGVIVKINNQLTLDSNTKYFHKLNIPKLDFSSQADLR           Human   (2821-2880)
KFIEGKLDTVASLQTEKNMVEFNNGMIVKINNPIILDSHTKYFHKLSIPRLDFSSKASFN           Hamster (frag 1)
KAIEGKSDTVASLHTEKNEVEFNNGMTVKVNNQLTLDSHTKYFHKLSVPRLDFSSKASLN           Mouse   (frag 1)

NEIKTLLKAGHIAWTSSGKGSWKWACPRFSDEGTHESQISFTIEGPLTSFGLSNKINSKH           Human   (2881-2940)
NEIKMLLEAGHVAWTSSGTGSWNWACPNFSDEGTHSSKISFTVEGPIAFFGLSNNINGKH           Hamster (frag 1)
NEIKTLLEAGHVALTSSGTGSWNWACPNFSDEGIHSSQISFTVDGPIAFVGLSNNINGKH           Mouse   (frag 1)

LRVNQNLVYESGSLNFSKLEIQSQVDSQHVGHSVLTAKGMALFGEGKAEFTGRHDAHLNG           Human   (2941-3000)
LRVIQKLAYESGFLNYSMLEVESKVESQHVGSSILTGKGTVLLREAKAEMTGEHNADLNG           Hamster (frag 1)
LRVIQKLTYESGFLNYSKFEVESKVESQHVGSSILTANGRALLKDAKAEMTGEHNANLNG           Mouse   (frag 1)

KVIGTLKNSLFFSAQPFEITASTNNEGNLKVRFPLRLTGKIDFLNNYALFLSPSAQQASW           Human   (3001-3060)
KVIGTLKNSLSFSAQPFMITASTNNDGNLKVSFPLKLTGKIDFLNNYALFLSPHAQQASW           Hamster (frag 1)
KVIGTLKNSLFFSAQPFEITASTNNEGNLKVGFPLKLTGKIDFLNNYALFLSPRAQQASW           Mouse   (frag 1)
```

FIG. 14A

Alignment of Human 2701-3540 SEQ ID NO:214 with Hamster SEQ ID NO:215 and Mouse SEQ ID NO:216 apoB-100 Sequences

```
LNDFQVPDLHIPEFQLPHISHTIEVPTFGKLYSILKIQSPLFTLDANADIGNGTTSANEA-     Human (2701-2760)
         EFQLPRLSHTIEIPAFGRLHGILKIQSPLFLIDANANIQNVTTLENKAE          Hamster (frag 1)
         EFQLPHLSHTIEIPAFGKLHSILKIQSPLFILDANANIQNVTTSGNKAE          Mouse (frag 1)

GIAASITAKGESKLEVLNFDFQANAQLSNPKINPLALKESVKFSSKYLRTEHGSEMLFFG      Human (2761-2820)
IVASIAAT-GESEIEALNFDFQAQAQFLELNPNPLILKESMNFSSKHARMEHEGEILFSG      Hamster (frag 1)
IVAS-VTAKGESQFEALNFDFQAQAQFLELNPHPPVLKESMNFSSKHVRMEHEGEIVFDG      Mouse (frag 1)

NAIEGKSNTVASLHTEKNTLELSNGVIVKINNQLTLDSNTKYFHKLNIPKLDFSSQADLR      Human (2821-2880)
KFIEGKLDTVASLQTEKNMVEFNNGMIVKINNPIILDSHTKYFHKLSIPRLDFSSKASFN      Hamster (frag 1)
KAIEGKSDTVASLHTEKNEVEFNNGMTVKVNNQLTLDSHTKYFHKLSVPRLDFSSKASLN      Mouse (frag 1)

NEIKTLLKAGHIAWTSSGKGSWKWACPRFSDEGTHESQISFTIEGPLTSFGLSNKINSKH      Human (2881-2940)
NEIKMLLEAGHVAWTSSGTGSWNWACPNFSDEGTHSSKISFTVEGPIAFFGLSNNINGKH      Hamster (frag 1)
KAIEGKSDTVASLHTEKNEVEFNNGMTVKVNNQLTLDSHTKYFHKLSVPRLDFSSKASLN      Mouse (frag 1)

LRVNQNLVYESGSLNFSKLEIQSQVDSQHVGHSVLTAKGMALFGEGKAEFTGRHDAHLNG      Human (2941-3000)
LRVIQKLAYESGFLNYSMLEVESKVESQHVGSSILTGKGTVLLREAKAEMTGEHNADLNG      Hamster (frag 1)
LRVIQKLTYESGFLNYSKFEVESKVESQHVGSSILTANGRALLKDAKAEMTGEHNANLNG      Mouse (frag 1)

KVIGTLKNSLFFSAQPFEITASTNNEGNLKVRFPLRLTGKIDFLNNYALFLSPSAQQASW      Human (3001-3060)
KVIGTLKNSLSFSAQPFMITASTNNDGNLKVSFPLKLTGKIDFLNNYALFLSPHAQQASW      Hamster (frag 1)
KVIGTLKNSLFFSAQPFEITASTNNEGNLKVGFPLKLTGKIDFLNNYALFLSPRAQQASW      Mouse (frag 1)
```

FIG. 14B

Alignment of Human 2701-3540 SEQ ID NO:214 with Hamster SEQ ID NO:215 and Mouse SEQ
ID NO:216 apoB-100 Sequence

```
QVSARFNQYKYNQNFSAGNNENIMEAHVGINGEANLDFLNIPLTIPEMRLPYTITTPPL        Human (3061-3120)
QVSARFNQYKYNQNFSAINNEHNIEAHVGMNGDANLDFLTIPLTIPEVKLPYIGLTTPLL       Hamster (frag 1)
QASTRFNQYKYNQNFSAINNEHNIEASIGMNGDANLDFLNIPLTIPEINLPYTEFKTPLL       Mouse (frag 1)

KDFSLWEKTGLKEFLKTTKQSFDLSVKAQYKNKHRHSITNPLAVLCEFISQSIKSFDRH        Human (3121-3180)
KDFSIWEETGLK------KQSFDLSVKAQYKKNRDRHSIAIPLNGFYEFILNNVDSGIGK      Hamster (frag 1)
KDFSIWEETGLKEFLKTTKQSFDLSVKAQYKNSDKHSIVVPLGMFYEFILNNVSNWDRK       Mouse (frag 1)

FEKNRNNALDFVTKSYNETKIKFDKYKAEKSQDELPRTFQIPGYTVPVVNEVSPFTIEM        Human (3181-3240)
IGKVRDSALDYLISSYNEAKNKFEN-----SLIQPSRTFQKRGYTIPFVNIEVTPFTVET      Hamster (frag 1)
FEKVRNNALHFLTTSYNEAKIKVDKYKTENSLNQPSGTFQNHGYTIPVVNIEVSPFAVET      Mouse (frag 1)

SAFGYVFPKAVSMPSFSILGSDVRVPSYTLILPSLELPVLHVPRNL-KLSLPHFKELCTIS     Human (3241-3300)
LASSHVIPKAINTPSVHILGPNVIVPSYRLVLPSLELPVLRVPRNLLKFSLPDFKELRTID    Hamster (frag 1)
LASRHVIPTAISTPSVTIPGPNIMVPSYKLVLPPLELPVFHGPGNLFKFFLPDFKGFNTID    Mouse (frag 1)

HIFIPAMGNITYDFSFKSSVITLNTNAELFNQSDIVAHLLSSSSSVIDALQYKLEGTTRL      Human (3301-3360)
NIYIPALGNFTYDFSFKSSVITLNTNVGLYNRSDIVAHFLSSSSFVTDALQYKLEGTSRL     Hamster (frag 1)
NIYIPAMGNFTYDFSFKSSVITLNTNAGLYNQSDIVAHFLSSSSFVTDALQYKLEGTSRL     Mouse (frag 1)

TRKRGLKLATALSLSNKFVEGSHNSTVSLTTKNMEVSVAKTTKAEI--PILRMNFKQELNGN    Human (3361-3420)
TRKRGLKLATADSLTNKFVKGNHDSTFSLTKKNMEASV-KTT-ANLHAPILTMNFKQELNGN   Hamster (frag 1)
MRKRGLKLATAVSLTNKFVKGSHDSTISLTKKNMEASV-RTT-ANLHAPIFSMNFKQELNGN   Mouse (frag 1)
```

FIG. 14C

Alignment of Human 2701-3540 SEQ ID NO:214 with Hamster SEQ ID NO:215 and Mouse
SEQ ID NO:216 apoB-100 Sequences

```
TKSKPTVSSSMEFKYDFNSSMLYSTAKGAVDHKLSLESLTSYFSIESSTKGDVKGSVLSR    Human (3421-3480)
AKSKPIVSSSIELNYDFNSSKLYSTAKGGVDHKFSLESLTSYFSIESSTKGNIKGSVLSQ    Hamster (frag 1)
TKSKPTVSSSIELNYDFNSSKLHSTATGGIDHKFSLESLTSYFSIESFTKGNIKSSFLSQ    Mouse (frag 1)
EYSGTIASEANTYLNSKSTRSSVKLQGTSKIDDIWNLEVKENFAGEATLQRIYSLWEHST    Human (3481-3540)
EYSGGSVASEANTYLNS                                               Hamster (frag 1)
EYSGGSVANEANVYLNS                                               Mouse (frag 1)
```

FIG. 14D

Alignment of Human 3481-4536 SEQ ID NO:217 with Rat SEQ ID NO:218 apoB-100
Sequences

```
EYSGTIASEANTYLNSKSTRSSVKLQGTSKIDDIWNLEVKENFAGEATLQRIYSLWEHST     Human (3481-3540)
           NSKGTRSSVRLQGASNFAGIWNFEVGENFAGEATLRRIYGTWEHNM     Rat (frag 2)

KNHLQLEGLFFTNGEHTSKATLELSPWQMSALVQHASQPSSFHDFPDLGQEVALNANTK     Human (3541-3600)
INHLQVFSYFDTKGKQTCRATLELSPWTMSTLLQVHVSQPSPLFDLHHFDQEVILKASTK     Rat (frag 2)

NQKIRWKNEVRIHSGSFQSQVELSNDQEKAHLDIAGSLEGHLRFLKNIILPVYDKSLWDF     Human (3601-3660)
NQKVSWKSEVQVESQVLQHNAHFSNDQEEVRLDIAGSLEG----------QLWDL         Rat (frag 2)

---------------------------------------------------------      Human
ENFFLPAFGKS-----------------------------------------------     Rat (frag 2)

LKLDVTTSIGRRQHLRVSTAFVYTKNPNGYSFSIPVKVLADKFITPGLKLNDLNSVLVMP    Human (3661-3720)
LR-ELLQIDGKRQYLQASTSLHYTKNPNGYLLSLPVQELTDRFIIPGLKLNDF-------    Rat (frag 2)

TFHVPFFTDLQVPSCKLDFREIQIYKKLRTSSFALNLPTLPEVKFPEVDVLTKYSQPEDSL   Human (3721-3780)
-----------SGIKIYKKLSTSPFALNLTMLPKVKFPGVDLLTQYSKPEGSS           Rat (frag 2)

IPFFEITVPESQLTVSRFTLPKSVSDGIAALDLNAVANKIADFELPTIIVPEQTIEIPSI    Human (3781-3840)
VPTFETTIPEIQLTVSQFTLPKSFPVGNTVFDLNKLTNLIADVDLPSITLPEQTIEIPSL    Rat (frag 2)

KFSVPAGIVIPSFQALTARFEVDSPVYNATWSASLKNKADYVETVLDSTCSSTVQFLEYE    Human (3841-3900)
EFSVPAGIFIPFFGELTAHVGMASPLYNVTWSTGWKNKADHVETFLDSTCSSTLQFLEYA    Rat (frag 2)
```

FIG. 14E

Alignment of Human 3481-4536 SEQ ID NO:217 with Rat SEQ ID NO:218 apoB-100 Sequences

```
LNVLGTHKIEDGTLASKTKGTLAHRDFSAEYEEDGKFEGLQEWEGKAHLNIKSPAFTDLH    Human (3901-3960)
LKVVGTHRIENDKFIYKIKGTLQHCDFNVKYNEDGIFEGLWDLEGEAHLDITSPALTDFH    Rat (frag 2)

LRYQKDKKGISTSAASPAVGTVGMDEDDDFSKWNFYYSPQSSPDKKLTIFKTELRVRE      Human (3961-4020)
LHYKEDKTSVSASASPAIGTVSLDASTDDQSVRLHVYFRPQSPPDNKLSIFKMEWRDKE     Rat (frag 2)

SDEETQIKVNWEEEAASGLLTSLKDNVPKATGVLYDYVNKYHWEHTGLTLREVSSKLRRN    Human (4021-4080)
SDGETYIKINWEEEAAFRLLDSLKSNVPKASEAVYDVKKYHLGH------ASSELRKS     Rat (frag 2)

LQNNAEWVYQGAIRQIDDIDVRFQKAASGTTGTYQEWKDKAQNLYQELLTQEGQASFQGL    Human (4081-4140)
LQNDAEH----AIRMVDEMNVNAQRVTRDTYQSL-YKKMLAQE--------SQSIPEKL    Rat (frag 2)

KDNVFDGLVRVTQKFHMKVKHLIDSLIDFLNFPRFQFPGKPGIYTREELCTMFIREVGTV    Human (4141-4200)
KKMVLGSLVRITQKYHMAVTWLMDSVIHFLKFNRVQFPGNAGTYTVDELYTIAMRETKKL    Rat (frag 2)

LSQVYSKVHNGSEILFSYFQDLVITLPFELRKHKLIDVISMYRELLKDLSKEAQEVFKAI    Human (4201-4260)
LSQLF----NGLGHLFSYVQDQV------EKSRVINDI--------TFKCPFSP         Rat (frag 2)

QSLKTTEVLRNLQDLLQFIFQLIEDNIKQLKEMKFTYLINYIQDEINTIFNDYIPYVFKL   Human (4261-4320)
TPCKLKDVLLIFREDLNILSNLGQQDINFTTILSDFQSFLERLLDIIEEKIEC-LKNN--   Rat (frag 2)

ESTCVPDHINMFFKTHIPFAFKS-------                                  Human
--------------------------                                      Rat (frag 2)
```

FIG. 14F

Alignment of Human 3481-4536 SEQ ID NO:217 with Rat SEQ ID NO:218 apoB-100 Sequences

```
LKENLCLNLHKFNEFIQNELQEASQELQQIHQYIMALREEYFDPSIVGWTVKYYELEEKI      Human (4321-4380)
LRENIYSVFSEFNDFVQSILQEGSYKLQQVHQYMKAFREEYFDPSVVGWTVKYYEIEEKM      Rat (frag 2)
VSLIKNLLVALKDFHSEYIVSASNFTSQLSSQVEQFLHRNIQEYLSILTDPDGKGKEKIA      Human (4381-4440)
VDLIKTLLAPLRDFYSEYSVTAADFASKMSTQVEQFVSRDIREYLSMLADINGKGREKVA     Rat (frag 2)
ELSATAQEIIKSQAIATKKIISDYHQQFRYKLQDFSDQLSDYYEKFIAESKRLIDLSIQN      Human (4441-4500)
ELSIVVKERIKSWSTAVAEITSDYLRQLHSKLQDFSDQLSGYYEKFVAESTRLIDLSIQN    Rat (frag 2)
YHTFLIYITELLKLQSTTVMN--PYMKLAPGELTIIL                             Human (4501-4536)
YHMFLRYIAELLKKLQVATANNVSPYLRFAQGELIITF                            Rat (frag 2)
```

FIG. 14G

Alignment of Human 4141-4536 SEQ ID NO:219 with Chicken SEQ ID NO:220 apoB-100 Sequences KDNVFDGLVRVTQKFHMKVKHLIDSLIDFLNFPRFQFPGKPGIYTREELCTMFIREVGTV    Human (4141-4200)
                                       IPGLSEKYTGEELYLMTTEKAAKT  Chicken (frag 1)

LSQVYSKVHNGSEILFSYFQDLVITLPFELRKHKLIDVISMYRELLKQDLSKEAQEVFKAI    Human (4201-4260)
ADICLSKLQEYFDALIAAISELEVRVPASETILRGRNVLDQIKEMLKHLQEKIRQTFVTL    Chicken (frag 1)

QSLKTTEVLRNLQDLLQFIEDNIKQLKEMKFTYLINYIQDEINTIFNDYIPYVFKL        Human (4261-4320)
QEADFAGKLNRLKQVVQKTFQKAGNMVRSLQSKNFEDIKVQMQQLYKDAMASDYAHKLRS    Chicken (frag 1)

LKENLCLNLHKFNEFIQNELQEASQELQQIHQYIMALREEYFDPSIVGWTVKYYELEEKI    Human (4321-4380)
LAENVKKYISQIKNFSQKTLQKLSENLQQLVLYIKALREEYFDPTTLGWSVKYYEVEDKV    Chicken (frag 1)

VSLIKNLLVALKDFHSEYIVSASNFTSQLSSQVEQFLHRNIQEYLSILTDPDGKGKEKIA    Human (4381-4440)
LGLLKNLMDTLVIWYNEYAKDLSDLVTRLTDQVRELVENYRQEYDLITDVEGKGRQKVM    Chicken (frag 1)

ELSATAQEIIKSQAIATKKIISDYHQQFRYKLQDFSDQLSDYYEKFIAESKRLIDLSIQN    Human (4441-4500)
ELSSAAQEKIRYWSAVAKRKINEHNRQVKAKLQEIYGQLSDSQEKLINVAKMLIDLTVEK    Chicken (frag 1)

YHTFLIYITELLKKLQSTTVMNPYMKLAPGELTIIL-----------                 Human (4501-4536)
YSTFMKYIFELLRWFEQATADSIKPYIAVREGELRIDVPFDWEYINQMPQKSREALRNKV    Chicken (frag 1)

-------------------------------------------                     Human
ELTRALIQQGVEQGTRKWEEMQAFIDEQLATEQLSFQQIVENIQKRMKT               Chicken (frag 1)

FIG. 14H

Alignment of Human 1561-1740 SEQ ID NO:221 with Rabbit SEQ ID NO:222 apoB-100 Sequences DMTFSKQNALLRSEYQADYESLRFFSLLSGSLNSHGLELNADILGTDKINSGAHKATLRI    Human (1561-1620)
DLTFSKQNALLRAEYQADYKSLRFFTLLSGLLNTHGLELNADILGTDKMNTAAHKATLRI    Rabbit (frag 1)
GQDGISTSATTNLKCSLLVLENELNAELGLSGASMKLTTNGRFREHNAKFSLDGKAALTE    Human (1621-1680)
GQNGVSTSATTSLRYSPLMLENELNAELALSGASMKLATNGRFKEHNAKFSLDGKATLTE    Rabbit (frag 1)
LSLGSAYQAMILGVDSKNIFNFKVSQEGLKLSNDMMGSYAEMKFDHTNSLNIAGLSLDFS    Human (1681-1740)
LSLGSAYQAMILGADSKNIFNF---------------------------------------    Rabbit (frag 1)

FIG. 14I

Alignment of Human 3301-3720 SEQ ID NO:223 with Rabbit SEQ ID NO:224 apoB-100 Sequences

```
HIFIPAMGNITYDFSFKSSVVITLNTNAELFNQSDIVAHLLSSSSSVIDALQYKLEGTTRL-     Human (3301-3360)
                                           MASEKGPSNKDYT           Rabbit (frag 2)

TRKRGLKLATALSLSNKFVEGSHNSTVSLTTKNMEVSVAKTTKAEIPILRMNFKQELNGN       Human (3361-3420)
LRRRI------EPWEFEVFFDPQELRKEACLLYEIKWGASSKTWRSSGKNTTNH-VEVN        Rabbit (frag 2)

-----                                                              Human
FLEKLT                                                             Rabbit (frag 2)

TKSKPTVSSSMEFKYDFNSSMLYSTAKGAVDHKLSLESLTSYFSIESSTKGDVKGSVLSR       Human (3421-3480)
-----                                                              Rabbit (frag 2)

EYSGTIASEANTYLNSKSTRSSVKLQGTSKIDDIWNLEVKENFAGEATLQRIYSLWEHST       Human (3481-3540)
RKEACLLYEIKWGASSKTWRSSGK-NTTNHVEVNF-LE-KLTSEGRLGPSTCCSI-----       Rabbit (frag 2)

KNHLQLEGLFFTNGEHTSKATLELSPWQMSALVQVHASQPSSFHDFPDLGQEVALNANTK       Human (3541-3600)
TWFLSWS--PCWECSMAIREFLSQHPGVTLIIFVARLFQHMDRRNRQGLKDLVTSGVTVR       Rabbit (frag 2)

NQKIRWKNEVRIHSGSFQSQVELSNDQEKAHLDIAGSLEGHLRFLKNIILPVYDKSLWDF       Human (3601-3660)
VMSVSEYCYCWENFVNYPPGKAAQWPRYPPRWMLMYALELYCIILGLPPC--------         Rabbit (frag 2)

LKLDVTTSIGRRQHLRVSTAFVYTKNPNGYSFSIPVKVLADKFITPGLKLNDLNSVLVMP       Human (3661-3720)
-----LKISRRHQKQL-----------TFFSLTPQYCHYKMIPPYILLATGLLQPSVPWR       Rabbit (frag 2)
```

FIG. 14J

LIPOPROTEINS AS NUCLEIC ACID VECTORS

The present application is a continuation-in-part of U.S. patent application Ser. No. 08/874,807 Entitled "Lipoproteins As Nucleic Acid Vectors" filed Jun. 13, 1997, now abandoned. The entire text of the above-referenced disclosure is specifically incorporated by reference herein without disclaimer.

BACKGROUND OF THE INVENTION

1. Field of the Invention

The present invention relates to materials and methods for the in vivo transport and delivery of nucleic acids. More particularly, it concerns the use of lipoproteins, including but not limited to, low density lipoproteins ("LDL"), and/or apolipoproteins for the in vivo transport of nucleic acids. In addition, the present invention relates to the use of lipoproteins in the early detection of cancer and/or metastatic cancer and/or arteriosclerosis.

2. Description of Related Art

The ultimate curative method for any genetic disorder, whether the disorder is inherited or results from a mutation, depends on an effective mode of replacing or augmenting non-functional gene(s). This process is now termed gene or genetic therapy. There are two important aspects to genetic therapy, the gene delivery system/vehicle and the gene control/expression program. Ideally, a replacement gene should become resident in the genome of the target cells/organism and be transferable to subsequent generations of cells and progeny, i.e., the change is incorporated into the germ cells or reproductive cells, the sperm and ovary. Although there have been several significant breakthroughs in this field, this area of biotechnology is still in its early development phase. The first step in any approach to gene replacement is the delivery of the specific gene (nucleic acid) to the cells.

Many techniques have been and are being developed to deliver and express genes in cells and specific tissues in mammals in vivo. Several general, non-specific methods for delivering genes have been reported involving aerosol nucleic acid delivery to cells (Stribling et al., 1992); calcium phosphate precipitation, using a steep change in ionic strength (Wigler et al., 1979); DEAE-dextran (Sompayrac et al., 1981); electroporation, forcing the nucleic acid into the cell by using an electric field or current (Neumann et al., 1982); microinjection, physically injecting the nucleic acid into a cell (Benvensty et al., 1986; Wolff et al., 1990); and polycationic molecules such as polylysine polypeptides (Curiel et al., 1992) and cationic lipids (Lee et al., 1996).

Liposomes, vesicles composed of synthetic or non-natural lipids such as long-chain fatty adds, can be used to carry the nucleic acid into the cell cytoplasm non-specifically (Felgner et al., 1987). A recent invention describes the delivery of a self-initiating and self-sustaining gene expression system which contains an RNA polymerase prebound to a DNA molecule using the aforementioned nucleotide delivery systems (U.S. Pat. No. 5,591,601).

Viral vectors in which specific nucleic acid sequences are incorporated into a neutralized or inactivated virus can use their viral entry mechanism to gain entry to the cell cytoplasm via specific cellular receptors to deliver nucleic acids (Schimotohono et al., 1981). The use of specific cellular receptors is apparently a more specific method for delivering genes. In this approach, the nucleic acid is bound either freely, through charge association, or alternatively it is chemically and non-reversibly conjugated to proteins with specific receptor proteins on the membrane of target cells for receptor-mediated uptake (Wu et al., 1988, Wu et al., 1989).

Techniques such as calcium phosphate precipitation, electroporation or DEAE-dextran transfection are not suitable for in vivo applications. Bombarding cells with nucleic acids under high pressure is a technique which has very limited applications in that it can only be applied topically and only a small number of cells can be targeted. Microinjection of nucleic acids into cells is mainly performed in vitro and requires actively dividing cells.

Gene delivery systems that use the viral entry mechanism of recombinant viral vectors have major disadvantages. Systems that utilize replication-defective adenoviral vectors can infect a wide variety of eukaryotic cell types including quiescent somatic cells utilizing the viral entry mechanism. However, adenoviral vector-based delivery systems are only successful in transient gene expression and repeated administration of the viral vector results in a strong immunological response of the host. In addition, the host will experience an adenoviral infection and can experience its symptoms if the recombinant vector undergoes homologous recombination with the wild-type virus strain. Systems that employ recombinant retroviral vectors can be used for stable integration of the gene of interest into the host's genome, but only actively dividing cells can be targeted. In addition, the disadvantages of the adenoviral vector systems also apply to retroviral vector systems (immune response, disease etc.).

Positively-charged polycationic molecules such as polylysine peptides which bind non-specifically to the negatively charged nucleic acids have been used to introduce DNA into the chromosome of the recipient cell or organism. Cationic lipid vesicles, liposomes and micelles have been used in aggregates with DNA and viral envelope glycoproteins in non-specific, delivery of genes. Liposomes, vesicles composed of synthetic or non-natural lipids, such as long-chain fatty acids, can be used to carry the nucleic acid into the cell cytoplasm non-specifically. In these systems, the liposomes are structured to "best fit" the nucleic acid and insertion into the cell is through non-specific uptake.

The interaction of the liposomal delivery systems discussed above with the nucleic acid to be delivered is non-specific. In addition, prior art techniques are designed to deliver multiple copies of the nucleic acid to the cell cytoplasm. Optimally, however, only one or two copies of a gene should be transfected per cell throughout the organism to replace a defective set of genes only in the specific cells and tissues where it would normally be expressed.

Thus there is a need for a safe and efficient gene delivery system that may be employed in the burgeoning filed of gene therapy.

SUMMARY OF THE PRESENT INVENTION

The present invention contemplates a gene delivery system for use in gene therapy. Thus in particular embodiments, the present invention provides a composition comprising an isolated polypeptide comprising at least one LDL or VLDL nucleic acid binding domain; and a nucleic acid comprising an LDL or VLDL binding sequence, wherein the nucleic acid is bound to the polypeptide. In particularly preferred embodiments, the polypeptide comprises an LDL nucleic acid binding domain. In other embodiments, the polypeptide comprises a VLDL nucleic acid binding domain. In particular aspects of the present invention, the nucleic acid comprises an expression region operably linked to a promoter active in eukaryotic cells. In more particular embodiments, the expression region encodes a polypeptide. In other preferred embodiments, the expression region comprises an antisense construct.

In those embodiments in which the expression region encodes a polypeptide, the polypeptide may be selected from the group consisting of α-globin, β-globin, γ-globin, granulocytei macrophage-colony stimulating factor (GM-CSF), tumor necrosis factor (TNF), IL-2, IL-3, IL-4, IL-5, IL-6, IL-7, IL-8, IL-9, IL-10, IL-11, IL-12, IL-13, IL-14, IL-15, β-interferon, γ-interferon, cytosine deaminase, adenosine deaminase, β-glucuronidase, hypoxanthine guanine phosphoribosyl transferase, galactose-l-phosphate uridyltransferase, glucocerbrosidase, glucose-6-phosphatase, thymidine kinase, lysosomal glucosidase, growth hormone, nerve growth factor, insulin, adrenocorticotropic hormone, parathormone, follicle-stimulating hormone, luteinizing hormone, epidermal growth factor, thyroid stimulating hormone of CFTR, EGFR, VEGFR, IL-2 receptor, estrogen receptor, Bax, Bak, Bcl-$X_s$, Bik, Bid, Bad, Harakiri, Ad E1B, an ICE-CED3 protease neomycin resistance, luciferase, adenine phosphoribosyl transferase (APRT), retinoblastoma, insulin, mast cell growth factor, p53, p16, p21, MMAC1, p73, zac1 and BRCAI.

In those embodiments in which the expression region comprises an antisense construct, the antisense construct may be complementary to a segment of an oncogene. In more preferred embodiments, the oncogene may be selected from the group consisting of ras, myc, neu, raf, erb, src, fms, jun, trk, ret, gsp, hst, bcl and abl.

The expression region may be linked to a promoter selected from the group consisting of CMV IE, LTR, SV40 IE, HSV tk, β-actin, human globin α, human globin β and human globin y promoter. In a defined embodiment, the nucleic acid binding domain is an apoB100 nucleic acid binding domain. In other embodiments, the composition of the present invention may further comprise one or more lipoproteins selected from the group consisting of apoA1, apoA-II, apoA-IV, acat, apoE, apoC-II, apoC-III and apo-D. In particularly preferred embodiment, the apoB100 is selected from the group consisting of human, rat and baboon apoB 100.

In particular aspects of the invention, the polypeptide comprises at least two nucleic acid binding domains. In particularly preferred embodiments, the nucleic acid binding domain contains a motif selected from the group consisting of a proline pipe helix DNA binding motif, a ISGF3γ-like DNA binding motif, a SREBP-like DNA binding motif, a coiled-coil motif and a nucleotide (ATP)-binding motif. In more defined embodiments, the binding domain may be selected from the group consisting of SEQ ID NO:78, SEQ ID NO:79, SEQ ID NO:80, SEQ ID NO:82, SEQ ID NO:83, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:105, SEQ ID NO:106, SEQ ID NO:107, SEQ ID NO:108, SEQ ID NO:109, SEQ ID NO:110, SEQ ID NO:111, SEQ ID NO:112, NO:113, SEQ ID NO:114, SEQ ID NO:115, SEQ ID NO:144, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:163, SEQ ID NO:164, SEQ ID NO:165, SEQ ID NO:166 and SEQ ID NO:175.

In other embodiments, the polypeptide may further comprise at least one nuclear localization sequence. More particularly, the nuclear localization sequence may be from apoB100. In more preferred embodiments, the nuclear localization sequence may be selected from the group consisting of SEQ ID NO:178, SEQ ID NO:179, SEQ ID NO:180, SEQ ID NO:194, SEQ ID NO:195, SEQ ID NO:196, SEQ ID NO:197, SEQ ID NO:198, SEQ ID NO:199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210.

Also contemplated by the present invention is a method for expressing a polypeptide in a human cell comprising the steps of providing a composition comprising (i) an isolated polypeptide comprising at least one LDL or VLDL nucleic acid binding domain and (ii) a nucleic acid comprising an expression cassette comprising a sequence encoding the polypeptide and a promoter active in eukaryotic cells, wherein the coding sequence is operably linked to the promoter, and wherein the nucleic acid sequence is bound to the LDL or VLDL; contacting the composition with the cell under conditions permitting transfer of the composition into the cell; and culturing the cell under conditions permitting the expression of the polypeptide.

In particularly preferred embodiments, the polypeptide independently, is a tumor suppressor, a cytokine, an enzyme, a hormone, a receptor, or an inducer of apoptosis. In preferred embodiments, the tumor suppressor may be selected from the group consisting of p53, p16, p21, MMAC1, p73, zac1, BRCAI and Rb. In preferred embodiments, the cytokine may be selected from the group consisting of IL-2, IL-2, IL-3, IL-4, IL-5, IL-6, IL-7, IL-8, IL-9, IL-10, IL-11, IL-12, IL-13, IL-14, IL-I5, TNF, GMCSF, β-interferon and γ-interferon. In other preferred embodiments, the enzyme may be selected from the group consisting of cytosine deaminase, adenosine deaminase, β-glucuronidase, hypoxanthine guanine phosphoribosyl transferase, galactose-1-phosphate uridyltransferase, glucocerbrosidase, glucose-6-phosphatase, thymidine kinase and lysosomal glucosidase. In still further preferred embodiments, the hormone may be selected from the group consisting of growth hormone, nerve growth factor, insulin, adrenocorticotropic hormone, parathormone, follicle-stimulating hormone, luteinizing hormone, epidermal growth factor and thyroid stimulating hormone. In defined embodiments, the receptor may be selected from the group consisting of CFTR, EGFR, VEGFR, IL-2 receptor and the estrogen receptor. In other preferred embodiments, the inducer of apoptosis may be selected from the group consisting of Bax, Bak, Bcl-$X_s$, Bik, Bid, Bad, Harakiri, Ad E1B and an ICE-CED3 protease.

In particularly preferred embodiments, the nucleic acid binding domain is an apoB 100 nucleic acid binding domain. In more preferred embodiments, the apoB 100 may be selected from the group consisting of human, rat and baboon low density apoB100. In still further preferred embodiments, the binding region is selected from the group consisting of a proline pipe helix DNA binding motif, a ISGF3γ-like DNA binding motif, a SREBP-like DNA binding motif, a coiled-coil motifs, and a nucleotide (ATP)-binding motif. In particular embodiments, the polypeptide further may comprise at least one nuclear localization sequence. In especially preferred embodiments, the nuclear localization sequence is derived from an apoB100 nuclear localization sequence. In specific embodiments, the polypeptide may be selected from the group consisting of α-globin, β-globin, γ-globin, neomycin resistance, luciferase, adenine phosphoribosyl transferase (APRT), and mast cell growth factor.

Also provided is a method for providing an expression construct to a human cell comprising providing a composition comprising (i) an isolated polypeptide comprising at least one LDL or VLDL nucleic acid binding domain and (ii) an expression cassette comprising a nucleic acid sequence encoding an expression region and a promoter active in eukaryotic cells, wherein the expression region is operably linked to the promoter, and wherein the nucleic acid sequence is bound to the LDL or VLDL; contacting the composition with the cell under conditions permitting transfer of the composition into the cell; and culturing the cell under conditions permitting the expression of the expression region.

In particularly preferred embodiments, the expression construct comprises an antisense construct. In more preferred embodiments, the antisense construct is derived from an oncogene. In exemplary embodiments, the oncogene may be selected from the group consisting ras, myc, neu, raf, erb, src, fms, jun, trk, ret, gsp, hst, bcl and abl. In other embodiments, the expression construct comprises a nucleic acid coding for a gene. In preferred aspects the gene encodes a polypeptide.

In particularly preferred embodiments, the nucleic acid binding domain is an apoB100 nucleic acid binding domain. The apoB100 may be selected from the group consisting of human, rat and baboon low density apoB100. In other preferred embodiments, the DNA binding region is selected from the group consisting of a proline pipe helix DNA binding motif, a ISGF3γ-like DNA binding motif, a SREBP-like DNA binding motif, a coiled-coil motifs, and a nucleotide (ATP)-binding motif.

Further the present invention contemplates a method for treating a human disease comprising providing a composition comprising (i) an isolated polypeptide comprising at least one LDL or VLDL nucleic acid binding domain and (ii) an expression cassette comprising a nucleic acid sequence encoding an expression region and a promoter active in eukaryotic cells, wherein the expression region is operably linked to the promoter, and wherein the nucleic acid sequence is bound to the LDL or VLDL; and administering the composition to a human subject having the disease under conditions permitting transfer of the composition into cells of the human subject.

In specific embodiments, the disease may be selected from the group consisting of cancer, diabetes, cystic fibrosis and arteriosclerosis. In preferred embodiments the polypeptide comprises at least two nucleic acid binding regions. In other preferred embodiments the polypeptide comprises at least one nuclear localization sequence. In particularly preferred embodiments, the nucleic acid encodes a gene. In other preferred embodiments, the expression construct comprises an antisense construct.

Another aspects of the present invention describes a pharmaceutical composition comprising an isolated polypeptide comprising at least one LDL or VLDL nucleic acid binding domain; and a nucleic acid comprising an LDL or VLDL binding sequence, wherein the nucleic acid is bound to the polypeptide; the pharmaceutical composition being dispersed in a suitable diluent.

Also contemplated by the present invention is a method of transforming a cell comprising providing a cell; contacting the cell with a composition comprising (i) an isolated polypeptide comprising at least one LDL or VLDL nucleic acid binding domain and (ii) an expression cassette comprising a nucleic acid sequence encoding an expression region and a promoter active in eukaryotic cells, wherein the expression region is operably linked to the promoter, and wherein the nucleic acid sequence is bound to the LDL or VLDL; wherein expression of the expression region is indicative of the transformation.

Yet another aspect of the present invention contemplates a method of transfecting a cell comprising the steps of providing a cell; contacting the cell with a composition comprising (i) an isolated polypeptide comprising at least one LDL or VLDL nucleic acid binding domain and (ii) an expression cassette comprising a nucleic acid sequence encoding an expression region and a promoter active in eukaryotic cells, wherein the expression region is operably linked to the promoter, and wherein the nucleic acid sequence is bound to the LDL or VLDL; wherein expression of the expression region is indicative of the transfection.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1 shows the amino acid sequence of apoB-100.

FIG. 2A–FIG. 2F is a homology alignment of SH3-like regions in apo B-100 with known SH3 domains of signal transduction proteins. FIG. 2A–FIG. 2D are the homology alignments and FIG. 2E–FIG. 2F identify the regions of apo B-100 and the proteins aligned.

FIGS. 3A–3C show a comparison of SH2-like regions in apo B-100 to known SH3 domains of signal transduction proteins. FIG. 3A and FIG. 3B are the homology alignments, FIG. 3C identifies the proteins and regions aligned.

FIG. 4A–FIG. 4B shows a comparison of the apo B-100 SH 1-like region to SH1 kinase domains of known signal transduction proteins. FIG. 4A and FIG. 4B shows the alignments;

FIG. 5A and FIG. 5B shows the inter-kringle proline-rich regions of Apo[a] compared with the proline rich region of SH3-binding protein (3BPI). FIG. 5A shows the alignment, FIG. 5B identifies the proteins and regions aligned.

FIG. 6 show an homology alignment of specific regions of apo B-100 and the activation regions located at the amino- and carboxyl- termini of signal transduction proteins.

FIG. 7 illustrates the homology of specific regions of apo B-100 with proline pipe helix motifs of Tus.

FIGS. 8A–8D show a homology alignment among one region of the DNA-binding protein ISGF3γ and similar regions in apo B-100.

FIGS. 9A–9C show a homology alignment among regions of the DNA-binding protein ISGF3γ and similar regions in apo B-100.

FIGS. 10A–FIG. 10N shows a sequence comparison of the DNA-binding domains of the SREBP1, SREBP2, and ADD1 proteins with similar regions found in apo B-100. FIG. 10B–10N shows a sequence comparison of the DNA-binding domains of SREBP1 with various apolipoproteins.

FIG. 11 shows a comparison of the primary structures of known coiled-coil regions of DNA-binding proteins and analogous regions in apo B-100.

FIGS. 12A–12B show a comparison of known ATP-binding loop motifs to similar regions in apo B-100.

FIGS. 13A–13E show a comparison of known nuclear localization signal sequences to similar regions in apo B-100.

FIGS. 14A, 14B–14C, 14D, 14E, 14F–14J show a comparison of human apo B-100 regions with sequenced regions of apo B-100 from other species.

DETAILED DESCRIPTION OF THE PREFERRED EMBODIMENT

Figure 15:
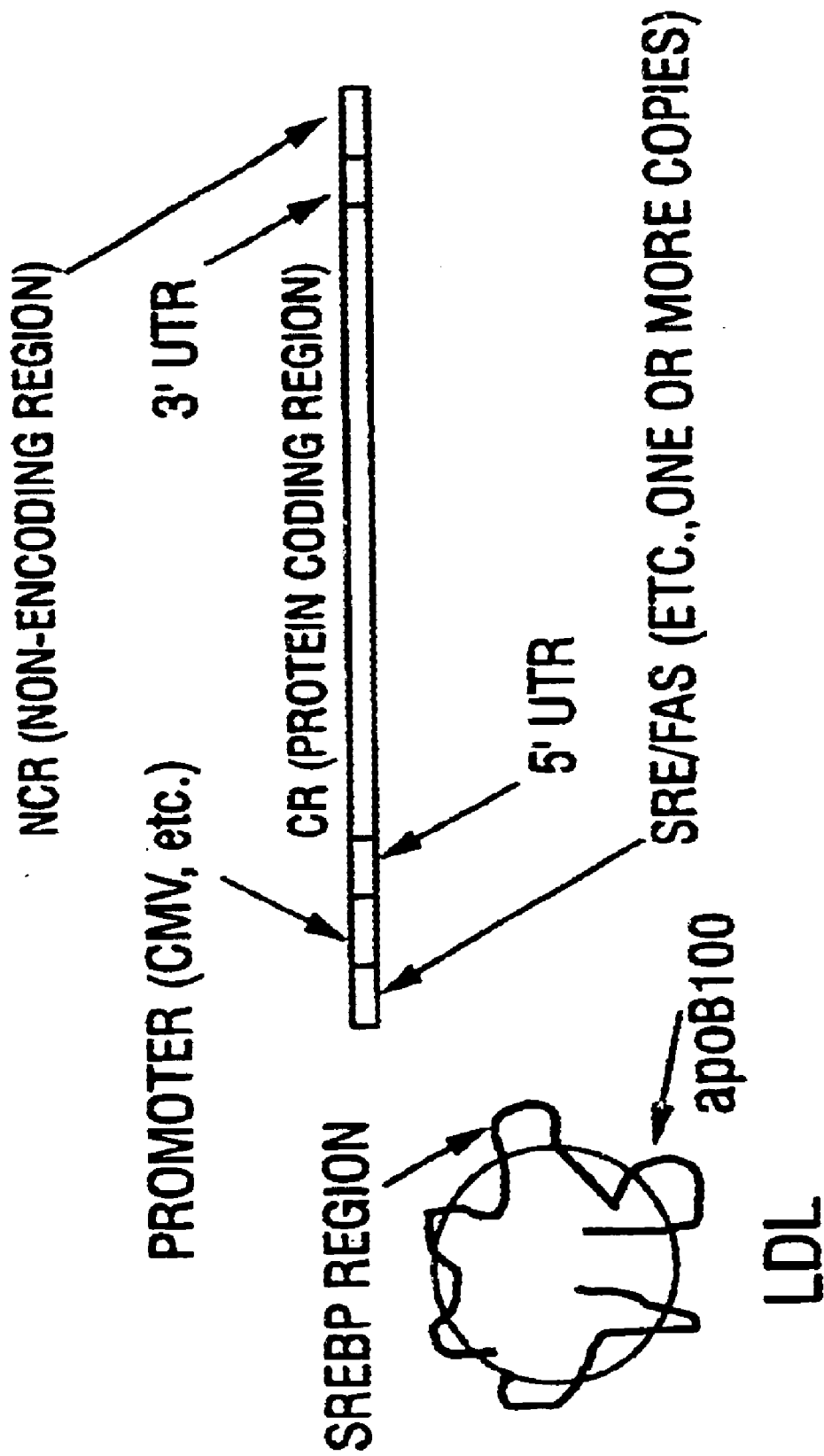
FIG. 15 shows the composition of the LDL gene delivery system of the instant invention LDL containing apo B-100 is depicted along with a DNA sequence containing a promoter, a protein coding region, a 3' untranslated region, and a non-coding region.

The present invention arises from the discovery that regions of apolipoproteins, the protein fraction of lipoprotein particles, are similar in primary structure and amino acid sequence to cellular proteins which are known to bind to DNA. Presently, the only known functions of lipoproteins VLDL, IDL, LDL and HDL are the solubilization and transport of hydrophobic lipids in plasma. The instant invention shows that LDLs, but not other lipoproteins, form a complex with DNA.

Herein, synthetic analogues of regions of DNA have been shown to bind to highly purified preparations of human, rat, and baboon LDL but not to other human lipoproteins such as VLDL and HDL, nor to mouse lipoproteins. In fact, the differences observed among the four species tested suggests that human, rat, and baboon lipoproteins behave very similarly in terms of DNA binding preference. Further, purified preparations of human, rat, and baboon LDLs are shown to complex with the promoter region of the human cytomegalovirus. Thus, the present invention demonstrates that human LDL complexes with specific regions of genomic DNA.

Because lipoproteins have specific cell membrane receptors and are actively and specifically internalized by many different cell types in mammals, and because the inventors show that LDL can bind DNA, these lipoproteins can be used as gene delivery vectors. More specifically, this invention relates to materials and methods for the use of lipoproteins, such as LDL, or, for example, apolipoproteins such as, but not limited to, apoB-100, apoAl, apoE, apoAIV, and apoC, or more specifically still, the DNA binding regions of these lipoproteins, as gene delivery vectors in vivo. As explained in greater detail below, the various embodiments of this invention include, but are not limited to, the delivery, of nucleic acids to a cell in the form of an LDL-lipoprotein complex, the specific delivery of DNA to the nucleus, and the specific localization of delivered DNA to specific nuclear sites.

Plasma levels of DNA increase in a variety of chronic diseases including lupus erythrematosis (Steinman, 1984), viral hepatitis (Neurath et al., 1984), and a variety of cancers (Leon et al., 1977; Shapiro et al., 1983; Stroun et al., 1987; Nawroz et al., 1996; Anker et al., 1997; Chen et al., 1996). It further has been shown that lipoproteins in the blood of non-tumor carrying organisms are not bound to nucleic acids. However, cancer-carrying individuals, and in particular individuals with metastatic cancers, release large amounts of nucleic acids, into the blood. Thus, this invention also relates to the observation that lipoproteins in the blood of cancer patients and especially metastatic cancer patients are bound to nucleic acids, including DNA. Accordingly, this invention also may be used to provide a simple screening test for the presence or absence of cancer, especially metastatic cancer, by isolating a patient's lipoproteins and determining whether the lipoproteins are bound to nucleic acids; the presence of lipoprotein-bound nucleic acid being correlative with the presence of cancer and/or metastatic cancer in the living body. Further embodiments of the present invention relate to the sequence specific detection of DNA bound to lipoproteins in a cancer patient as a method for the identification of specific types of cancer in a living body. These and other aspects of the present invention are discussed in greater detail below.

1. LIPOPROTEINS

Lipoproteins appear as micro-pseudomicellar particles in the blood plasma of all mammalian species including humans. Their major function is to transport lipids and other hydrophobic compounds (i.e., fat-soluble vitamins) through the aqueous environment of the blood stream to their specific target cells. The transported lipids can be used as a major substrate for energy metabolism (i.e., triglycerides), structural components for cell membranes (i.e., phospholipids and cholesterol), or as precursors for steroid hormones and bile acids (i.e., cholesterol). Although, lipoproteins vary widely in size and lipid content, they have a common general structure. Lipoprotein particles are believed to be spherical and consist of a hydrophobic core containing nonpolar lipids surrounded by a hydrophilic surface monolayer of polar lipids and proteins, which are called apolipoproteins.

Plasma lipoproteins may be separated into five major classes based on their density, size, and compositional and functional properties: 1) chylomicrons, 2) very low density lipoproteins (VLDL), 3) intermediate lipoproteins (IDL), 4) low density lipoproteins (LDL), and 5) high density lipoproteins (HDL). The different classes of lipoproteins show distinct compositional differences in apolipoprotein content. The specific role of each class of lipoproteins in lipid metabolism is determined by the interaction of these apolipoproteins with specific enzymes and cellular receptors.

a. ApoB100 Structure and Function

The major protein constituent of LDL is apoB-100. ApoB-100 is one of two known natural ligands for the LDL (apoE/apoB) receptor which is found on the surface of a wide variety of mammalian cell types (Brown and Goldstein, 1986). LDLs are taken up by a process called receptor-mediated endocytosis (Brown and Goldstein, 1986). Hence, lipoproteins may be able to function as naturally-occurring liposomes which contain protein constituents that can bind specifically to nucleic acids and can be internalized by a wide variety of eukaryotic cell types via specific receptor mediated processes.

Human apolipoprotein B-100 (apoB-100) is a major apoprotein component of very-low density lipoproteins (VLDL), intermediate density lipoproteins (IDL), low density lipoproteins (LDL), and lipoprotein[a] (Lp[a]). ApoB-100 is synthesized and incorporated into VLDL and Lp[a] by the liver. Human LDL can be described as a spherical particle composed of a hydrophobic core of cholesterol esters and triglycerides encapsulated by an amphipathic monolayer of phospholipids, glycolipids and cholesterol in which the apoB-100 is partially imbedded (Myant, 1990). In addition to one molecule of apoB-100, LDL is known to contain varying numbers of apo C-I, apo C-II, apo C-III, apo E, and apo D (Blanco-Vaca et al., 1992; Connelly et al., 1993; Blanco-Vaca et al., 1994).

The primary structure of apoB-100, SEQ ID NO:1 (FIG. 1) has been determined by amino acid sequence analysis (Yang et al., 1986; Yang et al., 1989) and inferred from its cDNA sequence (Yang et al., 1986; Yang et al., 1989; Knott et al., 1986). There appear to be several different isoforms of apo B-100. The isoform shown in FIG. 1 is the isoform used for all of the alignments in the specification. Homologous regions in the other isoforms, however, would align similarly.

The apparent molecular weight of apoB-100 is 512 kDa based on its amino acid composition of 4536 residues. The apoprotein contains 25 Cys residues (Coleman et al., 1990; Yang, 1990), at least 16 of which form intramolecular disulfide bonds, with the remaining cysteines present as free sulfhydryls, as additional (unassigned) intramolecular disulfides, or as intermolecular disulfide linkages to other apolipoproteins (Blanco-Vaca et al., 1992; Connelly et al., 1993). Several important functional regions on apoB-100 that have been identified include heparin-binding sites (Cardin et al., 1987; Weisgraber and Rail, 1987), glycosylation sites (Knott et al., 1986; Innerarity et al., 1986), and the LDL receptor-binding region (Blanco-Vaca et al., 1992; Knott et al., 1986, Milne et al., 1989).

ApoB-100, and apolipoprotein E (apoE), apolipoproteins present in the low-density lipoprotein group, function as ligands for the high-affinity receptor-mediated removal of certain lipoproteins from plasma by the liver and delivery of cholesterol and cholesterol esters to a variety of target tissues (Myant, 1990; Innerarity et al., 1986; Brown and Goldstein, 1986; Mahley, 1988). A general mechanism for the receptor mediated uptake of LDL is well-established (Myant, 1990; Innerarity et al., 1986; Brown and Goldstein, 1986; Mahley, 1988), and the role of the apoB-100 molecule in this mechanism also is well defined.

Specific binding of low density lipoproteins to their mammalian cell receptors depends on the presence and conformation of the apoB-100 ligands (Kinoshita et al., 1990). Several reports have shown that the interaction of apoB-100-lipoproteins with the up-regulated, high affinity LDL (apoB/apoE) receptor is modulated by the lipid composition of the particle (Teng et al., 1985; Marcel et al., 1988), by other apoproteins such as apo[a] in Lp[a] (Kostner and Grillhofer, 1991; Young et al., 1986) and apoe in β-VLDL (Innerarity et al., 1986; Mahley, 1988), and by monoclonal antibodies to specific regions of the apoB-100 molecule (Innerarity et al., 1986; Young et al., 1986).

In searching the apoB-100 sequence for regions of sequence similarity to other proteins, nucleic acid binding regions (deoxyribonucleic acids, DNA and ribonucleic acids, RNA), nucleotide-binding regions, and nuclear-localization regions in the amino acid sequence of apoB-100 and apoE, have been identified. The present invention demonstrates that highly purified preparations of human, rat, and baboon LDL bind specifically; to pure preparations of human genomic DNA. These properties impart to the lipoproteins the capacity to serve as delivery vehicles for genetic material.

Lipoprotein particles carry a variety of vitamins and steroid compounds in their pseudo-micelle lipid core which may function in the control of gene expression. These attributes impart to the lipoproteins a virus-like character as well as capacity. While the inventors do not wish to be bound by any particular theory, the many control elements and signal motifs in the primary structure of the apolipoproteins are suggestive of the ability of these proteins to transport nucleic acids, enter the cell, participate in signal transduction, enter the nuclear space, initiate incorporation of nucleic acid materials into the resident genome, and cause its subsequent expression. As used herein, the term "primary structure" refers to the amino acid sequence of the protein. The capacity of purified LDL to bind to human genomic DNA, along with apoB-100's homology to SH1, SH2, and SH3 signal transducer domains supports this hypothesis. These properties of apoB100, and methods of exploiting these properties, are discussed in further detail below.

2. NUCLEIC ACID BINDING REGIONS

The inventors have found that apo B-100 is also involved in DNA binding. DNA is the genetic blueprint that contains the information necessary for cell growth, differentiation, proliferation, and cellular response to environmental factors. The phenotypic differences between various cell types in higher eukaryotes are mainly due to differences in cellular gene expression.

The regulation of gene expression is predominantly controlled at the stage of initiation of transcription and is mediated by proteins which recognize specific DNA sequences. In order to recognize and bind to a specific DNA sequence a protein utilizes a structural motif. Over the past 15 years, several structural DNA binding motifs have been identified including as zinc fingers, helix-turn-helix, basic helix-loop-helix, KH RNA-binding motifs and leucine zippers and proline pipe helices. The inventors report here the identification of regions in apo B-100 with homology to various DNA binding motifs including: 1) Proline pipe helix DNA binding motifs, 2) ISGF3γ-like DNA binding motifs, 3) SREBP-like DNA binding motifs, 4) coiled-coil motifs, and 5) nucleotide (ATP)-binding motifs.

a. Nucleotide and ATP Binding Motifs

The inventors discovered that that there is a certain degree of homology between regions of apo B-100 and known ATP binding motifs found in other proteins including those involved in signal transduction and transcriptional-ribonucleotide synthesis (t-RNA synthetases. Typically, these proteins contain sites which interact with different regions of the nucleotide, i.e., negatively charged phosphate regions, the ribose (carbohydrate) hydroxyl groups, and the base. A second site binds to the substrate ligand such as any amino acid in the case of t-RNA synthetases and tyrosine, serine and threonine residues in the phosphorylation of proteins.

Examination of the apoB-100 primary structure reveals several regions which are similar in sequence to the known nucleotide and ATP binding motifs and are suggestive of a similar function. For example, ATP-binding sites are known to contain an essential ATP-binding lysine residue. In lyn, the site is $T_{269}$KVAVTLKPG (SEQ ID NO:54) and in lyk, it is $D_{386}$KVAIKTIREG (SEQ ID NO:55). A similar region can be found in apoB-100, DLNAVANKIAD (SEQ ID NO:56). The similarity of this region in apo B-100 with the ATP-binding sites on known tyrosine-kinases suggests that apo B-100 can bind to the nucleic acid, ATP.

A single ATP-binding region occurs between residues 3800 and 3840 which is located in the kinase domain of apoB-100. The sequence of this region with known ATP-binding regions of kinases is shown in FIG. 12. FIG. 12 shows a comparison of known ATP-binding loop motifs to similar regions in apo B-100. Bold letters indicate conserved amino acids, :critical amino acids (H and K) are indicated by the #, "*" indicates conserved amino acids, "-" indicates gaps introduced in the sequence in order to align the proteins, and identical amino acids between the sequences in "C" are listed below the alignment. Sequence identification numbers are listed in the right margin. The critical lysine residue is retained and the degree of similarity suggests a like function.

The ATP-binding motifs typical of t-RNA synthetases are characterized by the signature sequence HIGH (histidine, isoleucine, glycine histidine) SEQ ID NO:177, and a second motif which contains a critical lysine residue. These motifs are located within 300 residues and occur as proximal loops on the surface of the protein molecule. Several analogues of this signature sequence occur in the apoB-100 sequence (see FIG. 7 and FIG. 12). An extended comparison of apoB-100 regions which contain the HIGH signature sequence is made with the tyrosyl-tRNA synthetase sequence shown in FIG. 12.

b. Proline Pipe Helix Structures

The proline pipe helix is usually present in proteins that contain proline every fifth position (Myant, 1990) in the amino acid sequence that is at least 20 residues long $(PXXXXP)_n$ (SEQ ID NO:75) where n>4. In the proline pipe helix, 5.56 residues are required to make one complete left handed helical turn. The proline pipe helix is stabilized by a hydrogen bonding network between the C=O groups of residues in positions i+1, i+2, i+3 (where i is a proline or sometimes non-proline residue) with the NH groups in positions i+2, i+3, i+4, respectively, of the following turn (Blanco-Vaca et al., 1992). The unusually large turn of the helix results in the formation of a channel running along the helix that is about 6A in average diameter (Myant, 1990) and large enough to accommodate water (Blanco-Vaca et al., 1992) and possibly other molecules.

One function of the proline pipe helix is DNA binding. For example, the proline pipe helix in Tus is involved in tight binding to highly specific 22–23 base pair DNA known as Ter sites (Connelly et al., 1993; Blanco-Vaca et al., 1994). Because of its large diameter compared to the α-helix, the proline pipe helix spans the entire width of the major groove (Blanco-Vaca et al., 1992) and results in a tight and highly specific fit. This tight fit also results in a high correspondence between the positively charged amino acid residues of the proline pipe helix and the negatively charged phosphate groups of DNA (Blanco-Vaca et al., 1992). The occurrence of the proline pipe-DNA interactions in nature might be more widespread than presently thought and this interaction might play a very important biological function.

Careful examination. and analysis of the apoB-100 amino acid sequence shows that the 40-residue proline-rich segment P2682-I2719, or a portion of this segment, assumes a proline pipe helical conformation (see FIG. 7), PDFRLPEI-AIPEFIIPTLNLNDFQVPDLHIPEFQLPHISH (SEQ ID NO:76). Because the unique features of the proline pipe helix make it suitable for tight and highly specific DNA binding, this segment or motif in apoB-100 constitutes one of the DNA binding sites.

The functional implications of DNA binding by apoB-100 include, but are not limited to: 1) binding of DNA such as, for example, microsatellite DNA (Connelly et al., 1993; Blanco-Vaca et al., 1994) to apoB-100 or its fragment(s) for DNA transport from the cytoplasm to the nucleus; (2) binding of apoB-100 or its fragment(s) to the nuclear DNA to regulate transcription or effect other functions; or (3) binding of DNA to apoB-100 or its fragment(s) to transport DNA from the nucleus to the cytoplasm. Other functions as a consequence of apoB-100 DNA binding through the apoB-100 proline pipe helix are not precluded. Therefore, the proline pipe region of apoB-100 constitutes an important target for structure-based drug design and delivery systems.

C. ISGF3γ-like DNA Binding Motifs

ISGF3 is a multimeric transcription factor involved in the regulation of transcription of a large set of genes. This factor dissociated into two protein components termed ISGF3γ and ISGF3α. ISGF3γ is a 48 kDa protein that binds DNA recognizing the IFN-stimulated response element. ISGF3α does not bind DNA. Regions in apoB-100 have been found to be homologous to the DNA-binding domain of ISGF37 (FIG. 8 and FIG. 9).

FIG. 8 shows a homology alignment among one region of the DNA-binding protein ISGF3γ and similar regions in apo B-100. Basic amino acids are indicated in bold and * indicates conserved amino acids between the two regions and V indicates conserved amino acids that have switched positions between the two sequences aligned. Sequence identification numbers are identified in the legend to the figure.

FIG. 9 shows a homology alignment among regions of the DNA-binding protein ISGF3γ and similar regions in apo B-100. Basic amino acids are indicated in bold, "-" indicates gaps introduced in the sequence in order to align the two proteins. Sequence identification numbers are identified in the right margin.

This indicates apoB-100 can bind specific DNA sequences in a manner similar to ISGF3γ.

d. SREBP-Like DNA Binding Motifs

Another region within apoB-100 shows striking resemblance to the DNA binding domains of previously identified sterol regulatory element binding proteins (SREBP's; FIG. 10A and FIG. 10B). A sequence comparison of the DNA-binding domains of the SREBP1, SREBP2, ADD1 proteins with similar regions found in apo B-100 are shown in FIG. 10A where basic amino acids are indicated in bold, "*" indicates conserved amino acids, "-"indicates gaps introduced in the sequence in order to align the two proteins, and identical amino acids between the two sequence are listed below the alignment. FIG. 10B shows a sequence comparison of the DNA-binding domains of SREBP1 with various apolipoproteins where basic amino acids are indicated in bold, "*" indicates conserved amino acids, "-" indicates gaps introduced in the sequence in order to align the two proteins, V indicates conserved amino acids that have switched positions between the two sequences aligned, and identical amino acids between the two sequences are listed below the alignment. Sequence identification numbers are indicated in the legend to the figure. The full line of "*************" separates the different sequence alignments.

SREBP's are members of the basic helix-loop-helix-leucine zipper (bH-L-H-Zip) family of transcription factors and play a major role in the transcriptional regulation of a number of genes involved in cholesterol homeostasis as well as lipid biosynthesis. SREBP's contain 3 segments: 1) an $NH_2$ terminal bH-L-H-Zip DNA binding domain including an acidic transcription activating domain; 2) a middle segment containing two membrane spanning domains; and 3) a COOH terminal segment. In order for SREBP's to become functionally active transcription factors, their $NH_2$ terminal domain containing the bH-L-H-Zip region needs to be released from the endoplasmic reticulum or nuclear envelope. This process is mediated by a sterol-regulated protease. That apo B-100, like the SREBP's, binds DNA.

e. Coiled-coil Motif (Leucine Zipper)

The coiled-coil motif (Myant, 1990), sometimes referred to as the leucine zipper (Blanco-Vaca et al., 1992), is characterized by two α-helical chains that wrap around each other to form a left-handed supercoil. The amino acid sequence of coiled-coil forming proteins is characterized by the presence of heptad repeats, that is, three or more repeats of a seven-residue sequence where every third and every fourth position in the heptad is occupied by a hydrophobic residue (Blanco-Vaca et al., 1992; Connelly et al., 1993; Blanco-Vaca et al., 1994). The two a-helical chains that form the coiled-coil can align either in parallel or anti-parallel orientation and their stabilities are dependent on the presence of strategically located hydrophobic and electrostatic interactions (Yang et al., 1986; Yang et al., 1989; Knott et al., 1986; Coleman et al., 1990; Yang, 1990; Cardin et al., 1987; Weisgraber and Rall, 1987; Innerarity et al., 1986; Milne et al., 1989; Brown and Goldstein, 1986). The most attractive feature of the coiled-coil is that highly specific interactions can be tailored by redesigning this relatively simple motif.

The coiled-coil motif occurs widely in native proteins (Lupas et al., 1991; Cohen and Parry, 1986). It plays structural and finctional roles in fibrous proteins such as keratin, myosin, elastin, fibrinogen, tropomyosin, etc. The coiled-coil motif also serves as the dimerization domain for a number of transcription factors such as GCN4 (O'Shea et al., 1991; Ellenberger et al., 1992), GAL4 (Kraulis et al., 1992; Baleja and Sykes, 1991; Marmorstein et al., 1992), c-Fos-c-Jun (Glover and Harrison, 1995), where only the dimeric form binds to DNA and is active. It is found in globular proteins, such as tRNA synthetase (Cusack et al., 1990; Biou et al., 1994), and serves as anchors into the tRNA. Naturally occurring coiled-coils can also be found as three-stranded (Bullough et al., 1994a; Bullough et al., 1994b) or four-stranded (Banner et al, 1987) structures.

Sequence alignment analysis of apoB-100 predicts that there are at least eight coiled-coil structures of varying lengths in different regions of its amino acid sequence (FIG. 11). FIG. 11 shows a comparison of the primary structures of known coiled-coil regions of DNA-binding proteins and analogous regions in apo B-100. Bold letters indicate conserved amino acids. Sequence identification numbers are listed in the right margin.

While the inventors do not wish to be bound by any particular theory, it is likely that these coiled-coil domains play very important structural and functional roles that, in turn, are vital to the function of LDL. For example, the coiled-coil motif can serve as dimerization or multimerization sites that may be important in LDL solubilization or aggregation. The coiled-coil motif can also bind DNA, RNA or nucleotides and, therefore, plays a very important role in the regulation and energetics of protein synthesis. The coiled-coil motif can also serve as a template for transport of molecules within and between the cytoplasm and the nucleus. In addition, the coiled-coil motif can also serve as a (temporary) reservoir of ligands that may be important in the regulation of the metabolic pathways. This list is by no means exhaustive, but demonstrates the biological importance of the coiled-coil motif in apoB-100.

The discovery of the coiled-coil motif in apoB-100 and the important biological implications of its presence, apoB-100 by itself or as part of LDL, constitutes an important target for structure-based drug design, delivery, and diagnostic systems. Coiled-coil forming sequence in apoB-100 (as indicated in FIG. 11) can be used to design, study and manufacture coiled-coil based peptide or protein delivery systems for drugs, radioisotopes, oligonucleotides, genes, antigens, antibodies, epitopes for vaccines, sugars, carbohydrate analogs and other ligands to specific targets in cells, tissues and organs. Either single strand or multiple strands of the apoB-100 coiled-coil forming peptide sequences that can be used as components of or attached to the aforementioned ligands either by covalent or non-covalent methods.

Coiled-coil forming sequences in apoB-100 (FIG. 11), or fragments, analogs, or modifications therefore can be used as site-specific targets for the delivery of drugs, radioisotopes, oligonucleotides, genes, antigens, antibodies, epitopes for vaccines, sugars, carbohydrate analogs and other ligands. Site-specific targeting includes the use of coiled-coils, coiled-coil forming peptides, or any functional group that binds to the aforementioned coiled-coils sequences in apoB-100.

3. NUCLEAR LOCALIZATION SIGNALS

In addition to homology with DNA binding proteins, apoB-100 contains several regions that are homologous to known nuclear localization signals (FIG. 13). These signals include the NLS from human p53, Ab1, and apoj. FIG. 13 shows a comparison of known nuclear localization signal sequences to similar regions in apo B-100.

The bipartite nuclear localization signal contains two essential elements comprised of basic amino acids, H (histidine), R (Arginine), and K (Lysine) which are required for nuclear targeting. The signal motifs starts with two basic amino acids which are then followed by a ten to thirty amino acid spacer and a basic duster of five amino acids three of which must be basic. Approximately 50% of the known nuclear proteins listed in the protein databases have this motif, while less than 5% of non-nuclear proteins have it. FIG. 13A shows sequences in apoB-100 with the perfect 10 amino acid spacer between the bipartite nuclear localization sequence element.

There is no strict requirement for the spacer length other than perhaps flexibility in the amino acids, i.e., the dihedral angles. Indeed, there are basic amino acid clusters in the apo B-100 molecule that are separated by longer spacers and are nevertheless potential DNA-binding regions. FIG. 13B shows sequences in apoB-100 with more or less than 10 amino acids in the spacer region between the bipartite nuclear localization sequence element, and FIG. 13C shows sequences in apoB-100 with more or less than 10 amino acids in the spacer region between an imperfect "bipartite" nuclear localization sequence element.

Thus, these regions in apoB-100 are NLS sequences capable of directing DNA to the nucleus of a cell. Apolipoproteins present on human LDL can bind to DNA through the DNA binding motifs identified herein. The functional bH-L-H-Zip domain within apoB-100 can enter the nucleus, following proteolytic release and/or aided by the nuclear localization signal domains present within the apolipoproteins, and regulate transcription of the target genes.

In addition, apo B-100 appears to be conserved across species. FIG. 14 shows various regions of human apo B-100 aligned with the sequenced fragments of the apo B-100 from pig, rat, hamster, mouse, chicken and rabbit. Bold and underlined letters indicate positively charged, basic amino acids, and "-"indicates gaps introduced in the sequence in order to align the proteins;

4. HOMOLOGY TO SIGNAL TRANSDUCING PROTEINS

The inventors have found that in addition to homology with nuclear localization signals and DNA binding proteins, apoB-100 molecule has regions of sequence similarity to known motifs in a variety of signal transduction molecules. For example, regions of apo B-100 are homologous to src homology 3 (SH3) (FIG. 2), src homology 2 (SH2) (FIG. 3) and src homology 1 (SH1) (FIG. 4) kinase domains that are common to protein tyrosine kinases of the signal transduction system (Koch et al., 1991; Pawson, 1992; Schlessinger, 1994; Margolis, 1992; Waksman et al., 1993; Carpenter, 1992; Ugi et al., 1994; Lowenstein et al., 1992; Guevara, Jr. et al., 1994), as well as activation regions located at the amino-and carboxyl-termini of signal transduction proteins (FIG. 6).

FIG. 2 is a homology alignment of SH3-like regions in apo B-100 with known SH3 domains of signal transduction proteins, where "*" indicates conserved amino acids, "-"indicates gaps introduced in the sequence in order to align the two proteins, identical amino acids between the two sequences are listed below the alignment, and percent similarity is indicated in the right margin. This alignment is followed by a table identifying the regions of apoB-100 and the various proteins aligned to these regions along with their respective sequence identification numbers.

FIG. 3 shows a comparison of SH2-like regions in apo B-100 to known SH3 domains of signal transduction proteins, where structurally important motifs are indicated by double underline, basic amino acids are indicated in bold, "*" indicates conserved amino acids, "-" indicates gaps introduced in the sequence in order to align the two proteins, identical amino acids between the two sequences are listed below the alignment, and percent similarity is indicated in the right margin. The alignment is followed by a table identifying the reference proteins and regions of apoB-100 in the alignment along with their sequence identification numbers.

FIG. 4 shows a comparison of the apo B-100 SH1-like region to SH1 kinase domains of known signal transduction proteins where basic amino acids are indicated in bold, "*" indicates conserved amino acids, "-" indicates gaps introduced in the sequence in order to align the two proteins, and identical amino acids between the two sequences are listed above the alignment. The alignment is followed by a table identifying the reference proteins and the region of apoB-100 used for the alignment along with their respective sequence identification numbers.

FIG. 6 shows a homolog alignment of specific regions of apo B-100 and the activation regions located at the amino-and carboxyl-termini of signal transduction proteins where "*" indicates conserved amino acids, "-" indicates gaps introduced in the sequence in order to align the two proteins, and identical amino acids between the two sequences are listed above the alignment. Numbers in parenthesis indicate amino acid residues shown in the alignment and sequence identification numbers are listed in the right margin.

Discovery of these motifs in the apoB-100 sequences was based on a series of reports (Ye et al., 1988; Trieu and McConathy, 1990; Trieu et al., 1991) which showed that free pr6line inhibited binding of recombinant apo[a] to both Lp[a] and LDL. These results implied that proline within the apoB-100 sequence interacted with the kringle binding pocket. Molecular modeling was used to determine if proline is a ligand for the different apo[a] kringle types (Guevara, Jr. et al., 1993). These studies concluded that although free proline can be accommodated by the ligand binding site of several apo[a] kringle types, proline located within a polypeptide chain probably does not fit into any of the ligand binding sites of apo[a] kringles. As an alternative possibility, proline might bind at an allosteric site on the kringle structure (Guevara, Jr. et al., 1993), and thereby alter the ligand binding site of the kringle. A second possibility is that apo[a] kringles are not involved at all, but rather that the proline/threonine-rich inter-kringle regions (IKR's) associate with specific sites on apoB-100, and thereby enable recombinant apo[a] to bind to Lp[a] and LDL.

a. The SH3 Domain

The interkringle regions of Apo [a] have homology to 3BPI (FIG. 5). FIG. 5 shows the inter-kringle proline-rich regions of Apo[a] compared with the proline rich region of SH3-binding protein (3BPI) where the conserved prolines are indicated in bold and "-" indicates gaps introduced in the sequences in order to align the two proteins. Following the alignments is a table identifying the inter-kringle proline-rich regions of Apo[a] and the proline-rich region of 3BPI used for the alignment along with their respective sequence identification numbers.

Apo[a] is a hydrophilic, glycosylated apoprotein that is disulfide-linked to apo B-100 in the Lipoprotein[a] particle. The proline-rich hinge between kringle structures of the apo[a] are suggestive a of role in signaling. Cicchetti et al. (1992) and Ren et al. (1993) described a ten amino acid, proline-rich segment of the 3BP-1 protein which binds to an SH3 domain in Abl, a non-receptor protein tyrosine kinase involved in signal transduction. The proline-rich IKR's in apo[a] (McLean et al., 1987; Guevara, Jr. et al., 1992), like those in 3BP-1, contain the sequence PXP (SEQ ID NO:2) which is important for the interaction of these motifs with their corresponding SH3 domains.

Proline-rich binding proteins (BP's), SH3, and SH2 domains are regulatory domains in signaling proteins which mediate enzymatic activity, participate in intracellular protein-protein interactions, and bind to activated receptor protein-tyrosine kinases (Koch et al., 1991; Pawson, 1992; Schlessinger, 1994; Margolis, 1992; Waksman et al., 1993; Carpenter, 1992; Ugi et al., 1994; Lowenstein et al., 1992; Guevara, Jr. et al., 1994; Pleiman et al., 1994). The sequence similarities noted between apo[a] IKR's and the proline-rich segment of 3BP-1 suggest a similar function for these regions of the apo[d] in rion-covalent interactions between apo[a] and apoB-100, i.e., binding of a proline-rich region in apo[a] to an SHB-like region in apoB-100.

In apoB-100, at least 13 regions share high sequence similarities with SH3 domains. SH3 domains are found in several signal transduction proteins such as phophatidylinositol-3' kinase (PI3K) and the non-receptor tyrosine kinase Abl (see FIG. 1 and FIG. 4). This suggests that apo B-100 may have signal transduction properties.

b. The SH2 Domain

Many signal transduction proteins and other proteins such as tyrosine phosphatases and tensin also contain SH2 domains (Koch et al., 1991; Pawson, 1992; Schlessinger, 1994; Lowenstein et al., 1992), often flanked by SH3 domains. SH2 domains are typically comprised of about 100 amino acids. In the signaling process, SH2 domains bind to specific phosphotyrosine motifs of target proteins (Songyang et al., 1993; Escobedo et al., 1991). The apoB-100 sequence was examined for presence of SH2-like regions and numerous regions in the apoB-100 sequences were found to share some commonalties with SH2 domains of signaling proteins (FIG. 3). This suggests that apoB-100 may interact with phosphorylated proteins through SH2-like regions.

c. The SH1 Domain

Typically, signal transduction proteins also contain a kinase domain or src homology domain 1 (SH1) which is located in the carboxyl region of the protein and is comprised of about 300 amino acids (Rudd et al., 1993). SH1 domains are highly homologous. Regions of apo B-100 have been found that share homology with SH1 domains (FIG. 4). In addition, apo B-100 shares homolog with the catalytic loop or active site motif in these signaling proteins. For example, the active site motif of lyn (EC 2.7.1.1 12) is $R_{359}$KNYIHRDLRAAN (SEQ ID NO:52); a sequence that is highly conserved. An analogous region is found in apoB-100, $K_{3919}$GTLAHRDFSAE (SEQ ID NO:53).

Furthermore, apo B-100 shares amino acid sequence homolog with the activation regions located at the amino- and carboxyl- termini of signal transduction proteins (FIG. 6). Protein Kinase C and c-AMP-dependent kinase control sites are present at the amino-terminus of signal transduction proteins. Tyrosine kinase control sites are located in the carboxyl-terminus of these proteins. Typically, there is little sequence homology, at the amino-termini, but high homology is common at the carboxyl-termini of signaling protein kinases.

Regions of homology, within apo B-100 having sequence similarity to SH3, SH2 and SH1 domains and other cell signaling proteins, all point to the possibility that apo B-100 is involved in intracellular signaling.

5. PROTEIN EXPRESSION

As described above, the inventors have discovered that a particular region of the apoB-100 molecule is similar in sequence to the Steroid Regulatory Element Binding Proteins, SREBP1 and 2 and ADD1. Other regions of the apoB-I00 molecule are similar to specific regions in other known DNA binding proteins including, but not limited to ISGF3γ, coiled-coil regions of GCN4 and hMLKI, and the proline-pipe sequences of Tus. Further, the inventors found that the amino acid sequence of apolipoproteins, such as apoB-100 have regions involved with nucleotide binding and nuclear localization. For example, apolipoproteins such as apoB-100 show homology to the SH1 kinase domains of protein tyrosine kinases and the HIGH and KMSK motif plus critical lysine of tRNA synthetases both known to bind ATP as well as to the basic helix-loop-helix motif of sterol regulatory element binding proteins (SREBPs) known to localize to the nucleus where they are involved in the regulation of transcription.

a. Expression of apoB100

In certain embodiments of the present invention, it will be necessary to obtain apoB100 or lipoproteins containing apoB100 for use as DNA binding compositions. In particular embodiments as described herein below, such apoB100 may be obtained from the lipoprotein fraction of primate serum. As an alternative to purifying apoB100 from LDL fraction of serum, it is possible to generate pure fractions of apoB-100 by recombinant expression of the apoB100 gene. The apoB100 gene can be inserted into an appropriate expression system. The gene can be expressed in any number of different recombinant DNA expression systems to generate large amounts of the polypeptide product, which can then be purified and used as a DNA binding composition as described herein.

In one embodiment, specific amino acid sequence domains of an apoB100 polypeptide having for example, the sequence of SEQ ID NO:1, can be prepared. These may, for instance, be minor sequence variants of a polypeptide that arise due to natural variation within the population or they may be homologues found in other species. They also may be sequences that do not occur naturally but that are sufficiently similar that they function similarly and/or elicit an immune response that cross-reacts with natural forms of the polypeptide.

The, nucleotide binding, nuclear localization and signal transduction domains of the apoB100 molecule are discussed in detail herein below. Recombinant technologies, well known to those of skill in the art, may be used to produce recombinant apoB100 with one or more of these domains having sequences that optimize the DNA binding and/or nuclear localization capacities of the molecule. Furthermore, in certain instances it may be necessary to "customize" such domains in order to increase binding to a particular DNA sequence whilst decreasing the binding to other sequences. Alternatively, it may be preferable to alter a particular apoB100 polypeptide, in order to decrease its binding affinity for a particular molecule. Accordingly, sequence variants of these domains can be prepared by standard methods of site-directed mutagenesis such as those described below in the following section.

Amino acid sequence variants of an apoB100 polypeptide, or particular domains therein can be substitutional, insertional or deletion variants. Deletion variants lack one or more residues of the native protein which are not essential for function or immunogenic activity.

Substitutional variants typically contain the exchange of one amino acid for another at one or more sites within the protein, and may be designed to modulate one or more properties of the polypeptide such as stability against proteolytic cleavage. Substitutions preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

Insertional variants include fusion proteins such as those used to allow rapid purification of the polypeptide and also can include hybrid proteins containing sequences from other proteins and polypeptides which are homologues of the polypeptide. For example, an insertional variant could include portions of the amino acid sequence of the polypeptide, from one species, together with portions of the homologous polypeptide from another species. Other insertional variants can include those in which additional amino acids are introduced within the coding sequence of the polypeptide. These typically are smaller insertions than the fusion proteins described above and are introduced, for example, into a protease cleavage site. Alternatively, insertional variants of the present invention may be created in which one or more DNA binding domains and nuclear localization domain have been added to a native apoB100 molecule to alter particular characteristics of the molecule.

In one embodiment, major antigenic determinants of the polypeptide are identified by an empirical approach in which portions of the gene encoding the polypeptide are expressed in a recombinant host, and the resulting proteins tested for their ability to elicit an immune response. For example, PCR can be used to prepare a range of cDNAs encoding peptides lacking successively longer fragments of the C-terminus of the protein. The immunoprotective activity of each of these peptides then identifies those fragments or domains of the polypeptide that are essential for this activity. Further experiments in which only a small number of amino acids are removed at each iteration then allows the location of the antigenic determinants of the polypeptide.

Another embodiment for the preparation of polypeptides according to the invention is the use of peptide mimetics.

Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule.

Successful applications of the peptide mimetic concept have thus far focused on mimetics of β-turns within proteins, which are known to be highly antigenic. Likely β-turn structure within an polypeptide can be predicted by computer-based algorithms as discussed above. Once the component amino acids of the turn are determined, peptide mimetics can be constructed to achieve a similar spatial orientation of the essential elements of the amino acid side chains.

Modification and changes may be made in the structure of a gene and still obtain a fuictional molecule that encodes a protein or polypeptide with desirable characteristics. The following is a discussion based upon changing the amino acids of a protein to create an equivalent, or even an improved, second-generation molecule. The amino acid changes may be achieved by change the codons of the DNA sequence, according to the following data.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and its underlying DNA coding sequence, and nevertheless obtain a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte & Doolittle, 1982).

TABLE 1

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

b. apoB100 Variants

In order to determine the optimal DNA-binding sequences, recombinant fragments of apoB-100 or other apolipoproteins may be used in mobility shift assays or other common protein-DNA interaction assays, including, but not limited to, methylation interference assays, DNase-I footprinting assays, UV-crosslinking assays, Biotin/Streptavidin affinity systems, or screening expression libraries encoding DNA-binding proteins. The recombinant apolipoprotein fragments are expressed by cloning these cDNA fragments in commercially available eukaryotic expression vectors and employing recombinant DNA expression techniques well known to the art.

In addition, the recombinant fragments may be mutated by employing site-directed mutagenesis or oligonucleotide-directed mutagenesis techniques in order to improve their affinity for nucleic acids and used either in their original or mutated form. Mutations in the recombinant apolipoprotein fragments may include, but are not limited to, addition of endosomolytic and/or nuclear localization peptide sequences employing common recombinant DNA technology. The recombinant protein fragments are prebound to the nucleic acids of interest prior to their reassembly into freshly isolated lipoproteins and subsequent transfection. Alternatively, they are reassembled into lipoproteins prior to in vitro nucleic acid binding and subsequent transfection. Separation of protein-bound DNA from free DNA may be required prior to transfection and is accomplished by adsorption to nitrocellulose membranes or other common techniques including, but not limited to size-exclusion or density ultracentrifugation.

Site specific mutations can be made within the proposed DNA binding motifs or nuclear localization signal sequences of the apolipoproteins described in this invention, in order to improve their homology with known DNA binding motifs (e.g., SREBP-like DNA-binding motifs, ISGF3γ-like DNA-binding motifs) and nuclear localization signal sequences (e.g., NLS from human p53, Ap 1, IGFBP-3, ir, and apo J). Specific mutations in the DNA sequences of steroid regulatory elements (SRE) and IFN-stimulated response elements which affect the DNA-binding affinity of SREBP and ISGF3γ, respectively, have been described (Smith et al., 1990; Briggs et al., 1993; Wang et al., 1993; Veals et al., 1992).

Site-specific mutagenesis is a technique useful in the preparation of individual peptides, or biologically functional equivalent proteins or peptides, through specific mutagenesis of the underlying DNA. The technique further provides a ready ability to prepare and test sequence variants, incorporating one or more of the foregoing considerations, by introducing one or more nucleotide sequence change(s) into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art. As will be appreciated, the technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids are also routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected that include recombinant vectors bearing the mutated sequence arrangement.

The preparation of sequence variants of the selected gene using site-directed mutagenesis is provided as a means of producing potentially useful species and is not meant to be limiting, as there are other ways in which sequence variants of genes may be obtained. For example, recombinant vectors encoding the desired gene may be treated with mutagenic agents, such as hydroxylamine, to obtain sequence variants.

6. PURIFICATION OF LIPOPROTEINS

The purification of plasma LDL involves obtaining a composition of Lp(a) and subjecting the composition to reductive cleavage in a manner that allows the formation of cleavage products apo (a) and apoB100. These products are then separated to yield purified apo B100. Plasma lipoproteins may be isolated using standard sequential flotation ultracentrifugation methods as described (Schumaker and Puppione, 1986).

a. Purification of Lp(a)

Lp(a) is known to be made in the liver of primates. The LDL and VLDL in the plasma represents the primary source for the purification of Lp(a). Plasma may be collected from any primate source for the purposes of the invention, or indeed any other source suspected of possessing Lp(a). The Lp(a) component of the plasma can then be separated from other components of the plasma using ultracentrifugational flotation at a density of 1.21 g/mL for 20 hours at 50, 000 rpm followed by affinity chromatography using lysine-Sepharose™. Of course, the ultra centrifugational procedure is only exemplary and those of skill in the art will be able to vary them according to the particular equipment and study need without undue experimentation. The plasma may be supplemented with various inhibitors to prevent the Lp(a) from interacting with LDL components of the plasma.

Having separated Lp(a) from the other plasma components the Lp(a) sample is purified using affinity chromatography lysine-Sepharose™ chromatography. This separation is described in detail in PCT publication WO 97/17371, specifically incorporated herein by reference.

In some cases, it is desirable to use a method other than lysine-Sepharose™ chromatography for the purification of Lp(a), in such instances other chromatographic methods such FPLC may be employed. Such methods are disclosed in Scanu et al., 1993, incorporated herein by reference, and may be used in conjunction with the present invention to purify apo B100 from Lp(a).

The product purity can be assessed by for example, mobility on, 1% agarose gels, Western blots of SDS PAGE, utilizing anti-LDL antibodies.

b. Isolation of Apo B100 from Lp (a)

(i) Using Centrifugation

Following the purification of Lp(a), the apoB100 may be separated from the apo A fraction of the Lpa complex using reductive cleavage. The purified intact Lp(a) protein is subjected to reductive cleavage wherein a known volume of Lp(a) is incubated with a reductant. Exemplary reductants include homocysteine, N-acetyl cysteine, 2-mercaptoethanol, 3-mercaptopropionate, 2-aminoethanol, dithiothreitol, and DTE.

The reaction is incubated at room temperature for 10–20 minutes. This is followed by the addition of an inhibitor to prevent non-covalent, lysine mediated interactions between apo (a) and apoB100. ε-Aminocaproic acid (EACA) may be used as such an inhibitor. substituted by other lysine analogues, for example, compounds such as trans 4(aminomethyl)-cyclohexanecarboxylic acid, N-acetyl-L-lysine, p-benzylamine sulfonic acid, hexylamine, benzamidine, benzylamine, L-proline. Of course these are only exemplary lysine analogues and those of skill in the art may use other lysine analogues to prevent interaction between apo (a) and apoB100 proteins. The reaction conditions are described in greater detail in PCT publication number WO 97/17371. Of course, the conditions for the separation of apo (a) from the reaction mixture using sucrose density ultracentrifugation is only exemplary, and other methods commonly used by those of skill in the art may be used.

(ii) Isolation Using Chromatographic Methods

As an alternative to the above methods for the isolation of apo B100 from Lp(a) chromatographic methods may be utilized as exemplified below.

Heparin Sepharose™ Chromatography

Lp(a) may be treated with a reducing agent in the presence of a lysine analogue. For the purposes of this invention the lysine analog is supplied to prevent the interaction of apo (a) with apoB100. The reducing agent is supplied to break the disulfide bond of Lp (a). Lysine analogs for this invention include but are not limited to compounds such as EACA, trans 4(amino-methyl)-cyclohexanecarboxylic acid, N-acetyl-L-lysine, p-benzylamine sulfonic acid, hexylamine, benzamidine, benzylamine, L-proline or any other lysine analogue known to the artisan skilled in the art may be used. Example of reducing agents that may be used in this invention include, but are not limited to, homocysteine, N-acetyl cysteine, 2-mercaptoethanol, 3-mercaptopropionate, 2-aminoethanol, dithiothreitol, and DTE.

For example, the mixture of Lp (a), a reducing agent and a lysine analog is incubated for a suitable period of time in a suitable buffer of pH 7.4. A heparin-Sepharose™ column is equilibrated with a suitable buffer containing the lysine analog and the reducing agent. The mixture is applied to the equilibrated column, the column is washed with the same buffer and the first eluate is collected.

The first eluate from the column contains the apo (a) dissociated from Lp (a). The "free" apo (a) is dialyzed against an appropriate buffer. the dialysis product is pure apo (a) that may be freeze dried and stored at −20° C. or used immediately. The column is further washed with the buffer for a total of three column volumes followed by 3 volumes of 2M NaCl in the buffer. The high salt concentration serves to dissociate the remaining unreacted Lp(a) and LDL containing apoB100 free of apo (a).

Lysine-Sepharose™ Chromatography

An alternative to heparin-Sepharose™ chromatography is lysine chromatography. In this type of separation, Lp(a) is treated with a suitable reducing agent and then applied to a lysine Sepharose™ column that has been equilibrated with a suitable buffer of pH 7.4 containing the reducing agent. The column is washed with the same buffer and the first volume of elute is collected. This fraction contains LDL dissociated from apo (a). Further details of this type of chromatography for separating apolipoproteins may be found in PCT Publication WO 97/17371.

7. SCREENING NUCLEIC ACIDS THAT BIND LDL

Specifically contemplated by the present inventors are chip-based DNA technologies such as those described by Hacia et al. (1996) and Shoemaker et al. (1996). Chip technologies may be used to present DNA arrays for screening.

In a first embodiment, chip technologies may be employed to synthesize a variety of DNAs in order to test for their binding to an LDL with a specific apoB100 binding region. Briefly, these techniques involve quantitative methods for analyzing large numbers of nucleic acids rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

Thus, the invention may be applied for the screening of nucleic acids that bind to apoB100 containing lipoproteins. The LDL polypeptide or fragment may be either free in solution, fixed to a support, expressed in or on the surface of a cell, for example a bacterial cell. Either the LDL polypeptide or the nucleic acid may be labeled, thereby permitting determining of binding to the DNA molecules.

In another embodiment, the assay may measure the inhibition of binding of LDL to a natural or artificial substrate or binding partner. Competitive binding assays can be performed in which one of the agents (LDL, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small test nucleic acids (test compounds) are synthesized on a solid substrate, such as plastic pins or some other surface. Similarly, test compounds of the present invention are reacted with LDL and washed. Bound polypeptide is detected by various methods.

In an alternative embodiment, the invention may be applied for the screening for variants of ApoB 100 containing lipoproteins to determine a greater or lesser affinity for a particular iype of nucleic acid. These screening methods would be similar to those described above, except that the LDL peptide variants will be presented as an array with the nucleic acid binding regions being used to probe the array. Currently, one of the most widely used approaches for screening polypeptide libraries is to display polypeptides on the surface of filamentous bacteriophage (Smith, 1991; Smith, 1992). Ladner et al., (U.S. Pat. No. 5,403,484, specifically incorporated herein by reference) reported the display of proteins on the outer surface of a chosen bacterial cell, spore or phage, in order to identify and characterize binding proteins.

In an alternative embodiment, purified apoB100 or DNA-binding fragments thereof can be coated directly onto plates for use in the screening techniques. Alternatively, antibodies to the polypeptide can be used to immobilize the polypeptide to a solid phase. Also, fusion proteins containing a DNA binding region (preferably a terminal region) may be used to link peptides to a solid phase. Once linked, randomly sheared genomic DNA, transcripts or randomly generated oligomers may be contacted with the bound peptides. Any bound nucleic acid fragments can be identified by PCR using random primers if they are large enough. In the case where random oligomers are used, the oligomers, in addition to the random region, may comprise built in primer binding sites that can be used to amplify an intervening random region, thereby identifying the region binding to apoB100.

Thus, using the technologies described herein, it will be possible for one of skill in the art to screen for and isolate a variety of nucleic acids that bind to apoB100 and variants of apoB100 that exhibit nucleic acid binding capacity, including increased or decreased binding as compared to wild-type apoB100.

8. LDL-DNA COMPLEX FORMATION

In particular aspects of the present invention, lipoproteins are employed in order to trasnport DNA into cell in vitro and in vivo. In the present invention, optimal DNA/LDL binding has been established. In particular embodiments a 1:1 ratio of DNA:LDL protein molar ratio of 1:1 are incubated at 37° C. for 30 min in a buffered solution. An exemplary buffer may be 50 mM Tris-HCI at pH 7.4 containing 150 mM NaCl, and 10 mM $MgCl_2$. The concentrations of DNA and LDL protein may range form the pmolar range to the $\mu$molar range. In a preferred embodiment, 0.39 pmole DNA are incubated with 0.39 pmole LDL-protein.

The incubation conditions may be altered to increase or decrease the efficiency of DNA/LDL binding. For example the incubation may occur at temperatures ranging from 4° C. to 50° C., thus it is contemplated that the reaction mixture may be incubated at 4° C., 6° C., 8° C. 10° C., 12° C., 14° C., 16° C., 18° C., 20° C., 22° C., 24° C., 26° C., 28° C., 30° C., 32° C., 34° C., 36° C., 38° C., 40° C., 42° C., 44° C., 46° C., 48° C., 50° C.

The time of incubation may be varied from as little as 10 minutes to as long as 5 hours. Thus it is well within the skill of one in the art to incubate the mixture for varying degrees of time.

Other embodiments contemplate varying the concentration of MgC12 in the media. Thus the $MgCl_2$ concentration may vary from 1 mM to 100 mM. Thus, it is contemplated that the reaction mixture contains 5mM $MgCl_2$ 10 mM $MgCl_2$ 12 mM $MgCl_2$ 15 mM $MgCl_2$ 20 mM $MgCl_2$ 30 mM $MgCl_2$ 35 mM $MgCl_2$ 40 mM $MgCl_2$ 50 mM $MgCl_2$ 60 mM $MgCl_2$ 65 mM $MgCl_2$ 70 mM $MgCl_2$ 80 mM $MgCl_2$ 90 mM $MgCl_2$, or 100 mM $MgCl_2$.

9. GENE DELIVERY AND EXPRESSION IN EUKARYOTIC CELLS

The gene delivery system of the instant invention can be used to express any gene of interest in eukaryotic cells. The gene or its cDNA sequence is cloned into a plasmid containing the specific lipoprotein binding sequences (including, but not limited to SRE, E/C, FAS) and/or any eukaryotic regulatory sequence (for example, but not limited to HCMV, or tyrosine kinase promoter region) using DNA cloning techniques well known to the art. The orientation, number and location of the lipoprotein binding sequences may vary within the nucleic acid vector, but should not interrupt the protein coding sequence of the gene of interest.

The gene delivery system of the instant invention (see FIG. 15) can be used to transfect eukaryotic cells either in vivo or in vitro with any expression vector containing one or more of the aforementioned lipoprotein binding sequences. Expression vectors are designed using recombinant DNA cloning techniques known to the art and generally include five components linked in the following 5' to 3' orientation: i) an eukaryotic promoter sequence, 2) a sequence encoding a 5' untranslated RNA (UTR) which may include a first intron sequence followed by a consensus Kozak sequence and an initiation ATG, 3) a protein coding sequence, 4) a 3' UTR, and 5) a cognate transcription terminator sequence.

Lipoproteins are isolated from blood in a manner similar to the previously described procedures (see, Example 1) and bound to the nucleic acids of interest in a manner similar to the previously described DNA binding protocol (see, Example 2). Separation of protein-bound DNA from free DNA may be required prior to transfection and can be accomplished by adsorption to nitrocellulose membranes or other techniques well known to the art including, but not limited to size-exclusion or density ultracentrifugation.

a) Control Regions

In order for the gene delivery system of the present invention to effect expression of a transcript encoding a selected gene, the polynucleotides encoding these genes will be under the transcriptional control of a promoter. A "promoter" refers to a DNA sequence recognized by the synthetic machinery of the host cell, or introduced synthetic machinery, that is required to initiate the specific transcription of a gene. The phrase "under transcriptional control" means that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of, promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a therapeutic gene is not believed to be critical, so long as it is capable of expressing the polynucleotide in the targeted cell. Thus, where a human cell is targeted, it is preferable to position the polynucleotide coding region adjacent to and under the control of a promoter that is capable of being expressed in a human cell. Generally speaking, such a promoter might include either a human or viral promoter.

In preferred embodiments, the human cytomegalovirus (CMV) immediate early gene promoter, the SV40 early promoter and the Rous sarcoma virus long terminal repeat can be used to obtain high-level expression of the polynucleotide of interest. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of the therapeutic gene.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally, any promoter/enhancer combination (as per the Eukaryotic Promoter Data Base EPDB) could be used to drive expression of a particular construct. Use of a T3, T7 or SP6 cytoplasmic expression system is another possible embodiment. Eukaryotic cells can support cytoplasmic transcription from certain bacteriophage promoters if the appropriate bacteriophage polymerase is provided, either as part of the delivery complex or as an additional genetic expression vector.

According to the present invention, a number of different promoters are required. It is contemplated that these promoters may be the same or different, but the selection of particular promoters for particular uses may be advantageous.

b) IRES

In certain embodiments of the invention, the use of internal ribosome binding site (IRES) elements may prove advantageous in accordance with the present invention. These elements are used to create multigene, or polycistronic, messages. IRES elements are able to bypass the ribosome scanning model of 5' methylated Cap dependent translation. and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading. frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

In addition, it may be desirable to include polyadenylation signals in the vectors. These signals serve to terminate transcription and to stabilize mRNA transcripts produced from the vectors. A preferred polyadenylation signal is an SV40 polyadenylation signal.

c) Genes

The present invention contemplates the use of a variety of different genes inserted into the SV40 vector. For example, genes encoding enzymes, hormones, cytokines, oncogenes, receptors, tumor suppressors, transcription factors, drug selectable markers, toxins and various antigens are contemplated as suitable. genes for use according to the present invention. In addition, antisense constructs derived from oncogenes are other "genes" of interest according to the present invention.

A common gene currently being used in many gene therapy trials is p53, which currently is recognized as a tumor suppressor gene. High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or indirectly activate genes that suppress this growth. It has also been reported that transfection of DNA encoding wild-type p53 into cancer cell lines restores growth suppression control in such cells (Casey et al., 1991; Takahasi et al., 1992). It is thus proposed that the treatment of p53-associated cancers with wild type p53 in the compositions of the present invention will reduce the number of malignant cells or their growth rate.

$p16^{INK4}$ belongs to a newly described class of CDK-inhibitory proteins that also includes $p16^B$, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). Restoration of wild-type $p16^{INK4}$ function by transfection with a plasmid expression vector reduced colony formation by some human cancer cell lines (Okamoto, 1994; Arap, 1995).

Cell adhesion molecules, or CAM's are known to be involved in a complex network of molecular interactions that regulate organ development and cell differentiation (Edelman, 1985). Recent data indicate that aberrant expression of CAM's maybe involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumors growth in vitro and in vivo. Thus, the compositions of the present invention can be employed to mediated C-CAM suppression of tumor cell growth.

Other tumor suppressors that may be employed according to the present invention include RB, APC, DCC, NF-1, NF-2, WT-1, MEN-I, MEN-II, zacl, p73, VHL, MMAC1, FCC and MCC. Inducers of apoptosis, such as Bax, Bak, Bcl-$X_s$, Bik, Bid, Harakiri, Ad E1B, Bad and ICE-CED3 proteases, similarly could find use according to the present invention.

Various enzyme genes are of interest according to the present invention. Such enzymes include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase.

In another example, the expression vector may include a nucleotide sequence encoding for functional apolipoprotein A-I for the prevention or treatment of artherosclerosis. Atherosclerosis is a disease that is characterized by the development of atherosclerotic lesions which contain cholesterol esters and other lipids that are derived from the blood circulation. The plasma concentration of HDL is inversely correlated with the risk for development of atherosclerosis. HDL present in the blood circulation take up free cholesterol from extrahepatic cells which through the action of LCAT (lecithin-cholesterol acyltransferase) is converted to cholesterol esters and stored in the core of the HDL particles. The HDL cholesterol esters are transported either directly or indirectly via transfer to triglyceride rich lipoproteins (i.e., VLDL, IDL, LDL) to the liver by a process called "reverse cholesterol transport". Reverse cholesterol transport is of great importance for maintaining cholesterol homeostasis since the liver is the major organ for cholesterol excretion from the body via bile acids. Apo A-I is the major protein constituent of HDL and a cofactor LCAT. Therefore, increasing the plasma concentration of apo A-I containing HDL can increase the reverse cholesterol transport and reduce the risk for atherosclerosis.

Hormones are another group of gene that may be used in the SV40 vectors described herein. Included are growth hormone, prolactin, placental lactogen, luteinizing hormone, follicle-stimulating hormone, chorionic gonadotropin, thyroid-stimulating hormone, leptin, adrenocorticotropin (ACTH), angiotensin I and II, β-endorphin, β-melanocyte stimulating hormone (β-MSH), cholecystokinin, endothelin I, galanin, gastric inhibitory peptide (GIP), glucagon, insulin, lipotropins, neurophysins, somatostatin, calcitonin, calcitonin gene related peptide (CGRP), β-calcitonin gene related peptide, hypercalcemia of malignancy factor (1–40), parathyroid hormone-related protein (107–139) (PTH-rP), parathyroid hormone-related protein (107–111) (PTH-rP), glucagon-like peptide (GLP-1), pancreastatin, pancreatic peptide, peptide YY, PHM, secretin, vasoactive intestinal peptide (VIP), oxytocin, vasopressin (AVP), vasotocin, enkephalinamide, metorphinamide, alpha melanocyte stimulating hormone (alpha-MSH), atrial natriuretic factor (5–28) (ANF), amylin, amyloid P component (SAP-1), corticotropin releasing hormone (CRH), growth hormone releasing factor (GHRH), luteinizing hormone-releasing hormone (LHRH), neuropeptide Y, substance K (neurokinin A), substance P and thyrotropin releasing hormone (TRH).

Other classes of genes that are contemplated to be inserted into the SV40 vectors of the present invention include interleukins and cytokines. Interleukin I (IL-I), IL-2, IL-3, IL-4, IL-5, IL-6, IL-7, IL-8, IL-9, IL-10, IL-11 IL-12, GM-CSF and G-CSF.

Other therapeutics genes might include genes encoding antigens such as viral antigens, bacterial antigens, fungal antigens or parasitic antigens. Viruses include picomavirus, coronavirus, togavirus, flavirviru, rhabdovirus, paramyxovirus, orthomyxovirus, bunyavirus, arenvirus, reovirus, retrovirus, papovavirus, parvovirus, herpesvirus, poxvirus, hepadnavirus, and spongiform virus. Preferred viral targets include influenza, herpes simplex virus 1 and 2, measles, small pox, polio or HIV. Pathogens include trypanosomes, tapeworms, roundworms, helminths, Also, tumor markers, such as fetal antigen or prostate specific antigen, may be targeted in this manner. Preferred examples include HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. Preferably, vaccination of an individual would only be required infrequently, such as yearly or biennially, and provide long term immunologic protection against the infectious agent.

In yet another embodiment, the heterologous gene may include a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (Fvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Antibodies to a wide variety of molecules are contemplated, such as oncogenes, toxins, hormones, enzymes, viral or bacterial antigens, transcription factors or receptors.

d. Antisense

The instant invention can be used to transfect eukaryotic cells with ribonucleotide sequences including anti-sense RNA and ribozymes, that function to inhibit the translation of any mRNA of interest, either by direct binding (to the mRNA of interest), or blocking deoxyribonucleic acid (DNA) coding sequences preventing transcription.

Anti-sense RNA inhibits the translation of mRNA by direct binding to the mRNA of interest and preventing protein translation, either by inhibition of ribosome binding or the translocation of the targeted mRNA molecule which then becomes more susceptible to nuclease degradation.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing. Oncogenes such as ras, myc, neu, raf, erb, src, fms, jun, trk, ret, gsp, hst, bcl and abl also are suitable targets for antisense constructs.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

e. Ribozymes

Ribozymes are RNA molecules that catalyze the specific cleavage of RNA. Ribozyme activity is mediated through the hybridization of the ribozyme molecule to a specific sequence in the target RNA, followed by the endonucleolytic cleavage of the target RNA within that sequence. Potential RNA cleavage sites can be identified by searching for specific ribonucleotide sequences that include sequences such as GUU, GUC, and GUA within the target RNA. Hammerhead motif ribozyme molecules can then be designed that contain short RNA sequences (15–25 ribonucleotides) that are complementary to the region including the cleavage site of the target RNA.

Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et aL., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et aL., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Since the secondary structure of both target RNA as well as the anti-sense RNA is of great importance for the hybridization of both molecules, the predicted structural features can be analyzed and RNase protection assays can be used to determine hybridization efficiency. Anti-sense RNA and ribozymes can be synthesized employing chemical nucleic acid synthesis techniques well known to the art (ie., solid phase phosphoromidite synthesis) or the RNA molecules can be produced by in vitro and in vivo transcription of DNA sequences encoding the antisense RNA. DNA sequences encoding ribozymes or anti-sense RNA may be incorporated into an expression vector. The expression vector may be prebound to purified plasma lipoprotein fractions prior to transfection into eukaryotic cells.

f. Self-initiating and self-sustaining gene expression systems

The invention gene delivery system can also be used to delivery self-initiating and self-sustaining gene expression systems. Self-initiating and self-sustaining gene expression systems may be constructed by binding a RNA polymerase to a DNA construct in vitro prior to the introduction of the polynucleotide into the cell as described by Wagner et al. (U.S. Pat. No. 5,591,601). The RNA polymerase is bound to a DNA construct containing a cognate promoter of the RNA polymerase operably linked to a DNA sequence encoding for the RNA polymerase.

The expression of functional RNA polymerase in turn enables the expression of any gene of interest that contains a cognate promoter sequence recognized by the same RNA polymerase in eukaryotic host cells. DNA sequences encoding for both RNA polymerase and gene product of interest (i.e., protein of interest) may be contained within the same gene expression system. The gene expression system may be prebound to purified plasma lipoprotein fractions prior to transfection into eukaryotic cells.

g. Delivery of DNA to Cells in vivo

The invention gene delivery system can also be used to deliver DNA to cells in vivo. An expression vector containing the polynucleotide sequences of the gene of interest (e.g., reporter gene or a healthy copy of a defective gene) is prebound to LDL according to the protocols described herein. This DNA-LDL complex is then introduce into an organism for example, a rat, mouse or human by, for example, intravenous injection. At varying times post-injection, LDL is isolated from the blood and probed for DNA sequences of the type that were prebound to the LDL using standard molecular biological techniques such as, but not limited to, Southern blot hybridization or PCR™.

The LDL also can be immunoprecipitated with anti-LDL antibodies and then probed for specific DNA sequences bound to it. In order to determine cellular internalization and/or integration of the reporter gene sequences into the genomic DNA of cells of different tissues, total genomic DNA can be isolated from various tissues (according to standard molecular biology techniques) and probed for the presence of the reporter gene sequences using specific polynucleotide probes in PCR™ or Southern blot hybridization techniques. In addition, total cellular RNA can be isolated from various different tissues using standard molecular biology techniques and probed for the presence of specific mRNA encoded for by the reporter gene polynucleotide sequences using specific antisense polynucleotide probes in Northern blot hybridization techniques or ribonuclease (RNase) protection assays.

Expression of a functional protein encoded for by the gene of interest in different tissues can be analyzed using techniques well known to the art, such as, Western blot hybridization of cellular protein extracts with antibodies that bind specifically to the reporter gene product (i.e., protein of interest) or direct detection of intracellular fluorescence (e.g., when reporter genes are used that encode for blue or green fluorescent proteins (e.g., GFP from Clontech Inc.).

Several non-viral methods for the transfer of a DNA-LDL complex of the present invention into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al, 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the DNA-LDL complex has been delivered into the cell, the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the DNA-LDL complex is delivered to a cell and where in the cell the nucleic acid remains is dependent on the type of DNA molecule bound to the LDL.

In one embodiment of the invention, the DNA-LDL complex may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al., (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

Another embodiment of the invention for transferring a naked DNA-LDL complex into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang.et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exp:osure of the tissue or cells, to eliminate any intervening tissue between the gun and the target organ, i.e., ex vivo treatment. Again, DNA encoding a particular gene may be delivered via this method and still be incorporated by the present invention.

In a further embodiment of the invention, the DNA-LDL complex may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-DNA complexes.

Liposome-mediated nucleic acid delivery and expression of foreign DNA in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other DNA-LDL complexes which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues. Anderson et al., U.S. Pat. No. 5,399,346, and incorporated herein in its entirety, disclose ex vivo therapeutic methods.

10. PHARMACEUTICAL

The gene delivery system of the instant invention can be administered in vivo in various ways including, but not limited to, intravenous, pharyngeal, epidermal, intramuscular, intraperitoneal (IP), nasal, and/or rectal. The gene delivery system of the instant invention can also be used for in vitro transfections of eukaryotic cell types which possess specific lipoprotein receptors on their cytoplasmic membranes, but is not limited to these cell types.

Pharmaceutical products that may spring from the current invention may comprise naked polynucleotide containing single or multiple copies of the specific nucleotide sequences that bind to specific DNA-binding sites of the apolipoproteins present on plasma lipoproteins as described in the current invention. The polynucleotide may encode a biologically active peptide, antisense RNA, or ribozyme and will be provided in a physiologically acceptable administrable form.

Another pharmaceutical product that may spring from the current invention may comprise a highly purified plasma lipoprotein fraction, isolated according to the methodology, described herein from either the patients blood or other source, and a polynucleotide containing single or multiple copies of the specific nucleotide sequences that bind to specific DNA-binding sites of the apolipoproteins present on plasma lipoproteins, prebound to the purified lipoprotein fraction in a physiologically acceptable, administrable form.

Yet another pharmaceutical product may comprise a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form. Yet another pharmaceutical product may comprise a highly purified plasma lipoprotein fraction which contains recombinant apolipoprotein fragments containing single or multiple copies of specific DNA-binding motifs, prebound to a polynucleotide containing single or multiple copies of the specific nucleotide sequences, in a physiologically acceptable administrable form.

The dosage to be administered depends to a great extent on the body weight and physical condition of the subject being treated as well as the route of administration and frequency of treatment. A pharmaceutical composition comprising the naked polynucleotide prebound to a highly purified lipoprotein fraction may be administered in amounts ranging from 1 $\mu$g to 1 mg polynucleotide and 1 $\mu$g to 100 mg protein.

Administration of the therapeutic virus particle to a patient will follow general protocols for the administration of chemotherapeutics, taking into account the toxicity, if any, of the vector. It is anticipated that the treatment cycles would be repeated as necessary. It also is contemplated that various standard therapies, as well as surgical intervention, may be applied in combination with the described gene therapy.

Where clinical application of a gene therapy is contemplated, it will be necessary to prepare the complex as a pharmaceutical composition appropriate for the intended application. Generally this will entail preparing a pharmaceutical composition that is essentially free of pyrogens, as well as any other impurities that could be harmful to humans or animals. One also will generally desire to employ appropriate salts and buffers to render the complex stable and allow for complex uptake by target cells.

Aqueous compositions of the present invention comprise an effective amount of the compound, dissolved or dispersed in a pharmaceutically acceptable carrier or aqueous medium. Such compositions can also be referred to as inocula. The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

The compositions of the present invention may include classic pharmaceutical preparations. Dispersions also can be prepared in glycerol, liquid polyethylene glycols, and mixtures thereof and in oils. Under ordinary conditions of storage and use, these preparations contain a preservative to prevent the growth of microorganisms.

i) Disease States

A wide variety of disease states may be treated with compositions according to the present invention. In essence, any disease that can be treated by provision of a protein or nucleic acid is amenable to this approach. Disease states include a variety of genetic abnormalities such as diabetes, cancer, cystic fibrosis and various other diseases that could be treated by increasing or decreasing expression of a protein in a target cell.

Depending on the particular disease to be treated, administration of therapeutic compositions according to the present invention will be via any common route so long as the target tissue is available via that route. This includes oral, nasal, buccal, rectal, vaginal or topical. Topical administration would be particularly advantageous for treatment of skin cancers. Alternatively, administration will be by orthotopic, intradermal, subcutaneous, intramuscular, intraperitoneal or intravenous injection. Such compositions would normally be administered as pharmaceutically acceptable compositions that include physiologically acceptable carriers, buffers or other excipients.

In certain embodiments, ex vivo therapies also are contemplated. Ex vivo therapies involve the removal, from a patient, of target cells. The cells are treated outside the patient's body and then returned. One example of ex vivo therapy would involve a variation of autologous bone marrow transplant. Many times, ABMT fails because some cancer cells are present in the withdrawn bone marrow, and return of the bone marrow to the treated patient results in repopulation of the patient with cancer cells. In one embodiment, however, the withdrawn bone marrow cells could be treated while outside the patient with an LDL-DNA particle that targets and kills the cancer cell. Once the bone marrow cells are "purged," they can be reintroduced into the patient.

The treatments may include various "unit doses." Unit dose is defined as containing a predetermined-quantity of the therapeutic composition calculated to produce the desired responses in association with its administration, i.e., the appropriate route and treatment regimen. The quantity to be administered, and the particular route and formulation, are within the skill of those in the clinical arts. Also of import is the subject to be treated, in particular, the state of the subject and the protection desired. A unit dose need not be administered as a single injection but may comprise continuous infusion over a set period of time. Unit dose of the present invention may conveniently may be described in terms of 0.01 mg DNA/kg body weight to 0.4 mg DNA/kg body weight, with ranges in between these being contemplated such that 0.05, 0.10, 0.15, 0.20, 0.25, 0.5 mg/DNA/kg body weight are administered. Likewise the amount of LDL delivered can vary from about 0.2 to about 8.0 mg/kg body weight. Thus in particular embodiments, 0.4 mg, 0.5 mg, 0.8 mg, 1.0 mg, 1.5 mg, 2.0 mg, 2.5 mg, 3.0 mg, 4.0 mg, 5.0 mg, 5.5 mg, 6.0 mg, 6.5 mg, 7.0 mg and 7.5 mg of LDL may be delivered to an individual in vivo. The dosage of DNA:LDL to be administered depends to a great extent on the weight and physical condition of the subject being treated as well as the route of administration and the frequency of treatment. A pharmaceutical composition comprising the naked polynucleotide prebound to a highly purified lipoprotein fraction may be administered in amounts ranging from 1 $\mu$g to 1 mg polynucleotide to 1 $\mu$g to 100 mg protein. Thus, particular compositions may comprise 1 $\mu$g, 5 $\mu$g, 10 $\mu$g, 20 $\mu$g, 30 $\mu$g, 40 $\mu$g, 50 $\mu$g, 60 $\mu$g, 70 $\mu$g, 80 $\mu$g, 100 $\mu$g, 150 $\mu$g, 200 $\mu$g, 250 $\mu$g, 500 $\mu$g, 600 $\mu$g, 700 $\mu$g, 800 $\mu$g, 900 $\mu$g or 1000 $\mu$g polynucleotide that is bound independently to 1 $\mu$g, 5 $\mu$g, 10 $\mu$g, 20 $\mu$g, 3.0 $\mu$g, 40 $\mu$g 50 $\mu$g, 60 $\mu$g, 70 $\mu$g, 80 $\mu$g, 100 $\mu$g, 150 $\mu$g, 200 $\mu$g, 250 $\mu$g, 500 $\mu$g, 600 $\mu$g, 700 $\mu$g, 800 $\mu$g, 900 $\mu$g or 1000$\mu$g, 1.5 mg, 5 mg, 10 mg, 20mg, 30mg, 40 mg, 50 mg, 60 mg, 70 mg, 80 mg, 90 mg or 100 mg lipoprotein. Any amount of polynucleotide may be bound to any other amount of lipoprotein to achieve the pharmaceutical concentrations of the present invention.

ii) Cancer

One of the preferred embodiments of the present invention involves the use of the LDL vectors to deliver therapeutic genes to cancer cells. Target cancer cells include cancers of the lung, brain, prostate, kidney, liver, ovary, breast, skin, stomach, esophagus, head & neck, testicles, colon, cervix, lymphatic system and blood. Of particular interest are non-small cell lung carcinomas including squamous cell carcinomas, adenocarcinomas and large cell undifferentiated carcinomas.

According to the present invention, one may treat the cancer by directly injection a tumor with the LDL vector. Alternatively, the tumor may be infused or perfused with the vector using any suitable delivery vehicle. Local or regional administration, with respect to the tumor, also is contemplated. Finally, systemic administration may be performed. Continuous administration also may be applied where appropriate, for example, where a tumor is excised and the tumor bed is treated to eliminate residual, microscopic disease. Delivery via syringe or catherization is preferred. Such continuous perfusion may take place for a period from about 1–2 hours, to about 2–6 hours, to about 6–12 hours, to about 12–24 hours, to about 1–2 days, to about 1–2 weeks or longer following the initiation of treatment. Generally, the dose of the therapeutic composition via continuous perfusion will be equivalent to that given by a single or multiple injections, adjusted over a period of time during which the perfusion occurs.

For tumors of $\geq 4$ cm, the volume to be administered will be about 4–10 ml (preferably 10 ml), while for tumors of <4 cm, a volume of about 1–3 ml will be used (preferably 3 ml). Multiple injections delivered as single dose comprise about 0.1 to about 0.5 ml volumes. The LDL-DNA particles may advantageously be contacted by administering multiple injections to the tumor, spaced at approximately 1 cm intervals.

In certain embodiments, the tumor being treated may not, at least initially, be resectable. Treatments with therapeutic constructs may increase the resectability of the tumor due to shrinkage at the margins or by elimination of certain particularly invasive portions. Following treatments, resection may be possible. Additional treatments subsequent to resection will serve to eliminate microscopic residual disease at the tumor site.

A typical course of treatment, for a primary tumor or a post-excision tumor bed, will involve multiple doses. Typical primary tumor treatment involves a 6 dose application over a two week period. The two week regimen may be repeated one, two, three, four, five, six or more times. During a course of treatment, the need to complete the planned dosings may be reevaluated.

Cancer therapies also include a variety of combination therapies with both chemical and radiation based treatments. Combination chemotherapies include, for example, cisplatin (CDDP), carboplatin, procarbazine, mechlorethamine, cyclophosphamide, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin and methotrexate.

Combination radiation therapies may be x- and y-irradiation. Dosage ranges for x-irradiation range from daily doses of 2000 to 6000 roentgens for prolonged periods of time (3 to 4 weeks), to single doses of 2000 to 6000 roentgens. Dosages for radioisotopes vary widely, and depend on the half-life of the isotope, the strength and type of radiation emitted, and the uptake by neoplastic cells.

Various combinations may be employed, gene therapy is "A" and the radio- or chemotherapeutic agent is "B":

A/B/A  B/A/B  B/B/A  A/A/B  A/B/B  B/A/A  A/B/B/B  B/A/B/B

B/B/B/A  B/B/A/B  A/A/B/B  A/B/A/B  A/B/B/A  B/B/A/A

B/A/B/A  B/A/A/B  A/A/A/B  B/A/A/A  A/B/A/A  A/A/B/A

The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

The therapeutic compositions of the present invention are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg, 25 mg, 50 mg or up to about 100 mg of human serum albumin per milliliter of phosphate buffered saline.

Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to well known parameters.

Additional formulations are suitable for oral administration. Oral formulations include such, typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

11. EXAMPLES

The following examples are included to demonstrate preferred embodiments of the inventions. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

1. Isolation of Plasma Lipoproteins

Restriction endonucleases were purchased from Life Technologies, and Protease inhibitors (i.e., leupeptin, PMSF, and Trasylol) were purchased from Sigma Chemical Company. Plasma lipoproteins were isolated using standard sequential flotation ultracentrifugation methods as described (Schumaker and Puppione, 1986). Throughout the entire procedure samples were kept on ice or at 4° C. unless otherwise stated.

Subjects were fasted for at least 4 h prior to the start of the experimental procedures.: Blood was drawn into sterile, vacuumed glass tubes containing anticoagulants, e.g., 0.1% (ethylenedinitrolo)-tetracetic acid (EDTA) or heparin. Plasma was obtained by centrifugation (10 minutes at 3000× g) and immediately adjusted to 0.005% phenylrnethansulfonyl fluoride (PMSF), 10KIU Trasylol/ml, and 1 μg leupeptin/ml. VLDL, LDL, and HDL fractions were isolated by sequential flotation ultracentrifugation for 18 h at 40,000 rpm in a Beckmann centrifuge Model LS-80M after plasma samples were adjusted with potassium bromide (ICBr) to solution densities of 1.006, 1.019, and 1.215 g/ml respectively. Immediately following ultracentrifugation, individual lipoprotein fractions were collected and dialyzed extensively against phosphate buffered saline (pH 7.4) containing 0.001% sodium azide. Protein concentrations were determined using standard BCA protein assays (Pierce Chemical Company).

2. Dna-Binding Protocol

Lipoproteins and DNA were mixed together and incubated for 30 min at room temperature in 50 mmole/liter Tris (pH 7.4), 100–154 mmoles/liter sodium chloride (NaCl), 15 mmoles/liter magnesium chloride ($MgCl_2$). 6×Sample loading buffer (30% glycerol, 0.25% Xylene cyanole FF, 0.25% bromophenol blue) was added to the samples in a 1:5 V/V ratio. Samples were underloaded into 30 μl wells at the cathode edge of an 0.8% agarose gel containing 1 μg ethidium bromide/ml in Tris-Acetate buffer (pH 7.85) and electrophoresis was accomplished using 100 Volt constant until the negatively charged tracking dye had migrated at least 50% of distance from the loading well to the anodic edge of the gel.

3. Agarose Electrophoretogram of Human Lipoproteins

Agarose electrophoresis of human lipoproteins has been performed to illustrating the differential migration patterns of lipoprotein fractions VLDL, LDL, and HDL isolated from human plasma resolved using non-denaturing conditions.

Plasma lipoproteins were isolated from human blood according to the protocol described above. 6×Sample loading buffer (30% glycerol, 0.25% Xylene cyanole FF, 0.25% bromophenol blue) was added to the samples in a 1:5 V/V ratio. Samples were underloaded into 30 μl wells at the cathode edge of an 0.8% agarose gel in Tris-Acetate buffer (pH 7.85) and electrophoresis was accomplished using 100 Volt constant until the negatively charged tracking dye had migrated at least 50% of the distance from the loading well to the anodic edge of the gel.

Following electrophoresis, the agarose gel was stained for protein in a solution containing 50% V/V ethanol, 10% V/V acetic acid, and 0.25% Coomasie Brilliant Blue R-250 (CBB R-250, Bio-Rad Labs). Lane 1 contained human VLDL (10 μg protein), Lane 2 contained human LDL (35 μg protein), and Lane 3 contained human HDL (35 μg protein). Results illustrated the differential migration of lipoprotein fractions, VLDL, LDL, and HDL, isolated from human plasma resolved using non-denaturing conditions by agarose gel electrophoresis. Lipoproteins were visualized using a protein binding dye, Coomassie Brilliant Blue (CBB). The absence of other bands in each lane indicated the high degree of purity for each lipoprotein.

4. Radioisotope Labeling of Deoxyoligonucleotides

Complementary single stranded oligonucleotides were mixed (10 $\mu$g each) and incubated at 85° C. for 5 min in 10 mM Tris HCl (pH 7.4). Immediately following incubation, the samples were cooled down slowly to room temperature to obtain double stranded oligonucleotides. The double stranded oligonucleotides were then digested with BamHI and EcoRI for 1 h at 37° C. in 50 mM Tris HCl (pH 8.0), 100 mM NAG1, and 10 mM $MgCl_2$. Digested double stranded oligonucleotides were purified using a Qiaquick nucleotide removal kit from Qiagen Inc. according to manufacturer's protocol. The 5' protruding ends of the purified oligonucleotides were then labeled with $^{32}P$-$\alpha$dATP using a Prime-It II labeling kit containing Exo (-) Klenow enzyme from Stratagene Inc. according to the manufacturer's protocol. The specific activity of all oligonucleotides was determined by scintillation counting.

The DNA-binding studies were performed as described above except that the agarose gel was not stained with ethidium bromide. Instead, following electrophoresis, the agarose gel was dried under vacuum and exposed to X-ray film for 4 h at room temperature prior to protein staining in a solution containing 50% V/V ethanol, 10% V/V acetic acid, and 0.25% Coomassie Brilliant Blue R-250 (Bio-Rad Labs). Oligonucleotides and human LDL were present at 400,000 cpm and 40 $\mu$g protein per lane respectively.

5. Sonication of Plasma Lipoproteins

Solutions of plasma lipoproteins in phosphate-buffered saline containing 10 mM $MgCl_2$ were kept on ice and sonicated for various time periods ranging from 0 to 6 minutes in a Sonifier Model 350 sonicator (Branson Sonic Power Co.) at the following settings: duty cycle; 30%, pulsed, output control; level 2. Immediately following sonication, genomic DNA was added to the sonicated solutions, and the DNA-binding assay (see above) was started.

6. RT-PCR™ of Lipoprotein-bound RNA

Human liver RNA, complexed to human LDL or to human VLDL as described above, was subjected to agarose gel electrophoresis and extracted from the gel by solubilizing the gel for 20 min at 50° C. in 3 times the gel volume of QX-1 buffer (Qiagen) and by twice adding an equivalent volume of phenol/chloroform (pH 4.0). RNA was precipitated by adding an equivalent volume of 100% isopropanol and freezing the mixture overnight at −80° C. RNA pellets were dissolved in 50 $\mu$l of DEPC-treated water. For each reaction, the dissolved RNA (3 $\mu$l) was transcribed in reverse into single-stranded DNA by adding 100 mM KCl, 10 mM Tris-HCl (pH 8.3), 5 mM $MgCl_2$, 2.5 $\mu$M primer (oligo d(T) or random hexamers), 1 U/$\mu$l RNase inhibitor, 1 mM each of dATP, dCTP, dTTP, and dGTP, and 2.5 U/$\mu$l of MuLV reverse transcriptase in a total reaction volume of 20 $\mu$l. The single-stranded DNA samples were then amplified in 100 mM KCl, 10 mM Tris-HCl (pH 8.3), 2 mM $MgCl_2$, 0.15 $\mu$M each of the forward and reverse ISRE primers (see Table 2), 1 mM each of dATP, dCTP, dTTP, and dGTP, and 2.5 U/100 $\mu$l of AmpliTaq DNA polymerase in a total reaction volume of 100 $\mu$l. DNA amplification was carried out in a thermocycler in 30 consecutive cycles of denaturing at 95° C. for 60 sec, reannealing at 55° C. for 60 sec, primer extension at 72° C. for 120 sec, and a final extension at 72° C. for 7 min. For each PCR reaction, 10 $\mu$l of the reaction mixture was analyzed by electrophoresis on a 1% agarose gel in TBE buffer (45 mM Tris-borate and 1 mM EDTA, pH 8.0) while maintaining a 100-V constant for 1 h. The PCR products were visualized by staining the gel with ethidium bromide.

7. DNA Sequencing

DNA fragments obtained from the RT-PCR reactions were separated by electrophoresis on a 1% agarose gel and extracted from the gel by using a Qiagen gel extraction kit according to the manufacturer's protocol. DNA samples were analyzed on an Applied Biosystems Inc. model 373 automated DNA sequence apparatus after dye-terminator thermo cycle sequencing.

8. Cell Culture and Transfection Assays.

Human skin fibroblasts were cultured in complete growth medium consisting of Dulbecco's modified Eagle's medium that was supplemented with 10% fetal bovine serum, 100 $\mu$g/ml each of streptomycin and penicillin at 37° C. in an atmosphere of 5% $CO_2$ in a humidified incubator. Twenty-four hours before cell transfection, during exponential growth, the cultured cells were harvested by trypsinization, replated at a cell density of 1×106 cells in 35-mm culture dishes containing a glass coverslip, and cultured in complete growth medium. All transfection experiments were performed in triplicate as described.

9. LipoFectin Assay.

The pEGFP-N1 plasmid and LipoFectin were mixed together at a ratio of 1:4 (wt/wt) in 200 $\mu$l of serum-free medium and incubated for 15 min at room temperature. When the cells reached 40 to 60% confluence, they were transfected with a mixture of 5 $\mu$g of DNA and 20 $\mu$g of LipoFectin per 35-mm culture dish, each dish having been diluted in 1 ml of serum-free medium. Transfection was performed for 16 h at 37° C. Once transfection was achieved, the liposomes were removed from the culture dish by gentle washing and maintained in 2 ml of growth medium per 35-mm culture dish for 24 h at 37° C. Expression of GFP in the cells was determined by fluorescence microscopy 10. LDL Assay.

The pEGFP-N1 plasmid and LDL were mixed together at a ratio of 1:10 (wt/wt) in 100 $\mu$l of serum-free medium containing 10 mM $MgCl_2$ and incubated for 15 min at 37° C. When the cells were 40 to 60% confluent, they were transfected for 16 h at 37° C. with a mixture of 5 $\mu$g of DNA and 50 $\mu$g of LDL per 35-mm culture dish, each dish having been diluted in 1 ml of serum-free medium. Once transfection was achieved, the LDLs were removed by gentle washing and maintained in 2 ml of growth medium per 35-mm culture dish for 24 h at 37° C. At 24 h after transfection, the cells were washed with PBS and fixed in 2 ml of PBS containing 4% paraformaldehyde per 35-mm culture dish for 30 min. The coverslips were then removed from the culture dishes, washed with PBS, placed in an inverted orientation on glass slides, and examined by fluorescent microscopy to detect GFP.

11. In vivo Reporter Gene Expression.

Two-month-old female Sprague-Dawley rats were anesthetized with a combination anesthetic (42.8 mg/ml ketamine, 8.6 mg/ml xylazine, and 1.4 mg/ml acepromazine), and a prebound complex of purified rat LDL and linearized pEGFP-N1 plasmid DNA was injected intravenously (into the femoral vein), subcutaneously, intraperitoneally, and into the pharyngeal, nasal, and rectal mucosae (100 $\mu$g of LDL protein and 5 $\mu$g of DNA in 100 $\mu$l of PBS containing 10 mM $MgCl_2$ per site). Control animals were injected with linearized pEGFP-N1 plasmid DNA in which the HCMV IE promoter sequence was interrupted only by digestion with restriction enzymes. 5 μg of DNA in 100 μl of PBS containing 10 mM MgCl$_2$ per site. After 2, 5, or 7 days, all the treated and control rats were sacrificed, their blood was collected by means of cardiac puncture, and the tissues were excised and immobilized in OCT by means of snap freezing over liquid nitrogen or by immediate freezing in liquid nitrogen. The immobilized tissue samples were sectioned on a cryomicrotome, and the sections (5–8 μm thick) were fixed for 30 min in 4% paraformaldehyde and analyzed for expression of EGFP (green fluorescent protein) by fluorescent microscopy.

12. Fluorescent Microscopy.

Microscopy was performed by using an Olympus Model BH-2 fluorescent microscope (Olympus, USA) equipped with a digital camera (Hamamatsu, Model C5810) and a color printer (Image Master, Toshiba). The filter set used was a standard fluorescein isothiocyanate (FITC) set (Chroma Technology, Brattleboro, Vt., USA). The maximum excitation and emission wavelengths for this filter set were 485 nm (range 460–5 10 nm) and 540 nm (range 515–565 nm), respectively. Transfection efficiency was determined by calculating the average percentage of transduced cells of five different fields per 35-mm culture dish.

13. Detection of GFP.

Excised rat tissues were homogenized in 150 μl of PBS in a dounce homogenizer placed on ice. The homogenized tissues were centrifuged for 3 min at 13,000×g, and 50-μl aliquots were withdrawn and used in an ELISA assay to detect GFP. First, serial dilutions (range 1:10 to 1:1,000) of all samples were made in PBS. ELISA plates (96 wells) were coated with the samples (three wells/sample) by incubating the plates at room temperature for 3 h. The plated samples were then washed three times with 200 μl of 1×PBS containing 0.1% Tween 20 (PBST) and blocked with 200 μl of PBST containing 1% bovine serum albumin (BSA) for 2 h at room temperature while shaking gently. The washing procedure was repeated with 200 μl of PBST containing 0.1% BSA, and the plated samples were incubated with a 1:2,000 dilution of a recombinant GFP polyclonal antibody (IgG fraction, Clontech Inc., Palo Alto, Calif.) in PBST containing 0.1% BSA (50 μl of diluted mixture per well) for 18 h at 4° C. while shaking gently. The plated samples were washed and incubated with a 1:5000 dilution of HRP-conjugated goat anti-rabbit antibody (IgG fraction, Cappel, Durham, N.C.) in PBST containing 0.1% BSA for 1 h at room temperature while shaking gently. The washing procedure was repeated and was followed by a final wash with 1×PBS. GFP was detected after a 30-min incubation at room temperature in PBS containing σ-phenylenediamine as a chromogenic substrate.

Example 2

Binding of Human Genomic DNA to Human LDL

The binding of human genomic DNA (hg DNA) to human LDL has also been demonstrated. Each lane of the agarose gel contained hg DNA cut with AluI or HindIII. In addition, human VLDL and mouse LDL were run alongside the hg DNA.

Plasma lipoproteins were isolated from human or mouse blood according to the protocol described above. DNA-binding studies were performed using human genomic DNA digested with either AluI or HindIII. Following electrophoresis, the gel was stained for DNA with ethidium bromide prior to protein staining in a solution containing 50% V/V ethanol, 10% V/V acetic acid, and 0.25% Coomasie Brilliant Blue R-250 (CBB R-250, Bio-Rad Labs).

Each lane contained 5 μg human genomic DNA (hg DNA) cut with AluI or HindIII. In addition, human VLDL (10 μg protein per lane) human LDL (35 μg protein per lane) and mouse LDL (10 μg protein per lane) were also analysed.

Bands in this study showed specific binding of digested human DNA fragments and human LDL by gel-shift electrophoresis. DNA fragment obtained by AluI or HindIII digestion of human genomic DNA are shown to migrate toward the anode with much slower mobility when preincubated with human LDL but not when incubated with human VLDL, human HDL, or mouse LDL. The complexed DNA/lipoprotein band are first visualized using DNA-binding ethidium bromide and photographed using transmitted ultra-violet light for activation of the fluorescent dye. Lipoproteins were next visualized with CBB and photographed using transmitted visible light. The results shown in this figure indicate that aliquoti of AluI- and Hind III-digested human genomic DNA fragments comigrate with human LDL and are therefore bound to human LDL.

While AluI, and HindIII were used to digest genomic DNA in the studies shown here, the inventors of the instant invention have also used BamHI, and PvuI for genomic DNA digest. It is understood by those of skill in the art that there are many known restriction enzymes. All of which are capable of genomic DNA digestion resulting in DNA that can be successfully bound to LDL. DNA digested with AluI yields DNA of very small size (200–700 nucleotides) which allows isolation of the slower migrating digested DNA bound to LDL from the unbound digested DNA using agarose gel electrophoresis. Digestion of genomic DNA with HindIII yields genomic DNA of greater average size (1000–7000 nucleotides) which reaches the upper size limit for separation by agarose gel electrophoresis (the technique used here), however there are other known DNA separation techniques which would work similarly to accomplish the goal of separating free DNA from DNA bound to LDL. The choice of which separation technique to use is dependent only on the size of the DNA fragments resulting after digestion. In principal, undigested genomic DNA would also work.

Example 3

Binding of Plasmid DNA to Human LDL

Plasma LDL were isolated from human blood according to the protocol previously described in Example 1. DNA-binding studies were using DNA (pBluescript II KS, Stratagene Inc.) digested with Pvu I. Following electrophoresis, the agarose gel was stained for DNA with ethidium bromide prior to protein staining in a solution containing 50% V/V ethanol, 10% V/V acetic acid, and 0.25% Coomassie Brilliant Blue R-250 (CBB R-250, Bio-Rad Labs). The binding of plasmid DNA to human LDL was shown in agel which contained contains 0.5 μg molecular size DNA marker (Lane 1); 2 μg pKS DNA cut with Pvu I (Lanes 2–4); 35 μg human LDL (Lane 3) and 70 μg human LDL protein (Lane 4).

Results of the electrophoretogram illustrated specific binding of PvuI digested plasmid DNA (pBluescript II KS, Stratagene Inc.) and human LDL. Increased amounts of human LDL also caused an increase of DNA shifted to the LDL location and a decrease of the free Pvu I digested DNA band. Co-migration of the Pvu I digested DNA and human LDL are proof of a physical complex composed of LDL and DNA.

Example 4

Binding of CMV Promoter-regulatory Sequences to Human LDL

Plasma lipoproteins were isolated from human or mouse blood according to the protocol previously described in Example 1. DNA-binding studies were performed using plasmid DNA (either pBluescript II KS or pBKCMV, Stratagene Inc.) digested with BamHI. Following electrophoresis the agarose gel was stained for DNA with ethidium bromide prior to protein staining in a solution containing 50% V/V ethanol, 10% V/V acetic acid, and 0.25% Coomassie Brilliant Blue R-250 (CBB R-250, Bio-Rad Labs). Loading quantities per lane were as follows:

| plasmid DNA: | 1 µg DNA/lane |
|---|---|
| human VLDL | 35 µg protein/lane |
| human LDL | 35 µg protein/lane |
| mouse VLDL: | 8 µg protein/lane |
| mouse LDL: | 35 µg protein/lane |

This study used BamHI cut pIGS, BamHI cut pBKCMV, human VLDL, human LDL, mouse VLDL and mouse LDL.

A comparison of human LDL complexed with BamHI linearized plasmids, pBluescript II KS or pBKCMV. The inventors' results illustrated that specific binding of BamHI linearized plasmid DNA and human LDL occurs, but these BamHII linearized plasmids do not complex with either human VLDL, mouse VLDL or mouse LDL under the conditions previously described in the DNA-binding protocol (Example 2). Further, enhanced binding of human LDL and the BamHI linearized plasmid pBKCMV DNA which contains the cytomegalovirus promoter region SEQ ID NO:225 (Table 2) was observed as compared to the BamHI linearized plasmid pBluescript II KS DNA that does not contain the cytomegalovirus promoter region (lane 3). Because binding of DNA by LDL is enhanced in the presence of the CMV promoter, it is possible that LDL binds specifically to the CMV promoter sequence (SEQ ID NO:225, see Table 2).

Aliquots containing approximately 8 µg mouse VLDL protein were used in each DNA-binding assay mixtures resolved in lanes 4 and 9 as compared to 35 µg of total protein of allother lipoproteins (lanes 2, 3, 5, 7, 8, and 10). Due to the low physiological concentration of VLDL in mouse plasma and the limited loading capacity of the gel, it was not possible to load 35 µg of mouse VLDL protein per lane. Therefore, this study does not allow for a quantitative comparison of the plasmid DNA-binding capacity of mouse VLDL vs. human VLDL, human LDL, and mouse LDL.

Example 5

Binding of SRE, E/C, FAS, and ISRE Deoxynucleotide Sequences to Human LDL

Plasma lipoproteins were isolated from human or mouse blood according to the protocol previously described in Example 1. DNA-binding studies were performed using the synthetic oligonucleotides: SRE, E/C, and FAS (see Table 3 for nucleotide sequences).

TABLE 3

Deoxyribonucleic Acid Sequences of Synthetic Oligonucleotides used in Binding Studies with LDL

| SEQ ID NO | Oligo Name | Sequence (5'-3') |
|---|---|---|
| 226 | SRE-2A | GATCCAAATCACCCACTGCAACTCCTCCCCCTGCG |
| 227 | E/C-1A | GATCCATCCAATTGGGCAATCAGGAG |
| 228 | FAS-1A | GATCCGGTCTCCAATTGG |
| 229 | ISRE-1A | GATCCTCGGGAAAGGGAAACCGAAACTGAAGCCG |

DNA-binding studies were performed according to the previously described DNA-binding protocol (Example 2). Following electrophoresis, the agarose gel was stained for DNA with ethidium bromide prior to protein staining in a solution containing 50% V/V ethanol, 1096 V/V acetic acid, and 0.25% Coomassie Brilliant Blue R-250 (CBB R-250, Bio-Rad Labs). Oligonucleotides were present at 1 µg DNA per lane. Lanes containing human LDL contained 35 µg protein per lane and lanes containing mouse LDL contained 15 µg protein per lane.

The data generated showed the complexed synthetic, double-stranded oligonucleotide fragments and human LDL. The results strongly support that human LDL binds, to these DNA sequences in a highly specific fashion. The synthetic oligonucleotides SRE-2A, E/C-1A, FAS-1A, and ISRE-1A (Table 3, SEQ ID NO:226, SEQ ID NO:227, SEQ ID NO:228, and SEQ ID NO:229 respectively) bind to human LDL but do not bind to mouse LDL. DNA binding to human LDL is illustrated by the appearance of a fraction of slower mobility DNA that comigrates with human LDL.

In another embodiment of this same study, binding was determined using radioisotope labeling of the deoxynucleotide sequences as described in Example 1. The results from these DNA-binding studies show that human LDL binds to the synthetic oligonucleotides SRE-2A, E/C-1A, FAS-1A,

TABLE 2

Nucleotide Sequence of the Promoter Region (1300–1900) of the Human Cytomegalovirus SEQ ID NO:225

| GGATCTGACG | GTTCACTAAA | CCAGCTCTGC | TTATATAGAC | CTCCCACCGT |
|---|---|---|---|---|
| ACACGCCTAC | CGCCCATTTG | CGTCAATGGG | GCGGAGTTGT | TACGACATTT |
| TGGAAAGTCC | CGTTGATTTT | GGTGCCAAAA | CAAACTCCAT | TGACGTCAAT |
| GGGGTGGAGA | CTTGGAAATC | CCCGTGAGTC | AAACCGCTAT | CCACGCCCAT |
| TGATGTACTG | CCAAAACCGC | ATCACCATGG | TAATAGCGAT | GACTAATACG |
| TAGATGTACT | GCCAAGTAGG | AAAGTCCCAT | AAGGTCATGT | ACTGGGCATA |
| ATGCCAGGCG | GGCCATTTAC | CGTCATTGAC | GTCAATAGGG | GGCGTACTTG |
| GCATATGATA | CACTTGATGT | ACTGCCAAGT | GGGCAGTTTA | CCGTAAATAC |
| TCCACCCATT | GACGTCAATG | GAAAGTCCCT | ATTGGCGTTA | CTATGGGAAC |
| ATACGTCATT | ATTGACGTCA | ATGGGCGGGG | GTCGTTGGGC | GGTCAGCCAG |
| GCGGGCCATT | TACCGTAAGT | TATGTAACGC | GGAACTCCAT | ATATGGGCTA |
| TGAACTAATG | ACCCCGTAAT | TGATTACTAT | TAATAACTA | |

Major repeat regions are indicate in bold and underlined.

and ISRE-1A (Table 3, SEQ ID NO:226; SEQ ID NO:227; SEQ ID NO:228; SEQ ID NO:229) in a highly specific fashion. DNA binding to human LDL is illustrated by the appearance of a fraction of slower mobility DNA that comigrates with human LDL. The binding affinity of the 5 different synthetic oligonucleotides for human LDL can be determined by kinetic binding studies using quantitative autoradiography well known to those of skill in the art.

Example 6

Binding of Various Nucleotide Sequences to the LDL Isolated from Various Species Plasma lipoproteins were isolated from human, mouse, rat, or baboon blood according to the protocol previously described in Example 1. DNA-binding studies were performed according to the previously described DNA-binding protocol using the synthetic oligonucleotides: SRE, E/C, and FAS (see Table 3 for nucleotide sequences), genomic DNA, or plasmid DNA containing the CMV promoter. A summary of the binding studies of the instant invention are illustrated in Tables 4A and 4B, below. Table 4A illustrates the binding of human, mouse, rat and baboon LDL to various forms and sources of DNA, and Table 4B illustrates the DNA/LDL complexes made thus far.

TABLE 4A

Binding of Human, Mouse, Rat and Baboon LDL to Various Forms of DNA

| DNA | human LDL | mouse LDL | rat LDL | baboon LDL |
| --- | --- | --- | --- | --- |
| hg DNA | YES | NO | YES | YES |
| mg DNA | N.D. | N.D. | YES | N.D. |
| rg DNA | N.D. | N.D. | YES | N.D. |
| bg DNA | N.D. | N.D. | N.D. | YES |
| CMV | YES | NO | YES | YES |
| SRE | YES | NO | N.D. | NO |
| E/C | YES | NO | N.D. | NO |
| FAS | YES | NO | N.D. | NO | hg = human genomic DNA (digested with either AluI or HindIII,
mg = mouse genomic DNA digested with either AluI or HindIII,
rg = rat genomic DNA digested with either AluI or HindIII, and
bg = baboon genomic DNA digested with either AluI or HindIII
Yes = binding,
NO = no binding,
N.D. = binding not determined

TABLE 4B

Specific LDL/DNA Complexes That Have Been Made

| DNA | DNA Digested With | LDL |
| --- | --- | --- |
| human genomic | AluI | human |
| human genomic | HindIII | human |
| human genomic | Bam HI | human |
| human genomic | Pvu I | human |
| human genomic | AluI | rat |
| human genomic | HindIII | rat |
| human genomic | Bam HI | rat |
| human genomic | Pvu I | rat |
| human genomic | AluI | baboon |
| human genomic | HindIII | baboon |
| human genomic | Bam HI | baboon |
| human genomic | Pvu I | baboon |
| mouse genomic | AluI | rat |
| mouse genomic | HindIII | rat |
| rat genomic | AluI | rat |
| rat genomic | HindIII | rat |
| baboon genomic | AluI | baboon |
| baboon genomic | HindIII | baboon |

TABLE 4B-continued

Specific LDL/DNA Complexes That Have Been Made

| DNA | DNA Digested With | LDL |
| --- | --- | --- |
| pBSKS | Pvu I | human |
| pBSKS | Bam HI | human |
| pBKCMV | Bam HI | human |
| pBKCMV | Bam HI | rat |
| pBKCMV | Bam HI | baboon |
| SRE-2A oligo SEQ ID NO: 226 | none | human |
| E/C-1A oligo SEQ ID NO: 227 | none | human |
| FAS-1A oligo SEQ ID NO: 228 | none | human |
| ISRE-1A oligo SEQ ID NO: 229 | none | human |

Example 7

Detection of LDL-bound DNA in Human Blood

Plasma lipoproteins are isolated from human blood according to the protocol previously described in Example 1. 6×Sample loading buffer (30% glycerol, 0.25% Xylene cyanole FF, 0.25% bromophenol blue) is added to the samples in a 1:5 V/V ratio. Samples are underloaded into 30 µl wells at the cathode edge of an 0.8% agarose gel in Tris-Acetate buffer (pH 7.85) and electrophoresis is accomplished using 100 Volt constant until the negatively charged tracking dye migrates at least 50% of the distance from the loading well to the anodic edge of the gel. Following electrophoresis, is stained for DNA with ethidium bromide prior to protein staining in a solution containing 50% V/V ethanol, 10% V/V acetic add, and 0.25% Coomasie Brilliant Blue R-250 (CBB R-250, Bio-Rad Labs). If no DNA is detected by ethidium bromide staining, the agarose gel is subjected to Southern blot analysis using a labeled DNA probe. The DNA is labeled with a radioactive isotope (e.g., $^{32}P$), a non-radioactive tag (DIG) or with any other standard DNA-labeling method known to one of skill in the art. Randomly synthesized, short oligonucleotides are used as the probe to detect, in a general fashion, whether or not DNA is bound to the isolated LDL. Controls include lanes containing known quantities of DNA, lanes containing purified LDL digested with DNase I, and LDL bound to DNA made by mixing purified LDL and DNA according to the method described in Example 2.

LDL isolated from humans with cancer and subjected to the above protocol will have detectable DNA bound to the LDL in quantities greater than the amount of DNA bound to LDL isolated from humans without cancer.

Example 8

Detection of Specific Types of Cancers With Sequences Specific DNA Probes

Not only is it possible to identify the presence or absence of cancer in a living body using the invention technique (as described in Example 14 above), it is also possible to identify specific cancer types by using sequence specific DNA probes. For example, LDL-bound DNA isolated from a patient with colon cancer will have a different DNA sequence than the LDL-bound DNA isolated from a patient with a different cancer type, for example, breast cancer. Different DNA sequences bound to the LDL isolated from different cancer patients is determined by first isolating LDL from the blood of a person with an independently identified and known cancer type, using the protocol in Example 1. This isolated LDL is then digested with various non-specific proteases to remove the LDL while retaining the DNA. This DNA is then sequenced using standard sequencing techniques. A list of the DNA sequences along with the type of cancer it is associated with is made. This list is then used to synthesize probes that can differentiate among the various types of cancer. These probes are used in screening of a patient with an unknown cancer type, or in the early detection of metastatic cancer, or as a general early screening technique for the presence or absence of specific cancer types.

Example 9

Methods for the Determination of Metastatic Gene Transfer Via Lipoproteins as Native Vectors In order to determine the sequence of polynucleotides bound to endogenous LDL, plasma LDL and other apoB-containing lipoproteins are captured using a monoclonal antibody to a specific apoB epitope such as 2G8 which is immobilized on an inert, hydrophilic and highly porous polymer microbead. The LDL-DNA complex is then isolated by elution using affinity chromatography technology. DNA is further purified from the isolated LDL/DNA complex using standard DNA purification methodology such as phenol/chloroform extraction followed by ethanol precipitation. Alternatively, purified DNA is isolated from the affinity column using elution conditions that disrupt protein/DNA complexes but not protein/protein complexes (i.e., antibody/LDL complex). The polynucleotide sequences are determined using the SRE, E/C, FAS, and ISRE-1A oligonucleotides (SEQ ID NO:226, SEQ ID NO:227, SEQ ID NO:228, and SEQ ID NO:229, respectively) in a standard PCR™ methodology in order to amplify polynucleotides with unknown sequences. The amplified PCR™ products (i.e., polynucleotides) are then isolated by agarose gel electrophoresis and subsequent DNA sequencing techniques well known to the art.

Alternatively, identification of polynucleotide sequences that are bound to endogenous human LDL is via the specific binding of LDL to a plastic matrix such as a 96 well ELISA (enzyme linked immunosorbant assay) plates coated with specific antibodies that bind to human LDL. In this embodiment, freshly isolated plasma containing endogenous lipoproteins is used to bind to the anti-human LDL antibodies using standard ELISA procedures lipoproteins to the art. The presence and specific sequence of polynucleotides pre-bound to the endogenous LDL in each is determined by PCR ™ technology.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

Example 10

Low-density Lipoprotein Interacts With Human Cytomegalovirus Genomic DNA

DNA binding experiments with purified plasma lipoprotein fractions and human genomic DNA as well as several different plasmids indicate that purified LDL binds to human genomic DNA digested with different restriction enzymes (Alu I and Hind III).

Purified LDL also bound to several different plasmids but its binding affinity for plasmid DNA containing the HCMV IE promotor region was significantly higher. It was shown that the binding of both LDL and VLDL to the HCMV IE promotor region and SRE, MSRE, ISRE, MISRE, E/C, FAS, and MFAS oligonucleotides. The E/C oligonucleotide was used in these DNA binding studies because this oligonucleotide contains both a binding site for members of the C/EBP transcription factor family, which are involved in the regulation of differentiation-dependent adipocyte gene expression, as well as an overlapping E-box motif which is generally recognized by the eukaryotic basic helix-loop-helix (b-HLH) transcriptional regulators. LDL clearly have a greater affinity for all of the oligonucleotides tested than do VLDL. This is most likely due to interference with protein-DNA interaction caused by either the presence of other apolipoproteins on the surface of VLDL or an increased net charge as a result of the increased lipid content of VLDL.

The sequence specificity is illustrated by the fact that both LDL and VLDL show a decreased binding affinity for the mutated versions of the ISRE and FAS oligos (MISRE and MFAS respectively). In contrast, LDL showed an increased binding affinity for the mutated version of the SRE oligo (MSRE). It is possible that this mutated SRE sequence may be a better ligand for the putative DNA binding region of apo B present on LDL. The binding of both VLDL and LDL to the E/C oligonucleotide is not surprising since this oligo contains the E-box motif which is a known binding site for b-HLH proteins and similar b-HLH regions have been identified in apoB present on VLDL and LDL.

The affinity for the HCMV IE promotor is not immediately obvious since careful nalysis does not reveal an exact copy of either a SRE, ISRE, FAS, or E/C sequence. owever, the HCMV IE promotor region contains regulatory elements that are generally recognized by a large number of eukaryotic DNA-binding proteins, including a variety of different families of transcription factors, and it may therefore be possible that the identified b-HLH regions of apoB possess similar DNA binding properties.

Another possibility is that other yet unidentified regions of apoB are involved in the binding to the HCMV IE promotor region. The fact that HDL in contrast to VLDL and LDL do not bind to any of the oligos tested suggests that the DNA binding results from the specific interaction with apo B. These data support the hypothesis that apo B contains DNA binding domains which show homology with the DNA binding domains of SREBP-1, SREBP-2, ADD-1, and ISGF3γ and that apo B containing lipoproteins therefore bind to specific nucleotide sequences similar to those bound by these known DNA binding proteins.

Recent reports suggest a possible causal relationship between human cytomegalovirus (HCMV) and the development of atherosclerosis in humans. These reports together with data presented herein, which show that human LDL binds strongly to HCMV IE promotor sequences, led the inventors to investigate whether plasma LDL may play a role in the pathogenesis of HCMV induced atherosclerosis.

To test this hypothesis, the inventors looked for HCMV DNA sequences in the purified plasma LDL fraction of human subjects who tested seropositive for HCMV by polymerase chain reaction (PCR). The results of these studies show that a PCR product of the expected size (170 bp) could be detected with both primer sets (MTR2 and IE) in the purified plasma LDL fraction of HCMV seropositive subjects. However, this 170 bp DNA fragment could not be detected in the plasma samples of these subjects (lanes 6–8). These data suggest that the use of purified plasma LDL fractions for detection of CMV nucleic acid sequences by PCR techniques is more sensitive than when whole plasma samples are used. Furthermore, the increased yield of PCR products of the purified plasma LDL fractions strongly suggest that HCMV DNA is predominantly associated with LDL within the plasma pool of HCMV seropositive subjects.

Example 11

Low-density Lipoprotein as a Natural Gene Transfer Vector

The discovery of the nucleic acid-binding properties apo B-100 suggested that lipoproteins containing apoB100, as naturally occurring liposomes, may function as gene transfer agents. By using highly purified low-density lipoprotein as such an agent, the inventors were able to transfect cultured human skin fibroblasts in vitro and to express a green fluorescent protein reporter gene in vivo. The gene transfer mediated by low-density lipoprotein was more efficient that that mediated by LipoFectin. Low-density lipoprotein also did not exhibit any toxicity, immunogenicity, or serum inhibition.

1. DNA-binding

In the Examples above, it was shown that highly purified human LDL binds to nucleic acids in a specific fashion. In order to establish whether rat lipoproteins can bind nucleic acids in a similar fashion, DNA-binding experiments with different rat lipoprotein fractions were performed. A gel shift assay of linearized pBluescript KS and pBKCMV plasmid DNA and purified rat VLDL, LDL, and HDL fractions was performed. The data clearly demonstrate that the binding of nucleic acids is specific to the purified LDL fraction.

The binding of LDL to DNA is exhibited by the retarded electrophoretic migration of DNA in agarose gel that is caused by the formation of complexes of higher molecular weight. In contrast, purified fractions of VLDL and HDL did not bind any of the DNA samples tested. The fact that purified HDL did not bind DNA was expected, since endogenous HDL does not contain apo B-100. Surprisingly, there was no apparent binding of DNA to apo B-100-containing VLDL. It is possible that the DNA-binding assay, which employs ethidium bromide staining to detect DNA, lacks sensitivity or that VLDL does not bind to DNA under the conditions of the DNA-binding assay. Another explanation could be a difference in the conformation of apo B-100 present on LDL as opposed to VLDL because of a difference in the lipid composition and protein content of the two lipoprotein fractions.

2. In vitro Cell Transfection Studies.

Based on the findings of the DNA-binding assay, transfection studies were performed using a prebound complex of LDL and plasmid DNA that contained a reporter gene that encodes GFP.

The data generated illustrated the successful transfection of how human skin fibroblasts with LDL and pEGFP-N1 plasmid DNA. The transfection process was monitored by expression of the GFP encoding gene and is driven by the HCMV IE promoter. In addition to fluorescent microscopic analysis, expression of GFP was confirmed by a qualitative ELISA using a primary antibody against recombinant GFP and an HRP-conjugated secondary antibody with σ-phenylenediarnine as a chromogenic substrate.

Human skin fibroblasts transfected with LDL exhibited a significantly lower intensity of green fluorescence than did cells transfected with LipoFectin, indicating that the level of GFP expression was lower in these LDL-transfected cells. When the percentage of positively transfected cells were compared, however, transfection with LDL yielded a higher percentage of transfected cells than did transfection with LipoFectin (20 to 30% and 60 to 70%, respectively). In addition, LipoFectin-mediated transfection resulted in green fluorescence in the cell cytoplasm and in the nuclei, whereas LDL-mediated transfection resulted in green fluorescence predominantly in the cytoplasm.

Transfection assays in which LDL concentrations were as high as 250 g/ml of LDL protein produced no detectable effects on the confluence and viability of the cell cultures, whereas LipoFectin concentrations of 20 g/ml resulted in significant loss of cell viability. Control cells that were transfected with linearized pEGFP-NI plasmid DNA only exhibited no fluorescence.

3. In vivo Reporter Gene Expression.

To evaluate whether LDL could be used as a vehicle for in vivo gene delivery, a prebound rat LDL-pEGFP-N1 complex was administered to 2-month-old female Sprague-Dawley rats. Cryosections of the liver and heart tissues of the treated animals that had been excised 2 days after the LDL-pEGFP-N1 complex showed significant levels of green fluorescence indicative of EGFP expression as determined by fluorescent microscopy.

The expression of GFP in the different tissues was confirmed by a qualitative ELISA using a primary antibody against recombinant GFP and an HRP-conjugated secondary. antibody with σ-phenylenediamine as a chromogenic substrate. In contrast, only low levels of autofluorescence were observed in the cryosectioned tissues obtained from the control animals treated solely with linearized pEGFP-N1 DNA. These data demonstrate that purified LDL can be used in a prebound complex with DNA as an in vivo gene delivery system.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims

REFERENCES

U.S. Pat. No. 4,396,601
U.S. Pat. No. 4,403,035
U.S. Pat. No. 4,497,796
U.S. Pat. No. 4,663,292
U.S. Pat. No. 4,868,116
U.S. Pat. No. 4,885,248
U.S. Pat. No. 4,904,582
U.S. Pat. No. 5,023,243
U.S. Pat. No. 5,096,815
U.S. Pat. No. 5,149.782
U.S. Pat. No. 5,168,062

U.S. Pat. No. 5,198,346
U.S. Pat. No. 5,219,740
U.S. Pat. No. 5,252,479
U.S. Pat. No. 5,283,185
U.S. Pat. No. 5,298,422
U.S. Pat. No. 5,385,839
U.S. Pat. No. 5,482,853
U.S. Pat. No. 5,518,913
U.S. Pat. No. 5,521,291
U.S. Pat. No. 5,523,222
U.S. Pat. No. 5,547,932
U.S. Pat. No. 5,574,142
U.S. Pat. No. 5,578,475
U.S. Pat. No. 5,580,558
U.S. Pat. No. 5,580,859
U.S. Pat. No. 5,585,254
U.S. Pat. No. 5,585,362
U.S. Pat. No. 5,591,601
Baleja and Sykes, *Biochem. Cell Biol.*, 69(2–3):202–205, 1991.
Banner, Kolddnidis, Tsemoglou, *J. Mol. Biol.*, 196(3): 657–675, 1987.
Benvensty et al., *Proc. Natl. Acad. Sci. USA*, 83:9551–9555, 1986.
Biou, Yaremchuk, Tukaio, Cusack, *Science*, 263(5152): 1404–1410, 1994.
Blanco-Vaca et al., *Chem. Physics, Lipids*, 67/68:35–42, 1994.
Blanco-Vaca et al., *J. Lipid Res.*, 33:1785–17986, 1992.
Briggs et al., *J. Biol. Chem.*, 268:14490–14496, 1993.
Brown and Goldstein, *Science*, 232:34–47, 1986.
Bullough, Hughson, Skehel, Wiley, *Nature*, 371(6492): 37–43, 1994b.
Bullough, Hughson, Treharne, Ruigrok, Skehel, Wiley, *J. Mol. Biol.*, 236(4):1262–1265, 1994a.
Cardin et al., *Blochem.*, 26:5513–5518, 1987.
Carpenter, *FASEB J.*, 6:3283–3289, 1992.
Cicchetti et al., *Science*, 257:803–806, 1992.
Cohen and Parry, *TIBS*, 11:245–248, 1986.
Coleman et al., *Biochim. Biophy. Acta*, 1037:129–132, 1990.
Connelly et al., *J. Lipid Res.*, 34:1717–1727, 1993.
Cooper, "The SRC family of protein-tyrosine kinases," C.hapter 3, In: Peptides and Protein Phosphorylation, B. E. Kemp, ed., CRC Press, Inc., Boca Raton, Fla., pp. 85–113
Curiel et al., *Human Gene Therapy*, 3:147–154, 1992.
Cusack, Berthet-Colominas, Hartlein, Nassar, Leberman, *Nature*, 347(6290):249–255, 1990.
Ellenberger, Brandl, Struhl, Harrison, *Cell*, 71(7): 1223–37, 1992.
Escobedo et al., *Mol. Cell Biol.*, 11: 1125–1132, 1991.
Felgner et al., *Proc. Natl. Acad. Sci. USA*, 84:7413–7417, 1987.
Geahlen and Harrison, "Prorein-tyrosine kinases," C.hapter 10, In: Peptides and Protein Phosphorylation, B. E. Kemp, ed., CRC Press, Inc., Boca Raton, Fla., pp. 239–253.
Glover and Harrison, *Nature*, 373(6511):257–261, 1995.

Guevara, Jr. et al., *Arterioscler.*, 13:758–770, 1993.
Guevara, Jr. etal., *Proteins*, 12:188–199, 1992.
Guevara, Jr. et al., Src signal sequences in apoprotein B-100: "Does LDL or Lp[a] play a role in signal transduction," In: Multiple Risk Factors in Cardiovascular Disease, Yamamoto, ed., Churchill Livingston Japan, ICIC, 1994.
Hunter and Cooper, *Ann. Rev Biochem*, 54:897–930, 1985.
Innerarity et al., *Acta Med. Scand. Suppl.*, 715:51–59, 1986.
Kinoshitaet al., *J. Lipid Res.*, 31:701–708, 1990.
Knott et al., *Nature*, 323:734–738, 1986.
Koch et al., *Science*, 252:668–674, 1991.
Kostner and Grillhofer,*J. Biol. Chem.*, 266:21287–21292, 1991.
Kraulis, Raine, Gadhixji, Laue, *Nature*, 356(6368): 448–450, 1992.
Lee et al., *Human Gene Therapy*, 7:1701–1717, 1996.
Lowenstein et al., *Cell*, 70:431–442, 1992.
Lupas, Van Dyke, Stock, *Science*, 252(5010):1162–1164, 1991.
MacArthur and Thornton, *J. Mol. Biol.*, 218:397–412, 1991.
Mahley, *Science*, 240:622–630, 1988.
Marcel et al., *Arterioscl.*, 8:832, 1988.
Margolis, *Cell, Growth and Differentiation*, 3:73–80, 1992
Marmorstein, Carey, Ptashne, Harrison, *Nature*, 356 (6368):408–414, 1992.
McLean et al., *Nature*, 330:132–137, 1987.
Milne et al.,*J. Biol. Chem.*, 264(33):19754–19760, 1989.
Musacchio et al., *Nature*, 359:851–855, 1992.
Myant, "LDL: Physical and Chemical Characteristics, Chapter 5, In: Cholesterol Metabolsim, LDL, and the LDL Receptor, San Diego, Academic Press, pp. 99–111,1990.
Neumann et al., *EMBO J.*, 7:841–845, 1982.
Noble et al., *EMBO J.*, 12:2617–2624, 1993.
O'Shea, Klemm, Kim, Alber, *Science*, 254(5031): 539–544, 1991.
Pawson, *Current Opinion in Structural Biology*, 2:432–437, 1992.
Pleiman et al., *Science*, 263:1609–1612, 1994.
Ren et al., *Science*, 259:1157–1161, 1993.
Rudd et al., *Biochim. Biophys. Acta.*, 1155:239–266, 1993.
Schimotohono et al., *Cell*, 26:67–77, 1981.
Schlessinger, *Current Opinions in Genetics and Development*, 4:25–30, 1994.
Schumaker and Puppione, *Methods in Enzymology*, 128:155–170, 1986.
Smith et al., *J. Biol. Chem.*, 265:2306–2310, 1990.
Sompayrac etal., *Proc. Natl. Acad. Sci. USA*, 78:7575–7578, 1981.
Songyang et al., *Cell*, 72:767–778, 1993.
Stribling et al., *Proc. Natl. Acad. Sci. USA*, 89:11277–11281, 1992.
Teng et al, *J. Biol. Chem.*, 260:5067–5072, 1985.
Trieu and McConathy, *Biochem.*, 29(25):5919–5924, 1990.

Trieu et al., *J. Biol. Chem.*, 266(9):5480–5485, 1991.
Ugi et al., *FEBS Lett.*, 340:216–220, 1994.
Veals et al., *Mol. Cell. Biol.*, 12:3315–3324, 1992.
Waksman et al., *Cell*, 72:779–790, 1993.
Wang et al., *J. Biol. Chem.*, 268:14497–14504, 1993.
Weisgraber and Rall, Jr., *J. Biol. Chem.*, 262:11097–11103, 1987.
Wigler et al., *Proc. Natl. Acad Sci. USA*, 76:1373–1376, 1979.
Wolff et al., *Science*, 247:1465–1468, 1990.
Wu et al., *J. Biol. Chem.*, 263:14621–14624, 1988.
Wu et al., *J. Biol. Chem.*, 264:16985–16987, 1989.
Yang et al., *Arteriosclerosis*, 9(1):96–108, 1989.
Yang et al., *Nature*, 323:738–742, 1986.
Yang, *Proc. Natl. Acad. Sci. USA*, 87:5523–5527, 1990.
Ye et al., *J. Biol. Chem.*, 263(13):6337–6343, 1988.
Young et al., *Arterioscl.*, 6:178–188, 1986.
Yu et al., *Cell*, 76:933–945, 1994.

What is claimed is:

1. A method for expressing a selected polypeptide in a human cell comprising:
   a) providing a composition comprising (i) a polypeptide comprising a non-murine, native low density lipoprotein (LDL) and (ii) a nucleic acid comprising an expression cassette encoding said selected polypeptide, wherein said coding sequence is operably linked to a promoter, and wherein said nucleic acid is bound to said LDL;
   b) delivering said composition to said cell under conditions permitting transfer of said composition into said cell; and
   c) culturing said cell under conditions permitting the expression of said selected polypeptide.

2. The method of claim 1, wherein said selected polypeptide is a tumor suppressor.

3. The method of claim 1, wherein said selected polypeptide is a cytokine.

4. The method of claim 1, wherein said selected polypeptide is an enzyme.

5. The method of claim 1, wherein said selected polypeptide is a hormone.

6. The method of claim 1, wherein said selected polypeptide is a receptor.

7. The method of claim 1, wherein said selected polypeptide is an inducer of apoptosis.

8. The method of claim 2, wherein said tumor suppressor is selected from the group consisting of p53, p16, p21, MMAC1, p73, zacl, BRCAI and Rb.

9. The method of claim 3, wherein said cytokine is selected from the group consisting of IL-2, IL-2, IL-3, IL-4, IL-5, IL-6, IL-7, IL-8, IL-9, IL-10, IL-11, IL-12, IL-13, IL-14, IL-15, TNF, GMCSF, β-interferon and γ-interferon.

10. The method of claim 4, wherein said enzyme is selected from the group consisting of cytosine deaminase, adenosine deaminase, β-glucuronidase, hypoxanthine guanine phosphoribosyl transferase, galactose-1-phosphate uridyltransferase, glucocerbrosidase, glucose-6-phosphatase, thymidine kinase and lysosomal glucosidase.

11. The method of claim 5, wherein said hormone is selected from the group consisting of growth hormone, nerve growth factor, insulin, adrenocorticotropic hormone, parathormone, follicle-stimulating hormone, luteinizing hormone, epidermal growth factor and thyroid stimulating hormone.

12. The method of claim 6, wherein said receptor is selected from the group consisting of CFTR, EGFR, VEGFR, IL-2 receptor and the estrogen receptor.

13. The method of claim 7, wherein said inducer of apoptosis is selected from the group consisting of Bax, Bak, Bcl-$X_s$, Bik, Bid, Bad, Harakiri, Ad E1B and an ICE-CED3 protease.

14. The method of claim 1, wherein said promoter is selected from the group consisting of CMV IE, LTR, SV40 IE, HSV tk, β-actin, human globin α, human globin β and human globin γ promoter.

15. The method of claim 1, wherein said polypeptide further comprises at least one nuclear localization sequence.

16. The method of claim 15, wherein said nuclear localization sequence is an apoB100 nuclear localization sequence.

17. The method of claim 1, wherein said selected polypeptide is selected from the group consisting of α-globin, β-globin, γ-globin, neomycin resistance, luciferase, adenine phosphoribosyl transferase (APRT), mast cell growth factor.

18. A method for providing an expression construct to a human cell comprising:
   a) providing a composition comprising (i) a polypeptide comprising a non-murine, native low density lipoprotein (LDL) and (ii) a nucleic acid comprising an expression cassette, encoding an expression region and a promoter active in eukaryotic cells, wherein said expression region is operably linked to said promoter, and wherein said nucleic acid sequence is bound to said LDL; and
   b) delivering said composition to said cell under conditions permitting transfer of said composition into said cell.

19. The method of claim 18, wherein said expression construct comprises an antisense construct.

20. The method of claim 18, wherein said expression construct comprises an antisense oncogene construct.

21. The method of claim 20, wherein said oncogene is selected from the group consisting ras, myc, neu, raf erb, src, fms, jun, trk, ret, gsp, hst, bcl and abl.

22. The method of claim 18, wherein said expression construct comprises a nucleic acid coding for a polypeptide.

23. The method of claim 18, wherein said promoter is selected from the group consisting of CMV IE, LTR, SV40 IE, HSV tk, β-actin, human globin α, human globin β and human globin γ promoter.

24. The method of claim 18, wherein said polypeptide further comprises at least one nuclear localization sequence.

25. The method of claim 24, wherein said nuclear localization sequence is an apoB100 nuclear localization sequence.

26. The method of claim 18, wherein said polypeptide is selected from the group consisting of α-globin, β-globin, γ-globin, green fluorescent protein, neomycin resistance, luciferase, adenine phosphoribosyl transferase (APRT), mast cell growth factor.

27. A method inhibiting the growth of a tumor in vivo comprising:
   a) providing a composition comprising (i) a polypeptide comprising non-murine native low density lipoprotein (LDL) and (ii) a nucleic acid construct comprising an expression cassette encoding an anti-tumor expressible product and a promoter active in eukaryotic cells, wherein said nucleic acid construct is bound to said LDL; and
   b) delivering said composition to a human subject by local administration to said tumor under conditions permitting transfer of said composition into cells of said tumor,
whereby said tumor is inhibited by said expressible product.

28. The method of claim 27, wherein said promoter is selected from the group consisting of CMV IE, LTR, SV40 IE, HSV tk, β-actin, human globin α, human globin β and human globin γ promoter.

29. The method of claim 27, wherein said polypeptide comprises at least two nucleic acid binding regions.

30. The method of claim 27, wherein said polypeptide comprises at least one nuclear localization sequence.

31. The method of claims 30, wherein said nuclear localization sequence is an apoB100 nuclear localization sequence.

32. The method of claim 27, wherein said nucleic acid encodes a tumor suppressor gene, an inducer of apoptosis, or a cytokine.

33. The method of claim 27, wherein said expression construct comprises an antisense oncogene construct.

* * * * *

UNITED STATES PATENT AND TRADEMARK OFFICE
CERTIFICATE OF CORRECTION

PATENT NO.    : 6,635,623 B1
DATED         : October 21, 2003
INVENTOR(S)   : Juan Guevara Jr. Ron C. Hoogeveen and J. Paul Moore It is certified that error appears in the above-identified patent and that said Letters Patent is hereby corrected as shown below:

Title page,
Item [12], please delete "Hoogeveen" and insert -- Guevara -- therefor.
Item [75], Inventors, before "Ron C. Hoogeveen" please insert -- Juan Guevara Jr., Browvnsville, TX (US) -- therefor.
Item [56], References Cited, OTHER PUBLICATIONS,
"Sipehia," reference, please delete "byt" and insert -- by -- therefor.
"Chiu," reference, please delete "protetoals" and insert -- potential -- therefor.
"Verma," reference, please delete "therpy" and insert -- therapy -- therefor.
"Blanco-Vaca," reference, please delete "Characteriztion" and insert
-- Characterization -- therefor.
"Felgner," reference, please delete "hifhly" and insert -- highly -- therefor.

Column 3,
Line 7, please delete "granulocytei" and insert -- granulocyte -- therefor.

Column 19,
Line 20, please delete "fuictional" and insert -- functional -- therefor.

Column 24,
Line 39, please delete "iype" and insert -- type -- therefor.

Column 25,
Line 9, please delete "trasnport" and insert -- transport -- therefor.
Line 32, please delete "MgCl2" and insert -- $MgCl_2$ -- therefor.

Column 30,
Line 6, please delete "picomavirus" and insert -- picornavirus -- therefor.
Line 8, please delete "arenvirus" and insert -- adenovirus -- therefor.

Column 34,
Line 28, please delete "exp:osure" and insert -- exposure -- therefor.

Column 42,
Line 23, please delete "1x106" and insert -- $1x10^6$ -- therefor.

UNITED STATES PATENT AND TRADEMARK OFFICE
CERTIFICATE OF CORRECTION

PATENT NO.    : 6,635,623 B1
DATED         : October 21, 2003
INVENTOR(S)   : Juan Guevara Jr. Ron C. Hoogeveen and J. Paul Moore It is certified that error appears in the above-identified patent and that said Letters Patent is hereby corrected as shown below:

Column 50,
Line 34, please delete "nalysis" and insert -- analysis -- therefor.

Column 237,
Line 53, after "of" please delete -- IL-2 -- therefor.

Signed and Sealed this

Third Day of February, 2004

JON W. DUDAS
*Acting Director of the United States Patent and Trademark Office*

SEQUENCE LISTING (1) GENERAL INFORMATION:

(iii) NUMBER OF SEQUENCES: 229

(2) INFORMATION FOR SEQ ID NO:1:

(i) SEQUENCE CHARACTERISTICS:
        (A) LENGTH: 4536 amino acids
        (B) TYPE: amino acid
        (C) STRANDEDNESS:
        (D) TOPOLOGY: linear (xi) SEQUENCE DESCRIPTION: SEQ ID NO:1:

```
Glu Glu Glu Met Leu Glu Asn Val Ser Leu Val Cys Pro Lys Asp Ala
1               5                   10                  15

Thr Arg Phe Lys His Leu Arg Lys Tyr Thr Tyr Asn Tyr Glu Ala Glu
            20                  25                  30

Ser Ser Ser Gly Val Pro Gly Thr Ala Asp Ser Arg Ser Ala Thr Arg
            35                  40                  45

Ile Asn Cys Lys Val Glu Leu Glu Val Pro Gln Leu Cys Ser Phe Ile
    50                  55                  60

Leu Lys Thr Ser Gln Cys Thr Leu Lys Glu Val Tyr Gly Phe Asn Pro
65                  70                  75                  80

Glu Gly Lys Ala Leu Leu Lys Lys Thr Lys Asn Ser Glu Glu Phe Ala
            85                  90                  95

Ala Ala Met Ser Arg Tyr Glu Leu Lys Leu Ala Ile Pro Glu Gly Lys
            100                 105                 110

Gln Val Phe Leu Tyr Pro Glu Lys Asp Glu Pro Thr Tyr Ile Leu Asn
            115                 120                 125

Ile Lys Arg Gly Ile Ile Ser Ala Leu Leu Val Pro Pro Glu Thr Glu
            130                 135                 140

Glu Ala Lys Gln Val Leu Phe Leu Asp Thr Val Tyr Gly Asn Cys Ser
145                 150                 155                 160

Thr His Phe Thr Val Lys Thr Arg Lys Gly Asn Val Ala Thr Glu Ile
            165                 170                 175

Ser Thr Glu Arg Asp Leu Gly Gln Cys Asp Arg Phe Lys Pro Ile Arg
            180                 185                 190

Thr Gly Ile Ser Pro Leu Ala Leu Ile Lys Gly Met Thr Arg Pro Leu
            195                 200                 205

Ser Thr Leu Ile Ser Ser Gln Ser Cys Gln Tyr Thr Leu Asp Ala
            210                 215                 220

Lys Arg Lys His Val Ala Glu Ala Ile Cys Lys Glu Gln His Leu Phe
225                 230                 235                 240

Leu Pro Phe Ser Tyr Asn Asn Lys Tyr Gly Met Val Ala Gln Val Thr
            245                 250                 255
```

```
Gln Thr Leu Lys Leu Glu Asp Thr Pro Lys Ile Asn Ser Arg Phe Phe
            260                 265                 270
Gly Glu Gly Thr Lys Lys Met Gly Leu Ala Phe Glu Ser Thr Lys Ser
            275                 280                 285
Thr Ser Pro Pro Lys Gln Ala Glu Ala Val Leu Lys Thr Leu Gln Glu
            290                 295                 300
Leu Lys Lys Leu Thr Ile Ser Glu Gln Asn Ile Gln Arg Ala Asn Leu
305                 310                 315                 320
Phe Asn Lys Leu Val Thr Glu Leu Arg Gly Leu Ser Asp Glu Ala Val
                    325                 330                 335
Thr Ser Leu Leu Pro Gln Leu Ile Glu Val Ser Ser Pro Ile Thr Leu
                340                 345                 350
Gln Ala Leu Val Gln Cys Gly Gln Pro Gln Cys Ser Thr His Ile Leu
            355                 360                 365
Gln Trp Leu Lys Arg Val His Ala Asn Pro Leu Leu Ile Asp Val Val
            370                 375                 380
Thr Tyr Leu Val Ala Leu Ile Pro Glu Pro Ser Ala Gln Gln Leu Arg
385                 390                 395                 400
Glu Ile Phe Asn Met Ala Arg Asp Gln Arg Ser Arg Ala Thr Leu Tyr
                    405                 410                 415
Ala Leu Ser His Ala Val Asn Asn Tyr His Lys Thr Asn Pro Thr Gly
                420                 425                 430
Thr Gln Glu Leu Leu Asp Ile Ala Asn Tyr Leu Met Glu Gln Ile Gln
            435                 440                 445
Asp Asp Cys Thr Gly Asp Glu Asp Tyr Thr Tyr Leu Ile Leu Arg Val
            450                 455                 460
Ile Gly Asn Met Gly Gln Thr Met Glu Gln Leu Thr Pro Glu Leu Lys
465                 470                 475                 480
Ser Ser Ile Leu Lys Cys Val Gln Ser Thr Lys Pro Ser Leu Met Ile
                    485                 490                 495
Gln Lys Ala Ala Ile Gln Ala Leu Arg Lys Met Glu Pro Lys Asp Lys
                500                 505                 510
Asp Gln Glu Val Leu Leu Gln Thr Phe Leu Asp Asp Ala Ser Pro Gly
            515                 520                 525
Asp Lys Arg Leu Ala Ala Tyr Leu Met Leu Met Arg Ser Pro Ser Gln
            530                 535                 540
Ala Asp Ile Asn Lys Ile Val Gln Ile Leu Pro Trp Glu Gln Asn Glu
545                 550                 555                 560
Gln Val Lys Asn Phe Val Ala Ser His Ile Ala Asn Ile Leu Asn Ser
                    565                 570                 575
Glu Glu Leu Asp Ile Gln Asp Leu Lys Lys Leu Val Lys Glu Ala Leu
                580                 585                 590
Lys Glu Ser Gln Leu Pro Thr Val Met Asp Phe Arg Lys Phe Ser Arg
            595                 600                 605
Asn Tyr Gln Leu Tyr Lys Ser Val Ser Leu Pro Ser Leu Asp Pro Ala
            610                 615                 620
Ser Ala Lys Ile Glu Gly Asn Leu Ile Phe Asp Pro Asn Asn Tyr Leu
625                 630                 635                 640
Pro Lys Glu Ser Met Leu Lys Thr Thr Leu Thr Ala Phe Gly Phe Ala
                    645                 650                 655
Ser Ala Asp Leu Ile Glu Ile Gly Leu Glu Gly Lys Gly Phe Glu Pro
                660                 665                 670
```

```
Thr Leu Glu Ala Leu Phe Gly Lys Gln Gly Phe Phe Pro Asp Ser Val
            675                 680                 685

Asn Lys Ala Leu Tyr Trp Val Asn Gly Gln Val Pro Asp Gly Val Ser
        690                 695                 700

Lys Val Leu Val Asp His Phe Gly Tyr Thr Lys Asp Asp Lys His Glu
705                 710                 715                 720

Gln Asp Met Val Asn Gly Ile Met Leu Ser Val Glu Lys Leu Ile Lys
                725                 730                 735

Asp Leu Lys Ser Lys Glu Val Pro Glu Ala Arg Ala Tyr Leu Arg Ile
            740                 745                 750

Leu Gly Glu Glu Leu Gly Phe Ala Ser Leu His Asp Leu Gln Leu Leu
        755                 760                 765

Gly Lys Leu Leu Leu Met Gly Ala Arg Thr Leu Gln Gly Ile Pro Gln
    770                 775                 780

Met Ile Gly Glu Val Ile Arg Lys Gly Ser Lys Asn Asp Phe Phe Leu
785                 790                 795                 800

His Tyr Ile Phe Met Glu Asn Ala Phe Glu Leu Pro Thr Gly Ala Gly
                805                 810                 815

Leu Gln Leu Gln Ile Ser Ser Ser Gly Val Ile Ala Pro Gly Ala Lys
            820                 825                 830

Ala Gly Val Lys Leu Glu Val Ala Asn Met Gln Ala Glu Leu Val Ala
        835                 840                 845

Lys Pro Ser Val Ser Val Glu Phe Val Thr Asn Met Gly Ile Ile Ile
    850                 855                 860

Pro Asp Phe Ala Arg Ser Gly Val Gln Met Asn Thr Asn Phe Phe His
865                 870                 875                 880

Glu Ser Gly Leu Glu Ala His Val Ala Leu Lys Ala Gly Lys Leu Lys
                885                 890                 895

Phe Ile Ile Pro Ser Pro Lys Arg Pro Val Lys Leu Leu Ser Gly Gly
            900                 905                 910

Asn Thr Leu His Leu Val Ser Thr Thr Lys Thr Glu Val Ile Pro Pro
        915                 920                 925

Leu Ile Glu Asn Arg Gln Ser Trp Ser Val Cys Lys Gln Val Phe Pro
    930                 935                 940

Gly Leu Asn Tyr Cys Thr Ser Gly Ala Tyr Ser Asn Ala Ser Ser Thr
945                 950                 955                 960

Asp Ser Ala Ser Tyr Tyr Pro Leu Thr Gly Asp Thr Arg Leu Glu Leu
                965                 970                 975

Glu Leu Arg Pro Thr Gly Glu Ile Glu Gln Tyr Ser Val Ser Ala Thr
            980                 985                 990

Tyr Glu Leu Gln Arg Glu Asp Arg Ala Leu Val Asp Thr Leu Lys Phe
        995                 1000                1005

Val Thr Gln Ala Glu Gly Ala Lys Gln Thr Glu Ala Thr Met Thr Phe
    1010                1015                1020

Lys Tyr Asn Arg Gln Ser Met Thr Leu Ser Ser Glu Val Gln Ile Pro
1025                1030                1035                1040

Asp Phe Asp Val Asp Leu Gly Thr Ile Leu Arg Val Asn Asp Glu Ser
                1045                1050                1055

Thr Glu Gly Lys Thr Ser Tyr Arg Leu Thr Leu Asp Ile Gln Asn Lys
            1060                1065                1070

Lys Ile Thr Glu Val Ala Leu Met Gly His Leu Ser Cys Asp Thr Lys
        1075                1080                1085

Glu Glu Arg Lys Ile Lys Gly Val Ile Ser Ile Pro Arg Leu Gln Ala
```

-continued

```
            1090                1095               1100

Glu Ala Arg Ser Glu Ile Leu Ala His Trp Ser Pro Ala Lys Leu Leu
1105                1110                1115                1120

Leu Gln Met Asp Ser Ser Ala Thr Ala Tyr Gly Ser Thr Val Ser Lys
                1125                1130                1135

Arg Val Ala Trp His Tyr Asp Glu Glu Lys Ile Glu Phe Glu Trp Asn
            1140                1145                1150

Thr Gly Thr Asn Val Asp Thr Lys Lys Met Thr Ser Asn Phe Pro Val
                1155                1160                1165

Asp Leu Ser Asp Tyr Pro Lys Ser Leu His Met Tyr Ala Asn Arg Leu
            1170                1175                1180

Leu Asp His Arg Val Pro Glu Thr Asp Met Thr Phe Arg His Val Gly
1185                1190                1195                1200

Ser Lys Leu Ile Val Ala Met Ser Ser Trp Leu Gln Lys Ala Ser Gly
                1205                1210                1215

Ser Leu Pro Tyr Thr Gln Thr Leu Gln Asp His Leu Asn Ser Leu Lys
                1220                1225                1230

Glu Phe Asn Leu Gln Asn Met Gly Leu Pro Asp Phe His Ile Pro Glu
            1235                1240                1245

Asn Leu Phe Leu Lys Ser Asp Gly Arg Val Lys Tyr Thr Leu Asn Lys
            1250                1255                1260

Asn Ser Leu Lys Ile Glu Ile Pro Leu Pro Phe Gly Gly Lys Ser Ser
1265                1270                1275                1280

Arg Asp Leu Lys Met Leu Glu Thr Val Arg Thr Pro Ala Leu His Phe
                1285                1290                1295

Lys Ser Val Gly Phe His Leu Pro Ser Arg Glu Phe Gln Val Pro Thr
                1300                1305                1310

Phe Thr Ile Pro Lys Leu Tyr Gln Leu Gln Val Pro Leu Leu Gly Val
            1315                1320                1325

Leu Asp Leu Ser Thr Asn Val Tyr Ser Asn Leu Tyr Asn Trp Ser Ala
1330                1335                1340

Ser Tyr Ser Gly Gly Asn Thr Ser Thr Asp His Phe Ser Leu Arg Ala
1345                1350                1355                1360

Arg Tyr His Met Lys Ala Asp Ser Val Val Asp Leu Leu Ser Tyr Asn
                1365                1370                1375

Val Gln Gly Ser Gly Glu Thr Thr Tyr Asp His Lys Asn Thr Phe Thr
                1380                1385                1390

Leu Ser Cys Asp Gly Ser Leu Arg His Lys Phe Leu Asp Ser Asn Ile
            1395                1400                1405

Lys Phe Ser His Val Glu Lys Leu Gly Asn Asn Pro Val Ser Lys Gly
            1410                1415                1420

Leu Leu Ile Phe Asp Ala Ser Ser Ser Trp Gly Pro Gln Met Ser Ala
1425                1430                1435                1440

Ser Val His Leu Asp Ser Lys Lys Lys Gln His Leu Phe Val Lys Glu
                1445                1450                1455

Val Lys Ile Asp Gly Gln Phe Arg Val Ser Ser Phe Tyr Ala Lys Gly
            1460                1465                1470

Thr Tyr Gly Leu Ser Cys Gln Arg Asp Pro Asn Thr Gly Arg Leu Asn
            1475                1480                1485

Gly Glu Ser Asn Leu Arg Phe Asn Ser Ser Tyr Leu Gln Gly Thr Asn
            1490                1495                1500

Gln Ile Thr Gly Arg Tyr Glu Asp Gly Thr Leu Ser Leu Thr Ser Thr
1505                1510                1515                1520
```

-continued

```
Ser Asp Leu Gln Ser Gly Ile Ile Lys Asn Thr Ala Ser Leu Lys Tyr
            1525                1530                1535

Glu Asn Tyr Glu Leu Thr Leu Lys Ser Asp Thr Asn Gly Lys Tyr Lys
            1540                1545                1550

Asn Phe Ala Thr Ser Asn Lys Met Asp Met Thr Phe Ser Lys Gln Asn
            1555                1560                1565

Ala Leu Leu Arg Ser Glu Tyr Gln Ala Asp Tyr Glu Ser Leu Arg Phe
            1570                1575                1580

Phe Ser Leu Leu Ser Gly Ser Leu Asn Ser His Gly Leu Glu Leu Asn
1585                1590                1595                1600

Ala Asp Ile Leu Gly Thr Asp Lys Ile Asn Ser Gly Ala His Lys Ala
            1605                1610                1615

Thr Leu Arg Ile Gly Gln Asp Gly Ile Ser Thr Ser Ala Thr Thr Asn
            1620                1625                1630

Leu Lys Cys Ser Leu Leu Val Leu Glu Asn Glu Leu Asn Ala Glu Leu
            1635                1640                1645

Gly Leu Ser Gly Ala Ser Met Lys Leu Thr Thr Asn Gly Arg Phe Arg
            1650                1655                1660

Glu His Asn Ala Lys Phe Ser Leu Asp Gly Lys Ala Ala Leu Thr Glu
1665                1670                1675                1680

Leu Ser Leu Gly Ser Ala Tyr Gln Ala Met Ile Leu Gly Val Asp Ser
            1685                1690                1695

Lys Asn Ile Phe Asn Phe Lys Val Ser Gln Glu Gly Leu Lys Leu Ser
            1700                1705                1710

Asn Asp Met Met Gly Ser Tyr Ala Glu Met Lys Phe Asp His Thr Asn
            1715                1720                1725

Ser Leu Asn Ile Ala Gly Leu Ser Leu Asp Phe Ser Ser Lys Leu Asp
            1730                1735                1740

Asn Ile Tyr Ser Ser Asp Lys Phe Tyr Lys Gln Thr Val Asn Leu Gln
1745                1750                1755                1760

Leu Gln Pro Tyr Ser Leu Val Thr Thr Leu Asn Ser Asp Leu Lys Tyr
            1765                1770                1775

Asn Ala Leu Asp Leu Thr Asn Asn Gly Lys Leu Arg Leu Glu Pro Leu
            1780                1785                1790

Lys Leu His Val Ala Gly Asn Leu Lys Gly Ala Tyr Gln Asn Asn Glu
            1795                1800                1805

Ile Lys His Ile Tyr Ala Ile Ser Ser Ala Ala Leu Ser Ala Ser Tyr
            1810                1815                1820

Lys Ala Asp Thr Val Ala Lys Val Gln Gly Val Glu Phe Ser His Arg
1825                1830                1835                1840

Leu Asn Thr Asp Ile Ala Gly Leu Ala Ser Ala Ile Asp Met Ser Thr
            1845                1850                1855

Asn Tyr Asn Ser Asp Ser Leu His Phe Ser Asn Val Phe Arg Ser Val
            1860                1865                1870

Met Ala Pro Phe Thr Met Thr Ile Asp Ala His Thr Asn Gly Asn Gly
            1875                1880                1885

Lys Leu Ala Leu Trp Gly Glu His Thr Gly Gln Leu Tyr Ser Lys Phe
            1890                1895                1900

Leu Leu Lys Ala Glu Pro Leu Ala Phe Thr Phe Ser His Asp Tyr Lys
1905                1910                1915                1920

Gly Ser Thr Ser His His Leu Val Ser Arg Lys Ser Ile Ser Ala Ala
            1925                1930                1935
```

-continued

Leu Glu His Lys Val Ser Ala Leu Leu Thr Pro Ala Glu Gln Thr Gly
            1940                1945                1950

Thr Trp Lys Leu Lys Thr Gln Phe Asn Asn Asn Glu Tyr Ser Gln Asp
            1955                1960                1965

Leu Asp Ala Tyr Asn Thr Lys Asp Lys Ile Gly Val Glu Leu Thr Gly
            1970                1975                1980

Arg Thr Leu Ala Asp Leu Thr Leu Leu Asp Ser Pro Ile Lys Val Pro
1985                1990                1995                2000

Leu Leu Leu Ser Glu Pro Ile Asn Ile Ile Asp Ala Leu Glu Met Arg
            2005                2010                2015

Asp Ala Val Glu Lys Pro Gln Glu Phe Thr Ile Val Ala Phe Val Lys
            2020                2025                2030

Tyr Asp Lys Asn Gln Asp Val His Ser Ile Asn Leu Pro Phe Phe Glu
            2035                2040                2045

Thr Leu Gln Glu Tyr Phe Glu Arg Asn Arg Gln Thr Ile Ile Val Val
            2050                2055                2060

Val Glu Asn Val Gln Arg Asn Leu Lys His Ile Asn Ile Asp Gln Phe
2065                2070                2075                2080

Val Arg Lys Tyr Arg Ala Ala Leu Gly Lys Leu Pro Gln Gln Ala Asn
            2085                2090                2095

Asp Tyr Leu Asn Ser Phe Asn Trp Glu Arg Gln Val Ser His Ala Lys
            2100                2105                2110

Glu Lys Leu Thr Ala Leu Thr Lys Lys Tyr Arg Ile Thr Glu Asn Asp
            2115                2120                2125

Ile Gln Ile Ala Leu Asp Asp Ala Lys Ile Asn Phe Asn Glu Lys Leu
            2130                2135                2140

Ser Gln Leu Gln Thr Tyr Met Ile Gln Phe Asp Gln Tyr Ile Lys Asp
2145                2150                2155                2160

Ser Tyr Asp Leu His Asp Leu Lys Ile Ala Ile Ala Asn Ile Ile Asp
            2165                2170                2175

Glu Ile Ile Glu Lys Leu Lys Ser Leu Asp Glu His Tyr His Ile Arg
            2180                2185                2190

Val Asn Leu Val Lys Thr Ile His Asp Leu His Leu Phe Ile Glu Asn
            2195                2200                2205

Ile Asp Phe Asn Lys Ser Gly Ser Ser Thr Ala Ser Trp Ile Gln Asn
            2210                2215                2220

Val Asp Thr Lys Tyr Gln Ile Arg Ile Gln Ile Gln Glu Lys Leu Gln
2225                2230                2235                2240

Gln Leu Lys Arg His Ile Gln Asn Ile Asp Ile Gln His Leu Ala Gly
            2245                2250                2255

Lys Leu Lys Gln His Ile Glu Ala Ile Asp Val Arg Val Leu Leu Asp
            2260                2265                2270

Gln Leu Gly Thr Thr Ile Ser Phe Glu Arg Ile Asn Asp Val Leu Glu
            2275                2280                2285

His Val Lys His Phe Val Ile Asn Leu Ile Gly Asp Phe Glu Val Ala
            2290                2295                2300

Glu Lys Ile Asn Ala Phe Arg Ala Lys Val His Glu Leu Ile Glu Arg
2305                2310                2315                2320

Tyr Glu Val Asp Gln Gln Ile Gln Val Leu Met Asp Lys Leu Val Glu
            2325                2330                2335

Leu Thr His Gln Tyr Lys Leu Lys Glu Thr Ile Gln Lys Leu Ser Asn
            2340                2345                2350

Val Leu Gln Gln Val Lys Ile Lys Asp Tyr Phe Glu Lys Leu Val Gly

```
                    2355                2360                 2365
Phe Ile Asp Asp Ala Val Lys Lys Leu Asn Glu Leu Ser Phe Lys Thr
2370                2375                2380

Phe Ile Glu Asp Val Asn Lys Phe Leu Asp Met Leu Ile Lys Lys Leu
2385                2390                2395                 2400

Lys Ser Phe Asp Tyr His Gln Phe Val Asp Glu Thr Asn Asp Lys Ile
                2405                2410                2415

Arg Glu Val Thr Gln Arg Leu Asn Gly Glu Ile Gln Ala Leu Glu Leu
                2420                2425                2430

Pro Gln Lys Ala Glu Ala Leu Lys Leu Phe Leu Glu Thr Lys Ala
                2435                2440                2445

Thr Val Ala Val Tyr Leu Glu Ser Leu Gln Asp Thr Lys Ile Thr Leu
                2450                2455                2460

Ile Ile Asn Trp Leu Gln Glu Ala Leu Ser Ser Ala Ser Leu Ala His
2465                2470                2475                 2480

Met Lys Ala Lys Phe Arg Glu Thr Leu Glu Asp Thr Arg Asp Arg Met
                2485                2490                2495

Tyr Asp Met Asp Ile Gln Gln Glu Leu Gln Arg Tyr Leu Ser Leu Val
                2500                2505                2510

Gly Gln Val Tyr Ser Thr Leu Val Thr Tyr Ile Ser Asp Trp Trp Thr
                2515                2520                2525

Leu Ala Ala Lys Asn Leu Thr Asp Phe Ala Glu Gln Tyr Ser Ile Gln
                2530                2535                2540

Asp Trp Ala Lys Arg Met Lys Ala Leu Val Glu Gln Gly Phe Thr Val
2545                2550                2555                 2560

Pro Glu Ile Lys Thr Ile Leu Gly Thr Met Pro Ala Phe Glu Val Ser
                2565                2570                2575

Leu Gln Ala Leu Gln Lys Ala Thr Phe Gln Thr Pro Asp Phe Ile Val
                2580                2585                2590

Pro Leu Thr Asp Leu Arg Ile Pro Ser Val Gln Ile Asn Phe Lys Asp
                2595                2600                2605

Leu Lys Asn Ile Lys Ile Pro Ser Arg Phe Ser Thr Pro Glu Phe Thr
                2610                2615                2620

Ile Leu Asn Thr Phe His Ile Pro Ser Phe Thr Ile Asp Phe Val Glu
2625                2630                2635                 2640

Met Lys Val Lys Ile Ile Arg Thr Ile Asp Gln Met Gln Asn Ser Glu
                2645                2650                2655

Leu Gln Trp Pro Val Pro Asp Ile Tyr Leu Arg Asp Leu Lys Val Glu
                2660                2665                2670

Asp Ile Pro Leu Ala Arg Ile Thr Leu Pro Asp Phe Arg Leu Pro Glu
                2675                2680                2685

Ile Ala Ile Pro Glu Phe Ile Ile Pro Thr Leu Asn Leu Asn Asp Phe
                2690                2695                2700

Gln Val Pro Asp Leu His Ile Pro Glu Phe Gln Leu Pro His Ile Ser
2705                2710                2715                 2720

His Thr Ile Glu Val Pro Thr Phe Gly Lys Leu Tyr Ser Ile Leu Lys
                2725                2730                2735

Ile Gln Ser Pro Leu Phe Thr Leu Asp Ala Asn Ala Asp Ile Gly Asn
                2740                2745                2750

Gly Thr Thr Ser Ala Asn Glu Ala Gly Ile Ala Ala Ser Ile Thr Ala
                2755                2760                2765

Lys Gly Glu Ser Lys Leu Glu Val Leu Asn Phe Asp Phe Gln Ala Asn
                2770                2775                2780
```

```
Ala Gln Leu Ser Asn Pro Lys Ile Asn Pro Leu Ala Leu Lys Glu Ser
2785                2790                2795                2800

Val Lys Phe Ser Ser Lys Tyr Leu Arg Thr Glu His Gly Ser Glu Met
            2805                2810                2815

Leu Phe Phe Gly Asn Ala Ile Glu Gly Lys Ser Asn Thr Val Ala Ser
        2820                2825                2830

Leu His Thr Glu Lys Asn Thr Leu Glu Leu Ser Asn Gly Val Ile Val
            2835                2840                2845

Lys Ile Asn Asn Gln Leu Thr Leu Asp Ser Asn Thr Lys Tyr Phe His
2850                2855                2860

Lys Leu Asn Ile Pro Lys Leu Asp Phe Ser Ser Gln Ala Asp Leu Arg
2865                2870                2875                2880

Asn Glu Ile Lys Thr Leu Leu Lys Ala Gly His Ile Ala Trp Thr Ser
                2885                2890                2895

Ser Gly Lys Gly Ser Trp Lys Trp Ala Cys Pro Arg Phe Ser Asp Glu
            2900                2905                2910

Gly Thr His Glu Ser Gln Ile Ser Phe Thr Ile Glu Gly Pro Leu Thr
            2915                2920                2925

Ser Phe Gly Leu Ser Asn Lys Ile Asn Ser Lys His Leu Arg Val Asn
    2930                2935                2940

Gln Asn Leu Val Tyr Glu Ser Gly Ser Leu Asn Phe Ser Lys Leu Glu
2945                2950                2955                2960

Ile Gln Ser Gln Val Asp Ser Gln His Val Gly His Ser Val Leu Thr
                2965                2970                2975

Ala Lys Gly Met Ala Leu Phe Gly Glu Gly Lys Ala Glu Phe Thr Gly
            2980                2985                2990

Arg His Asp Ala His Leu Asn Gly Lys Val Ile Gly Thr Leu Lys Asn
            2995                3000                3005

Ser Leu Phe Phe Ser Ala Gln Pro Phe Glu Ile Thr Ala Ser Thr Asn
        3010                3015                3020

Asn Glu Gly Asn Leu Lys Val Arg Phe Pro Leu Arg Leu Thr Gly Lys
3025                3030                3035                3040

Ile Asp Phe Leu Asn Asn Tyr Ala Leu Phe Leu Ser Pro Ser Ala Gln
            3045                3050                3055

Gln Ala Ser Trp Gln Val Ser Ala Arg Phe Asn Gln Tyr Lys Tyr Asn
            3060                3065                3070

Gln Asn Phe Ser Ala Gly Asn Asn Glu Asn Ile Met Glu Ala His Val
            3075                3080                3085

Gly Ile Asn Gly Glu Ala Asn Leu Asp Phe Leu Asn Ile Pro Leu Thr
        3090                3095                3100

Ile Pro Glu Met Arg Leu Pro Tyr Thr Ile Ile Thr Thr Pro Pro Leu
3105                3110                3115                3120

Lys Asp Phe Ser Leu Trp Glu Lys Thr Gly Leu Lys Glu Phe Leu Lys
            3125                3130                3135

Thr Thr Lys Gln Ser Phe Asp Leu Ser Val Lys Ala Gln Tyr Lys Lys
            3140                3145                3150

Asn Lys His Arg His Ser Ile Thr Asn Pro Leu Ala Val Leu Cys Glu
            3155                3160                3165

Phe Ile Ser Gln Ser Ile Lys Ser Phe Asp Arg His Phe Glu Lys Asn
        3170                3175                3180

Arg Asn Asn Ala Leu Asp Phe Val Thr Lys Ser Tyr Asn Glu Thr Lys
3185                3190                3195                3200
```

-continued

Ile Lys Phe Asp Lys Tyr Lys Ala Glu Lys Ser His Asp Glu Leu Pro
            3205                3210                3215

Arg Thr Phe Gln Ile Pro Gly Tyr Thr Val Pro Val Asn Val Glu
            3220                3225            3230

Val Ser Pro Phe Thr Ile Glu Met Ser Ala Phe Gly Tyr Val Phe Pro
            3235                3240            3245

Lys Ala Val Ser Met Pro Ser Phe Ser Ile Leu Gly Ser Asp Val Arg
            3250                3255            3260

Val Pro Ser Tyr Thr Leu Ile Leu Pro Ser Leu Glu Leu Pro Val Leu
3265            3270            3275            3280

His Val Pro Arg Asn Leu Lys Leu Ser Leu Pro His Phe Lys Glu Leu
            3285                3290            3295

Cys Thr Ile Ser His Ile Phe Ile Pro Ala Met Gly Asn Ile Thr Tyr
            3300                3305            3310

Asp Phe Ser Phe Lys Ser Ser Val Ile Thr Leu Asn Thr Asn Ala Glu
            3315                3320            3325

Leu Phe Asn Gln Ser Asp Ile Val Ala His Leu Leu Ser Ser Ser Ser
            3330                3335            3340

Ser Val Ile Asp Ala Leu Gln Tyr Lys Leu Glu Gly Thr Thr Arg Leu
3345            3350            3355            3360

Thr Arg Lys Arg Gly Leu Lys Leu Ala Thr Ala Leu Ser Leu Ser Asn
            3365                3370            3375

Lys Phe Val Glu Gly Ser His Asn Ser Thr Val Ser Leu Thr Thr Lys
            3380                3385            3390

Asn Met Glu Val Ser Val Ala Lys Thr Thr Lys Ala Glu Ile Pro Ile
            3395                3400            3405

Leu Arg Met Asn Phe Lys Gln Glu Leu Asn Gly Asn Thr Lys Ser Lys
            3410                3415            3420

Pro Thr Val Ser Ser Met Glu Phe Lys Tyr Asp Phe Asn Ser Ser
3425            3430            3435            3440

Met Leu Tyr Ser Thr Ala Lys Gly Ala Val Asp His Lys Leu Ser Leu
            3445                3450            3455

Glu Ser Leu Thr Ser Tyr Phe Ser Ile Glu Ser Ser Thr Lys Gly Asp
            3460                3465            3470

Val Lys Gly Ser Val Leu Ser Arg Glu Tyr Ser Gly Thr Ile Ala Ser
            3475                3480            3485

Glu Ala Asn Thr Tyr Leu Asn Ser Lys Ser Thr Arg Ser Ser Val Lys
            3490                3495            3500

Leu Gln Gly Thr Ser Lys Ile Asp Asp Ile Trp Asn Leu Glu Val Lys
3505            3510            3515            3520

Glu Asn Phe Ala Gly Glu Ala Thr Leu Gln Arg Ile Tyr Ser Leu Trp
            3525                3530            3535

Glu His Ser Thr Lys Asn His Leu Gln Leu Glu Gly Leu Phe Phe Thr
            3540                3545            3550

Asn Gly Glu His Thr Ser Lys Ala Thr Leu Glu Leu Ser Pro Trp Gln
            3555                3560            3565

Met Ser Ala Leu Val Gln Val His Ala Ser Gln Pro Ser Ser Phe His
            3570                3575            3580

Asp Phe Pro Asp Leu Gly Gln Glu Val Ala Leu Asn Ala Asn Thr Lys
3585            3590            3595            3600

Asn Gln Lys Ile Arg Trp Lys Asn Glu Val Arg Ile His Ser Gly Ser
            3605                3610            3615

Phe Gln Ser Gln Val Glu Leu Ser Asn Asp Gln Glu Lys Ala His Leu

-continued

```
                3620                3625                3630
Asp Ile Ala Gly Ser Leu Glu Gly His Leu Arg Phe Leu Lys Asn Ile
                3635                3640                3645
Ile Leu Pro Val Tyr Asp Lys Ser Leu Trp Asp Phe Leu Lys Leu Asp
                3650                3655                3660
Val Thr Thr Ser Ile Gly Arg Arg Gln His Leu Arg Val Ser Thr Ala
3665                3670                3675                3680
Phe Val Tyr Thr Lys Asn Pro Asn Gly Tyr Ser Phe Ser Ile Pro Val
                3685                3690                3695
Lys Val Leu Ala Asp Lys Phe Ile Thr Pro Gly Leu Lys Leu Asn Asp
                3700                3705                3710
Leu Asn Ser Val Leu Val Met Pro Thr Phe His Val Pro Phe Thr Asp
                3715                3720                3725
Leu Gln Val Pro Ser Cys Lys Leu Asp Phe Arg Glu Ile Gln Ile Tyr
                3730                3735                3740
Lys Lys Leu Arg Thr Ser Ser Phe Ala Leu Asn Leu Pro Thr Leu Pro
3745                3750                3755                3760
Glu Val Lys Phe Pro Glu Val Asp Val Leu Thr Lys Tyr Ser Gln Pro
                3765                3770                3775
Glu Asp Ser Leu Ile Pro Phe Phe Glu Ile Thr Val Pro Glu Ser Gln
                3780                3785                3790
Leu Thr Val Ser Gln Phe Thr Leu Pro Lys Ser Val Ser Asp Gly Ile
                3795                3800                3805
Ala Ala Leu Asp Leu Asn Ala Val Ala Asn Lys Ile Ala Asp Phe Glu
                3810                3815                3820
Leu Pro Thr Ile Ile Val Pro Glu Gln Thr Ile Glu Ile Pro Ser Ile
3825                3830                3835                3840
Lys Phe Ser Val Pro Ala Gly Ile Val Ile Pro Ser Phe Gln Ala Leu
                3845                3850                3855
Thr Ala Arg Phe Glu Val Asp Ser Pro Val Tyr Asn Ala Thr Trp Ser
                3860                3865                3870
Ala Ser Leu Lys Asn Lys Ala Asp Tyr Val Glu Thr Val Leu Asp Ser
                3875                3880                3885
Thr Cys Ser Ser Thr Val Gln Phe Leu Glu Tyr Glu Leu Asn Val Leu
                3890                3895                3900
Gly Thr His Lys Ile Glu Asp Gly Thr Leu Ala Ser Lys Thr Lys Gly
3905                3910                3915                3920
Thr Leu Ala His Arg Asp Phe Ser Ala Glu Tyr Glu Glu Asp Gly Lys
                3925                3930                3935
Phe Glu Gly Leu Gln Glu Trp Glu Gly Lys Ala His Leu Asn Ile Lys
                3940                3945                3950
Ser Pro Ala Phe Thr Asp Leu His Leu Arg Tyr Gln Lys Asp Lys Lys
                3955                3960                3965
Gly Ile Ser Thr Ser Ala Ala Ser Pro Ala Val Gly Thr Val Gly Met
                3970                3975                3980
Asp Met Asp Glu Asp Asp Asp Phe Ser Lys Trp Asn Phe Tyr Tyr Ser
3985                3990                3995                4000
Pro Gln Ser Ser Pro Asp Lys Lys Leu Thr Ile Phe Lys Thr Glu Leu
                4005                4010                4015
Arg Val Arg Glu Ser Asp Glu Glu Thr Gln Ile Lys Val Asn Trp Glu
                4020                4025                4030
Glu Glu Ala Ala Ser Gly Leu Leu Thr Ser Leu Lys Asp Asn Val Pro
                4035                4040                4045
```

```
-continued

Lys Ala Thr Gly Val Leu Tyr Asp Tyr Val Asn Lys Tyr His Trp Glu
    4050            4055            4060

His Thr Gly Leu Thr Leu Arg Glu Val Ser Ser Lys Leu Arg Arg Asn
4065            4070            4075            4080

Leu Gln Asn Asn Ala Glu Trp Val Tyr Gln Gly Ala Ile Arg Gln Ile
        4085            4090            4095

Asp Asp Ile Asp Val Arg Phe Gln Lys Ala Ala Ser Gly Thr Thr Gly
            4100            4105            4110

Thr Tyr Gln Glu Trp Lys Asp Lys Ala Gln Asn Leu Tyr Gln Glu Leu
        4115            4120            4125

Leu Thr Gln Glu Gly Gln Ala Ser Phe Gln Gly Leu Lys Asp Asn Val
        4130            4135            4140

Phe Asp Gly Leu Val Arg Val Thr Gln Lys Phe His Met Lys Val Lys
4145            4150            4155            4160

His Leu Ile Asp Ser Leu Ile Asp Phe Leu Asn Phe Pro Arg Phe Gln
            4165            4170            4175

Phe Pro Gly Lys Pro Gly Ile Tyr Thr Arg Glu Glu Leu Cys Thr Met
            4180            4185            4190

Phe Ile Arg Glu Val Gly Thr Val Leu Ser Gln Val Tyr Ser Lys Val
            4195            4200            4205

His Asn Gly Ser Glu Ile Leu Phe Ser Tyr Phe Gln Asp Leu Val Ile
        4210            4215            4220

Thr Leu Pro Phe Glu Leu Arg Lys His Lys Leu Ile Asp Val Ile Ser
4225            4230            4235            4240

Met Tyr Arg Glu Leu Leu Lys Asp Leu Ser Lys Glu Ala Gln Glu Val
            4245            4250            4255

Phe Lys Ala Ile Gln Ser Leu Lys Thr Thr Glu Val Leu Arg Asn Leu
        4260            4265            4270

Gln Asp Leu Leu Gln Phe Ile Phe Gln Leu Ile Glu Asp Asn Ile Lys
        4275            4280            4285

Gln Leu Lys Glu Met Lys Phe Thr Tyr Leu Ile Asn Tyr Ile Gln Asp
        4290            4295            4300

Glu Ile Asn Thr Ile Phe Asn Asp Tyr Ile Pro Tyr Val Phe Lys Leu
4305            4310            4315            4320

Leu Lys Glu Asn Leu Cys Leu Asn Leu His Lys Phe Asn Glu Phe Ile
            4325            4330            4335

Gln Asn Glu Leu Gln Glu Ala Ser Gln Glu Leu Gln Gln Ile His Gln
        4340            4345            4350

Tyr Ile Met Ala Leu Arg Glu Glu Tyr Phe Asp Pro Ser Ile Val Gly
        4355            4360            4365

Trp Thr Val Lys Tyr Tyr Glu Leu Glu Glu Lys Ile Val Ser Leu Ile
    4370            4375            4380

Lys Asn Leu Leu Val Ala Leu Lys Asp Phe His Ser Glu Tyr Ile Val
4385            4390            4395            4400

Ser Ala Ser Asn Phe Thr Ser Gln Leu Ser Ser Gln Val Glu Gln Phe
            4405            4410            4415

Leu His Arg Asn Ile Gln Glu Tyr Leu Ser Ile Leu Thr Asp Pro Asp
            4420            4425            4430

Gly Lys Gly Lys Glu Lys Ile Ala Glu Leu Ser Ala Thr Ala Gln Glu
        4435            4440            4445

Ile Ile Lys Ser Gln Ala Ile Ala Thr Lys Lys Ile Ile Ser Asp Tyr
        4450            4455            4460
```

```
His Gln Gln Phe Arg Tyr Lys Leu Gln Asp Phe Ser Asp Gln Leu Ser
4465                4470                4475                4480

Asp Tyr Tyr Glu Lys Phe Ile Ala Glu Ser Lys Arg Leu Ile Asp Leu
                4485                4490                4495

Ser Ile Gln Asn Tyr His Thr Phe Leu Ile Tyr Ile Thr Glu Leu Leu
                4500                4505                4510

Lys Lys Leu Gln Ser Thr Thr Val Met Asn Pro Tyr Met Lys Leu Ala
            4515                4520                4525

Pro Gly Glu Leu Thr Ile Ile Leu
            4530                4535
```

(2) INFORMATION FOR SEQ ID NO:2:

(i) SEQUENCE CHARACTERISTICS:
        (A) LENGTH: 3 amino acids
        (B) TYPE: amino acid
        (C) STRANDEDNESS:
        (D) TOPOLOGY: linear (xi) SEQUENCE DESCRIPTION: SEQ ID NO:2:

```
Pro Xaa Pro
1
```

(2) INFORMATION FOR SEQ ID NO:3:

(i) SEQUENCE CHARACTERISTICS:
        (A) LENGTH: 46 amino acids
        (B) TYPE: amino acid
        (C) STRANDEDNESS:
        (D) TOPOLOGY: linear (xi) SEQUENCE DESCRIPTION: SEQ ID NO:3:

```
Lys Tyr Thr Tyr Asn Tyr Glu Ala Glu Ser Ser Ser Gly Val Pro Gly
1               5                   10                  15

Thr Ala Asp Ser Arg Ser Ala Thr Arg Ile Asn Cys Lys Val Glu Leu
                20                  25                  30

Glu Val Pro Gln Leu Cys Ser Phe Ile Leu Lys Thr Ser Gln
            35                  40                  45
```

(2) INFORMATION FOR SEQ ID NO:4:

(i) SEQUENCE CHARACTERISTICS:
        (A) LENGTH: 45 amino acids
        (B) TYPE: amino acid
        (C) STRANDEDNESS:
        (D) TOPOLOGY: linear (xi) SEQUENCE DESCRIPTION: SEQ ID NO:4:

```
Ala Tyr Asp Phe Asn Tyr Pro Ile Lys Lys Asp Ser Ser Ser Gln Leu
1               5                   10                  15

Leu Ser Val Gln Gln Gly Glu Thr Ile Tyr Ile Leu Asn Lys Asn Ser
                20                  25                  30

Ser Gly Trp Trp Asp Gly Leu Val Ile Asp Asp Ser Asn
            35                  40                  45
```

(2) INFORMATION FOR SEQ ID NO:5:

(i) SEQUENCE CHARACTERISTICS:
        (A) LENGTH: 45 amino acids
        (B) TYPE: amino acid
        (C) STRANDEDNESS:
        (D) TOPOLOGY: linear (xi) SEQUENCE DESCRIPTION: SEQ ID NO:5:

```
Val Tyr Gly Phe Asn Pro Glu Gly Lys Ala Leu Leu Lys Lys Thr Lys
1               5                   10                  15

Asn Ser Glu Glu Phe Ala Ala Ala Met Ser Arg Tyr Glu Leu Lys Leu
            20                  25                  30

Ala Ile Pro Glu Gly Lys Gln Val Phe Leu Tyr Pro Glu
        35                  40                  45
```

(2) INFORMATION FOR SEQ ID NO:6:

(i) SEQUENCE CHARACTERISTICS:
        (A) LENGTH: 47 amino acids
        (B) TYPE: amino acid
        (C) STRANDEDNESS:
        (D) TOPOLOGY: linear (xi) SEQUENCE DESCRIPTION: SEQ ID NO:6:

```
Leu Tyr Asp Phe Val Ala Ser Gly Asp Asn Thr Leu Ser Ile Thr Lys
1               5                   10                  15

Gly Glu Lys Leu Arg Val Leu Gly Tyr Asn His Tyr Asn Gly Glu Trp
            20                  25                  30

Cys Glu Ala Gln Thr Lys Asn Gly Gln Gly Trp Val Pro Ser Asn
        35                  40                  45
```

(2) INFORMATION FOR SEQ ID NO:7:

(i) SEQUENCE CHARACTERISTICS:
        (A) LENGTH: 44 amino acids
        (B) TYPE: amino acid
        (C) STRANDEDNESS:
        (D) TOPOLOGY: linear (xi) SEQUENCE DESCRIPTION: SEQ ID NO:7:

```
Phe Leu Pro Phe Ser Tyr Asn Asn Lys Tyr Gly Met Val Ala Gln Val
1               5                   10                  15

Thr Gln Thr Leu Lys Leu Glu Asp Thr Pro Lys Ile Asn Ser Arg Phe
            20                  25                  30

Phe Gly Glu Gly Thr Lys Lys Met Gly Leu Ala Phe
        35                  40
```

(2) INFORMATION FOR SEQ ID NO:8:

(i) SEQUENCE CHARACTERISTICS:
        (A) LENGTH: 43 amino acids
        (B) TYPE: amino acid
        (C) STRANDEDNESS:
        (D) TOPOLOGY: linear (xi) SEQUENCE DESCRIPTION: SEQ ID NO:8:

```
Leu Phe Asp Tyr Lys Ala Gln Arg Glu Asp Glu Leu Thr Phe Thr Lys
1               5                   10                  15

Ser Ala Ile Ile Gln Asn Val Glu Lys Gln Glu Gly Gly Trp Trp Arg
            20                  25                  30

Gly Asp Tyr Gly Gly Lys Lys Gln Leu Trp Phe
        35                  40
```

(2) INFORMATION FOR SEQ ID NO:9:

(i) SEQUENCE CHARACTERISTICS:
        (A) LENGTH: 45 amino acids
        (B) TYPE: amino acid
        (C) STRANDEDNESS:
        (D) TOPOLOGY: linear (xi) SEQUENCE DESCRIPTION: SEQ ID NO:9:

Phe Leu Pro Phe Ser Tyr Asn Asn Lys Tyr Gly Met Val Ala Gln Val
1               5                   10                  15

Thr Gln Thr Leu Lys Leu Glu Asp Thr Pro Lys Ile Asn Ser Arg Phe
                20                  25                  30

Phe Gly Glu Gly Thr Lys Lys Met Gly Leu Ala Phe Glu
            35                  40                  45

(2) INFORMATION FOR SEQ ID NO:10:

(i) SEQUENCE CHARACTERISTICS:
        (A) LENGTH: 46 amino acids
        (B) TYPE: amino acid
        (C) STRANDEDNESS:
        (D) TOPOLOGY: linear (xi) SEQUENCE DESCRIPTION: SEQ ID NO:10:

Leu His Ser Tyr Glu Pro Ser His Asp Gly Asp Leu Gly Phe Glu Lys
1               5                   10                  15

Gly Glu Gln Leu Arg Ile Leu Glu Gln Ser Gly Glu Trp Trp Lys Ala
                20                  25                  30

Gln Ser Leu Thr Thr Gly Gln Glu Gly Phe Ile Pro Phe Asn
            35                  40                  45

(2) INFORMATION FOR SEQ ID NO:11:

(i) SEQUENCE CHARACTERISTICS:
        (A) LENGTH: 62 amino acids
        (B) TYPE: amino acid
        (C) STRANDEDNESS:
        (D) TOPOLOGY: linear (xi) SEQUENCE DESCRIPTION: SEQ ID NO:11:

Tyr Thr Tyr Leu Ile Leu Arg Val Ile Gly Asn Met Gly Gln Thr Met
1               5                   10                  15

Glu Gln Leu Thr Pro Glu Leu Lys Ser Ser Ile Leu Lys Cys Val Gln
                20                  25                  30

Ser Thr Lys Pro Ser Leu Met Ile Gln Lys Ala Ala Ile Gln Ala Leu
            35                  40                  45

Arg Lys Met Glu Pro Lys Asp Lys Asp Gln Glu Val Leu Leu
50                  55                  60

(2) INFORMATION FOR SEQ ID NO:12:

(i) SEQUENCE CHARACTERISTICS:
        (A) LENGTH: 53 amino acids
        (B) TYPE: amino acid
        (C) STRANDEDNESS:
        (D) TOPOLOGY: linear (xi) SEQUENCE DESCRIPTION: SEQ ID NO:12:

Val Val Ala Leu Phe Asp Tyr Ala Ala Val Asn Asp Arg Asp Leu Gln
1               5                   10                  15

Val Leu Lys Gly Glu Lys Leu Gln Val Leu Arg Ser Thr Gly Asp Trp
                20                  25                  30

Trp Leu Ala Arg Ser Leu Val Thr Gly Arg Glu Gly Tyr Val Pro Ser
            35                  40                  45

Asn Phe Val Ala Pro
50

(2) INFORMATION FOR SEQ ID NO:13:

(i) SEQUENCE CHARACTERISTICS:
            (A) LENGTH: 50 amino acids
            (B) TYPE: amino acid
            (C) STRANDEDNESS:
            (D) TOPOLOGY: linear (xi) SEQUENCE DESCRIPTION: SEQ ID NO:13:

Ala Phe Gly Phe Ala Ser Ala Asp Leu Ile Glu Ile Gly Leu Glu Gly
1               5                   10                  15

Lys Gly Phe Glu Pro Thr Leu Glu Ala Leu Phe Gly Lys Gln Gly Phe
            20                  25                  30

Phe Pro Asp Ser Val Asn Lys Ala Leu Tyr Trp Val Asn Gly Gln Val
        35                  40                  45

Pro Asp
    50

(2) INFORMATION FOR SEQ ID NO:14:

(i) SEQUENCE CHARACTERISTICS:
            (A) LENGTH: 48 amino acids
            (B) TYPE: amino acid
            (C) STRANDEDNESS:
            (D) TOPOLOGY: linear (xi) SEQUENCE DESCRIPTION: SEQ ID NO:14:

Leu Tyr Asp Phe Ala Ala Glu Asn Pro Asp Glu Leu Thr Phe Asn Glu
1               5                   10                  15

Gly Ala Val Val Thr Val Ile Asn Lys Ser Asn Pro Asp Trp Trp Glu
            20                  25                  30

Gly Glu Leu Asn Gly Gln Arg Gly Val Phe Pro Ala Ser Tyr Val Glu
        35                  40                  45

(2) INFORMATION FOR SEQ ID NO:15:

(i) SEQUENCE CHARACTERISTICS:
            (A) LENGTH: 46 amino acids
            (B) TYPE: amino acid
            (C) STRANDEDNESS:
            (D) TOPOLOGY: linear (xi) SEQUENCE DESCRIPTION: SEQ ID NO:15:

Phe Gly Tyr Thr Lys Asp Asp Lys His Glu Gln Asp Met Val Asn Gly
1               5                   10                  15

Ile Met Leu Ser Val Glu Lys Leu Ile Lys Asp Leu Lys Ser Lys Glu
            20                  25                  30

Val Pro Glu Ala Arg Ala Tyr Leu Arg Ile Leu Gly Glu Glu
        35                  40                  45

(2) INFORMATION FOR SEQ ID NO:16:

(i) SEQUENCE CHARACTERISTICS:
            (A) LENGTH: 49 amino acids
            (B) TYPE: amino acid
            (C) STRANDEDNESS:
            (D) TOPOLOGY: linear (xi) SEQUENCE DESCRIPTION: SEQ ID NO:16:

Tyr Asp Tyr Lys Lys Glu Glu Glu Asp Ile Asp Leu His Leu Gly Asp
1               5                   10                  15

Ile Leu Thr Val Asn Lys Gly Ser Leu Val Ala Leu Gly Phe Ser Asp
            20                  25                  30

Gly Gln Glu Ala Lys Pro Glu Glu Ile Gly Trp Leu Asn Gly Tyr Asn

Glu (2) INFORMATION FOR SEQ ID NO:17:

(i) SEQUENCE CHARACTERISTICS:
        (A) LENGTH: 52 amino acids
        (B) TYPE: amino acid
        (C) STRANDEDNESS:
        (D) TOPOLOGY: linear (xi) SEQUENCE DESCRIPTION: SEQ ID NO:17:

```
Phe Asp Tyr His Gln Phe Val Asp Glu Thr Asn Asp Lys Ile Arg Glu
 1               5                  10                  15

Val Thr Gln Arg Leu Asn Gly Glu Ile Gln Ala Leu Glu Leu Pro Gln
                20                  25                  30

Lys Ala Glu Ala Leu Lys Leu Phe Leu Glu Thr Lys Ala Thr Val
            35                  40                  45

Ala Val Tyr Leu
        50
```

(2) INFORMATION FOR SEQ ID NO:18:

(i) SEQUENCE CHARACTERISTICS:
        (A) LENGTH: 46 amino acids
        (B) TYPE: amino acid
        (C) STRANDEDNESS:
        (D) TOPOLOGY: linear (xi) SEQUENCE DESCRIPTION: SEQ ID NO:18:

```
Tyr Asp Tyr Gln Glu Lys Ser Pro Arg Glu Val Thr Met Lys Lys Gly
 1               5                  10                  15

Asp Ile Leu Thr Leu Leu Asn Ser Thr Asn Lys Asp Trp Trp Lys Val
                20                  25                  30

Glu Val Asn Asp Arg Gln Gly Phe Val Pro Ala Ala Tyr Val
            35                  40                  45
```

(2) INFORMATION FOR SEQ ID NO:19:

(i) SEQUENCE CHARACTERISTICS:
        (A) LENGTH: 51 amino acids
        (B) TYPE: amino acid
        (C) STRANDEDNESS:
        (D) TOPOLOGY: linear (xi) SEQUENCE DESCRIPTION: SEQ ID NO:19:

```
Tyr Asp Met Asp Ile Gln Gln Glu Leu Gln Arg Tyr Leu Ser Leu Val
 1               5                  10                  15

Gly Gln Val Tyr Ser Thr Leu Val Thr Tyr Ile Ser Asp Trp Trp Thr
                20                  25                  30

Leu Ala Ala Lys Asn Leu Thr Asp Phe Ala Glu Gln Tyr Ser Ile Gln
            35                  40                  45

Asp Trp Ala
        50
```

(2) INFORMATION FOR SEQ ID NO:20:

(i) SEQUENCE CHARACTERISTICS:
        (A) LENGTH: 51 amino acids
        (B) TYPE: amino acid
        (C) STRANDEDNESS:
        (D) TOPOLOGY: linear (xi) SEQUENCE DESCRIPTION: SEQ ID NO:20:

Phe Asp Tyr Lys Ala Gln Arg Glu Asp Glu Leu Thr Phe Thr Lys Ser
1               5                   10                  15

Ala Ile Ile Gln Asn Val Glu Lys Gln Asp Gly Gly Trp Trp Arg Gly
            20                  25                  30

Asp Tyr Gly Gly Lys Lys Gln Leu Trp Phe Pro Ser Asn Tyr Val Glu
        35                  40                  45

Glu Met Ile
50

(2) INFORMATION FOR SEQ ID NO:21:

(i) SEQUENCE CHARACTERISTICS:
        (A) LENGTH: 55 amino acids
        (B) TYPE: amino acid
        (C) STRANDEDNESS:
        (D) TOPOLOGY: linear (xi) SEQUENCE DESCRIPTION: SEQ ID NO:21:

Tyr Asp Met Asp Ile Gln Gln Glu Leu Gln Arg Tyr Leu Ser Leu Val
1               5                   10                  15

Gly Gln Val Tyr Ser Thr Leu Val Thr Tyr Ile Ser Asp Trp Trp Thr
            20                  25                  30

Leu Ala Ala Lys Asn Leu Thr Asp Phe Ala Glu Gln Tyr Ser Ile Gln
        35                  40                  45

Asp Trp Ala Lys Arg Met Lys
    50                  55

(2) INFORMATION FOR SEQ ID NO:22:

(i) SEQUENCE CHARACTERISTICS:
        (A) LENGTH: 53 amino acids
        (B) TYPE: amino acid
        (C) STRANDEDNESS:
        (D) TOPOLOGY: linear (xi) SEQUENCE DESCRIPTION: SEQ ID NO:22:

Ile Gln Asp Tyr Glu Pro Arg Leu Thr Asp Glu Ile Arg Ile Ser Leu
1               5                   10                  15

Gly Glu Lys Val Lys Ile Leu Ala Thr His Thr Asp Gly Trp Cys Leu
            20                  25                  30

Val Glu Lys Cys Asn Thr Arg Lys Gly Thr Ile His Val Ser Val Asp
        35                  40                  45

Asp Lys Arg Tyr Leu
50

(2) INFORMATION FOR SEQ ID NO:23:

(i) SEQUENCE CHARACTERISTICS:
        (A) LENGTH: 49 amino acids
        (B) TYPE: amino acid
        (C) STRANDEDNESS:
        (D) TOPOLOGY: linear (xi) SEQUENCE DESCRIPTION: SEQ ID NO:23:

Tyr Asp Tyr Glu Ala Arg Thr Glu Asp Asp Leu Thr Phe Thr Lys Gly
1               5                   10                  15

Glu Lys Phe His Ile Leu Asn Asn Thr Glu Gly Asp Trp Trp Glu Ala
            20                  25                  30

Arg Ser Leu Ser Ser Gly Lys Thr Gly Cys Ile Pro Ser Asn Tyr Val
        35                  40                  45

Ala (2) INFORMATION FOR SEQ ID NO:24:

(i) SEQUENCE CHARACTERISTICS:
        (A) LENGTH: 45 amino acids
        (B) TYPE: amino acid
        (C) STRANDEDNESS:
        (D) TOPOLOGY: linear (xi) SEQUENCE DESCRIPTION: SEQ ID NO:24:

```
Thr Tyr Asp Phe Ser Phe Lys Ser Ser Val Ile Thr Leu Asn Thr Asn
1               5                  10                 15

Ala Glu Leu Phe Asn Gln Ser Asp Ile Val Ala His Leu Leu Ser Ser
            20                  25                 30

Ser Ser Ser Val Ile Asp Ala Leu Gln Tyr Lys Leu Glu
        35                  40                 45
```

(2) INFORMATION FOR SEQ ID NO:25:

(i) SEQUENCE CHARACTERISTICS:
        (A) LENGTH: 47 amino acids
        (B) TYPE: amino acid
        (C) STRANDEDNESS:
        (D) TOPOLOGY: linear (xi) SEQUENCE DESCRIPTION: SEQ ID NO:25:

```
Asp Phe Asn Tyr Pro Ile Lys Lys Asp Ser Ser Ser Gln Leu Leu Ser
1               5                  10                 15

Val Gln Gln Gly Glu Thr Ile Tyr Ile Leu Asn Lys Asn Ser Ser Gly
            20                  25                 30

Trp Trp Asp Gly Leu Val Ile Asp Asp Ser Asn Gly Lys Val Asn
        35                  40                 45
```

(2) INFORMATION FOR SEQ ID NO:26:

(i) SEQUENCE CHARACTERISTICS:
        (A) LENGTH: 49 amino acids
        (B) TYPE: amino acid
        (C) STRANDEDNESS:
        (D) TOPOLOGY: linear (xi) SEQUENCE DESCRIPTION: SEQ ID NO:26:

```
Lys Tyr Asp Phe Asn Ser Ser Met Leu Tyr Ser Thr Ala Lys Gly Ala
1               5                  10                 15

Val Asp His Lys Leu Ser Leu Glu Ser Leu Thr Ser Tyr Phe Ser Ile
            20                  25                 30

Glu Ser Ser Thr Lys Gly Asp Val Lys Gly Ser Val Leu Ser Arg Glu
        35                  40                 45

Tyr
```

(2) INFORMATION FOR SEQ ID NO:27:

(i) SEQUENCE CHARACTERISTICS:
        (A) LENGTH: 52 amino acids
        (B) TYPE: amino acid
        (C) STRANDEDNESS:
        (D) TOPOLOGY: linear (xi) SEQUENCE DESCRIPTION: SEQ ID NO:27:

```
Glu Pro Tyr Val Ala Ile Lys Ala Tyr Thr Ala Val Glu Gly Asp Glu
1               5                  10                 15
```

Val Ser Leu Leu Glu Gly Glu Ala Val Glu Val Ile His Lys Leu Leu
            20                  25                  30

Asp Gly Trp Trp Val Ile Arg Lys Asp Asp Val Thr Gly Tyr Phe Pro
            35                  40                  45

Ser Met Tyr Leu
    50

(2) INFORMATION FOR SEQ ID NO:28:

(i) SEQUENCE CHARACTERISTICS:
        (A) LENGTH: 54 amino acids
        (B) TYPE: amino acid
        (C) STRANDEDNESS:
        (D) TOPOLOGY: linear (xi) SEQUENCE DESCRIPTION: SEQ ID NO:28:

Leu Trp Asp Phe Leu Lys Leu Asp Val Thr Thr Ser Ile Gly Arg Arg
1               5                   10                  15

Gln His Leu Arg Val Ser Thr Ala Phe Val Tyr Thr Lys Asn Pro Asn
            20                  25                  30

Gly Tyr Ser Phe Ser Ile Pro Val Lys Val Leu Ala Asp Lys Phe Ile
            35                  40                  45

Thr Pro Gly Leu Lys Leu
    50

(2) INFORMATION FOR SEQ ID NO:29:

(i) SEQUENCE CHARACTERISTICS:
        (A) LENGTH: 55 amino acids
        (B) TYPE: amino acid
        (C) STRANDEDNESS:
        (D) TOPOLOGY: linear (xi) SEQUENCE DESCRIPTION: SEQ ID NO:29:

Leu Tyr Asp Phe Lys Ala Glu Lys Ala Asp Glu Leu Thr Thr Tyr Val
1               5                   10                  15

Gly Glu Asn Leu Phe Ile Cys Ala His His Asn Cys Glu Trp Phe Ile
            20                  25                  30

Ala Lys Pro Ile Gly Arg Leu Gly Gly Pro Gly Leu Val Pro Val Gly
            35                  40                  45

Phe Val Ser Ile Ile Asp Ile
    50              55

(2) INFORMATION FOR SEQ ID NO:30:

(i) SEQUENCE CHARACTERISTICS:
        (A) LENGTH: 47 amino acids
        (B) TYPE: amino acid
        (C) STRANDEDNESS:
        (D) TOPOLOGY: linear (xi) SEQUENCE DESCRIPTION: SEQ ID NO:30:

Val Leu Tyr Asp Tyr Val Asn Lys Tyr His Trp Glu His Thr Gly Leu
1               5                   10                  15

Thr Leu Arg Glu Val Ser Ser Lys Leu Arg Arg Asn Leu Gln Asn Asn
            20                  25                  30

Ala Glu Trp Val Tyr Gln Gly Ala Ile Arg Gln Ile Asp Asp Ile
            35                  40                  45

(2) INFORMATION FOR SEQ ID NO:31:

(i) SEQUENCE CHARACTERISTICS:

(A) LENGTH: 40 amino acids
            (B) TYPE: amino acid
            (C) STRANDEDNESS:
            (D) TOPOLOGY: linear (xi) SEQUENCE DESCRIPTION: SEQ ID NO:31:

Val Leu Tyr Asp Phe Lys Ala Glu Lys Ala Asp Glu Leu Thr Thr Tyr
1               5                   10                  15

Val Gly Glu Asn Leu Phe Ile Cys Ala His His Asn Cys Glu Trp Phe
            20                  25                  30

Ile Ala Lys Pro Ile Gly Arg Leu
        35                  40

(2) INFORMATION FOR SEQ ID NO:32:

(i) SEQUENCE CHARACTERISTICS:
        (A) LENGTH: 43 amino acids
        (B) TYPE: amino acid
        (C) STRANDEDNESS:
        (D) TOPOLOGY: linear (xi) SEQUENCE DESCRIPTION: SEQ ID NO:32:

Lys Pro Gly Ile Tyr Thr Arg Glu Glu Leu Cys Thr Met Phe Ile Arg
1               5                   10                  15

Glu Val Gly Thr Val Leu Ser Gln Val Tyr Ser Lys Val His Asn Gly
            20                  25                  30

Ser Glu Ile Leu Phe Ser Tyr Phe Gln Asp Leu
        35                  40

(2) INFORMATION FOR SEQ ID NO:33:

(i) SEQUENCE CHARACTERISTICS:
        (A) LENGTH: 52 amino acids
        (B) TYPE: amino acid
        (C) STRANDEDNESS:
        (D) TOPOLOGY: linear (xi) SEQUENCE DESCRIPTION: SEQ ID NO:33:

Leu Phe Gly Phe Val Pro Glu Thr Lys Glu Glu Leu Gln Val Met Pro
1               5                   10                  15

Gly Asn Ile Val Phe Val Leu Lys Lys Gly Asn Asp Asn Trp Ala Thr
            20                  25                  30

Val Met Phe Asn Gly Gln Lys Gly Leu Val Pro Cys Asn Tyr Leu Glu
        35                  40                  45

Pro Val Glu Leu
    50

(2) INFORMATION FOR SEQ ID NO:34:

(i) SEQUENCE CHARACTERISTICS:
        (A) LENGTH: 43 amino acids
        (B) TYPE: amino acid
        (C) STRANDEDNESS:
        (D) TOPOLOGY: linear (xi) SEQUENCE DESCRIPTION: SEQ ID NO:34:

Gly Lys Pro Gly Ile Tyr Thr Arg Glu Glu Leu Cys Thr Met Phe Ile
1               5                   10                  15

Arg Glu Val Gly Thr Val Leu Ser Gln Val Tyr Ser Lys Val His Asn
            20                  25                  30

Gly Ser Glu Ile Leu Phe Ser Tyr Phe Gln Asp
        35                  40

(2) INFORMATION FOR SEQ ID NO:35:

(i) SEQUENCE CHARACTERISTICS:
        (A) LENGTH: 52 amino acids
        (B) TYPE: amino acid
        (C) STRANDEDNESS:
        (D) TOPOLOGY: linear (xi) SEQUENCE DESCRIPTION: SEQ ID NO:35:

```
Ala Lys Phe Asp Tyr Val Ala Gln Gln Glu Gln Leu Asp Ile Lys
1               5                  10                  15

Lys Asn Glu Arg Leu Trp Leu Leu Asp Ser Lys Ser Trp Trp Arg
                20                  25                  30

Val Arg Asn Ser Met Asn Lys Thr Gly Phe Val Pro Ser Asn Tyr Val
            35                  40                  45

Glu Arg Lys Asn
        50
```

(2) INFORMATION FOR SEQ ID NO:36:

(i) SEQUENCE CHARACTERISTICS:
        (A) LENGTH: 85 amino acids
        (B) TYPE: amino acid
        (C) STRANDEDNESS:
        (D) TOPOLOGY: linear (xi) SEQUENCE DESCRIPTION: SEQ ID NO:36:

```
Trp Tyr His Ala Ser Leu Thr Arg Ala Gln Ala Glu His Met Leu Met
1               5                  10                  15

Arg Val Pro Arg Asp Gly Ala Phe Leu Val Arg Lys Arg Asn Glu Pro
                20                  25                  30

Asn Ser Tyr Ala Ile Ser Phe Arg Ala Glu Gly Lys Ile Lys His Cys
            35                  40                  45

Arg Val Gln Gln Glu Gly Thr Val Met Leu Gly Asn Ser Glu Phe Asp
        50                  55                  60

Ser Leu Val Asp Leu Ile Ser Tyr Tyr Glu Lys His Pro Leu Tyr Arg
65                  70                  75                  80

Lys Met Lys Leu Arg
                85
```

(2) INFORMATION FOR SEQ ID NO:37:

(i) SEQUENCE CHARACTERISTICS:
        (A) LENGTH: 106 amino acids
        (B) TYPE: amino acid
        (C) STRANDEDNESS:
        (D) TOPOLOGY: linear (xi) SEQUENCE DESCRIPTION: SEQ ID NO:37:

```
Phe Phe Gly Glu Gly Thr Lys Lys Met Gly Leu Ala Phe Glu Ser Thr
1               5                  10                  15

Lys Ser Thr Ser Pro Pro Lys Gln Ala Glu Ala Val Leu Lys Thr Leu
                20                  25                  30

Gln Glu Leu Lys Lys Leu Thr Ile Ser Glu Gln Asn Ile Gln Arg Ala
            35                  40                  45

Asn Leu Phe Asn Lys Leu Val Thr Glu Leu Arg Gly Leu Ser Asp Glu
        50                  55                  60

Ala Val Thr Ser Leu Leu Pro Gln Leu Ile Glu Val Ser Ser Pro Ile
65                  70                  75                  80

Thr Leu Gln Ala Leu Val Gln Cys Gly Gln Pro Cys Ser Thr His Ile
```

```
                    85                  90                  95
Leu Gln Trp Leu Lys Arg Val His Ala Asn
                   100                 105

(2) INFORMATION FOR SEQ ID NO:38:

(i) SEQUENCE CHARACTERISTICS:
        (A) LENGTH: 91 amino acids
        (B) TYPE: amino acid
        (C) STRANDEDNESS:
        (D) TOPOLOGY: linear (xi) SEQUENCE DESCRIPTION: SEQ ID NO:38:

Trp Phe His Gly Lys Ile Ser Lys Gln Glu Ala Tyr Asn Leu Leu Met
1               5                  10                  15

Thr Val Gly Gln Ala Cys Ser Phe Leu Val Arg Pro Ser Asp Asn Thr
            20                  25                  30

Pro Gly Asp Tyr Ser Leu Tyr Phe Arg Thr Ser Glu Asn Ile Gln Arg
        35                  40                  45

Phe Lys Ile Cys Pro Thr Pro Asn Asn Gln Phe Met Met Gly Gly Arg
    50                  55                  60

Tyr Tyr Asn Ser Ser Ile Gly Asp Ile Ile Asp His Tyr Arg Lys Glu
65                  70                  75                  80

Gln Ile Val Glu Gly Tyr Tyr Leu Lys Glu Pro
                85                  90

(2) INFORMATION FOR SEQ ID NO:39:

(i) SEQUENCE CHARACTERISTICS:
        (A) LENGTH: 93 amino acids
        (B) TYPE: amino acid
        (C) STRANDEDNESS:
        (D) TOPOLOGY: linear (xi) SEQUENCE DESCRIPTION: SEQ ID NO:39:

Ile Met Leu Ser Val Glu Lys Leu Ile Lys Asp Leu Lys Ser Lys Glu
1               5                  10                  15

Val Pro Glu Ala Arg Ala Tyr Leu Arg Ile Leu Gly Glu Glu Leu Gly
            20                  25                  30

Phe Ala Ser Leu His Asp Leu Gln Leu Leu Gly Lys Leu Leu Leu Met
        35                  40                  45

Gly Ala Arg Thr Leu Gln Gly Ile Pro Gln Met Ile Gly Glu Val Ile
    50                  55                  60

Arg Lys Gly Ser Lys Asn Asp Phe Phe Leu His Tyr Ile Phe Met Glu
65                  70                  75                  80

Asn Ala Phe Glu Leu Pro Thr Gly Ala Gly Leu Gln Leu
                85                  90

(2) INFORMATION FOR SEQ ID NO:40:

(i) SEQUENCE CHARACTERISTICS:
        (A) LENGTH: 89 amino acids
        (B) TYPE: amino acid
        (C) STRANDEDNESS:
        (D) TOPOLOGY: linear (xi) SEQUENCE DESCRIPTION: SEQ ID NO:40:

Trp Phe His Gly Lys Ile Ser Lys Gln Glu Ala Tyr Asn Leu Leu Met
1               5                  10                  15

Thr Val Gly Gln Ala Cys Ser Phe Leu Val Arg Pro Ser Asp Asn Thr
            20                  25                  30
```

```
Pro Gly Asp Tyr Ser Leu Tyr Phe Arg Thr Ser Glu Asn Ile Gln Arg
        35                  40                  45

Phe Lys Ile Cys Pro Thr Pro Asn Asn Gln Phe Met Met Gly Gly Arg
    50                  55                  60

Tyr Tyr Asn Ser Ser Ile Gly Asp Ile Ile Asp His Tyr Arg Lys Glu
65                  70                  75                  80

Gln Ile Val Glu Gly Tyr Tyr Leu Lys
                85
```

(2) INFORMATION FOR SEQ ID NO:41:

(i) SEQUENCE CHARACTERISTICS:
        (A) LENGTH: 77 amino acids
        (B) TYPE: amino acid
        (C) STRANDEDNESS:
        (D) TOPOLOGY: linear (xi) SEQUENCE DESCRIPTION: SEQ ID NO:41:

```
Tyr Phe His Lys Leu Asn Ile Pro Lys Leu Asp Phe Ser Ser Gln Ala
1               5                   10                  15

Asp Leu Arg Asn Glu Ile Lys Thr Leu Leu Lys Ala Gly His Ile Ala
            20                  25                  30

Trp Thr Ser Ser Gly Lys Gly Ser Trp Lys Trp Ala Cys Pro Arg Phe
        35                  40                  45

Ser Asp Glu Gly Thr His Glu Ser Gln Ile Ser Phe Thr Ile Glu Gly
    50                  55                  60

Pro Leu Thr Ser Phe Gly Leu Ser Asn Lys Ile Asn Ser
65                  70                  75
```

(2) INFORMATION FOR SEQ ID NO:42:

(i) SEQUENCE CHARACTERISTICS:
        (A) LENGTH: 98 amino acids
        (B) TYPE: amino acid
        (C) STRANDEDNESS:
        (D) TOPOLOGY: linear (xi) SEQUENCE DESCRIPTION: SEQ ID NO:42:

```
Trp Tyr Trp Gly Asp Ile Ser Arg Glu Glu Val Asn Glu Lys Leu Arg
1               5                   10                  15

Asp Thr Pro Asp Gly Thr Phe Leu Val Arg Asp Ala Ser Ser Lys Ile
            20                  25                  30

Gln Gly Asp Tyr Leu Thr Leu Arg Lys Gly Gly Asn Asn Lys Leu Ile
        35                  40                  45

Lys Val Phe His Arg Asp Gly Lys Tyr Gly Phe Ser Glu Pro Leu Thr
    50                  55                  60

Phe Cys Ser Val Val Asp Leu Ile Thr His Tyr Arg His Glu Ser Leu
65                  70                  75                  80

Ala Gln Tyr Asn Ala Lys Leu Asp Thr Arg Leu Leu Tyr Pro Val Ser
                85                  90                  95

Lys Tyr
```

(2) INFORMATION FOR SEQ ID NO:43:

(i) SEQUENCE CHARACTERISTICS:
        (A) LENGTH: 100 amino acids
        (B) TYPE: amino acid
        (C) STRANDEDNESS:
        (D) TOPOLOGY: linear (xi) SEQUENCE DESCRIPTION: SEQ ID NO:43:

Phe Phe Ser Ala Gln Pro Phe Glu Ile Thr Ala Ser Thr Asn Asn Glu
1               5                   10                  15

Gly Asn Leu Lys Val Arg Phe Pro Leu Arg Leu Thr Gly Lys Ile Asp
                20                  25                  30

Phe Leu Asn Asn Tyr Ala Leu Phe Leu Ser Pro Ser Ala Gln Gln Ala
            35                  40                  45

Ser Trp Gln Val Ser Ala Arg Phe Asn Gln Tyr Lys Tyr Asn Gln Asn
        50                  55                  60

Phe Ser Ala Gly Asn Asn Glu Asn Ile Met Glu Ala His Val Gly Ile
65                  70                  75                  80

Asn Gly Glu Ala Asn Leu Asp Phe Leu Asn Ile Pro Leu Thr Ile Pro
                85                  90                  95

Glu Met Arg Leu
            100

(2) INFORMATION FOR SEQ ID NO:44:

(i) SEQUENCE CHARACTERISTICS:
        (A) LENGTH: 106 amino acids
        (B) TYPE: amino acid
        (C) STRANDEDNESS:
        (D) TOPOLOGY: linear (xi) SEQUENCE DESCRIPTION: SEQ ID NO:44:

Trp Phe His Gly Lys Leu Gly Ala Gly Arg Asp Gly Arg His Ile Ala
1               5                   10                  15

Glu Arg Leu Leu Thr Glu Tyr Cys Ile Glu Thr Gly Ala Pro Asp Gly
                20                  25                  30

Ser Phe Leu Val Arg Glu Ser Glu Thr Phe Val Gly Asp Tyr Thr Leu
            35                  40                  45

Ser Phe Trp Arg Asn Gly Lys Val Gln His Cys Arg Ile His Ser Arg
        50                  55                  60

Gln Asp Ala Gly Thr Pro Lys Phe Phe Leu Thr Asp Asn Leu Val Phe
65                  70                  75                  80

Asp Ser Leu Tyr Asp Leu Ile Thr His Tyr Gln Gln Val Pro Leu Arg
                85                  90                  95

Cys Asn Glu Phe Glu Met Arg Leu Ser Glu
            100                 105

(2) INFORMATION FOR SEQ ID NO:45:

(i) SEQUENCE CHARACTERISTICS:
        (A) LENGTH: 91 amino acids
        (B) TYPE: amino acid
        (C) STRANDEDNESS:
        (D) TOPOLOGY: linear (xi) SEQUENCE DESCRIPTION: SEQ ID NO:45:

Phe Pro Gly Lys Pro Gly Ile Tyr Thr Arg Glu Glu Leu Cys Thr Met
1               5                   10                  15

Phe Ile Arg Glu Val Gly Thr Val Leu Ser Gln Val Tyr Ser Lys Val
                20                  25                  30

His Asn Gly Ser Glu Ile Leu Phe Ser Tyr Phe Gln Asp Leu Val Ile
            35                  40                  45

Thr Leu Pro Phe Glu Leu Arg Lys His Lys Leu Ile Asp Val Ile Ser
        50                  55                  60

Met Tyr Arg Glu Leu Leu Lys Asp Leu Ser Lys Glu Ala Gln Glu Val

```
                65                  70                  75                  80
Phe Lys Ala Ile Gln Ser Leu Lys Thr Thr Glu
                    85                  90

(2) INFORMATION FOR SEQ ID NO:46:

(i) SEQUENCE CHARACTERISTICS:
        (A) LENGTH: 203 amino acids
        (B) TYPE: amino acid
        (C) STRANDEDNESS:
        (D) TOPOLOGY: linear (xi) SEQUENCE DESCRIPTION: SEQ ID NO:46:

Val Ser Asp Gly Ile Ala Ala Leu Asp Leu Asn Ala Val Ala Asn Lys
1               5                   10                  15

Ile Ala Asp Phe Glu Leu Pro Thr Ile Ile Val Pro Glu Gln Thr Ile
                20                  25                  30

Glu Ile Pro Ser Ile Lys Phe Ser Val Pro Ala Gly Ile Val Ile Pro
                35                  40                  45

Ser Phe Gln Ala Leu Thr Ala Arg Phe Glu Val Asp Ser Pro Val Tyr
    50                  55                  60

Asn Ala Thr Trp Ser Ala Ser Leu Lys Asn Lys Ala Asp Tyr Val Glu
65                  70                  75                  80

Thr Val Leu Asp Ser Thr Cys Ser Ser Thr Val Gln Phe Leu Glu Tyr
                85                  90                  95

Glu Leu Asn Val Leu Gly Thr His Lys Ile Glu Asp Gly Thr Leu Ala
                100                 105                 110

Ser Lys Thr Lys Gly Thr Leu Ala His Arg Asp Phe Ser Ala Glu Tyr
            115                 120                 125

Glu Glu Asp Gly Lys Phe Glu Gly Leu Gln Glu Trp Glu Gly Lys Ala
    130                 135                 140

His Leu Asn Ile Lys Ser Pro Ala Phe Thr Asp Leu His Leu Arg Tyr
145                 150                 155                 160

Gln Lys Asp Lys Lys Gly Ile Ser Thr Ser Ala Ala Ser Pro Ala Val
                165                 170                 175

Gly Thr Val Gly Met Asp Met Asp Glu Asp Asp Phe Ser Lys Trp
                180                 185                 190

Asn Phe Tyr Tyr Ser Pro Gln Ser Ser Pro Asp
                195                 200

(2) INFORMATION FOR SEQ ID NO:47:

(i) SEQUENCE CHARACTERISTICS:
        (A) LENGTH: 214 amino acids
        (B) TYPE: amino acid
        (C) STRANDEDNESS:
        (D) TOPOLOGY: linear (xi) SEQUENCE DESCRIPTION: SEQ ID NO:47:

Leu Gly Gln Gly Cys Phe Gly Glu Val Trp Met Gly Thr Trp Asn Gly
1               5                   10                  15

Thr Thr Arg Val Ala Ile Lys Thr Leu Lys Pro Gly Thr Met Ser Pro
                20                  25                  30

Glu Ala Phe Leu Gln Glu Ala Gln Val Met Lys Lys Leu Arg His Glu
                35                  40                  45

Lys Leu Val Gln Leu Tyr Ala Val Val Ser Glu Glu Pro Ile Tyr Ile
            50                  55                  60

Val Thr Glu Tyr Met Ser Lys Gly Ser Leu Leu Asp Phe Leu Lys Gly
```

```
                65                    70                     75                       80
Glu Thr Gly Lys Tyr Leu Arg Leu Pro Gln Leu Val Asp Met Ala Ala
                    85                     90                     95

Gln Ile Ala Ser Gly Met Ala Tyr Val Glu Arg Met Asn Tyr Val His
                100                    105                    110

Arg Asp Leu Arg Ala Ala Asn Ile Leu Val Gly Glu Asn Leu Val Cys
                115                    120                    125

Lys Val Ala Asp Phe Gly Leu Ala Arg Leu Ile Glu Asp Asn Glu Tyr
    130                    135                    140

Thr Ala Arg Gln Gly Ala Lys Phe Pro Ile Lys Trp Thr Ala Pro Glu
145                    150                    155                    160

Ala Ala Leu Tyr Gly Arg Phe Thr Ile Lys Ser Asp Val Trp Ser Phe
                165                    170                    175

Gly Ile Leu Leu Thr Glu Leu Thr Thr Lys Gly Arg Val Pro Tyr Pro
                180                    185                    190

Gly Met Val Asn Arg Glu Val Leu Asp Gln Val Glu Arg Gly Tyr Arg
                195                    200                    205

Met Pro Cys Pro Pro Glu
    210
```

(2) INFORMATION FOR SEQ ID NO:48:

(i) SEQUENCE CHARACTERISTICS:
        (A) LENGTH: 213 amino acids
        (B) TYPE: amino acid
        (C) STRANDEDNESS:
        (D) TOPOLOGY: linear (xi) SEQUENCE DESCRIPTION: SEQ ID NO:48:

```
Leu Gly Asn Gly Gln Phe Gly Glu Val Trp Met Gly Thr Trp Asn Gly
1                   5                      10                     15

Asn Thr Lys Val Ala Ile Lys Thr Leu Lys Pro Gly Thr Met Ser Pro
                20                     25                     30

Glu Ser Phe Leu Glu Glu Ala Gln Ile Met Lys Lys Leu Lys His Asp
                35                     40                     45

Lys Leu Val Gln Leu Tyr Ala Val Val Ser Glu Glu Pro Ile Tyr Ile
    50                     55                     60

Val Thr Glu Tyr Met Asn Lys Gly Ser Leu Leu Asp Phe Leu Lys Asp
65                     70                     75                     80

Gly Glu Gly Arg Ala Leu Lys Leu Pro Asn Leu Val Asp Met Ala Ala
                85                     90                     95

Gln Val Ala Ala Gly Met Ala Tyr Ile Glu Arg Met Asn Tyr Ile His
                100                    105                    110

Arg Asp Leu Arg Ser Ala Asn Ile Leu Val Gly Asn Gly Leu Ile Cys
                115                    120                    125

Lys Ile Ala Asp Phe Gly Leu Ala Arg Leu Ile Glu Asp Asn Glu Tyr
    130                    135                    140

Thr Ala Arg Gln Gly Ala Lys Phe Pro Ile Lys Trp Thr Ala Pro Glu
145                    150                    155                    160

Ala Ala Leu Tyr Gly Arg Phe Thr Ile Lys Ser Asp Val Trp Ser Phe
                165                    170                    175

Gly Ile Leu Leu Thr Glu Leu Val Thr Lys Gly Arg Val Pro Tyr Pro
                180                    185                    190

Gly Met Asn Asn Arg Glu Val Leu Glu Gln Val Glu Arg Gly Tyr Arg
                195                    200                    205
```

```
Met Pro Cys Pro Gln
    210

(2) INFORMATION FOR SEQ ID NO:49:

(i) SEQUENCE CHARACTERISTICS:
        (A) LENGTH: 213 amino acids
        (B) TYPE: amino acid
        (C) STRANDEDNESS:
        (D) TOPOLOGY: linear (xi) SEQUENCE DESCRIPTION: SEQ ID NO:49:

Leu Gly Ala Gly Gln Phe Gly Glu Val Trp Met Ala Thr Tyr Asn Lys
1               5                   10                  15

His Thr Lys Val Ala Val Lys Thr Met Lys Pro Gly Ser Met Ser Val
            20                  25                  30

Glu Ala Phe Leu Ala Glu Ala Asn Val Met Lys Thr Leu Gln His Asp
        35                  40                  45

Lys Leu Val Lys Leu His Ala Val Val Thr Lys Glu Pro Ile Tyr Ile
    50                  55                  60

Ile Thr Glu Phe Met Ala Lys Gly Ser Leu Leu Asp Phe Leu Lys Ser
65                  70                  75                  80

Asp Glu Gly Ser Lys Gln Pro Leu Pro Lys Leu Ile Asp Phe Ser Ala
                85                  90                  95

Gln Ile Ala Glu Gly Met Ala Phe Ile Glu Gln Arg Asn Tyr Ile His
            100                 105                 110

Arg Asp Leu Arg Ala Ala Asn Ile Leu Val Ser Ala Ser Leu Val Cys
        115                 120                 125

Lys Ile Ala Asp Phe Gly Leu Ala Arg Val Ile Glu Asp Asn Glu Tyr
    130                 135                 140

Thr Ala Arg Glu Gly Ala Lys Phe Pro Ile Lys Trp Thr Ala Pro Glu
145                 150                 155                 160

Ala Ile Asn Phe Gly Ser Phe Thr Ile Lys Ser Asp Val Trp Ser Phe
                165                 170                 175

Gly Ile Leu Leu Met Glu Ile Val Thr Tyr Gly Arg Ile Pro Tyr Pro
            180                 185                 190

Gly Met Ser Asn Pro Glu Val Ile Arg Ala Leu Glu Arg Gly Tyr Arg
        195                 200                 205

Met Pro Arg Pro Glu
    210

(2) INFORMATION FOR SEQ ID NO:50:

(i) SEQUENCE CHARACTERISTICS:
        (A) LENGTH: 218 amino acids
        (B) TYPE: amino acid
        (C) STRANDEDNESS:
        (D) TOPOLOGY: linear (xi) SEQUENCE DESCRIPTION: SEQ ID NO:50:

Leu Gly Ala Gly Gln Phe Gly Glu Val Trp Met Gly Tyr Tyr Asn Asn
1               5                   10                  15

Ser Thr Lys Val Ala Val Lys Thr Leu Lys Pro Gly Thr Met Ser Val
            20                  25                  30

Gln Ala Phe Leu Glu Glu Ala Asn Leu Met Lys Thr Leu Gln His Asp
        35                  40                  45

Lys Leu Val Arg Leu Tyr Ala Val Val Thr Arg Glu Glu Pro Ile Tyr
    50                  55                  60
```

```
Ile Ile Thr Glu Tyr Met Ala Lys Gly Ser Leu Leu Asp Phe Leu Lys
65                  70                  75                  80

Ser Asp Glu Gly Gly Lys Val Leu Leu Pro Lys Leu Ile Asp Phe Ser
                85                  90                  95

Ala Gln Ile Ala Glu Gly Met Ala Tyr Ile Glu Arg Lys Asn Tyr Ile
            100                 105                 110

His Arg Asp Leu Arg Ala Ala Asn Val Leu Val Ser Glu Ser Leu Met
            115                 120                 125

Cys Lys Ile Ala Asp Phe Gly Leu Ala Arg Val Ile Glu Asp Asn Glu
        130                 135                 140

Tyr Thr Ala Arg Glu Gly Ala Lys Phe Pro Ile Lys Trp Thr Ala Pro
145                 150                 155                 160

Glu Ala Ile Asn Phe Gly Cys Phe Thr Ile Lys Ser Asp Val Trp Ser
                165                 170                 175

Phe Gly Ile Leu Leu Tyr Glu Ile Val Thr Tyr Gly Lys Ile Pro Tyr
            180                 185                 190

Pro Gly Arg Thr Asn Ala Asp Val Met Thr Ala Leu Ser Gln Gly Tyr
            195                 200                 205

Arg Met Pro Arg Val Glu Asn Cys Pro Asp
    210                 215

(2) INFORMATION FOR SEQ ID NO:51:

(i) SEQUENCE CHARACTERISTICS:
        (A) LENGTH: 213 amino acids
        (B) TYPE: amino acid
        (C) STRANDEDNESS:
        (D) TOPOLOGY: linear (xi) SEQUENCE DESCRIPTION: SEQ ID NO:51:

Leu Gly Ala Gly Gln Phe Gly Glu Val Trp Met Gly Tyr Tyr Asn Gly
1               5                   10                  15

His Thr Lys Val Ala Val Lys Ser Leu Lys Gln Gly Ser Met Ser Pro
            20                  25                  30

Asp Ala Phe Leu Ala Glu Ala Asn Leu Met Lys Gln Leu Gln His Gln
        35                  40                  45

Arg Leu Val Arg Leu Tyr Ala Val Val Thr Gln Glu Pro Ile Tyr Ile
    50                  55                  60

Ile Thr Glu Tyr Met Glu Asn Gly Ser Leu Val Asp Phe Leu Lys Thr
65                  70                  75                  80

Pro Ser Gly Ile Lys Leu Thr Ile Asn Lys Leu Leu Asp Met Ala Ala
                85                  90                  95

Gln Ile Ala Glu Gly Met Ala Phe Ile Glu Glu Arg Asn Tyr Ile His
            100                 105                 110

Arg Asp Leu Arg Ala Ala Asn Ile Leu Val Ser Asp Thr Leu Ser Cys
        115                 120                 125

Lys Ile Ala Asp Phe Gly Leu Ala Arg Leu Ile Glu Asp Asn Glu Tyr
    130                 135                 140

Thr Ala Arg Glu Gly Ala Lys Phe Pro Ile Lys Trp Thr Ala Pro Glu
145                 150                 155                 160

Ala Ile Asn Tyr Gly Thr Phe Thr Ile Lys Ser Asp Val Trp Ser Phe
                165                 170                 175

Gly Ile Leu Leu Thr Glu Ile Val Thr His Gly Arg Ile Pro Tyr Pro
            180                 185                 190

Gly Met Thr Asn Pro Glu Val Ile Gln Asn Leu Glu Arg Gly Tyr Arg
            195                 200                 205
```

Met Val Arg Pro Asp
    210

(2) INFORMATION FOR SEQ ID NO:52:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:52:

Arg Lys Asn Tyr Ile His Arg Asp Leu Arg Ala Ala Asn
1               5                   10

(2) INFORMATION FOR SEQ ID NO:53:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:53:

Lys Gly Thr Leu Ala His Arg Asp Phe Ser Ala Glu
1               5                   10

(2) INFORMATION FOR SEQ ID NO:54:

(i) SEQUENCE CHARACTERISTICS:
        (A) LENGTH: 11 amino acids
        (B) TYPE: amino acid
        (C) STRANDEDNESS:
        (D) TOPOLOGY: linear (xi) SEQUENCE DESCRIPTION: SEQ ID NO:54:

Thr Lys Val Ala Val Lys Thr Leu Lys Pro Gly
1               5                   10

(2) INFORMATION FOR SEQ ID NO:55:

(i) SEQUENCE CHARACTERISTICS:
        (A) LENGTH: 11 amino acids
        (B) TYPE: amino acid
        (C) STRANDEDNESS:
        (D) TOPOLOGY: linear (xi) SEQUENCE DESCRIPTION: SEQ ID NO:55:

Asp Lys Val Ala Ile Lys Thr Ile Arg Glu Gly
1               5                   10

(2) INFORMATION FOR SEQ ID NO:56:

(i) SEQUENCE CHARACTERISTICS:
        (A) LENGTH: 11 amino acids
        (B) TYPE: amino acid
        (C) STRANDEDNESS:
        (D) TOPOLOGY: linear (xi) SEQUENCE DESCRIPTION: SEQ ID NO:56:

Asp Leu Asn Ala Val Ala Asn Lys Ile Ala Asp
1               5                   10

(2) INFORMATION FOR SEQ ID NO:57:

(i) SEQUENCE CHARACTERISTICS:
        (A) LENGTH: 34 amino acids (B) TYPE: amino acid
        (C) STRANDEDNESS:
        (D) TOPOLOGY: linear (xi) SEQUENCE DESCRIPTION: SEQ ID NO:57:

Thr Ser Leu Arg Ala Pro Thr Met Pro Pro Leu Pro Pro Val Pro
1               5                  10                 15

Pro Gln Pro Ala Arg Arg Gln Ser Arg Arg Leu Pro Ala Ser Pro Val
            20                  25                  30

Ile Ser (2) INFORMATION FOR SEQ ID NO:58:

(i) SEQUENCE CHARACTERISTICS:
        (A) LENGTH: 36 amino acids
        (B) TYPE: amino acid
        (C) STRANDEDNESS:
        (D) TOPOLOGY: linear (xi) SEQUENCE DESCRIPTION: SEQ ID NO:58:

Ser Asp Ala Glu Gly Thr Ala Val Ala Pro Pro Thr Val Thr Pro Val
1               5                  10                 15

Pro Ser Leu Glu Ala Pro Ser Glu Gln Ala Pro Thr Glu Gln Arg Pro
            20                  25                  30

Gly Val Gln Glu
        35

(2) INFORMATION FOR SEQ ID NO:59:

(i) SEQUENCE CHARACTERISTICS:
        (A) LENGTH: 36 amino acids
        (B) TYPE: amino acid
        (C) STRANDEDNESS:
        (D) TOPOLOGY: linear (xi) SEQUENCE DESCRIPTION: SEQ ID NO:59:

Ser Asp Ala Glu Gly Thr Ala Val Ala Pro Pro Thr Ile Thr Pro Ile
1               5                  10                 15

Pro Ser Leu Glu Ala Pro Ser Glu Gln Ala Pro Thr Glu Gln Arg Pro
            20                  25                  30

Gly Val Gln Glu
        35

(2) INFORMATION FOR SEQ ID NO:60:

(i) SEQUENCE CHARACTERISTICS:
        (A) LENGTH: 36 amino acids
        (B) TYPE: amino acid
        (C) STRANDEDNESS:
        (D) TOPOLOGY: linear (xi) SEQUENCE DESCRIPTION: SEQ ID NO:60:

Ser Asp Ala Glu Trp Thr Ala Phe Val Pro Pro Asn Val Ile Leu Ala
1               5                  10                 15

Pro Ser Leu Glu Ala Phe Phe Glu Gln Ala Leu Thr Glu Thr Pro
            20                  25                  30

Gly Val Gln Asp
        35

(2) INFORMATION FOR SEQ ID NO:61:

(i) SEQUENCE CHARACTERISTICS:
        (A) LENGTH: 36 amino acids (B) TYPE: amino acid
        (C) STRANDEDNESS:
        (D) TOPOLOGY: linear (xi) SEQUENCE DESCRIPTION: SEQ ID NO:61:

Leu Val Thr Glu Ser Ser Val Leu Ala Thr Leu Thr Val Val Pro Asp
1               5                   10                  15

Pro Ser Thr Glu Ala Ser Ser Glu Glu Ala Pro Thr Glu Gln Ser Pro
            20                  25                  30

Gly Val Gln Asp
        35

(2) INFORMATION FOR SEQ ID NO:62:

(i) SEQUENCE CHARACTERISTICS:
        (A) LENGTH: 36 amino acids
        (B) TYPE: amino acid
        (C) STRANDEDNESS:
        (D) TOPOLOGY: linear (xi) SEQUENCE DESCRIPTION: SEQ ID NO:62:

Pro Val Met Glu Ser Thr Leu Leu Thr Thr Pro Thr Val Val Pro Val
1               5                   10                  15

Pro Ser Thr Glu Leu Pro Ser Glu Glu Ala Pro Thr Glu Asn Ser Thr
            20                  25                  30

Gly Val Gln Asp
        35

(2) INFORMATION FOR SEQ ID NO:63:

(i) SEQUENCE CHARACTERISTICS:
        (A) LENGTH: 36 amino acids
        (B) TYPE: amino acid
        (C) STRANDEDNESS:
        (D) TOPOLOGY: linear (xi) SEQUENCE DESCRIPTION: SEQ ID NO:63:

Pro Val Thr Glu Ser Ser Val Leu Thr Thr Pro Thr Val Ala Pro Val
1               5                   10                  15

Pro Ser Thr Glu Ala Pro Ser Glu Gln Ala Pro Pro Glu Lys Ser Pro
            20                  25                  30

Val Val Gln Asp
        35

(2) INFORMATION FOR SEQ ID NO:64:

(i) SEQUENCE CHARACTERISTICS:
        (A) LENGTH: 37 amino acids
        (B) TYPE: amino acid
        (C) STRANDEDNESS:
        (D) TOPOLOGY: linear (xi) SEQUENCE DESCRIPTION: SEQ ID NO:64:

Ser Glu Thr Glu Ser Gly Val Leu Glu Thr Pro Thr Val Val Pro Glu
1               5                   10                  15

Pro Ser Met Glu Ala His Ser Glu Ala Ala Pro Thr Glu Gln Thr Pro
            20                  25                  30

Val Val Arg Arg Gln
        35

(2) INFORMATION FOR SEQ ID NO:65:

(i) SEQUENCE CHARACTERISTICS:

(A) LENGTH: 37 amino acids
        (B) TYPE: amino acid
        (C) STRANDEDNESS:
        (D) TOPOLOGY: linear (xi) SEQUENCE DESCRIPTION: SEQ ID NO:65:

Pro Lys Asp Ala Thr Arg Phe Lys His Leu Arg Lys Tyr Thr Tyr Asn
1               5                   10                  15

Tyr Glu Ala Glu Ser Ser Ser Gly Val Pro Gly Thr Ala Asp Ser Arg
            20                  25                  30

Ser Ala Thr Arg Ile
            35

(2) INFORMATION FOR SEQ ID NO:66:

(i) SEQUENCE CHARACTERISTICS:
        (A) LENGTH: 37 amino acids
        (B) TYPE: amino acid
        (C) STRANDEDNESS:
        (D) TOPOLOGY: linear (xi) SEQUENCE DESCRIPTION: SEQ ID NO:66:

Pro Lys Asp Ala Thr Arg Phe Lys His Leu Arg Lys Tyr Thr Tyr Asn
1               5                   10                  15

Tyr Glu Ala Glu Ser Ser Ser Gly Val Pro Gly Thr Ala Asp Ser Arg
            20                  25                  30

Ser Ala Thr Arg Ile
            35

(2) INFORMATION FOR SEQ ID NO:67:

(i) SEQUENCE CHARACTERISTICS:
        (A) LENGTH: 34 amino acids
        (B) TYPE: amino acid
        (C) STRANDEDNESS:
        (D) TOPOLOGY: linear (xi) SEQUENCE DESCRIPTION: SEQ ID NO:67:

Pro Lys Asp Ala Ser Gln Arg Arg Arg Ser Leu Glu Pro Ala Glu Asn
1               5                   10                  15

Val His Gly Ala Gly Gly Gly Ala Phe Pro Ala Ser Gln Thr Pro Ser
            20                  25                  30

Lys Pro (2) INFORMATION FOR SEQ ID NO:68:

(i) SEQUENCE CHARACTERISTICS:
        (A) LENGTH: 32 amino acids
        (B) TYPE: amino acid
        (C) STRANDEDNESS:
        (D) TOPOLOGY: linear (xi) SEQUENCE DESCRIPTION: SEQ ID NO:68:

Asp Lys Glu Ala Thr Lys Leu Thr Glu Glu Arg Asp Gly Ser Leu Asn
1               5                   10                  15

Gln Ser Ser Gly Tyr Arg Tyr Gly Thr Asp Pro Thr Pro Gln His Tyr
            20                  25                  30

(2) INFORMATION FOR SEQ ID NO:69:

(i) SEQUENCE CHARACTERISTICS:
        (A) LENGTH: 39 amino acids
        (B) TYPE: amino acid
        (C) STRANDEDNESS:

(D) TOPOLOGY: linear (xi) SEQUENCE DESCRIPTION: SEQ ID NO:69:

Ile Gln Asn Tyr His Thr Phe Leu Ile Tyr Ile Thr Glu Leu Leu Lys
1               5                   10                  15

Lys Leu Gln Ser Thr Thr Val Met Asn Pro Tyr Met Lys Leu Ala Pro
                20                  25                  30

Gly Glu Leu Thr Ile Ile Leu
            35

(2) INFORMATION FOR SEQ ID NO:70:

(i) SEQUENCE CHARACTERISTICS:
        (A) LENGTH: 31 amino acids
        (B) TYPE: amino acid
        (C) STRANDEDNESS:
        (D) TOPOLOGY: linear (xi) SEQUENCE DESCRIPTION: SEQ ID NO:70:

Pro Glu Glu Arg Pro Thr Phe Glu Tyr Leu Gln Ala Phe Leu Glu Asp
1               5                   10                  15

Tyr Phe Thr Ser Thr Glu Pro Gln Tyr Gln Pro Gly Glu Asn Leu
                20                  25                  30

(2) INFORMATION FOR SEQ ID NO:71:

(i) SEQUENCE CHARACTERISTICS:
        (A) LENGTH: 31 amino acids
        (B) TYPE: amino acid
        (C) STRANDEDNESS:
        (D) TOPOLOGY: linear (xi) SEQUENCE DESCRIPTION: SEQ ID NO:71:

Pro Glu Glu Arg Pro Thr Phe Glu Tyr Leu Gln Ser Phe Leu Glu Asp
1               5                   10                  15

Tyr Phe Thr Ala Thr Glu Pro Gln Tyr Gln Pro Gly Glu Asn Leu
                20                  25                  30

(2) INFORMATION FOR SEQ ID NO:72:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:72:

Pro Glu Glu Arg Pro Thr Phe Glu Tyr Ile Gln Ser Val Leu Asp Asp
1               5                   10                  15

Phe Tyr Thr Ala Thr Glu Ser Gln Tyr Gln Gln Gln Pro
                20                  25

(2) INFORMATION FOR SEQ ID NO:73:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:73:

Ala Glu Glu Arg Pro Thr Phe Asp Tyr Leu Gln Ser Val Leu Asp Asp
1               5                   10                  15

Phe Tyr Thr Ala Thr Glu Gly Gln Tyr Gln Gln Gln Pro 20              25

(2) INFORMATION FOR SEQ ID NO:74:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:74:

Pro Glu Asp Arg Pro Thr Phe Asp Tyr Leu Arg Ser Val Leu Glu Asp
1               5                   10                  15

Phe Phe Thr Ala Thr Glu Gly Gln Tyr Gln Pro Gln Pro
            20              25

(2) INFORMATION FOR SEQ ID NO:75:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:75:

Pro Xaa Xaa Xaa Xaa Pro
1               5

(2) INFORMATION FOR SEQ ID NO:76:

(i) SEQUENCE CHARACTERISTICS:
        (A) LENGTH: 40 amino acids
        (B) TYPE: amino acid
        (C) STRANDEDNESS:
        (D) TOPOLOGY: linear (xi) SEQUENCE DESCRIPTION: SEQ ID NO:76:

Pro Asp Phe Arg Leu Pro Glu Ile Ala Ile Pro Glu Phe Ile Ile Pro
1               5                   10                  15

Thr Leu Asn Leu Asn Asp Phe Gln Val Pro Asp Leu His Ile Pro Glu
            20                  25                  30

Phe Gln Leu Pro His Ile Ser His
        35                  40

(2) INFORMATION FOR SEQ ID NO:77:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:77:

Pro Gln Asn Ala Lys Leu Lys Ile Lys Arg Pro Val Lys Val Gln Pro
1               5                   10                  15

Ile Ala Arg Val Trp Tyr
            20

(2) INFORMATION FOR SEQ ID NO:78:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:78:

Pro Asp Phe Arg Leu Pro Glu Ile Ala Ile Pro Glu Phe Ile Ile Pro
1               5                   10                  15

Thr Leu Asn Leu Asn Asp
            20

(2) INFORMATION FOR SEQ ID NO:79:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:79:

Asn Asp Phe Gln Val Pro Asp Leu His Ile Pro Glu Phe Gln Leu Pro
1               5                   10                  15

His Ile Ser His Thr Ile
            20

(2) INFORMATION FOR SEQ ID NO:80:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:80:

Pro Ser Leu Glu Leu Pro Val Leu His Val Pro Arg Asn Leu Lys Leu
1               5                   10                  15

Ser Leu Pro His Phe Lys
            20

(2) INFORMATION FOR SEQ ID NO:81:

(i) SEQUENCE CHARACTERISTICS:
        (A) LENGTH: 379 amino acids
        (B) TYPE: amino acid
        (C) STRANDEDNESS:
        (D) TOPOLOGY: linear (xi) SEQUENCE DESCRIPTION: SEQ ID NO:81:

Met Ala Ser Gly Arg Ala Arg Cys Thr Arg Lys Leu Arg Asn Trp Val
1               5                   10                  15

Val Glu Gln Val Glu Ser Gly Gln Phe Pro Gly Val Cys Trp Asp Asp
                20                  25                  30

Thr Ala Lys Thr Met Phe Arg Ile Pro Trp Lys His Ala Gly Lys Gln
            35                  40                  45

Asp Phe Arg Glu Ser Gln Asp Ala Ala Phe Phe Lys Ala Trp Ala Ile
    50                  55                  60

Phe Lys Gly Lys Tyr Lys Glu Gly Asp Lys Glu Val Pro Glu Arg Gly
65                  70                  75                  80

Arg Met Asp Val Ala Glu Pro Tyr Lys Val Tyr Gln Leu Leu Pro Pro
                85                  90                  95

Gly Ile Val Ser Gly Gln Pro Gly Thr Gln Lys Val Pro Ser Lys Arg
            100                 105                 110

Gln His Ser Ser Val Ser Ser Glu Arg Lys Glu Glu Asp Ala Met Gln
    115                 120                 125

Asn Cys Thr Leu Ser Pro Ser Val Leu Gln Asp Ser Leu Asn Asn Glu
130                 135                 140

```
Glu Gly Ala Ser Gly Gly Ala Val His Ser Asp Ile Gly Ser Ser Ser
145                 150                 155                 160

Ser Ser Ser Ser Pro Glu Pro Gln Glu Val Thr Asp Thr Thr Glu Ala
            165                 170                 175

Pro Phe Gln Gly Asp Gln Arg Ser Leu Glu Phe Leu Leu Pro Pro Glu
            180                 185                 190

Pro Asp Tyr Ser Leu Leu Leu Thr Phe Ile Tyr Asn Gly Arg Val Val
            195                 200                 205

Gly Glu Ala Gln Val Gln Ser Leu Asp Cys Arg Leu Val Ala Glu Pro
        210                 215                 220

Ser Gly Ser Glu Ser Ser Met Glu Gln Val Leu Phe Pro Lys Pro Gly
225                 230                 235                 240

Pro Glu Pro Thr Gln Arg Leu Leu Ser Gln Leu Glu Arg Gly Ile Leu
            245                 250                 255

Val Ala Ser Asn Pro Arg Gly Leu Phe Val Gln Arg Leu Cys Pro Ile
            260                 265                 270

Pro Ile Ser Trp Asn Ala Pro Gln Ala Pro Pro Gly Pro Gly Pro His
        275                 280                 285

Leu Leu Pro Ser Asn Glu Cys Val Glu Leu Phe Arg Thr Ala Tyr Phe
290                 295                 300

Cys Arg Asp Leu Val Arg Tyr Phe Gln Gly Leu Gly Pro Pro Pro Lys
305                 310                 315                 320

Phe Gln Val Thr Leu Asn Phe Trp Glu Glu Ser His Gly Ser Ser His
            325                 330                 335

Thr Pro Gln Asn Leu Ile Thr Val Lys Met Glu Gln Ala Phe Ala Arg
            340                 345                 350

Tyr Leu Lys Met Glu Gln Ala Phe Ala Arg Tyr Leu Leu Glu Gln Thr
        355                 360                 365

Pro Glu Gln Gln Ala Ala Ile Leu Ser Leu Val
    370                 375
```

(2) INFORMATION FOR SEQ ID NO:82:

(i) SEQUENCE CHARACTERISTICS:
        (A) LENGTH: 383 amino acids
        (B) TYPE: amino acid
        (C) STRANDEDNESS:
        (D) TOPOLOGY: linear (xi) SEQUENCE DESCRIPTION: SEQ ID NO:82:

```
Val Ser Leu Val Cys Pro Lys Asp Ala Thr Arg Phe Lys His Leu Arg
1               5                   10                  15

Lys Tyr Thr Tyr Asn Tyr Glu Ala Glu Ser Ser Ser Gly Val Pro Gly
            20                  25                  30

Thr Ala Asp Ser Arg Ser Ala Thr Arg Ile Asn Cys Lys Val Glu Leu
            35                  40                  45

Glu Val Pro Gln Leu Cys Ser Phe Ile Leu Lys Thr Ser Gln Cys Thr
        50                  55                  60

Leu Lys Glu Val Tyr Gly Phe Asn Pro Glu Gly Lys Ala Leu Leu Lys
65                  70                  75                  80

Lys Thr Lys Asn Ser Glu Glu Phe Ala Ala Ala Met Ser Arg Tyr Glu
            85                  90                  95

Leu Lys Leu Ala Ile Pro Glu Gly Lys Gln Val Phe Leu Tyr Pro Glu
            100                 105                 110

Lys Asp Glu Pro Thr Tyr Ile Leu Asn Ile Lys Arg Gly Ile Ile Ser
```

```
                115                 120                 125
Ala Leu Leu Val Pro Pro Glu Thr Glu Ala Lys Gln Val Leu Phe
    130                 135                 140

Leu Asp Thr Val Tyr Gly Asn Cys Ser Thr His Phe Thr Val Lys Thr
145                 150                 155                 160

Arg Lys Gly Asn Val Ala Thr Glu Ile Ser Thr Glu Arg Asp Leu Gly
                165                 170                 175

Gln Cys Asp Arg Phe Lys Pro Ile Arg Thr Gly Ile Ser Pro Leu Ala
                180                 185                 190

Leu Ile Lys Gly Met Thr Arg Pro Leu Ser Thr Leu Ile Ser Ser Ser
            195                 200                 205

Gln Ser Cys Gln Tyr Thr Leu Asp Ala Lys Arg Lys His Val Ala Glu
            210                 215                 220

Ala Ile Cys Lys Glu Gln His Leu Phe Leu Pro Phe Ser Tyr Lys Asn
225                 230                 235                 240

Lys Tyr Gly Met Val Ala Gln Val Thr Gln Thr Leu Lys Leu Glu Asp
                245                 250                 255

Thr Pro Lys Ile Asn Ser Arg Phe Phe Gly Glu Gly Thr Lys Lys Met
            260                 265                 270

Gly Leu Ala Phe Glu Ser Thr Lys Ser Thr Ser Pro Pro Lys Gln Ala
            275                 280                 285

Glu Ala Val Leu Lys Thr Leu Gln Glu Leu Lys Lys Leu Thr Ile Ser
290                 295                 300

Glu Gln Asn Ile Gln Arg Ala Asn Leu Phe Asn Lys Leu Val Thr Glu
305                 310                 315                 320

Leu Arg Gly Leu Ser Asp Glu Ala Val Thr Ser Leu Leu Pro Gln Leu
                325                 330                 335

Ile Glu Val Ser Ser Pro Ile Thr Leu Gln Ala Leu Val Gln Cys Gly
            340                 345                 350

Gln Pro Gln Cys Ser Thr His Ile Leu Lys Arg Val His Ala Asn Pro
            355                 360                 365

Leu Leu Ile Asp Val Val Thr Tyr Leu Val Ala Leu Ile Pro Glu
            370                 375                 380

(2) INFORMATION FOR SEQ ID NO:83:

(i) SEQUENCE CHARACTERISTICS:
        (A) LENGTH: 394 amino acids
        (B) TYPE: amino acid
        (C) STRANDEDNESS:
        (D) TOPOLOGY: linear (xi) SEQUENCE DESCRIPTION: SEQ ID NO:83:

Phe Gly Leu Ser Asn Lys Ile Asn Ser Lys His Leu Arg Val Asn Gln
1               5                   10                  15

Asn Leu Val Tyr Glu Ser Gly Ser Leu Asn Phe Ser Lys Leu Glu Ile
                20                  25                  30

Gln Ser Gln Val Asp Ser Gln His Val Gly His Ser Val Leu Thr Ala
            35                  40                  45

Lys Gly Met Ala Leu Phe Gly Glu Gly Lys Ala Glu Phe Thr Gly Arg
        50                  55                  60

His Asp Ala His Leu Asn Gly Lys Val Ile Gly Thr Leu Lys Asn Ser
65                  70                  75                  80

Leu Phe Phe Ser Ala Gln Pro Phe Glu Ile Thr Ala Ser Thr Asn Asn
                85                  90                  95
```

```
Glu Gly Asn Leu Lys Val Arg Phe Pro Leu Arg Leu Thr Gly Lys Ile
            100                 105                 110

Asp Phe Leu Asn Asn Tyr Ala Leu Phe Leu Ser Pro Ser Ala Gln Gln
            115                 120                 125

Ala Ser Trp Gln Val Ser Ala Arg Phe Asn Gln Tyr Lys Tyr Asn Gln
            130                 135                 140

Asn Phe Ser Ala Gly Asn Asn Glu Asn Ile Met Glu Ala His Val Gly
145                 150                 155                 160

Ile Asn Gly Glu Ala Asn Leu Asp Phe Leu Asn Ile Pro Leu Thr Ile
                165                 170                 175

Pro Glu Met Arg Leu Pro Tyr Thr Ile Ile Thr Thr Pro Pro Leu Lys
                180                 185                 190

Asp Phe Ser Leu Trp Glu Lys Thr Gly Leu Lys Glu Phe Leu Lys Thr
            195                 200                 205

Thr Lys Gln Ser Phe Asp Leu Ser Val Lys Ala Gln Tyr Lys Lys Asn
            210                 215                 220

Lys His Arg His Ser Ile Asn Pro Leu Ala Val Leu Cys Glu Phe Ile
225                 230                 235                 240

Ser Gln Ser Ile Lys Ser Phe Asp Arg His Phe Glu Lys Asn Arg Asn
                245                 250                 255

Asn Ala Leu Asp Phe Val Thr Lys Ser Tyr Asn Glu Thr Lys Ile Lys
                260                 265                 270

Phe Asp Lys Tyr Lys Ala Glu Lys Ser His Asp Glu Leu Pro Arg Thr
            275                 280                 285

Phe Gln Ile Pro Gly Tyr Thr Val Pro Val Val Asn Val Glu Val Ser
            290                 295                 300

Pro Phe Thr Ile Glu Met Ser Ala Phe Gly Tyr Val Phe Pro Lys Ala
305                 310                 315                 320

Val Ser Met Pro Ser Phe Ser Ile Leu Gly Ser Asp Val Arg Val Pro
                325                 330                 335

Ser Tyr Thr Leu Ile Leu Pro Ser Leu Glu Leu Pro Val Leu His Val
                340                 345                 350

Pro Arg Asn Leu Lys Leu Ser Leu Pro His Phe Lys Glu Leu Cys Thr
            355                 360                 365

Ile Ser His Ile Phe Ile Pro Ala Met Gly Asn Ile Thr Tyr Asp Phe
            370                 375                 380

Ser Phe Lys Ser Ser Val Ile Thr Leu Asn
385                 390
```

(2) INFORMATION FOR SEQ ID NO:84:

(i) SEQUENCE CHARACTERISTICS:
        (A) LENGTH: 51 amino acids
        (B) TYPE: amino acid
        (C) STRANDEDNESS:
        (D) TOPOLOGY: linear (xi) SEQUENCE DESCRIPTION: SEQ ID NO:84:

```
Met Ala Ser Gly Arg Ala Arg Cys Thr Arg Lys Leu Arg Asn Trp Val
1               5                   10                  15

Val Glu Gln Val Glu Ser Gly Gln Phe Pro Gly Val Cys Trp Asp Asp
            20                  25                  30

Thr Ala Lys Thr Met Phe Arg Ile Pro Trp Lys His Ala Gly Lys Gln
            35                  40                  45

Asp Phe Arg
50
```

(2) INFORMATION FOR SEQ ID NO:85:

(i) SEQUENCE CHARACTERISTICS:
        (A) LENGTH: 48 amino acids
        (B) TYPE: amino acid
        (C) STRANDEDNESS:
        (D) TOPOLOGY: linear (xi) SEQUENCE DESCRIPTION: SEQ ID NO:85:

```
Pro Lys Asp Ala Thr Arg Phe Lys His Leu Arg Lys Tyr Thr Tyr Asn
1               5                   10                  15

Tyr Glu Ala Glu Ser Ser Ser Gly Val Pro Gly Thr Ala Asp Ser Arg
                20                  25                  30

Ser Ala Thr Arg Ile Asn Cys Lys Val Glu Leu Glu Val Leu Pro Gln
                35                  40                  45
```

(2) INFORMATION FOR SEQ ID NO:86:

(i) SEQUENCE CHARACTERISTICS:
        (A) LENGTH: 37 amino acids
        (B) TYPE: amino acid
        (C) STRANDEDNESS:
        (D) TOPOLOGY: linear (xi) SEQUENCE DESCRIPTION: SEQ ID NO:86:

```
Pro Glu Gly Lys Ala Leu Leu Lys Lys Thr Lys Asn Ser Glu Glu Phe
1               5                   10                  15

Ala Ala Ala Met Ser Arg Tyr Glu Leu Lys Leu Ala Ile Pro Glu Gly
                20                  25                  30

Lys Gln Val Phe Leu
                35
```

(2) INFORMATION FOR SEQ ID NO:87:

(i) SEQUENCE CHARACTERISTICS:
        (A) LENGTH: 38 amino acids
        (B) TYPE: amino acid
        (C) STRANDEDNESS:
        (D) TOPOLOGY: linear (xi) SEQUENCE DESCRIPTION: SEQ ID NO:87:

```
Cys Ser Thr His Phe Thr Val Lys Thr Arg Lys Gly Asn Val Ala Thr
1               5                   10                  15

Glu Ile Ser Thr Glu Arg Asp Leu Gly Gln Cys Asp Arg Phe Lys Pro
                20                  25                  30

Ile Arg Thr Gly Ile Ser
                35
```

(2) INFORMATION FOR SEQ ID NO:88:

(i) SEQUENCE CHARACTERISTICS:
        (A) LENGTH: 51 amino acids
        (B) TYPE: amino acid
        (C) STRANDEDNESS:
        (D) TOPOLOGY: linear (xi) SEQUENCE DESCRIPTION: SEQ ID NO:88:

```
Cys Ser Thr His Ile Leu Gln Trp Leu Lys Arg Val His Ala Asn Pro
1               5                   10                  15

Leu Leu Ile Asp Val Val Thr Tyr Leu Val Ala Leu Ile Pro Glu Pro
                20                  25                  30

Ser Ala Gln Gln Leu Arg Glu Ile Phe Asn Met Ala Arg Asp Gln Arg
```

```
            35                  40                  45
Ser Arg Ala
    50

(2) INFORMATION FOR SEQ ID NO:89:

(i) SEQUENCE CHARACTERISTICS:
        (A) LENGTH: 38 amino acids
        (B) TYPE: amino acid
        (C) STRANDEDNESS:
        (D) TOPOLOGY: linear (xi) SEQUENCE DESCRIPTION: SEQ ID NO:89:

His Leu Ser Cys Asp Thr Lys Glu Glu Arg Lys Ile Lys Gly Val Ile
1               5                   10                  15

Ser Ile Pro Arg Leu Gln Ala Glu Ala Arg Ser Glu Ile Leu Ala His
            20                  25                  30

Trp Ser Pro Ala Lys Leu
            35

(2) INFORMATION FOR SEQ ID NO:90:

(i) SEQUENCE CHARACTERISTICS:
        (A) LENGTH: 47 amino acids
        (B) TYPE: amino acid
        (C) STRANDEDNESS:
        (D) TOPOLOGY: linear (xi) SEQUENCE DESCRIPTION: SEQ ID NO:90:

Ser Val His Leu Asp Ser Lys Lys Gln His Leu Phe Val Lys Glu
1               5                   10                  15

Val Lys Ile Asp Gly Gln Phe Arg Val Ser Ser Phe Tyr Ala Lys Gly
            20                  25                  30

Thr Tyr Gly Leu Ser Cys Gln Arg Asp Pro Asn Thr Gly Arg Leu
            35                  40                  45

(2) INFORMATION FOR SEQ ID NO:91:

(i) SEQUENCE CHARACTERISTICS:
        (A) LENGTH: 40 amino acids
        (B) TYPE: amino acid
        (C) STRANDEDNESS:
        (D) TOPOLOGY: linear (xi) SEQUENCE DESCRIPTION: SEQ ID NO:91:

Lys His Ile Asn Ile Asp Gln Phe Val Arg Lys Tyr Arg Ala Ala Leu
1               5                   10                  15

Gly Lys Leu Pro Gln Gln Ala Asn Asp Tyr Leu Ser Phe Asn Trp Glu
            20                  25                  30

Arg Gln Val Ser His Ala Lys Glu
            35                  40

(2) INFORMATION FOR SEQ ID NO:92:

(i) SEQUENCE CHARACTERISTICS:
        (A) LENGTH: 40 amino acids
        (B) TYPE: amino acid
        (C) STRANDEDNESS:
        (D) TOPOLOGY: linear (xi) SEQUENCE DESCRIPTION: SEQ ID NO:92:

Lys Leu Thr Ala Leu Thr Lys Lys Tyr Arg Ile Thr Glu Asn Asp Ile
1               5                   10                  15
```

```
Gln Ile Ala Leu Asp Asp Ala Lys Ile Asn Phe Asn Glu Lys Leu Ser
         20                  25                  30

Gln Leu Gln Thr Tyr Met Ile Gln
         35              40
```

(2) INFORMATION FOR SEQ ID NO:93:

(i) SEQUENCE CHARACTERISTICS:
        (A) LENGTH: 50 amino acids
        (B) TYPE: amino acid
        (C) STRANDEDNESS:
        (D) TOPOLOGY: linear (xi) SEQUENCE DESCRIPTION: SEQ ID NO:93:

```
Glu Arg Ile Asn Asp Val Leu Glu His Val Lys His Phe Val Ile Asn
1               5                  10                  15

Leu Ile Gly Asp Phe Glu Val Ala Glu Lys Ile Asn Ala Phe Arg Ala
         20                  25                  30

Lys Val His Glu Leu Ile Glu Arg Tyr Glu Val Asp Gln Gln Ile Gln
         35                  40                  45

Val Leu
    50
```

(2) INFORMATION FOR SEQ ID NO:94:

(i) SEQUENCE CHARACTERISTICS:
        (A) LENGTH: 50 amino acids
        (B) TYPE: amino acid
        (C) STRANDEDNESS:
        (D) TOPOLOGY: linear (xi) SEQUENCE DESCRIPTION: SEQ ID NO:94:

```
Asn Lys Phe Leu Asp Met Leu Ile Lys Lys Leu Lys Ser Phe Asp Tyr
1               5                  10                  15

His Gln Phe Val Asp Glu Thr Asn Asp Lys Ile Arg Glu Val Thr Gln
         20                  25                  30

Arg Leu Asn Gly Glu Ile Gln Ala Leu Glu Leu Pro Gln Lys Ala Glu
         35                  40                  45

Ala Leu
    50
```

(2) INFORMATION FOR SEQ ID NO:95:

(i) SEQUENCE CHARACTERISTICS:
        (A) LENGTH: 23 amino acids
        (B) TYPE: amino acid
        (C) STRANDEDNESS:
        (D) TOPOLOGY: linear (xi) SEQUENCE DESCRIPTION: SEQ ID NO:95:

```
Ser Asn Lys Ile Asn Ser Lys His Leu Arg Val Asn Gln Asn Leu Val
1               5                  10                  15

Tyr Glu Ser Gly Ser Leu Asn
         20
```

(2) INFORMATION FOR SEQ ID NO:96:

(i) SEQUENCE CHARACTERISTICS:
        (A) LENGTH: 47 amino acids
        (B) TYPE: amino acid
        (C) STRANDEDNESS:
        (D) TOPOLOGY: linear (xi) SEQUENCE DESCRIPTION: SEQ ID NO:96:

```
Phe Ser Lys Leu Glu Ile Gln Ser Gln Val Asp Ser Gln His Val Gly
1               5                   10                  15

His Ser Val Leu Thr Ala Lys Gly Met Ala Leu Phe Gly Glu Gly Gly
            20                  25                  30

Lys Ala Glu Phe Thr Gly Arg His Asp Ala His Leu Asn Gly Lys
            35                  40                  45
```

(2) INFORMATION FOR SEQ ID NO:97:

(i) SEQUENCE CHARACTERISTICS:
        (A) LENGTH: 50 amino acids
        (B) TYPE: amino acid
        (C) STRANDEDNESS:
        (D) TOPOLOGY: linear (xi) SEQUENCE DESCRIPTION: SEQ ID NO:97:

```
Val Lys Ala Gln Tyr Lys Lys Asn Lys His Arg His Ser Ile Thr Asn
1               5                   10                  15

Pro Leu Ala Val Leu Cys Glu Phe Ile Ser Gln Ser Ile Lys Ser Phe
            20                  25                  30

Asp Arg His Phe Glu Lys Asn Arg Asn Asn Ala Leu Asp Phe Val Thr
            35                  40                  45

Lys Ser
    50
```

(2) INFORMATION FOR SEQ ID NO:98:

(i) SEQUENCE CHARACTERISTICS:
        (A) LENGTH: 51 amino acids
        (B) TYPE: amino acid
        (C) STRANDEDNESS:
        (D) TOPOLOGY: linear (xi) SEQUENCE DESCRIPTION: SEQ ID NO:98:

```
Lys Leu Glu Gly Thr Thr Arg Leu Thr Arg Lys Arg Gly Leu Lys Leu
1               5                   10                  15

Ala Thr Ala Leu Ser Leu Ser Asn Lys Phe Val Glu Gly Ser His Asn
            20                  25                  30

Ser Thr Val Ser Leu Thr Thr Lys Asn Met Glu Val Ser Val Ala Lys
            35                  40                  45

Thr Thr Lys
    50
```

(2) INFORMATION FOR SEQ ID NO:99:

(i) SEQUENCE CHARACTERISTICS:
        (A) LENGTH: 51 amino acids
        (B) TYPE: amino acid
        (C) STRANDEDNESS:
        (D) TOPOLOGY: linear (xi) SEQUENCE DESCRIPTION: SEQ ID NO:99:

```
Lys Leu Asp Val Thr Thr Ser Ile Gly Arg Arg Gln His Leu Arg Val
1               5                   10                  15

Ser Thr Ala Phe Val Tyr Thr Lys Asn Pro Asn Gly Tyr Ser Phe Ser
            20                  25                  30

Ile Pro Val Lys Val Leu Ala Asp Lys Phe Ile Thr Pro Gly Leu Lys
            35                  40                  45

Leu Asn Asp
    50
```

(2) INFORMATION FOR SEQ ID NO:100:

(i) SEQUENCE CHARACTERISTICS:
        (A) LENGTH: 49 amino acids
        (B) TYPE: amino acid
        (C) STRANDEDNESS:
        (D) TOPOLOGY: linear (xi) SEQUENCE DESCRIPTION: SEQ ID NO:100:

```
Phe Arg Glu Ile Gln Ile Tyr Lys Lys Leu Arg Thr Ser Ser Phe Ala
1               5                   10                  15

Leu Asn Leu Pro Thr Leu Pro Glu Val Lys Phe Pro Glu Val Asp Val
            20                  25                  30

Leu Thr Lys Tyr Ser Gln Pro Glu Asp Ser Leu Ile Pro Phe Phe Glu
        35                  40                  45

Ile
```

(2) INFORMATION FOR SEQ ID NO:101:

(i) SEQUENCE CHARACTERISTICS:
        (A) LENGTH: 48 amino acids
        (B) TYPE: amino acid
        (C) STRANDEDNESS:
        (D) TOPOLOGY: linear (xi) SEQUENCE DESCRIPTION: SEQ ID NO:101:

```
Leu His Leu Arg Tyr Gln Lys Asp Lys Lys Gly Ile Ser Thr Ser Ala
1               5                   10                  15

Ala Ser Pro Ala Val Gly Thr Val Gly Met Asp Met Asp Glu Asp Asp
            20                  25                  30

Asp Phe Ser Lys Trp Asn Phe Tyr Tyr Ser Pro Gln Ser Ser Pro Asp
        35                  40                  45
```

(2) INFORMATION FOR SEQ ID NO:102:

(i) SEQUENCE CHARACTERISTICS:
        (A) LENGTH: 48 amino acids
        (B) TYPE: amino acid
        (C) STRANDEDNESS:
        (D) TOPOLOGY: linear (xi) SEQUENCE DESCRIPTION: SEQ ID NO:102:

```
Leu Arg Glu Val Ser Ser Lys Leu Arg Arg Asn Leu Gln Asn Asn Ala
1               5                   10                  15

Glu Trp Val Tyr Gln Gly Ala Ile Arg Gln Ile Asp Asp Ile Asp Val
            20                  25                  30

Arg Phe Gln Lys Ala Ala Ser Gly Thr Thr Gly Thr Tyr Gln Glu Trp
        35                  40                  45
```

(2) INFORMATION FOR SEQ ID NO:103:

(i) SEQUENCE CHARACTERISTICS:
        (A) LENGTH: 50 amino acids
        (B) TYPE: amino acid
        (C) STRANDEDNESS:
        (D) TOPOLOGY: linear (xi) SEQUENCE DESCRIPTION: SEQ ID NO:103:

```
Arg Val Thr Gln Lys Phe His Met Lys Val Lys His Leu Ile Asp Ser
1               5                   10                  15

Leu Ile Asp Phe Leu Asn Phe Pro Arg Phe Gln Phe Pro Gly Lys Pro
            20                  25                  30
```

```
Gly Ile Tyr Thr Arg Glu Glu Leu Cys Thr Met Phe Ile Arg Glu Val
        35                  40                  45

Gly Thr
    50
```

(2) INFORMATION FOR SEQ ID NO:104:

(i) SEQUENCE CHARACTERISTICS:
        (A) LENGTH: 49 amino acids
        (B) TYPE: amino acid
        (C) STRANDEDNESS:
        (D) TOPOLOGY: linear (xi) SEQUENCE DESCRIPTION: SEQ ID NO:104:

```
Trp Lys His Ala Gly Lys Gln Asp Phe Arg Glu Ser Gln Asp Ala Ala
1               5                   10                  15

Ala Phe Phe Lys Ala Trp Ala Ile Phe Lys Gly Lys Tyr Lys Glu Gly
            20                  25                  30

Asp Lys Glu Val Pro Glu Arg Gly Arg Met Asp Val Ala Glu Pro Tyr
        35                  40                  45

Lys
```

(2) INFORMATION FOR SEQ ID NO:105:

(i) SEQUENCE CHARACTERISTICS:
        (A) LENGTH: 48 amino acids
        (B) TYPE: amino acid
        (C) STRANDEDNESS:
        (D) TOPOLOGY: linear (xi) SEQUENCE DESCRIPTION: SEQ ID NO:105:

```
Glu His Val Lys His Phe Val Ile Asn Leu Ile Gly Asp Phe Glu Val
1               5                   10                  15

Ala Glu Lys Ile Asn Ala Phe Arg Ala Lys Val His Glu Leu Ile Glu
            20                  25                  30

Arg Tyr Glu Val Asp Gln Gln Ile Gln Val Leu Met Asp Lys Leu Val
        35                  40                  45
```

(2) INFORMATION FOR SEQ ID NO:106:

(i) SEQUENCE CHARACTERISTICS:
        (A) LENGTH: 52 amino acids
        (B) TYPE: amino acid
        (C) STRANDEDNESS:
        (D) TOPOLOGY: linear (xi) SEQUENCE DESCRIPTION: SEQ ID NO:106:

```
Val Arg Lys Tyr Arg Ala Ala Leu Gly Lys Leu Pro Gln Gln Ala Asn
1               5                   10                  15

Asp Tyr Leu Asn Ser Phe Asn Trp Glu Arg Gln Val Ser His Ala Lys
            20                  25                  30

Glu Lys Leu Thr Ala Leu Thr Lys Lys Tyr Arg Ile Thr Glu Asn Asp
        35                  40                  45

Ile Gln Ile Ala
    50
```

(2) INFORMATION FOR SEQ ID NO:107:

(i) SEQUENCE CHARACTERISTICS:
        (A) LENGTH: 57 amino acids
        (B) TYPE: amino acid
        (C) STRANDEDNESS:
        (D) TOPOLOGY: linear (xi) SEQUENCE DESCRIPTION: SEQ ID NO:107:

Tyr Ile Lys Asp Ser Tyr Asp Leu His Asp Leu Lys Ile Ala Ile Ala
1               5                   10                  15

Asn Ile Ile Asp Glu Ile Ile Glu Lys Leu Lys Ser Leu Asp Glu His
                20                  25                  30

Tyr His Ile Arg Val Asn Leu Val Lys Thr Ile His Asp Leu His Leu
            35                  40                  45

Phe Ile Glu Asn Ile Asp Phe Asn Lys
        50                  55

(2) INFORMATION FOR SEQ ID NO:108:

(i) SEQUENCE CHARACTERISTICS:
        (A) LENGTH: 33 amino acids
        (B) TYPE: amino acid
        (C) STRANDEDNESS:
        (D) TOPOLOGY: linear (xi) SEQUENCE DESCRIPTION: SEQ ID NO:108:

Lys Ile Thr Leu Ile Ile Asn Trp Leu Gln Glu Ala Leu Ser Ser Ala
1               5                   10                  15

Ser Leu Ala His Met Lys Ala Lys Phe Arg Glu Thr Leu Glu Asp Thr
                20                  25                  30

Arg (2) INFORMATION FOR SEQ ID NO:109:

(i) SEQUENCE CHARACTERISTICS:
        (A) LENGTH: 32 amino acids
        (B) TYPE: amino acid
        (C) STRANDEDNESS:
        (D) TOPOLOGY: linear (xi) SEQUENCE DESCRIPTION: SEQ ID NO:109:

Thr Asp His Phe Ser Leu Arg Ala Arg Tyr His Met Lys Ala Asp Ser
1               5                   10                  15

Val Val Asp Leu Ser Tyr Asn Val Gln Gly Ser Gly Glu Thr Thr Tyr
                20                  25                  30

(2) INFORMATION FOR SEQ ID NO:110:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO:110:

Lys Leu Thr Thr Asn Gly Arg Phe Arg Glu His Asn Ala Lys Phe Ser
1               5                   10                  15

Leu Asp Gly Lys
            20

(2) INFORMATION FOR SEQ ID NO:111:

(i) SEQUENCE CHARACTERISTICS:
        (A) LENGTH: 52 amino acids
        (B) TYPE: amino acid
        (C) STRANDEDNESS:
        (D) TOPOLOGY: linear (xi) SEQUENCE DESCRIPTION: SEQ ID NO:111:

```
Asp Thr Lys Tyr Gln Ile Arg Ile Gln Ile Gln Glu Lys Leu Gln Gln
  1               5                  10                  15

Leu Lys Arg His Ile Gln Asn Ile Asp Ile Gln His Leu Ala Gly Lys
                 20                  25                  30

Leu Lys Gln His Ile Glu Ala Ile Asp Val Arg Val Leu Leu Asp Gln
                 35                  40                  45

Leu Gly Thr Thr
             50
```

(2) INFORMATION FOR SEQ ID NO:112:

(i) SEQUENCE CHARACTERISTICS:
        (A) LENGTH: 45 amino acids
        (B) TYPE: amino acid
        (C) STRANDEDNESS:
        (D) TOPOLOGY: linear (xi) SEQUENCE DESCRIPTION: SEQ ID NO:112:

```
Phe His Asp Phe Pro Asp Leu Gly Gln Glu Val Ala Leu Asn Ala Asn
  1               5                  10                  15

Thr Lys Asn Gln Lys Ile Arg Trp Lys Asn Glu Val Arg Ile His Ser
                 20                  25                  30

Gly Ser Phe Gln Ser Gln Val Glu Leu Ser Asn Asp Gln
                 35                  40                  45
```

(2) INFORMATION FOR SEQ ID NO:113:

(i) SEQUENCE CHARACTERISTICS:
        (A) LENGTH: 34 amino acids
        (B) TYPE: amino acid
        (C) STRANDEDNESS:
        (D) TOPOLOGY: linear (xi) SEQUENCE DESCRIPTION: SEQ ID NO:113:

```
Lys Asp Asn Val Phe Asp Gly Leu Val Arg Val Thr Gln Lys Phe His
  1               5                  10                  15

Met Lys Val Lys His Leu Ile Asp Ser Leu Ile Asp Phe Leu Asn Phe
                 20                  25                  30

Pro Arg
```

(2) INFORMATION FOR SEQ ID NO:114:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:114:

```
His Arg Asn Ile Gln Glu Tyr Leu Ser Ile Leu Thr Asp Pro Asp Gly
  1               5                  10                  15

Lys Gly Lys Glu Lys Ile Ala Glu Leu Ser Ala Thr Ala Gln Glu Ile
                 20                  25                  30

Ile Lys Ser
         35
```

(2) INFORMATION FOR SEQ ID NO:115:

(i) SEQUENCE CHARACTERISTICS:
        (A) LENGTH: 210 amino acids
        (B) TYPE: amino acid
        (C) STRANDEDNESS:
        (D) TOPOLOGY: linear (xi) SEQUENCE DESCRIPTION: SEQ ID NO:115:

```
Glu Phe Thr Ile Val Ala Phe Val Lys Tyr Asp Lys Asn Gln Asp Val
1               5                   10                  15

His Ser Ile Asn Leu Pro Phe Phe Glu Thr Leu Gln Glu Tyr Phe Glu
            20                  25                  30

Arg Asn Arg Gln Thr Ile Val Val Glu Asn Val Gln Arg Asn Leu
        35                  40                  45

Lys His Ile Asn Ile Asp Gln Phe Val Arg Lys Tyr Arg Ala Ala Leu
    50                  55                  60

Gly Lys Leu Pro Gln Gln Ala Asn Asp Tyr Leu Asn Ser Phe Asn Trp
65                  70                  75                  80

Glu Arg Gln Val Ser His Ala Lys Glu Lys Leu Thr Ala Leu Thr Lys
                85                  90                  95

Lys Tyr Arg Ile Thr Glu Asn Asp Ile Gln Ile Ala Leu Asp Asp Ala
                100                 105                 110

Lys Ile Asn Phe Asn Glu Lys Leu Ser Gln Leu Gln Thr Tyr Met Ile
            115                 120                 125

Gln Phe Asp Gln Tyr Ile Lys Asp Ser Tyr Asp Leu His Asp Leu Lys
    130                 135                 140

Ile Ala Ile Ala Asn Ile Ile Asp Glu Ile Ile Glu Lys Leu Lys Ser
145                 150                 155                 160

Leu Asp Glu His Tyr His Ile Arg Val Asn Leu Val Lys Thr Ile His
                165                 170                 175

Asp Leu His Leu Phe Ile Glu Asn Ile Asp Phe Asn Lys Ser Gly Ser
            180                 185                 190

Ser Thr Ala Ser Trp Ile Gln Asn Val Asp Thr Lys Tyr Gln Ile Arg
        195                 200                 205

Ile Gln
    210
```

(2) INFORMATION FOR SEQ ID NO:116:

(i) SEQUENCE CHARACTERISTICS:
        (A) LENGTH: 174 amino acids
        (B) TYPE: amino acid
        (C) STRANDEDNESS:
        (D) TOPOLOGY: linear (xi) SEQUENCE DESCRIPTION: SEQ ID NO:116:

```
Gly Pro Leu Pro Thr Leu Val Ser Gly Gly Thr Ile Leu Ala Thr Val
1               5                   10                  15

Pro Leu Val Val Asp Ala Glu Lys Leu Pro Ile Asn Arg Leu Ala Ala
            20                  25                  30

Gly Ser Lys Ala Pro Ala Ser Ala Gln Ser Arg Gly Glu Lys Arg Thr
        35                  40                  45

Ala His Asn Ala Ile Glu Lys Arg Tyr Arg Ser Ser Ile Asn Asp Lys
    50                  55                  60

Ile Ile Glu Leu Lys Asp Leu Val Val Gly Thr Glu Ala Lys Leu Asn
65                  70                  75                  80

Lys Ser Ala Val Leu Arg Lys Ala Ile Asp Tyr Ile Arg Phe Leu Gln
                85                  90                  95

His Ser Asn Gln Lys Leu Lys Gln Glu Asn Leu Ser Leu Arg Thr Ala
                100                 105                 110

Val His Lys Ser Lys Ser Leu Lys Asp Leu Val Ser Ala Cys Gly Ser
            115                 120                 125
```

```
Gly Gly Asn Thr Asp Val Leu Met Glu Gly Val Lys Thr Glu Val Glu
        130                 135                 140

Asp Thr Leu Thr Pro Pro Ser Asp Ala Gly Ser Pro Phe Gln Ser
145                 150                 155                 160

Ser Pro Leu Ser Leu Gly Ser Arg Gly Ser Gly Ser Gly Gly
                165                 170
```

(2) INFORMATION FOR SEQ ID NO:117:

(i) SEQUENCE CHARACTERISTICS:
        (A) LENGTH: 172 amino acids
        (B) TYPE: amino acid
        (C) STRANDEDNESS:
        (D) TOPOLOGY: linear (xi) SEQUENCE DESCRIPTION: SEQ ID NO:117:

```
Gln Val Pro Thr Leu Val Gly Ser Ser Gly Thr Ile Leu Thr Thr Met
1               5                   10                  15

Pro Val Met Met Gly Gln Glu Lys Val Pro Ile Lys Gln Val Pro Gly
                20                  25                  30

Gly Val Lys Gln Leu Glu Pro Pro Lys Glu Gly Glu Arg Arg Thr Thr
            35                  40                  45

His Asn Ile Ile Glu Lys Arg Tyr Arg Ser Ser Ile Asn Asp Lys Ile
        50                  55                  60

Ile Glu Leu Lys Asp Leu Val Met Gly Thr Asp Ala Lys Met His Lys
65                  70                  75                  80

Ser Gly Val Leu Arg Lys Ala Ile Asp Tyr Ile Lys Tyr Leu Gln Gln
                85                  90                  95

Val Asn His Lys Leu Arg Gln Glu Asn Met Val Leu Lys Leu Ala Asn
                100                 105                 110

Gln Lys Asn Lys Leu Leu Lys Gly Ile Asp Leu Gly Ser Leu Val Asp
            115                 120                 125

Asn Glu Val Asp Leu Lys Ile Glu Asp Phe Asn Gln Asn Val Leu Leu
130                 135                 140

Met Ser Pro Pro Ala Ser Asp Ser Gly Ser Gln Ala Gly Phe Ser Pro
145                 150                 155                 160

Tyr Ser Ile Asp Ser Glu Pro Gly Ser Pro Leu Leu
                165                 170
```

(2) INFORMATION FOR SEQ ID NO:118:

(i) SEQUENCE CHARACTERISTICS:
        (A) LENGTH: 173 amino acids
        (B) TYPE: amino acid
        (C) STRANDEDNESS:
        (D) TOPOLOGY: linear (xi) SEQUENCE DESCRIPTION: SEQ ID NO:118:

```
Gly Pro Leu Gln Thr Leu Val Ser Gly Thr Ile Leu Ala Thr Val
1               5                   10                  15

Pro Leu Val Val Asp Thr Asp Lys Leu Pro Ile His Arg Leu Ala Ala
                20                  25                  30

Gly Gly Lys Ala Leu Gly Ser Ala Gln Ser Arg Gly Glu Lys Arg Thr
            35                  40                  45

Ala His Asn Ala Ile Glu Lys Arg Tyr Arg Ser Ser Ile Asn Asp Lys
        50                  55                  60

Ile Val Glu Leu Lys Asp Leu Val Val Gly Thr Glu Ala Lys Leu Asn
65                  70                  75                  80
```

```
Lys Ser Ala Val Leu Arg Lys Ala Ile Asp Tyr Ile Arg Phe Leu Gln
                85                  90                  95

His Ser Asn Gln Lys Leu Lys Gln Glu Asn Leu Thr Leu Arg Ser Ala
            100                 105                 110

His Lys Ser Lys Ser Leu Lys Asp Leu Val Ser Ala Cys Gly Ser Gly
        115                 120                 125

Gly Gly Thr Asp Val Ser Met Glu Gly Met Lys Pro Glu Val Val Glu
    130                 135                 140

Thr Leu Thr Pro Pro Ser Asp Ala Gly Ser Pro Ser Gln Ser Ser
145                 150                 155                 160

Pro Leu Ser Leu Gly Ser Arg Gly Ser Ser Gly Gly
                165                 170
```

(2) INFORMATION FOR SEQ ID NO:119:

(i) SEQUENCE CHARACTERISTICS:
        (A) LENGTH: 243 amino acids
        (B) TYPE: amino acid
        (C) STRANDEDNESS:
        (D) TOPOLOGY: linear (xi) SEQUENCE DESCRIPTION: SEQ ID NO:119:

```
Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
    130                 135                 140

Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
            180                 185                 190

His Ala Lys Ala Thr Glu His Leu Ser Thr Leu Ser Glu Lys Ala Lys
        195                 200                 205

Pro Ala Leu Glu Asp Leu Arg Gln Gly Leu Leu Pro Val Leu Glu Ser
    210                 215                 220

Phe Lys Val Ser Phe Leu Ser Ala Leu Glu Glu Tyr Thr Lys Lys Leu
225                 230                 235                 240

Asn Thr Gln
```

(2) INFORMATION FOR SEQ ID NO:120:

(i) SEQUENCE CHARACTERISTICS:
        (A) LENGTH: 269 amino acids
        (B) TYPE: amino acid
        (C) STRANDEDNESS:
        (D) TOPOLOGY: linear (xi) SEQUENCE DESCRIPTION: SEQ ID NO:120:

Gln Gln Val Pro Val Leu Leu Gln Pro His Phe Ile Lys Ala Asp Ser
1               5                   10                  15

Leu Leu Leu Thr Ala Met Lys Thr Asp Gly Ala Thr Val Lys Ala Ala
                20                  25                  30

Gly Leu Ser Pro Leu Val Ser Gly Thr Thr Val Gln Thr Gly Pro Leu
            35                  40                  45

Pro Thr Leu Val Ser Gly Gly Thr Ile Leu Ala Thr Val Pro Leu Val
    50                  55                  60

Val Asp Ala Glu Lys Leu Pro Ile Asn Arg Leu Ala Ala Gly Ser Lys
65                  70                  75                  80

Ala Pro Ala Ser Ala Gln Ser Arg Gly Glu Lys Arg Thr Ala His Asn
                85                  90                  95

Ala Ile Glu Lys Arg Tyr Arg Ser Ser Ile Asn Asp Lys Ile Ile Glu
                100                 105                 110

Leu Lys Asp Leu Val Val Gly Thr Glu Ala Lys Leu Asn Lys Ser Ala
            115                 120                 125

Val Leu Arg Lys Ala Ile Asp Tyr Ile Arg Phe Leu Gln His Ser Asn
130                 135                 140

Gln Lys Leu Lys Gln Glu Asn Leu Ser Leu Arg Thr Ala Val His Lys
145                 150                 155                 160

Ser Lys Ser Leu Lys Asp Leu Val Ser Ala Cys Gly Ser Gly Gly Asn
                165                 170                 175

Thr Asp Val Leu Met Glu Gly Val Lys Thr Glu Val Glu Asp Thr Leu
                180                 185                 190

Thr Pro Pro Pro Ser Asp Ala Gly Ser Pro Phe Gln Ser Ser Pro Leu
            195                 200                 205

Ser Leu Gly Ser Arg Gly Ser Gly Ser Gly Gly Ser Gly Ser Asp Ser
210                 215                 220

Glu Pro Asp Ser Pro Val Phe Glu Asp Ser Lys Ala Lys Pro Glu Gln
225                 230                 235                 240

Arg Pro Ser Leu His Ser Arg Gly Met Leu Asp Arg Ser Arg Leu Leu
                245                 250                 255

Ala Leu Cys Thr Leu Val Phe Leu Cys Leu Ser Cys Asn
                260                 265

(2) INFORMATION FOR SEQ ID NO:121:

(i) SEQUENCE CHARACTERISTICS:
        (A) LENGTH: 77 amino acids
        (B) TYPE: amino acid
        (C) STRANDEDNESS:
        (D) TOPOLOGY: linear (xi) SEQUENCE DESCRIPTION: SEQ ID NO:121:

Gln Ala Lys Glu Pro Cys Val Glu Ser Leu Val Ser Gln Tyr Phe Gln
1               5                   10                  15

Thr Val Thr Asp Tyr Gly Lys Asp Leu Met Glu Lys Val Lys Ser Pro
                20                  25                  30

Glu Leu Gln Ala Glu Ala Lys Ser Tyr Phe Glu Lys Ser Lys Glu Gln
            35                  40                  45

Leu Thr Pro Leu Ile Lys Lys Ala Gly Thr Glu Leu Val Asn Phe Leu
    50                  55                  60

Ser Tyr Phe Val Glu Leu Gly Thr Gln Pro Ala Thr Gln
65                  70                  75

(2) INFORMATION FOR SEQ ID NO:122:

(i) SEQUENCE CHARACTERISTICS:
        (A) LENGTH: 71 amino acids
        (B) TYPE: amino acid
        (C) STRANDEDNESS:
        (D) TOPOLOGY: linear (xi) SEQUENCE DESCRIPTION: SEQ ID NO:122:

Glu Ala Lys Leu Asn Lys Ser Ala Val Leu Arg Lys Ala Ile Asp Tyr
1               5                   10                  15

Ile Arg Phe Leu Gln His Ser Asn Gln Lys Leu Lys Gln Glu Asn Leu
                20                  25                  30

Ser Leu Arg Thr Ala Val His Lys Ser Lys Ser Leu Lys Asp Leu Val
            35                  40                  45

Ser Ala Cys Gly Ser Gly Gly Asn Thr Asp Val Leu Met Glu Gly Val
    50                  55                  60

Lys Thr Glu Val Glu Asp Thr
65                  70

(2) INFORMATION FOR SEQ ID NO:123:

(i) SEQUENCE CHARACTERISTICS:
        (A) LENGTH: 397 amino acids
        (B) TYPE: amino acid
        (C) STRANDEDNESS:
        (D) TOPOLOGY: linear (xi) SEQUENCE DESCRIPTION: SEQ ID NO:123:

Gln Lys Ser Glu Leu Thr Gln Gln Leu Asn Ala Leu Phe Gln Asp Lys
1               5                   10                  15

Leu Gly Glu Val Asn Thr Tyr Ala Gly Asp Leu Gln Lys Lys Leu Val
                20                  25                  30

Pro Phe Ala Thr Glu Leu His Glu Arg Leu Ala Lys Asp Ser Glu Lys
            35                  40                  45

Leu Lys Glu Glu Ile Gly Lys Glu Leu Glu Glu Leu Arg Ala Arg Leu
    50                  55                  60

Leu Pro His Ala Asn Glu Val Ser Gln Lys Ile Gly Asp Asn Leu Arg
65                  70                  75                  80

Glu Leu Gln Gln Arg Leu Glu Pro Tyr Ala Asp Gln Leu Arg Thr Gln
                85                  90                  95

Val Asn Thr Gln Ala Glu Gln Leu Arg Arg Gln Leu Asp Pro Leu Ala
                100                 105                 110

Gln Arg Met Glu Arg Val Leu Arg Glu Asn Ala Asp Ser Leu Gln Ala
            115                 120                 125

Ser Leu Arg Pro His Ala Asp Glu Leu Lys Ala Lys Ile Asp Gln Asn
    130                 135                 140

Val Glu Glu Leu Lys Gly Arg Leu Thr Pro Tyr Ala Asp Glu Phe Lys
145                 150                 155                 160

Val Lys Ile Asp Gln Thr Val Glu Glu Leu Arg Arg Ser Leu Ala Pro
                165                 170                 175

Tyr Ala Gln Asp Thr Gln Glu Lys Leu Asn His Gln Leu Glu Gly Leu
                180                 185                 190

-continued

```
Thr Phe Gln Met Lys Lys Asn Ala Glu Glu Leu Lys Ala Arg Ile Ser
            195                 200                 205

Ala Ser Ala Glu Ile Asp Gln Thr Val Glu Glu Leu Arg Arg Ser Leu
210                 215                 220

Ala Pro Tyr Ala Gln Asp Thr Gln Glu Lys Leu Asn His Gln Leu Glu
225                 230                 235                 240

Gly Leu Thr Phe Gln Met Lys Lys Asn Ala Glu Glu Leu Lys Ala Arg
            245                 250                 255

Ile Ser Ala Ser Ala Glu Glu Leu Arg Gln Arg Leu Ala Pro Leu Ala
            260                 265                 270

Glu Asp Val Arg Gly Asn Leu Lys Gly Asn Thr Glu Gly Leu Gln Lys
            275                 280                 285

Ser Leu Ala Glu Leu Gly Gly His Leu Asp Gln Gln Val Glu Glu Phe
290                 295                 300

Arg Arg Arg Val Glu Pro Tyr Gly Glu Asn Phe Asn Lys Ala Leu Val
305                 310                 315                 320

Gln Gln Met Glu Gln Leu Arg Gln Lys Leu Gly Pro His Ala Gly Asp
            325                 330                 335

Val Glu Gly His Leu Ser Phe Leu Glu Lys Asp Leu Arg Asp Lys Val
            340                 345                 350

Asn Ser Phe Phe Ser Thr Phe Lys Glu Lys Glu Ser Gln Asp Lys Thr
            355                 360                 365

Leu Ser Leu Pro Glu Leu Glu Gln Gln Gln Glu Gln Gln Gln Glu Gln
            370                 375                 380

Gln Gln Glu Gln Val Gln Met Leu Ala Pro Leu Glu Ser
385                 390                 395

(2) INFORMATION FOR SEQ ID NO:124:

(i) SEQUENCE CHARACTERISTICS:
        (A) LENGTH: 412 amino acids
        (B) TYPE: amino acid
        (C) STRANDEDNESS:
        (D) TOPOLOGY: linear (xi) SEQUENCE DESCRIPTION: SEQ ID NO:124:

Glu Lys Leu Pro Ile Asn Arg Leu Ala Ala Gly Ser Lys Ala Pro Ala
1               5                   10                  15

Ser Ala Gln Ser Arg Gly Glu Lys Arg Thr Ala His Asn Ala Ile Glu
            20                  25                  30

Lys Arg Tyr Arg Ser Ser Ile Asn Asp Lys Ile Ile Glu Leu Lys Asp
            35                  40                  45

Leu Val Val Gly Thr Glu Ala Lys Leu Asn Lys Ser Ala Val Leu Arg
        50                  55                  60

Lys Ala Ile Asp Tyr Ile Arg Phe Leu Gln His Ser Asn Gln Lys Leu
65                  70                  75                  80

Lys Gln Glu Asn Leu Ser Leu Arg Thr Ala Val His Lys Ser Lys Ser
            85                  90                  95

Leu Lys Asp Leu Val Ser Ala Cys Gly Ser Gly Gly Asn Thr Asp Val
            100                 105                 110

Leu Met Glu Gly Val Lys Thr Glu Val Glu Asp Thr Leu Thr Pro Pro
            115                 120                 125

Pro Ser Asp Ala Lys Pro Phe Gln Ser Ser Pro Leu Ser Leu Lys Arg
            130                 135                 140

Lys Lys Gly Lys Lys Asp Ser Glu Pro Asp Ser Pro Val Phe Glu Asp
```

```
                    145                 150                 155                 160
Ser Lys Ala Lys Pro Glu Gln Arg Pro Ser Leu His Ser Arg Gly Met
                165                 170                 175

Leu Asp Arg Ser Arg Leu Ala Leu Cys Thr Leu Val Phe Leu Cys Leu
            180                 185                 190

Ser Cys Asn Pro Leu Ala Ser Leu Leu Gly Ala Arg Gly Leu Pro Ser
        195                 200                 205

Pro Ser Asp Thr Thr Ser Val Tyr His Ser Pro Gly Arg Asn Val Leu
    210                 215                 220

Gly Thr Glu Arg Asp Gly Pro Gly Trp Ala Gln Ala Val Gln Leu Phe
225                 230                 235                 240

Leu Cys Asp Leu Leu Leu Val Ala Thr Ser Leu Trp Arg Gln Gln Gln
                245                 250                 255

Pro Pro Ala Pro Ala Pro Ala Gln Gly Ala Ser Ser Arg Pro Gln
            260                 265                 270

Ala Ser Ala Leu Glu Ile Arg Gly Phe Gln Arg Asp Leu Ser Ser Leu
        275                 280                 285

Arg Arg Leu Ala Gln Ser Phe Arg Pro Ala Met Arg Arg Val Phe Leu
    290                 295                 300

His Glu Ala Thr Ala Arg Leu Met Ala Gly Ala Ser Pro Thr Arg Thr
305                 310                 315                 320

His Gln Leu Leu Asp Arg Ser Leu Arg Arg Ala Gly Pro Gly Gly
                325                 330                 335

Lys Gly Gly Ala Ala Glu Leu Glu Pro Arg Pro Thr Arg Arg Glu His
            340                 345                 350

Ala Glu Ala Leu Leu Leu Ala Ser Cys Tyr Leu Pro Pro Gly Phe Leu
        355                 360                 365

Ser Ala Pro Gly Gln Arg Val Gly Met Leu Ala Glu Ala Arg Thr Leu
    370                 375                 380

Glu Lys Leu Gly Asp Arg Arg Leu Leu His Asp Cys Gln Gln Met Leu
385                 390                 395                 400

Met Arg Leu Gly Gly Gly Thr Thr Val Thr Ser Ser
                405                 410

(2) INFORMATION FOR SEQ ID NO:125:

(i) SEQUENCE CHARACTERISTICS:
        (A) LENGTH: 124 amino acids
        (B) TYPE: amino acid
        (C) STRANDEDNESS:
        (D) TOPOLOGY: linear (xi) SEQUENCE DESCRIPTION: SEQ ID NO:125:

Glu Lys Met Ser Leu Arg Asn Arg Leu Ser Lys Ser Arg Glu Asn Pro
1               5                   10                  15

Glu Glu Asp Glu Asp Gln Arg Asn Pro Ala Lys Glu Ser Leu Glu Thr
            20                  25                  30

Pro Ser Asn Gly Arg Ile Asp Ile Lys Gln Leu Ile Ala Lys Lys Ile
        35                  40                  45

Lys Leu Thr Ala Glu Asn Gly Arg Ile Asp Ile Lys Gln Leu Ile Ala
    50                  55                  60

Lys Lys Ile Lys Leu Thr Ala Glu Ala Glu Glu Leu Lys Pro Phe Phe
65                  70                  75                  80

Met Lys Glu Val Gly Ser His Phe Asp Asp Phe Val Thr Asn Leu Ile
                85                  90                  95
```

```
Glu Lys Ser Ala Ser Leu Asp Asn Lys Ala His Ser Phe Val Arg Glu
            100                 105                 110

Asn Val Pro Arg Val Leu Asn Ser Ala Lys Glu Lys
            115                 120
```

(2) INFORMATION FOR SEQ ID NO:126:

(i) SEQUENCE CHARACTERISTICS:
        (A) LENGTH: 135 amino acids
        (B) TYPE: amino acid
        (C) STRANDEDNESS:
        (D) TOPOLOGY: linear (xi) SEQUENCE DESCRIPTION: SEQ ID NO:126:

```
Glu Lys Leu Pro Ile Asn Arg Leu Ala Ala Gly Ser Lys Ala Pro Ala
1               5                   10                  15

Ser Ala Gln Ser Arg Gly Glu Lys Arg Thr Ala His Asn Ala Ile Glu
            20                  25                  30

Lys Arg Tyr Arg Ser Ser Ile Asn Asp Lys Ile Ile Glu Leu Lys Asp
            35                  40                  45

Leu Val Val Gly Thr Glu Ala Lys Leu Asn Lys Ser Tyr Ile Arg Phe
50                  55                  60

Leu Gln His Ser Asn Gln Lys Leu Lys Gln Glu Asn Leu Ser Leu Arg
65                  70                  75                  80

Thr Ala Val His Lys Ser Lys Ser Leu Lys Asp Leu Val Ser Ala Cys
            85                  90                  95

Gly Ser Gly Gly Asn Thr Asp Val Leu Met Glu Gly Val Lys Thr Glu
            100                 105                 110

Val Glu Asp Lys Ala Lys Pro Glu Gln Arg Pro Ser Leu His Ser Arg
            115                 120                 125

Gly Met Leu Asp Arg Ser Arg
130                 135
```

(2) INFORMATION FOR SEQ ID NO:127:

(i) SEQUENCE CHARACTERISTICS:
        (A) LENGTH: 26 amino acids
        (B) TYPE: amino acid
        (C) STRANDEDNESS:
        (D) TOPOLOGY: linear (xi) SEQUENCE DESCRIPTION: SEQ ID NO:127:

```
Arg Arg His Cys Pro Leu Lys Asn Pro Thr Phe Leu Asp Tyr Val Arg
1               5                   10                  15

Pro Arg Ser Trp Thr Cys Arg Tyr Val Phe
            20                  25
```

(2) INFORMATION FOR SEQ ID NO:128:

(i) SEQUENCE CHARACTERISTICS:
        (A) LENGTH: 25 amino acids
        (B) TYPE: amino acid
        (C) STRANDEDNESS:
        (D) TOPOLOGY: linear (xi) SEQUENCE DESCRIPTION: SEQ ID NO:128:

```
Arg Arg Arg Ala Gly Pro Gly Gly Lys Gly Gly Ala Val Ala Glu Leu
1               5                   10                  15

Glu Pro Arg Pro Thr Arg Arg Glu His
            20                  25
```

(2) INFORMATION FOR SEQ ID NO:129:

(i) SEQUENCE CHARACTERISTICS:
        (A) LENGTH: 114 amino acids
        (B) TYPE: amino acid
        (C) STRANDEDNESS:
        (D) TOPOLOGY: linear (xi) SEQUENCE DESCRIPTION: SEQ ID NO:129:

```
Ala Met Leu Gly Gln Ser Thr Glu Glu Leu Arg Val Arg Leu Ala Ser
 1               5                  10                  15

His Leu Arg Lys Leu Arg Lys Arg Leu Leu Arg Asp Ala Asp Asp Leu
             20                  25                  30

Gln Lys Arg Leu Ala Val Tyr Gln Ala Gly Ala Arg Glu Gly Ala Glu
         35                  40                  45

Arg Gly Leu Ser Ala Ile Arg Glu Arg Leu Gly Pro Leu Val Glu Gln
 50                  55                  60

Gly Arg Val Arg Ala Ala Thr Val Gly Ser Leu Ala Gly Gln Pro Leu
 65                  70                  75                  80

Gln Glu Arg Ala Gln Ala Trp Gly Glu Arg Leu Arg Ala Arg Met Glu
             85                  90                  95

Glu Met Gly Ser Arg Thr Arg Asp Arg Leu Asp Glu Val Lys Glu Gln
            100                 105                 110

Val Ala
```

(2) INFORMATION FOR SEQ ID NO:130:

(i) SEQUENCE CHARACTERISTICS:
        (A) LENGTH: 107 amino acids
        (B) TYPE: amino acid
        (C) STRANDEDNESS:
        (D) TOPOLOGY: linear (xi) SEQUENCE DESCRIPTION: SEQ ID NO:130:

```
Lys Leu Pro Ile Asn Arg Leu Ala Ala Gly Ser Lys Ala Pro Ala Ser
 1               5                  10                  15

Ala Gln Ser Arg Gly Glu Lys Arg Thr Ala His Asn Ala Ile Glu Lys
             20                  25                  30

Arg Tyr Arg Ser Ser Ile Asn Asp Lys Ile Ile Glu Leu Lys Asp Leu
         35                  40                  45

Val Val Gly Thr Glu Ala Lys Leu Asn Lys Ser Ala Val Leu Arg Lys
 50                  55                  60

Ala Ile Asp Tyr Ile Arg Phe Leu Gln His Ser Asn Gln Lys Leu Lys
 65                  70                  75                  80

Gln Glu Asn Leu Ser Leu Arg Thr Ala Val His Lys Ser Lys Ser Leu
             85                  90                  95

Lys Asp Leu Val Ser Ala Cys Gly Ser Gly Gly
            100                 105
```

(2) INFORMATION FOR SEQ ID NO:131:

(i) SEQUENCE CHARACTERISTICS:
        (A) LENGTH: 42 amino acids
        (B) TYPE: amino acid
        (C) STRANDEDNESS:
        (D) TOPOLOGY: linear (xi) SEQUENCE DESCRIPTION: SEQ ID NO:131:

```
Thr Gln Gln Pro Gln Gln Asp Glu Met Pro Ser Pro Thr Phe Leu Thr
 1               5                  10                  15
```

```
Gln Val Lys Glu Ser Leu Ser Ser Tyr Trp Glu Ser Ala Lys Thr Ala
            20                  25                  30
Ala Gln Asn Leu Tyr Glu Lys Thr Tyr Leu
            35                  40
```

(2) INFORMATION FOR SEQ ID NO:132:

(i) SEQUENCE CHARACTERISTICS:
        (A) LENGTH: 45 amino acids
        (B) TYPE: amino acid
        (C) STRANDEDNESS:
        (D) TOPOLOGY: linear (xi) SEQUENCE DESCRIPTION: SEQ ID NO:132:

```
Ser Gln Ile Gln Gln Val Pro Val Leu Leu Gln Pro His Phe Ile Lys
1               5                   10                  15
Ala Asp Ser Leu Leu Leu Thr Ala Met Lys Thr Asp Gly Ala Thr Val
            20                  25                  30
Lys Ala Ala Gly Leu Ser Pro Leu Val Ser Gly Thr Thr
            35                  40                  45
```

(2) INFORMATION FOR SEQ ID NO:133:

(i) SEQUENCE CHARACTERISTICS:
        (A) LENGTH: 45 amino acids
        (B) TYPE: amino acid
        (C) STRANDEDNESS:
        (D) TOPOLOGY: linear (xi) SEQUENCE DESCRIPTION: SEQ ID NO:133:

```
Ser Leu Leu Ser Phe Met Gln Gly Tyr Met Lys His Ala Thr Lys Thr
1               5                   10                  15
Ala Lys Asp Ala Leu Ser Ser Val Gln Glu Ser Gln Val Ala Gln Gln
            20                  25                  30
Ala Arg Gly Trp Val Thr Asp Gly Phe Ser Ser Leu Lys
            35                  40                  45
```

(2) INFORMATION FOR SEQ ID NO:134:

(i) SEQUENCE CHARACTERISTICS:
        (A) LENGTH: 47 amino acids
        (B) TYPE: amino acid
        (C) STRANDEDNESS:
        (D) TOPOLOGY: linear (xi) SEQUENCE DESCRIPTION: SEQ ID NO:134:

```
Ala Pro Ala Ser Ala Gln Ser Arg Gly Glu Lys Arg Thr Ala His Asn
1               5                   10                  15
Ala Ile Glu Lys Arg Tyr Arg Ser Ser Ile Asn Asp Lys Ile Ile Glu
            20                  25                  30
Leu Lys Asp Leu Val Val Gly Thr Glu Ala Lys Leu Asn Lys Ser
            35                  40                  45
```

(2) INFORMATION FOR SEQ ID NO:135:

(i) SEQUENCE CHARACTERISTICS:
        (A) LENGTH: 28 amino acids
        (B) TYPE: amino acid
        (C) STRANDEDNESS:
        (D) TOPOLOGY: linear (xi) SEQUENCE DESCRIPTION: SEQ ID NO:135:

```
Asp Tyr Trp Ser Thr Val Lys Asp Lys Phe Ser Glu Phe Trp Asp Leu
1               5                   10                  15
```

```
Asp Pro Glu Val Arg Pro Thr Ser Ala Val Ala Ala
            20                  25
```

(2) INFORMATION FOR SEQ ID NO:136:

(i) SEQUENCE CHARACTERISTICS:
        (A) LENGTH: 32 amino acids
        (B) TYPE: amino acid
        (C) STRANDEDNESS:
        (D) TOPOLOGY: linear (xi) SEQUENCE DESCRIPTION: SEQ ID NO:136:

```
Glu Ile Tyr Val Ala Ala Ala Leu Arg Val Lys Thr Ser Leu Pro Arg
1               5                   10                  15
Ala Leu His Phe Leu Thr Arg Phe Phe Leu Ser Ser Ala Arg Gln Ala
            20                  25                  30
```

(2) INFORMATION FOR SEQ ID NO:137:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:137:

```
Glu Lys Ile Pro Thr
1               5
```

(2) INFORMATION FOR SEQ ID NO:138:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:138:

```
Glu Lys Leu Pro Ile
1               5
```

(2) INFORMATION FOR SEQ ID NO:139:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:139:

```
Glu Asn Gly Arg Cys Ile Gln Ala Asn Tyr Ser Leu Met Glu Asn Gly
1               5                   10                  15
Lys Ile Lys Val Leu Asn Gln Glu Leu Arg Ala Asp Gly
            20                  25
```

(2) INFORMATION FOR SEQ ID NO:140:

(i) SEQUENCE CHARACTERISTICS:
        (A) LENGTH: 31 amino acids
        (B) TYPE: amino acid
        (C) STRANDEDNESS:
        (D) TOPOLOGY: linear (xi) SEQUENCE DESCRIPTION: SEQ ID NO:140:

```
Ala Val Leu Arg Lys Ala Ile Asp Tyr Ile Arg Phe Leu Gln His Ser
1               5                   10                  15
```

Asn Gln Lys Leu Lys Gln Glu Asn Leu Ser Leu Arg Thr Ala Val
            20                  25                  30

(2) INFORMATION FOR SEQ ID NO:141:

(i) SEQUENCE CHARACTERISTICS:
        (A) LENGTH: 32 amino acids
        (B) TYPE: amino acid
        (C) STRANDEDNESS:
        (D) TOPOLOGY: linear (xi) SEQUENCE DESCRIPTION: SEQ ID NO:141:

Met Lys Gln Leu Glu Asp Lys Val Glu Glu Leu Leu Ser Lys Asn Tyr
1               5                   10                  15

His Leu Glu Asn Glu Val Ala Arg Leu Lys Lys Leu Val Gly Glu Arg
            20                  25                  30

(2) INFORMATION FOR SEQ ID NO:142:

(i) SEQUENCE CHARACTERISTICS:
        (A) LENGTH: 32 amino acids
        (B) TYPE: amino acid
        (C) STRANDEDNESS:
        (D) TOPOLOGY: linear (xi) SEQUENCE DESCRIPTION: SEQ ID NO:142:

Lys His Glu Ile Gln Glu Met Phe Asp Gln Leu Arg Ala Lys Glu Lys
1               5                   10                  15

Glu Leu Arg Thr Trp Glu Glu Leu Thr Arg Ala Ala Leu Gln Gln
            20                  25                  30

(2) INFORMATION FOR SEQ ID NO:143:

(i) SEQUENCE CHARACTERISTICS:
        (A) LENGTH: 32 amino acids
        (B) TYPE: amino acid
        (C) STRANDEDNESS:
        (D) TOPOLOGY: linear (xi) SEQUENCE DESCRIPTION: SEQ ID NO:143:

Glu Glu Leu Leu Arg Arg Arg Glu Gln Glu Leu Ala Glu Arg Glu Ile
1               5                   10                  15

Asp Ile Leu Glu Arg Glu Leu Asn Ile Ile His Gln Leu Cys Gln
            20                  25                  30

(2) INFORMATION FOR SEQ ID NO:144:

(i) SEQUENCE CHARACTERISTICS:
        (A) LENGTH: 32 amino acids
        (B) TYPE: amino acid
        (C) STRANDEDNESS:
        (D) TOPOLOGY: linear (xi) SEQUENCE DESCRIPTION: SEQ ID NO:144:

Arg Ile Gln Ile Gln Glu Lys Leu Gln Gln Leu Lys Arg His Ile Gln
1               5                   10                  15

Asn Ile Asp Ile Gln His Leu Ala Gly Lys Leu Lys Gln His Ile Glu
            20                  25                  30

(2) INFORMATION FOR SEQ ID NO:145:

(i) SEQUENCE CHARACTERISTICS:
        (A) LENGTH: 35 amino acids
        (B) TYPE: amino acid
        (C) STRANDEDNESS:

(D) TOPOLOGY: linear (xi) SEQUENCE DESCRIPTION: SEQ ID NO:145:

Val Leu Gln Gln Val Lys Ile Lys Asp Tyr Phe Glu Lys Leu Val Gly
1               5                   10                  15

Phe Ile Asp Asp Ala Val Lys Lys Leu Asn Glu Leu Ser Phe Lys Thr
                20                  25                  30

Phe Ile Glu
        35

(2) INFORMATION FOR SEQ ID NO:146:

(i) SEQUENCE CHARACTERISTICS:
        (A) LENGTH: 31 amino acids
        (B) TYPE: amino acid
        (C) STRANDEDNESS:
        (D) TOPOLOGY: linear (xi) SEQUENCE DESCRIPTION: SEQ ID NO:146:

Glu Leu Ser Phe Lys Thr Phe Ile Glu Asp Val Asn Lys Phe Leu Asp
1               5                   10                  15

Met Leu Ile Lys Lys Leu Lys Ser Phe Asp Tyr His Gln Phe Val
                20                  25                  30

(2) INFORMATION FOR SEQ ID NO:147:

(i) SEQUENCE CHARACTERISTICS:
        (A) LENGTH: 28 amino acids
        (B) TYPE: amino acid
        (C) STRANDEDNESS:
        (D) TOPOLOGY: linear (xi) SEQUENCE DESCRIPTION: SEQ ID NO:147:

His Gln Phe Val Asp Glu Thr Asn Asp Lys Ile Arg Glu Val Thr Gln
1               5                   10                  15

Arg Leu Asn Gly Glu Ile Gln Ala Leu Glu Leu Pro
                20                  25

(2) INFORMATION FOR SEQ ID NO:148:

(i) SEQUENCE CHARACTERISTICS:
        (A) LENGTH: 31 amino acids
        (B) TYPE: amino acid
        (C) STRANDEDNESS:
        (D) TOPOLOGY: linear (xi) SEQUENCE DESCRIPTION: SEQ ID NO:148:

Ala Ala Lys Asn Leu Thr Asp Phe Ala Glu Gln Tyr Ser Ile Gln Asp
1               5                   10                  15

Trp Ala Lys Arg Met Lys Ala Leu Val Glu Gln Gly Phe Thr Val
                20                  25                  30

(2) INFORMATION FOR SEQ ID NO:149:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:149:

Ser Ala Ser Leu Ala His Met Lys Ala Lys Phe Arg Glu Thr Leu Glu
1               5                   10                  15

Asp Thr Arg Asp Arg Met Tyr Asp Met Asp Ile Gln Gln Glu Leu Gln

```
                    20                  25                  30
Arg Tyr Leu
        35

(2) INFORMATION FOR SEQ ID NO:150:

(i) SEQUENCE CHARACTERISTICS:
        (A) LENGTH: 35 amino acids
        (B) TYPE: amino acid
        (C) STRANDEDNESS:
        (D) TOPOLOGY: linear (xi) SEQUENCE DESCRIPTION: SEQ ID NO:150:

Cys Leu Asn Leu His Lys Phe Asn Glu Phe Ile Gln Asn Glu Leu Gln
1               5                  10                  15

Glu Ala Ser Gln Glu Leu Gln Gln Ile His Gln Tyr Ile Met Ala Leu
                20                  25                  30

Arg Glu Glu
        35

(2) INFORMATION FOR SEQ ID NO:151:

(i) SEQUENCE CHARACTERISTICS:
        (A) LENGTH: 33 amino acids
        (B) TYPE: amino acid
        (C) STRANDEDNESS:
        (D) TOPOLOGY: linear (xi) SEQUENCE DESCRIPTION: SEQ ID NO:151:

Phe Leu Ile Tyr Ile Thr Glu Leu Leu Lys Lys Leu Gln Ser Thr Thr
1               5                  10                  15

Val Met Asn Pro Tyr Met Lys Leu Ala Pro Gly Glu Leu Thr Ile Ile
                20                  25                  30

Leu (2) INFORMATION FOR SEQ ID NO:152:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:152:

Arg Leu Leu Asp His Arg Val Pro Glu Thr Asp Met Thr Phe Arg His
1               5                  10                  15

Val Gly Ser Lys Leu Ile Val Ala Met Ser Ser Trp Leu Gln
                20                  25                  30

(2) INFORMATION FOR SEQ ID NO:153:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:153:

Leu Asn Phe Ser Lys Leu Glu Ile Gln Ser Gln Val Asp Ser Gln His
1               5                  10                  15

Val Gly His Ser Val Leu Thr Ala Lys Gly Met Ala Leu Phe
                20                  25                  30
```

```
(2) INFORMATION FOR SEQ ID NO:154:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:154:

Asn Gln Asn Phe Ser Ala Gly Asn Asn Glu Asn Ile Met Glu Ala His
1               5                  10                  15

Val Gly Ile Asn Gly Glu Ala Asn Leu Asp Phe Leu Asn Ile
            20                  25                  30

(2) INFORMATION FOR SEQ ID NO:155:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:155:

Met Val Val Thr Arg Ile Ala Pro Ser Pro Thr Gly Asp Pro His Val
1               5                  10                  15

Gly Thr Ala Tyr Ile Ala Leu Phe Asn Tyr Ala Trp Ala
            20                  25

(2) INFORMATION FOR SEQ ID NO:156:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:156:

Thr Thr Val His Thr Arg Phe Pro Pro Glu Pro Asn Gly Tyr Leu His
1               5                  10                  15

Ile Gly His Ala Lys Ser Ile Cys Leu Asn Phe Gly Ile Ala
            20                  25                  30

(2) INFORMATION FOR SEQ ID NO:157:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:157:

Lys Ile Lys Leu Tyr Cys Gly Val Asp Pro Thr Ala Gln Ser Leu His
1               5                  10                  15

Leu Gly Asn Leu Val Pro Met Val Leu Leu His Phe Tyr Val
            20                  25                  30

(2) INFORMATION FOR SEQ ID NO:158:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:158:

Pro Ile Ala Leu Tyr Cys Gly Phe Asp Pro Thr Ala Asp Ser Leu His
```

```
1               5                  10                 15
Leu Gly His Leu Val Pro Leu Leu Cys Leu Lys Arg Gly Gln
            20                 25                 30
```

(2) INFORMATION FOR SEQ ID NO:159:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:159:

```
Arg Val Thr Leu Tyr Cys Gly Phe Asp Pro Thr Ala Asp Ser Leu His
1               5                  10                 15
Ile Gly Asn Leu Ala Ala Ile Leu Thr Leu Arg Arg Phe Gln
            20                 25                 30
```

(2) INFORMATION FOR SEQ ID NO:160:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:160:

```
Arg Ile Gly Ala Tyr Val Gly Ile Asp Pro Thr Ala Pro Ser Leu His
1               5                  10                 15
Val Gly His Leu Leu Pro Leu Met Pro Leu Phe Trp Met Tyr
            20                 25                 30
```

(2) INFORMATION FOR SEQ ID NO:161:

(i) SEQUENCE CHARACTERISTICS:
        (A) LENGTH: 30 amino acids
        (B) TYPE: amino acid
        (C) STRANDEDNESS:
        (D) TOPOLOGY: linear (xi) SEQUENCE DESCRIPTION: SEQ ID NO:161:

```
Pro Ile Ala Leu Tyr Cys Gly Phe Asp Pro Thr Ala Asp Ser Leu His
1               5                  10                 15
Leu Gly His Leu Val Pro Leu Leu Cys Leu Lys Arg Phe Gln
            20                 25                 30
```

(2) INFORMATION FOR SEQ ID NO:162:

(i) SEQUENCE CHARACTERISTICS:
        (A) LENGTH: 31 amino acids
        (B) TYPE: amino acid
        (C) STRANDEDNESS:
        (D) TOPOLOGY: linear (xi) SEQUENCE DESCRIPTION: SEQ ID NO:162:

```
Pro Leu Lys Val Lys Leu Gly Ala Asp Pro Thr Ala Pro Asp Ile His
1               5                  10                 15
Ile Gly His His Thr Val Val Leu Asn Lys Leu Arg Gln Phe Gln
            20                 25                 30
```

(2) INFORMATION FOR SEQ ID NO:163:

(i) SEQUENCE CHARACTERISTICS:
        (A) LENGTH: 43 amino acids
        (B) TYPE: amino acid (C) STRANDEDNESS:
            (D) TOPOLOGY: linear (xi) SEQUENCE DESCRIPTION: SEQ ID NO:163:

Val Ser Lys Gly Leu Leu Ile Phe Asp Ala Ser Ser Met Gly Pro
1               5                   10                  15

Gln Met Ser Ala Ser Val His Leu Asp Ser Lys Lys Gln His Leu
                20                  25                  30

Phe Val Lys Glu Val Lys Ile Asp Gly Gln Phe
            35                  40

(2) INFORMATION FOR SEQ ID NO:164:

(i) SEQUENCE CHARACTERISTICS:
            (A) LENGTH: 43 amino acids
            (B) TYPE: amino acid
            (C) STRANDEDNESS:
            (D) TOPOLOGY: linear (xi) SEQUENCE DESCRIPTION: SEQ ID NO:164:

Thr Ile Ile Thr Thr Pro Pro Leu Lys Asp Phe Ser Leu Trp Glu Lys
1               5                   10                  15

Thr Gly Leu Lys Glu Phe Leu Lys Thr Thr Lys Gln Ser Phe Asp Leu
                20                  25                  30

Ser Val Lys Ala Gln Tyr Lys Lys Asn Lys His
            35                  40

(2) INFORMATION FOR SEQ ID NO:165:

(i) SEQUENCE CHARACTERISTICS:
            (A) LENGTH: 39 amino acids
            (B) TYPE: amino acid
            (C) STRANDEDNESS:
            (D) TOPOLOGY: linear (xi) SEQUENCE DESCRIPTION: SEQ ID NO:165:

Lys Asn Arg Asn Asn Ala Leu Asp Phe Val Thr Lys Ser Tyr Asn Glu
1               5                   10                  15

Thr Lys Ile Lys Phe Asp Lys Tyr Lys Ala Glu Lys Ser Gln Asp Glu
                20                  25                  30

Leu Pro Arg Thr Phe Gln Ile
            35

(2) INFORMATION FOR SEQ ID NO:166:

(i) SEQUENCE CHARACTERISTICS:
            (A) LENGTH: 36 amino acids
            (B) TYPE: amino acid
            (C) STRANDEDNESS:
            (D) TOPOLOGY: linear (xi) SEQUENCE DESCRIPTION: SEQ ID NO:166:

Asp Ala Leu Gln Tyr Lys Leu Glu Gly Thr Thr Arg Leu Thr Arg Lys
1               5                   10                  15

Arg Gly Leu Lys Leu Ala Thr Ala Leu Ser Leu Ser Asn Lys Phe Val
                20                  25                  30

Glu Gly Ser His
            35

(2) INFORMATION FOR SEQ ID NO:167:

(i) SEQUENCE CHARACTERISTICS:
            (A) LENGTH: 42 amino acids (B) TYPE: amino acid
        (C) STRANDEDNESS:
        (D) TOPOLOGY: linear (xi) SEQUENCE DESCRIPTION: SEQ ID NO:167:

Arg Ala Phe Gly Trp Glu Ala Pro Arg Phe Tyr His Met Pro Leu Leu
1               5                   10                  15

Arg Asn Pro Asp Lys Thr Lys Ile Ser Lys Arg Lys Ser His Thr Ser
            20                  25                  30

Leu Asp Trp Tyr Lys Ala Glu Gly Phe Leu
        35                  40

(2) INFORMATION FOR SEQ ID NO:168:

(i) SEQUENCE CHARACTERISTICS:
        (A) LENGTH: 42 amino acids
        (B) TYPE: amino acid
        (C) STRANDEDNESS:
        (D) TOPOLOGY: linear (xi) SEQUENCE DESCRIPTION: SEQ ID NO:168:

Asp Asn Ile Thr Ile Pro Val His Pro Arg Gln Tyr Glu Phe Ser Arg
1               5                   10                  15

Leu Asn Leu Glu Tyr Thr Val Met Ser Lys Arg Lys Leu Asn Leu Leu
            20                  25                  30

Val Thr Asp Lys His Val Glu Gly Trp Asp
        35                  40

(2) INFORMATION FOR SEQ ID NO:169:

(i) SEQUENCE CHARACTERISTICS:
        (A) LENGTH: 40 amino acids
        (B) TYPE: amino acid
        (C) STRANDEDNESS:
        (D) TOPOLOGY: linear (xi) SEQUENCE DESCRIPTION: SEQ ID NO:169:

Lys Asn Lys Gly Leu Pro Phe Gly Ile Thr Val Pro Leu Leu Thr Thr
1               5                   10                  15

Ala Thr Gly Glu Lys Phe Gly Lys Ser Ala Gly Asn Ala Val Phe Ile
            20                  25                  30

Asp Pro Ser Ile Asn Thr Ala Tyr
        35                  40

(2) INFORMATION FOR SEQ ID NO:170:

(i) SEQUENCE CHARACTERISTICS:
        (A) LENGTH: 41 amino acids
        (B) TYPE: amino acid
        (C) STRANDEDNESS:
        (D) TOPOLOGY: linear (xi) SEQUENCE DESCRIPTION: SEQ ID NO:170:

Arg Leu His Gln Asn Gln Val Phe Gly Leu Thr Val Pro Leu Ile Thr
1               5                   10                  15

Lys Ala Asp Gly Thr Lys Phe Gly Lys Thr Glu Gly Gly Ala Val Trp
            20                  25                  30

Leu Asp Pro Lys Lys Thr Ser Pro Tyr
        35                  40

(2) INFORMATION FOR SEQ ID NO:171:

(i) SEQUENCE CHARACTERISTICS:

(A) LENGTH: 42 amino acids
        (B) TYPE: amino acid
        (C) STRANDEDNESS:
        (D) TOPOLOGY: linear (xi) SEQUENCE DESCRIPTION: SEQ ID NO:171:

Lys Thr Lys Gly Glu Ala Arg Ala Phe Gly Leu Thr Ile Pro Leu Val
1               5                  10                  15

Thr Lys Ala Asp Gly Thr Lys Phe Gly Lys Thr Glu Ser Gly Thr Ile
            20                  25                  30

Trp Leu Asp Lys Glu Lys Thr Ser Pro Tyr
            35                  40

(2) INFORMATION FOR SEQ ID NO:172:

(i) SEQUENCE CHARACTERISTICS:
        (A) LENGTH: 41 amino acids
        (B) TYPE: amino acid
        (C) STRANDEDNESS:
        (D) TOPOLOGY: linear (xi) SEQUENCE DESCRIPTION: SEQ ID NO:172:

Lys Thr Ala Leu Asp Glu Cys Val Gly Phe Thr Val Pro Leu Leu Thr
1               5                  10                  15

Asp Ser Ser Gly Ala Lys Phe Gly Lys Ser Ala Gly Asn Ala Ile Trp
            20                  25                  30

Leu Asp Pro Tyr Gln Thr Ser Val Phe
            35                  40

(2) INFORMATION FOR SEQ ID NO:173:

(i) SEQUENCE CHARACTERISTICS:
        (A) LENGTH: 41 amino acids
        (B) TYPE: amino acid
        (C) STRANDEDNESS:
        (D) TOPOLOGY: linear (xi) SEQUENCE DESCRIPTION: SEQ ID NO:173:

Arg Leu His Gln Asn Gln Val Phe Gly Leu Thr Val Pro Leu Ile Thr
1               5                  10                  15

Lys Ala Asp Gly Thr Lys Phe Gly Lys Thr Glu Gly Gly Ala Val Trp
            20                  25                  30

Leu Asp Pro Lys Lys Thr Ser Pro Tyr
            35                  40

(2) INFORMATION FOR SEQ ID NO:174:

(i) SEQUENCE CHARACTERISTICS:
        (A) LENGTH: 42 amino acids
        (B) TYPE: amino acid
        (C) STRANDEDNESS:
        (D) TOPOLOGY: linear (xi) SEQUENCE DESCRIPTION: SEQ ID NO:174:

Ser Ala Gly Lys Lys Pro Gln Val Ala Ile Thr Leu Pro Leu Leu Val
1               5                  10                  15

Gly Leu Asp Gly Glu Lys Lys Met Ser Lys Ser Leu Gly Asn Tyr Ile
            20                  25                  30

Gly Val Thr Glu Ala Pro Ser Asp Met Phe
            35                  40

(2) INFORMATION FOR SEQ ID NO:175:

(i) SEQUENCE CHARACTERISTICS:
    (A) LENGTH: 35 amino acids
    (B) TYPE: amino acid
    (C) STRANDEDNESS:
    (D) TOPOLOGY: linear (xi) SEQUENCE DESCRIPTION: SEQ ID NO:175:

Arg Val Ser Thr Ala Phe Val Tyr Thr Lys Asn Pro Asn Gly Tyr Ser
1               5                   10                  15

Phe Ser Ile Pro Val Lys Val Leu Ala Asp Lys Phe Ile Thr Pro Gly
            20                  25                  30

Leu Lys Leu
        35

(2) INFORMATION FOR SEQ ID NO:176:

(i) SEQUENCE CHARACTERISTICS:
        (A) LENGTH: 29 amino acids
        (B) TYPE: amino acid
        (C) STRANDEDNESS:
        (D) TOPOLOGY: linear (xi) SEQUENCE DESCRIPTION: SEQ ID NO:176:

Lys Leu Gly Gln Gly Cys Phe Gly Glu Val Trp Met Gly Thr Trp Asn
1               5                   10                  15

Gly Thr Thr Arg Val Ala Ile Lys Thr Leu Lys Pro Gly
            20                  25

(2) INFORMATION FOR SEQ ID NO:177:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:177:

His Ile Gly His
1

(2) INFORMATION FOR SEQ ID NO:178:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:178:

His Lys Asn Thr Ser Thr Leu Ser Cys Asp Gly Ser Leu Arg His Lys
1               5                   10                  15

Phe (2) INFORMATION FOR SEQ ID NO:179:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:179:

Arg Lys Leu Lys His Ile Asn Ile Asp Gln Phe Val Arg Lys Tyr Arg
1               5                   10                  15

Ala (2) INFORMATION FOR SEQ ID NO:180:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:180:

```
Arg His Ile Gln Asn Ile Asp Ile Gln His Leu Ala Gly Lys Leu Lys
1               5                   10                  15
Gln His
```

(2) INFORMATION FOR SEQ ID NO:181:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:181:

```
Lys Lys Gly Phe Tyr Lys Lys Lys Gln Cys Arg Pro Ser Lys Gly Arg
1               5                   10                  15
Lys
```

(2) INFORMATION FOR SEQ ID NO:182:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:182:

```
Lys Lys Pro Leu Asp Gly Glu Tyr Phe Thr Leu Gln Ile Arg Gly Arg
1               5                   10                  15
Glu Arg
```

(2) INFORMATION FOR SEQ ID NO:183:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:183:

```
Lys Arg Ala Leu Pro Asn Asn Thr Ser Ser Ser Pro Gln Pro Lys Lys
1               5                   10                  15
Lys
```

(2) INFORMATION FOR SEQ ID NO:184:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:184:

```
Lys Lys Thr Asn Leu Phe Ser Ala Leu Ile Lys Lys Lys Lys Lys Thr
1               5                   10                  15
```

Ala (2) INFORMATION FOR SEQ ID NO:185:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:185:

Arg Lys Thr Leu Leu Asn Ser Leu Glu Glu Ala Lys Lys Lys Glu
1               5                   10                  15

Asp (2) INFORMATION FOR SEQ ID NO:186:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:186:

Arg Arg Glu Leu Asp Glu Ser Leu Gln Val Ala Glu Arg Leu Thr Arg
1               5                   10                  15

Lys (2) INFORMATION FOR SEQ ID NO:187:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:187:

Arg Arg Ser Tyr Ala Leu Val Ser Leu Ser Phe Phe Arg Lys Leu Arg
1               5                   10                  15

Leu (2) INFORMATION FOR SEQ ID NO:188:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:188:

Arg Arg Tyr Gly Asp Glu Glu Leu His Leu Cys Val Ser Arg Lys His
1               5                   10                  15

Phe (2) INFORMATION FOR SEQ ID NO:189:

(i) SEQUENCE CHARACTERISTICS:
        (A) LENGTH: 17 amino acids
        (B) TYPE: amino acid
        (C) STRANDEDNESS:
        (D) TOPOLOGY: linear (xi) SEQUENCE DESCRIPTION: SEQ ID NO:189:

Lys Arg Val Ala Lys Arg Lys Leu Ile Glu Gln Asn Arg Glu Arg Arg
1               5                   10                  15

Arg (2) INFORMATION FOR SEQ ID NO:190:

(i) SEQUENCE CHARACTERISTICS:
       (A) LENGTH: 17 amino acids
       (B) TYPE: amino acid
       (C) STRANDEDNESS:
       (D) TOPOLOGY: linear (xi) SEQUENCE DESCRIPTION: SEQ ID NO:190:

His Arg Ser Thr Asn Ala Gln Gly Ser His Trp Lys Gln Arg Arg Lys
1               5                   10                  15
Phe (2) INFORMATION FOR SEQ ID NO:191:

(i) SEQUENCE CHARACTERISTICS:
       (A) LENGTH: 17 amino acids
       (B) TYPE: amino acid
       (C) STRANDEDNESS:
       (D) TOPOLOGY: linear (xi) SEQUENCE DESCRIPTION: SEQ ID NO:191:

Lys Arg Pro Pro Ile Ser Asp Ser Glu Glu Leu Ser Ala Lys Lys Arg
1               5                   10                  15
Lys (2) INFORMATION FOR SEQ ID NO:192:

(i) SEQUENCE CHARACTERISTICS:
       (A) LENGTH: 17 amino acids
       (B) TYPE: amino acid
       (C) STRANDEDNESS:
       (D) TOPOLOGY: linear (xi) SEQUENCE DESCRIPTION: SEQ ID NO:192:

Lys Lys Gly Lys Lys Pro Lys Thr Glu Lys Glu Asp Lys Val Lys His
1               5                   10                  15
Ile (2) INFORMATION FOR SEQ ID NO:193:

(i) SEQUENCE CHARACTERISTICS:
       (A) LENGTH: 17 amino acids
       (B) TYPE: amino acid
       (C) STRANDEDNESS:
       (D) TOPOLOGY: linear (xi) SEQUENCE DESCRIPTION: SEQ ID NO:193:

Arg Lys Arg Met Arg Asn Arg Ile Ala Ala Ser Lys Cys Arg Lys Arg
1               5                   10                  15
Lys (2) INFORMATION FOR SEQ ID NO:194:

(i) SEQUENCE CHARACTERISTICS:
       (A) LENGTH: 18 amino acids
       (B) TYPE: amino acid
       (C) STRANDEDNESS:
       (D) TOPOLOGY: linear (xi) SEQUENCE DESCRIPTION: SEQ ID NO:194:

Arg His Ile Gln Asn Ile Asp Ile Gln His Leu Ala Gly Lys Leu Lys

```
1               5               10              15
Gln His (2) INFORMATION FOR SEQ ID NO:195:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:195:

Lys Lys Ile Thr Glu Val Ala Leu Met Gly His Leu Ser Cys Asp Thr
1               5                   10                  15

Lys Glu Glu Arg Lys
            20

(2) INFORMATION FOR SEQ ID NO:196:

(i) SEQUENCE CHARACTERISTICS:
        (A) LENGTH: 14 amino acids
        (B) TYPE: amino acid
        (C) STRANDEDNESS:
        (D) TOPOLOGY: linear (xi) SEQUENCE DESCRIPTION: SEQ ID NO:196:

Lys His Ile Asn Ile Asp Gln Phe Val Arg Lys Tyr Arg Ala
1               5                   10

(2) INFORMATION FOR SEQ ID NO:197:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:197:

His Arg Asn Ile Gln Glu Tyr Leu Ser Ile Leu Thr Asp Pro Asp Gly
1               5                   10                  15

Lys Gly Lys Glu Lys
            20

(2) INFORMATION FOR SEQ ID NO:198:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:198:

Lys Glu Val Tyr Gly Phe Asn Pro Glu Gly Lys Ala Leu Leu Lys Lys
1               5                   10                  15

Thr Lys (2) INFORMATION FOR SEQ ID NO:199:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:199:
```

```
Lys Val Leu Val Asp His Phe Gly Tyr Thr Lys Asp Asp Lys His Glu
1               5                   10                  15
Asp Met
```

(2) INFORMATION FOR SEQ ID NO:200:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:200:

```
Arg Gln Val Ser His Ala Lys Glu Lys Leu Thr Ala Leu Thr Lys Lys
1               5                   10                  15
Tyr Arg
```

(2) INFORMATION FOR SEQ ID NO:201:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:201:

```
Lys Tyr Gln Ile Arg Ile Gln Ile Gln Glu Lys Leu Gln Gln Leu Lys
1               5                   10                  15
Arg His
```

(2) INFORMATION FOR SEQ ID NO:202:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:202:

```
Lys Tyr Gln Ile Arg Ile Gln Ile Gln Glu Lys Leu Gln Gln Leu Lys
1               5                   10                  15
Arg His
```

(2) INFORMATION FOR SEQ ID NO:203:

(i) SEQUENCE CHARACTERISTICS:
        (A) LENGTH: 20 amino acids
        (B) TYPE: amino acid
        (C) STRANDEDNESS:
        (D) TOPOLOGY: linear (xi) SEQUENCE DESCRIPTION: SEQ ID NO:203:

```
Lys Gly Met Ala Leu Phe Gly Glu Gly Lys Ala Glu Phe Thr Gly Arg
1               5                   10                  15
His Asp Ala His
            20
```

(2) INFORMATION FOR SEQ ID NO:204:

(i) SEQUENCE CHARACTERISTICS:
        (A) LENGTH: 18 amino acids
        (B) TYPE: amino acid
        (C) STRANDEDNESS:
        (D) TOPOLOGY: linear (xi) SEQUENCE DESCRIPTION: SEQ ID NO:204:

Lys Gln Ser Phe Asp Leu Ser Val Lys Ala Gln Tyr Lys Lys Asn Lys
1               5                   10                  15
His Arg (2) INFORMATION FOR SEQ ID NO:205:

(i) SEQUENCE CHARACTERISTICS:
            (A) LENGTH: 15 amino acids
            (B) TYPE: amino acid
            (C) STRANDEDNESS:
            (D) TOPOLOGY: linear (xi) SEQUENCE DESCRIPTION: SEQ ID NO:205:

Lys Leu Glu Gly Thr Thr Arg Leu Thr Arg Lys Arg Gly Leu Lys
1               5                   10                  15

(2) INFORMATION FOR SEQ ID NO:206:

(i) SEQUENCE CHARACTERISTICS:
            (A) LENGTH: 15 amino acids
            (B) TYPE: amino acid
            (C) STRANDEDNESS:
            (D) TOPOLOGY: linear (xi) SEQUENCE DESCRIPTION: SEQ ID NO:206:

Lys Leu Asp Val Thr Thr Ser Ile Gly Arg Arg Gln His Leu Arg
1               5                   10                  15

(2) INFORMATION FOR SEQ ID NO:207:

(i) SEQUENCE CHARACTERISTICS:
            (A) LENGTH: 15 amino acids
            (B) TYPE: amino acid
            (C) STRANDEDNESS:
            (D) TOPOLOGY: linear (xi) SEQUENCE DESCRIPTION: SEQ ID NO:207:

Lys Lys Leu Asp Phe Arg Glu Ile Gln Ile Tyr Lys Lys Leu Arg
1               5                   10                  15

(2) INFORMATION FOR SEQ ID NO:208:

(i) SEQUENCE CHARACTERISTICS:
            (A) LENGTH: 16 amino acids
            (B) TYPE: amino acid
            (C) STRANDEDNESS:
            (D) TOPOLOGY: linear (xi) SEQUENCE DESCRIPTION: SEQ ID NO:208:

Lys Ser Pro Ala Thr Asp Leu His Leu Arg Tyr Gln Lys Asp Lys Lys
1               5                   10                  15

(2) INFORMATION FOR SEQ ID NO:209:

(i) SEQUENCE CHARACTERISTICS:
            (A) LENGTH: 20 amino acids
            (B) TYPE: amino acid
            (C) STRANDEDNESS:
            (D) TOPOLOGY: linear (xi) SEQUENCE DESCRIPTION: SEQ ID NO:209:

Lys Tyr His Trp Glu His Thr Gly Leu Thr Leu Arg Glu Val Ser Ser
1               5                   10                  15
Lys Leu Arg Arg
            20

(2) INFORMATION FOR SEQ ID NO:210:

(i) SEQUENCE CHARACTERISTICS:
        (A) LENGTH: 21 amino acids
        (B) TYPE: amino acid
        (C) STRANDEDNESS:
        (D) TOPOLOGY: linear (xi) SEQUENCE DESCRIPTION: SEQ ID NO:210:

```
Lys Asp Asn Val Phe Asp Gly Leu Val Arg Val Thr Gln Lys Phe His
1               5                   10                  15

Met Lys Val Lys His
            20
```

(2) INFORMATION FOR SEQ ID NO:211:

(i) SEQUENCE CHARACTERISTICS:
        (A) LENGTH: 180 amino acids
        (B) TYPE: amino acid
        (C) STRANDEDNESS:
        (D) TOPOLOGY: linear (xi) SEQUENCE DESCRIPTION: SEQ ID NO:211:

```
Ser Ile Asn Leu Pro Phe Phe Glu Thr Leu Gln Glu Tyr Phe Glu Arg
1               5                   10                  15

Asn Arg Gln Thr Ile Ile Val Val Glu Asn Val Gln Arg Asn Leu
            20                  25                  30

Lys His Ile Asn Ile Asp Gln Phe Val Arg Lys Tyr Arg Ala Ala Leu
            35                  40                  45

Gly Lys Leu Pro Gln Gln Ala Asn Asp Tyr Leu Asn Ser Phe Asn Trp
50                  55                  60

Glu Arg Gln Val Ser His Ala Lys Glu Lys Leu Thr Ala Leu Thr Lys
65                  70                  75                  80

Lys Tyr Arg Ile Thr Glu Asn Asp Ile Gln Ile Ala Leu Asp Asp Ala
                85                  90                  95

Lys Ile Asn Phe Asn Glu Lys Leu Ser Gln Leu Gln Thr Tyr Met Ile
                100                 105                 110

Gln Phe Asp Gln Tyr Ile Lys Asp Ser Tyr Asp Leu His Asp Leu Lys
            115                 120                 125

Ile Ala Ile Ala Asn Ile Ile Asp Glu Ile Ile Glu Lys Leu Lys Ser
130                 135                 140

Leu Asp Glu His Tyr His Ile Arg Val Asn Leu Val Lys Thr Ile His
145                 150                 155                 160

Asp Leu His Leu Phe Ile Glu Asn Ile Asp Phe Asn Lys Ser Gly Ser
                165                 170                 175

Ser Thr Ala Ser
            180
```

(2) INFORMATION FOR SEQ ID NO:212:

(i) SEQUENCE CHARACTERISTICS:
        (A) LENGTH: 94 amino acids
        (B) TYPE: amino acid
        (C) STRANDEDNESS:
        (D) TOPOLOGY: linear (xi) SEQUENCE DESCRIPTION: SEQ ID NO:212:

```
Pro Gln Gln Val Asn Asp Tyr Leu Ser Thr Phe Ser Trp Glu Arg Gln
1               5                   10                  15
```

-continued

```
Val Leu Ser Ala Lys Lys His Ser Asp Phe Met Glu Asp Tyr Arg
            20                  25                  30

Ile Thr Glu Asn Asp Val Arg Ile Ala Leu Asp Asn Ala Lys Ile Asn
            35                  40                  45

Leu Asn Glu Lys Leu Thr Gln Leu Gln Thr Tyr Val Ile Gln Phe Asp
50                  55                  60

Gln Tyr Ile Lys Asp Asn Tyr Asp Leu His Asp Phe Lys Thr Ala Ile
65                  70                  75                  80

Ala Arg Ile Ile Asp Glu Ile Ile Ala Thr Leu Lys Ile Leu
                85                  90
```

(2) INFORMATION FOR SEQ ID NO:213:

(i) SEQUENCE CHARACTERISTICS:
        (A) LENGTH: 85 amino acids
        (B) TYPE: amino acid
        (C) STRANDEDNESS:
        (D) TOPOLOGY: linear (xi) SEQUENCE DESCRIPTION: SEQ ID NO:213:

```
Lys Tyr Arg Val Ala Leu Ser Arg Leu Pro Gln Gln Ile His Asp Tyr
1               5                   10                  15

Leu Asn Ala Ser Asp Trp Glu Arg Gln Val Ala Gly Ala Lys Glu Lys
            20                  25                  30

Leu Thr Ser Phe Met Glu Asn Tyr Arg Ile Thr Asp Asn Asp Val Leu
            35                  40                  45

Ile Ala Leu Asp Ser Ala Lys Ile Asn Leu Asn Glu Lys Leu Ser Gln
50                  55                  60

Leu Glu Thr Tyr Ala Ile Gln Phe Asp Gln Tyr Ile Arg Asp Asn Tyr
65                  70                  75                  80

Asp Ala Gln Asp Leu
                85
```

(2) INFORMATION FOR SEQ ID NO:214:

(i) SEQUENCE CHARACTERISTICS:
        (A) LENGTH: 840 amino acids
        (B) TYPE: amino acid
        (C) STRANDEDNESS:
        (D) TOPOLOGY: linear (xi) SEQUENCE DESCRIPTION: SEQ ID NO:214:

```
Leu Asn Asp Phe Gln Val Pro Asp Leu His Ile Pro Glu Phe Gln Leu
1               5                   10                  15

Pro His Ile Ser His Thr Ile Glu Val Pro Thr Phe Gly Lys Leu Tyr
            20                  25                  30

Ser Ile Leu Lys Ile Gln Ser Pro Leu Phe Thr Leu Asp Ala Asn Ala
            35                  40                  45

Asp Ile Gly Asn Gly Thr Thr Ser Ala Asn Glu Ala Gly Ile Ala Ala
            50                  55                  60

Ser Ile Thr Ala Lys Gly Glu Ser Lys Leu Glu Val Leu Asn Phe Asp
65                  70                  75                  80

Phe Gln Ala Asn Ala Gln Leu Ser Asn Pro Lys Ile Asn Pro Leu Ala
                85                  90                  95

Leu Lys Glu Ser Val Lys Phe Ser Ser Lys Tyr Leu Arg Thr Glu His
                100                 105                 110

Gly Ser Glu Met Leu Phe Phe Gly Asn Ala Ile Glu Gly Lys Ser Asn
            115                 120                 125
```

-continued

```
Thr Val Ala Ser Leu His Thr Glu Lys Asn Thr Leu Glu Leu Ser Asn
            130                 135                 140
Gly Val Ile Val Lys Ile Asn Asn Gln Leu Thr Leu Asp Ser Asn Thr
145                 150                 155                 160
Lys Tyr Phe His Lys Leu Asn Ile Pro Lys Leu Asp Phe Ser Ser Gln
                165                 170                 175
Ala Asp Leu Arg Asn Glu Ile Lys Thr Leu Leu Lys Ala Gly His Ile
            180                 185                 190
Ala Trp Thr Ser Ser Gly Lys Gly Ser Trp Lys Trp Ala Cys Pro Arg
        195                 200                 205
Phe Ser Asp Glu Gly Thr His Glu Ser Gln Ile Ser Phe Thr Ile Glu
    210                 215                 220
Gly Pro Leu Thr Ser Phe Gly Leu Ser Asn Lys Ile Asn Ser Lys His
225                 230                 235                 240
Leu Arg Val Asn Gln Asn Leu Val Tyr Glu Ser Gly Ser Leu Asn Phe
                245                 250                 255
Ser Lys Leu Glu Ile Gln Ser Gln Val Asp Ser Gln His Val Gly His
            260                 265                 270
Ser Val Leu Thr Ala Lys Gly Met Ala Leu Phe Gly Glu Gly Lys Ala
        275                 280                 285
Glu Phe Thr Gly Arg His Asp Ala His Leu Asn Gly Lys Val Ile Gly
    290                 295                 300
Thr Leu Lys Asn Ser Leu Phe Phe Ser Ala Gln Pro Phe Glu Ile Thr
305                 310                 315                 320
Ala Ser Thr Asn Asn Glu Gly Asn Leu Lys Val Arg Phe Pro Leu Arg
                325                 330                 335
Leu Thr Gly Lys Ile Asp Phe Leu Asn Asn Tyr Ala Leu Phe Leu Ser
            340                 345                 350
Pro Ser Ala Gln Gln Ala Ser Trp Gln Val Ser Ala Arg Phe Asn Gln
        355                 360                 365
Tyr Lys Tyr Asn Gln Asn Phe Ser Ala Gly Asn Asn Glu Asn Ile Met
    370                 375                 380
Glu Ala His Val Gly Ile Asn Gly Glu Ala Asn Leu Asp Phe Leu Asn
385                 390                 395                 400
Ile Pro Leu Thr Ile Pro Glu Met Arg Leu Pro Tyr Thr Ile Ile Thr
                405                 410                 415
Thr Pro Pro Leu Lys Asp Phe Ser Leu Trp Glu Lys Thr Gly Leu Lys
            420                 425                 430
Glu Phe Leu Lys Thr Thr Lys Gln Ser Phe Asp Leu Ser Val Lys Ala
        435                 440                 445
Gln Tyr Lys Lys Asn Lys His Arg His Ser Ile Thr Asn Pro Leu Ala
    450                 455                 460
Val Leu Cys Glu Phe Ile Ser Gln Ser Ile Lys Ser Phe Asp Arg His
465                 470                 475                 480
Phe Glu Lys Asn Arg Asn Asn Ala Leu Asp Phe Val Thr Lys Ser Tyr
                485                 490                 495
Asn Glu Thr Lys Ile Lys Phe Asp Lys Tyr Lys Ala Glu Lys Ser His
            500                 505                 510
Asp Glu Leu Pro Arg Thr Phe Gln Ile Pro Gly Tyr Thr Val Pro Val
        515                 520                 525
Val Asn Val Glu Val Ser Pro Phe Thr Ile Glu Met Ser Ala Phe Gly
    530                 535                 540
Tyr Val Phe Pro Lys Ala Val Ser Met Pro Ser Phe Ser Ile Leu Gly
```

```
545                 550                 555                 560
Ser Asp Val Arg Val Pro Ser Tyr Thr Leu Ile Leu Pro Ser Leu Glu
                565                 570                 575

Leu Pro Val Leu His Val Pro Arg Asn Leu Lys Leu Ser Leu Pro His
                580                 585                 590

Phe Lys Glu Leu Cys Thr Ile Ser His Ile Phe Ile Pro Ala Met Gly
            595                 600                 605

Asn Ile Thr Tyr Asp Phe Ser Phe Lys Ser Ser Val Ile Thr Leu Asn
        610                 615                 620

Thr Asn Ala Glu Leu Phe Asn Gln Ser Asp Ile Val Ala His Leu Leu
625                 630                 635                 640

Ser Ser Ser Ser Val Ile Asp Ala Leu Gln Tyr Lys Leu Glu Gly
                645                 650                 655

Thr Thr Arg Leu Thr Arg Lys Arg Gly Leu Lys Leu Ala Thr Ala Leu
                660                 665                 670

Ser Leu Ser Asn Lys Phe Val Glu Gly Ser His Asn Ser Thr Val Ser
            675                 680                 685

Leu Thr Thr Lys Asn Met Glu Val Ser Val Ala Lys Thr Thr Lys Ala
        690                 695                 700

Glu Ile Pro Ile Leu Arg Met Asn Phe Lys Gln Glu Leu Asn Gly Asn
705                 710                 715                 720

Thr Lys Ser Lys Pro Thr Val Ser Ser Met Glu Phe Lys Tyr Asp
                725                 730                 735

Phe Asn Ser Ser Met Leu Tyr Ser Thr Ala Lys Gly Ala Val Asp His
                740                 745                 750

Lys Leu Ser Leu Glu Ser Leu Thr Ser Tyr Phe Ser Ile Glu Ser Ser
                755                 760                 765

Thr Lys Gly Asp Val Lys Gly Ser Val Leu Ser Arg Glu Tyr Ser Gly
                770                 775                 780

Thr Ile Ala Ser Glu Ala Asn Thr Tyr Leu Asn Ser Lys Ser Thr Arg
785                 790                 795                 800

Ser Ser Val Lys Leu Gln Gly Thr Ser Lys Ile Asp Asp Ile Trp Asn
                805                 810                 815

Leu Glu Val Lys Glu Asn Phe Ala Gly Glu Ala Thr Leu Gln Arg Ile
                820                 825                 830

Tyr Ser Leu Trp Glu His Ser Thr
            835                 840

(2) INFORMATION FOR SEQ ID NO:215:

(i) SEQUENCE CHARACTERISTICS:
        (A) LENGTH: 773 amino acids
        (B) TYPE: amino acid
        (C) STRANDEDNESS:
        (D) TOPOLOGY: linear (xi) SEQUENCE DESCRIPTION: SEQ ID NO:215:

Glu Phe Gln Leu Pro Arg Leu Ser His Thr Ile Glu Ile Pro Ala Phe
1               5                   10                  15

Gly Arg Leu His Gly Ile Leu Lys Ile Gln Ser Pro Leu Phe Ile Leu
                20                  25                  30

Asp Ala Asn Ala Asn Ile Gln Asn Val Thr Thr Leu Glu Asn Lys Ala
            35                  40                  45

Glu Ile Val Ala Ser Ile Ala Ala Thr Gly Glu Ser Glu Ile Glu Ala
        50                  55                  60
```

```
Leu Asn Phe Asp Phe Gln Ala Gln Ala Gln Phe Leu Glu Leu Asn Pro
 65                  70                  75                  80

Asn Pro Leu Ile Leu Lys Glu Ser Met Asn Phe Ser Ser Lys His Ala
                 85                  90                  95

Arg Met Glu His Glu Gly Glu Ile Leu Phe Ser Gly Lys Phe Ile Glu
            100                 105                 110

Gly Lys Leu Asp Thr Val Ala Ser Leu Gln Thr Glu Lys Asn Met Val
            115                 120                 125

Glu Phe Asn Asn Gly Met Ile Val Lys Ile Asn Asn Pro Ile Ile Leu
130                 135                 140

Asp Ser His Thr Lys Tyr Phe His Lys Leu Ser Ile Pro Arg Leu Asp
145                 150                 155                 160

Phe Ser Ser Lys Ala Ser Phe Asn Asn Glu Ile Lys Met Leu Leu Glu
                165                 170                 175

Ala Gly His Val Ala Trp Thr Ser Ser Gly Thr Gly Ser Trp Asn Trp
            180                 185                 190

Ala Cys Pro Asn Phe Ser Asp Glu Gly Thr His Ser Ser Lys Ile Ser
            195                 200                 205

Phe Thr Val Glu Gly Pro Ile Ala Phe Phe Gly Leu Ser Asn Asn Ile
            210                 215                 220

Asn Gly Lys His Leu Arg Val Ile Gln Lys Leu Ala Tyr Glu Ser Gly
225                 230                 235                 240

Phe Leu Asn Tyr Ser Met Leu Glu Val Glu Ser Lys Val Glu Ser Gln
                245                 250                 255

His Val Gly Ser Ser Ile Leu Thr Gly Lys Gly Thr Val Leu Leu Arg
            260                 265                 270

Glu Ala Lys Ala Glu Met Thr Gly Glu His Asn Ala Asp Leu Asn Gly
            275                 280                 285

Lys Val Ile Gly Thr Leu Lys Asn Ser Leu Ser Phe Ser Ala Gln Pro
            290                 295                 300

Phe Met Ile Thr Ala Ser Thr Asn Asn Asp Gly Asn Leu Lys Val Ser
305                 310                 315                 320

Phe Pro Leu Lys Leu Thr Gly Lys Ile Asp Phe Leu Asn Asn Tyr Ala
                325                 330                 335

Leu Phe Leu Ser Pro His Ala Gln Gln Ala Ser Trp Gln Val Ser Ala
            340                 345                 350

Arg Phe Asn Tyr Lys Tyr Asn Gln Asn Phe Ser Ala Ile Asn Asn Glu
            355                 360                 365

His Asn Ile Glu Ala His Val Gly Met Asn Gly Asp Ala Asn Leu Asp
            370                 375                 380

Phe Leu Thr Ile Pro Leu Thr Ile Pro Glu Val Lys Leu Pro Tyr Ile
385                 390                 395                 400

Gly Leu Thr Thr Pro Leu Leu Lys Asp Phe Ser Ile Trp Glu Glu Thr
                405                 410                 415

Gly Leu Lys Lys Gln Ser Phe Asp Leu Ser Val Lys Ala Gln Tyr Lys
            420                 425                 430

Lys Asn Arg Asp Arg His Ser Ile Ala Ile Pro Leu Asn Gly Phe Tyr
            435                 440                 445

Glu Phe Ile Leu Asn Asn Val Asp Ser Gly Ile Gly Lys Ile Gly Lys
            450                 455                 460

Val Arg Asp Ser Ala Leu Asp Tyr Leu Ile Ser Ser Tyr Asn Glu Ala
465                 470                 475                 480

Lys Asn Lys Phe Glu Asn Ser Leu Ile Gln Pro Ser Arg Thr Phe Gln
```

```
                    485                 490                 495
Lys Arg Gly Tyr Thr Ile Pro Phe Val Asn Ile Glu Val Thr Pro Phe
                500                 505                 510

Thr Val Glu Thr Leu Ala Ser Ser His Val Ile Pro Lys Ala Ile Asn
                515                 520                 525

Thr Pro Ser Val His Ile Leu Gly Pro Asn Val Ile Val Pro Ser Tyr
                530                 535                 540

Arg Leu Val Leu Pro Ser Leu Glu Leu Pro Val Leu Arg Val Pro Arg
545                 550                 555                 560

Asn Leu Lys Phe Ser Leu Pro Asp Phe Lys Glu Leu Arg Thr Ile
                565                 570                 575

Asp Asn Ile Tyr Ile Pro Ala Leu Gly Asn Phe Thr Tyr Asp Phe Ser
                580                 585                 590

Phe Lys Ser Ser Val Ile Thr Leu Asn Thr Asn Val Gly Leu Tyr Asn
                595                 600                 605

Arg Ser Asp Ile Val Ala His Phe Leu Ser Ser Ser Phe Val Thr
610                 615                 620

Asp Ala Leu Gln Tyr Lys Leu Glu Gly Thr Ser Arg Leu Thr Arg Lys
625                 630                 635                 640

Arg Gly Leu Lys Leu Ala Thr Ala Asp Ser Leu Thr Asn Lys Phe Val
                645                 650                 655

Lys Gly Asn His Asp Ser Thr Phe Ser Leu Thr Lys Lys Asn Met Glu
                660                 665                 670

Ala Ser Val Lys Thr Thr Ala Asn Leu His Ala Pro Ile Leu Thr Met
                675                 680                 685

Asn Phe Lys Gln Glu Leu Asn Gly Asn Ala Lys Ser Lys Pro Ile Val
                690                 695                 700

Ser Ser Ser Ile Glu Leu Asn Tyr Asp Phe Asn Ser Ser Lys Leu Tyr
705                 710                 715                 720

Ser Thr Ala Lys Gly Gly Val Asp His Lys Phe Ser Leu Glu Ser Leu
                725                 730                 735

Thr Ser Tyr Phe Ser Ile Glu Ser Ser Thr Lys Gly Asn Ile Lys Gly
                740                 745                 750

Ser Val Leu Ser Gln Glu Tyr Ser Gly Ser Val Ala Ser Glu Ala Asn
                755                 760                 765

Thr Tyr Leu Asn Ser
770

(2) INFORMATION FOR SEQ ID NO:216:

(i) SEQUENCE CHARACTERISTICS:
        (A) LENGTH: 785 amino acids
        (B) TYPE: amino acid
        (C) STRANDEDNESS:
        (D) TOPOLOGY: linear (xi) SEQUENCE DESCRIPTION: SEQ ID NO:216:

Glu Phe Gln Leu Pro His Leu Ser His Thr Ile Glu Ile Pro Ala Phe
1               5                  10                  15

Gly Lys Leu His Ser Ile Leu Lys Ile Gln Ser Pro Leu Phe Ile Leu
                20                  25                  30

Asp Ala Asn Ala Asn Ile Gln Asn Val Thr Thr Ser Gly Asn Lys Ala
            35                  40                  45

Glu Ile Val Ala Ser Val Thr Ala Lys Gly Glu Ser Gln Phe Glu Ala
        50                  55                  60
```

-continued

```
Leu Asn Phe Asp Phe Gln Ala Gln Ala Gln Phe Leu Glu Leu Asn Pro
 65                  70                  75                  80

His Pro Pro Val Leu Lys Glu Ser Met Asn Phe Ser Ser Lys His Val
                 85                  90                  95

Arg Met Glu His Glu Gly Glu Ile Val Phe Asp Gly Lys Ala Ile Glu
            100                 105                 110

Gly Lys Ser Asp Thr Val Ala Ser Leu His Thr Glu Lys Asn Glu Val
        115                 120                 125

Glu Phe Asn Asn Gly Met Thr Val Lys Val Asn Asn Gln Leu Thr Leu
130                 135                 140

Asp Ser His Thr Lys Tyr Phe His Lys Leu Ser Val Pro Arg Leu Asp
145                 150                 155                 160

Phe Ser Ser Lys Ala Ser Leu Asn Asn Glu Ile Lys Thr Leu Leu Glu
                165                 170                 175

Ala Gly His Val Ala Leu Thr Ser Ser Gly Thr Gly Ser Trp Asn Trp
            180                 185                 190

Ala Cys Pro Asn Phe Ser Asp Glu Gly Ile His Ser Ser Gln Ile Ser
        195                 200                 205

Phe Thr Val Asp Gly Pro Ile Ala Phe Val Gly Leu Ser Asn Asn Ile
210                 215                 220

Asn Gly Lys His Leu Arg Val Ile Gln Lys Leu Thr Tyr Glu Ser Gly
225                 230                 235                 240

Phe Leu Asn Tyr Ser Lys Phe Glu Val Glu Ser Lys Val Glu Ser Gln
                245                 250                 255

His Val Gly Ser Ser Ile Leu Thr Ala Asn Gly Arg Ala Leu Leu Lys
            260                 265                 270

Asp Ala Lys Ala Glu Met Thr Gly Glu His Asn Ala Asn Leu Asn Gly
        275                 280                 285

Lys Val Ile Gly Thr Leu Lys Asn Ser Leu Phe Phe Ser Ala Gln Pro
290                 295                 300

Phe Glu Ile Thr Ala Ser Thr Asn Asn Glu Gly Asn Leu Lys Val Gly
305                 310                 315                 320

Phe Pro Leu Lys Leu Thr Gly Lys Ile Asp Phe Leu Asn Asn Tyr Ala
                325                 330                 335

Leu Phe Leu Ser Pro Arg Ala Gln Gln Ala Ser Trp Gln Ala Ser Thr
            340                 345                 350

Arg Phe Asn Gln Tyr Lys Tyr Asn Gln Asn Phe Ser Ala Ile Asn Asn
        355                 360                 365

Glu His Asn Ile Glu Ala Ser Ile Gly Met Asn Gly Asp Ala Asn Leu
370                 375                 380

Asp Phe Leu Asn Ile Pro Leu Thr Ile Pro Glu Ile Asn Leu Pro Tyr
385                 390                 395                 400

Thr Glu Phe Lys Thr Pro Leu Leu Lys Asp Phe Ser Ile Trp Glu Glu
                405                 410                 415

Thr Gly Leu Lys Glu Phe Leu Lys Thr Thr Lys Gln Ser Phe Asp Leu
            420                 425                 430

Ser Val Lys Ala Gln Tyr Lys Lys Asn Ser Asp Lys His Ser Ile Val
        435                 440                 445

Val Pro Leu Gly Met Phe Tyr Glu Phe Ile Leu Asn Asn Val Asn Ser
450                 455                 460

Trp Asp Arg Lys Phe Glu Lys Val Arg Asn Asn Ala Leu His Phe Leu
465                 470                 475                 480

Thr Thr Ser Tyr Asn Glu Ala Lys Ile Lys Val Asp Lys Tyr Lys Thr
```

-continued

```
                    485                 490                 495
Glu Asn Ser Leu Asn Gln Pro Ser Gly Thr Phe Gln Asn His Gly Tyr
                500                 505                 510

Thr Ile Pro Val Val Asn Ile Glu Val Ser Pro Phe Ala Val Glu Thr
            515                 520                 525

Leu Ala Ser Arg His Val Ile Pro Thr Ala Ile Ser Thr Pro Ser Val
            530                 535                 540

Thr Ile Pro Gly Pro Asn Ile Met Val Pro Ser Tyr Lys Leu Val Leu
545                 550                 555                 560

Pro Pro Leu Glu Leu Pro Val Phe His Gly Pro Gly Asn Leu Phe Lys
                565                 570                 575

Phe Phe Leu Pro Asp Phe Lys Gly Phe Asn Thr Ile Asp Asn Ile Tyr
                580                 585                 590

Ile Pro Ala Met Gly Asn Phe Thr Tyr Asp Phe Ser Phe Lys Ser Ser
            595                 600                 605

Val Ile Thr Leu Asn Thr Asn Ala Gly Leu Tyr Asn Gln Ser Asp Ile
            610                 615                 620

Val Ala His Phe Leu Ser Ser Ser Phe Val Thr Asp Ala Leu Gln
625                 630                 635                 640

Tyr Lys Leu Glu Gly Thr Ser Arg Leu Met Arg Lys Arg Gly Leu Lys
                645                 650                 655

Leu Ala Thr Ala Val Ser Leu Thr Asn Lys Phe Val Lys Gly Ser His
                660                 665                 670

Asp Ser Thr Ile Ser Leu Thr Lys Lys Asn Met Glu Ala Ser Val Arg
            675                 680                 685

Thr Thr Ala Asn Leu His Ala Pro Ile Phe Ser Met Asn Phe Lys Gln
            690                 695                 700

Glu Leu Asn Gly Asn Thr Lys Ser Lys Pro Thr Val Ser Ser Ser Ile
705                 710                 715                 720

Glu Leu Asn Tyr Asp Phe Asn Ser Ser Lys Leu His Ser Thr Ala Thr
                725                 730                 735

Gly Gly Ile Asp His Lys Phe Ser Leu Glu Ser Leu Thr Ser Tyr Phe
                740                 745                 750

Ser Ile Glu Ser Phe Thr Lys Gly Asn Ile Lys Ser Ser Phe Leu Ser
            755                 760                 765

Gln Glu Tyr Ser Gly Ser Val Ala Asn Glu Ala Asn Val Tyr Leu Asn
770                 775                 780

Ser
785

(2) INFORMATION FOR SEQ ID NO:217:

(i) SEQUENCE CHARACTERISTICS:
        (A) LENGTH: 1056 amino acids
        (B) TYPE: amino acid
        (C) STRANDEDNESS:
        (D) TOPOLOGY: linear (xi) SEQUENCE DESCRIPTION: SEQ ID NO:217:

Glu Tyr Ser Gly Thr Ile Ala Ser Glu Ala Asn Thr Tyr Leu Asn Ser
1               5                   10                  15

Lys Ser Thr Arg Ser Ser Val Lys Leu Gln Gly Thr Ser Lys Ile Asp
                20                  25                  30

Asp Ile Trp Asn Leu Glu Val Lys Glu Asn Phe Ala Gly Glu Ala Thr
            35                  40                  45
```

-continued

```
Leu Gln Arg Ile Tyr Ser Leu Trp Glu His Ser Thr Lys Asn His Leu
     50                  55                  60
Gln Leu Glu Gly Leu Phe Phe Thr Asn Gly Glu His Thr Ser Lys Ala
 65                  70                  75                  80
Thr Leu Glu Leu Ser Pro Trp Gln Met Ser Ala Leu Val Gln Val His
                 85                  90                  95
Ala Ser Gln Pro Ser Ser Phe His Asp Phe Pro Asp Leu Gly Gln Glu
                100                 105                 110
Val Ala Leu Asn Ala Asn Thr Lys Asn Gln Lys Ile Arg Trp Lys Asn
                115                 120                 125
Glu Val Arg Ile His Ser Gly Ser Phe Gln Ser Gln Val Glu Leu Ser
130                 135                 140
Asn Asp Gln Glu Lys Ala His Leu Asp Ile Ala Gly Ser Leu Glu Gly
145                 150                 155                 160
His Leu Arg Phe Leu Lys Asn Ile Ile Leu Pro Val Tyr Asp Lys Ser
                165                 170                 175
Leu Trp Asp Phe Leu Lys Leu Asp Val Thr Thr Ser Ile Gly Arg Arg
                180                 185                 190
Gln His Leu Arg Val Ser Thr Ala Phe Val Tyr Thr Lys Asn Pro Asn
                195                 200                 205
Gly Tyr Ser Phe Ser Ile Pro Val Lys Val Leu Ala Asp Lys Phe Ile
    210                 215                 220
Thr Pro Gly Leu Lys Leu Asn Asp Leu Asn Ser Val Leu Val Met Pro
225                 230                 235                 240
Thr Phe His Val Pro Phe Thr Asp Leu Gln Val Pro Ser Cys Lys Leu
                245                 250                 255
Asp Phe Arg Glu Ile Gln Ile Tyr Lys Lys Leu Arg Thr Ser Ser Phe
                260                 265                 270
Ala Leu Asn Leu Pro Thr Leu Pro Glu Val Lys Phe Pro Glu Val Asp
                275                 280                 285
Val Leu Thr Lys Tyr Ser Gln Pro Glu Asp Ser Leu Ile Pro Phe Phe
    290                 295                 300
Glu Ile Thr Val Pro Glu Ser Gln Leu Thr Val Ser Gln Phe Thr Leu
305                 310                 315                 320
Pro Lys Ser Val Ser Asp Gly Ile Ala Ala Leu Asp Leu Asn Ala Val
                325                 330                 335
Ala Asn Lys Ile Ala Asp Phe Glu Leu Pro Thr Ile Ile Val Pro Glu
                340                 345                 350
Gln Thr Ile Glu Ile Pro Ser Ile Lys Phe Ser Val Pro Ala Gly Ile
                355                 360                 365
Val Ile Pro Ser Phe Gln Ala Leu Thr Ala Arg Phe Glu Val Asp Ser
    370                 375                 380
Pro Val Tyr Asn Ala Thr Trp Ser Ala Ser Leu Lys Asn Lys Ala Asp
385                 390                 395                 400
Tyr Val Glu Thr Val Leu Asp Ser Thr Cys Ser Ser Thr Val Gln Phe
                405                 410                 415
Leu Glu Tyr Glu Leu Asn Val Leu Gly Thr His Lys Ile Glu Asp Gly
                420                 425                 430
Thr Leu Ala Ser Lys Thr Lys Gly Thr Leu Ala His Arg Asp Phe Ser
                435                 440                 445
Ala Glu Tyr Glu Glu Asp Gly Lys Phe Glu Gly Leu Gln Glu Trp Glu
    450                 455                 460
Gly Lys Ala His Leu Asn Ile Lys Ser Pro Ala Phe Thr Asp Leu His
```

```
                                 -continued 465                470                475                480

Leu Arg Tyr Gln Lys Asp Lys Lys Gly Ile Ser Thr Ser Ala Ala Ser
                485                490                495

Pro Ala Val Gly Thr Val Gly Met Asp Met Asp Glu Asp Asp Asp Phe
                500                505                510

Ser Lys Trp Asn Phe Tyr Tyr Ser Pro Gln Ser Ser Pro Asp Lys Lys
                515                520                525

Leu Thr Ile Phe Lys Thr Glu Leu Arg Val Arg Glu Ser Asp Glu Glu
                530                535                540

Thr Gln Ile Lys Val Asn Trp Glu Glu Ala Ala Ser Gly Leu Leu
545                550                555                560

Thr Ser Leu Lys Asp Asn Val Pro Lys Ala Thr Gly Val Leu Tyr Asp
                565                570                575

Tyr Val Asn Lys Tyr His Trp Glu His Thr Gly Leu Thr Leu Arg Glu
                580                585                590

Val Ser Ser Lys Leu Arg Arg Asn Leu Gln Asn Asn Ala Glu Trp Val
                595                600                605

Tyr Gln Gly Ala Ile Arg Gln Ile Asp Asp Ile Asp Val Arg Phe Gln
                610                615                620

Lys Ala Ala Ser Gly Thr Thr Gly Thr Tyr Gln Glu Trp Lys Asp Lys
625                630                635                640

Ala Gln Asn Leu Tyr Gln Glu Leu Leu Thr Gln Glu Gly Gln Ala Ser
                645                650                655

Phe Gln Gly Leu Lys Asp Asn Val Phe Asp Gly Leu Val Arg Val Thr
                660                665                670

Gln Lys Phe His Met Lys Val Lys His Leu Ile Asp Ser Leu Ile Asp
                675                680                685

Phe Leu Asn Phe Pro Arg Phe Gln Phe Pro Gly Lys Pro Gly Ile Tyr
                690                695                700

Thr Arg Glu Glu Leu Cys Thr Met Phe Ile Arg Glu Val Gly Thr Val
705                710                715                720

Leu Ser Gln Val Tyr Ser Lys Val His Asn Gly Ser Glu Ile Leu Phe
                725                730                735

Ser Tyr Phe Gln Asp Leu Val Ile Thr Leu Pro Phe Glu Leu Arg Lys
                740                745                750

His Lys Leu Ile Asp Val Ile Ser Met Tyr Arg Glu Leu Leu Lys Asp
                755                760                765

Leu Ser Lys Glu Ala Gln Glu Val Phe Lys Ala Ile Gln Ser Leu Lys
                770                775                780

Thr Thr Glu Val Leu Arg Asn Leu Gln Asp Leu Leu Gln Phe Ile Phe
785                790                795                800

Gln Leu Ile Glu Asp Asn Ile Lys Gln Leu Lys Glu Met Lys Phe Thr
                805                810                815

Tyr Leu Ile Asn Tyr Ile Gln Asp Glu Ile Asn Thr Ile Phe Asn Asp
                820                825                830

Tyr Ile Pro Tyr Val Phe Lys Leu Leu Lys Glu Asn Leu Cys Leu Asn
                835                840                845

Leu His Lys Phe Asn Glu Phe Ile Gln Asn Glu Leu Gln Glu Ala Ser
                850                855                860

Gln Glu Leu Gln Gln Ile His Gln Tyr Ile Met Ala Leu Arg Glu Glu
865                870                875                880

Tyr Phe Asp Pro Ser Ile Val Gly Trp Thr Val Lys Tyr Tyr Glu Leu
                885                890                895
```

```
Glu Glu Lys Ile Val Ser Leu Ile Lys Asn Leu Leu Val Ala Leu Lys
            900                 905                 910

Asp Phe His Ser Glu Tyr Ile Val Ser Ala Ser Asn Phe Thr Ser Gln
            915                 920                 925

Leu Ser Ser Gln Val Glu Gln Phe Leu His Arg Asn Ile Gln Glu Tyr
            930                 935                 940

Leu Ser Ile Leu Thr Asp Pro Asp Gly Lys Gly Lys Glu Lys Ile Ala
945                 950                 955                 960

Glu Leu Ser Ala Thr Ala Gln Glu Ile Ile Lys Ser Gln Ala Ile Ala
            965                 970                 975

Thr Lys Lys Ile Ile Ser Asp Tyr His Gln Gln Phe Arg Tyr Lys Leu
            980                 985                 990

Gln Asp Phe Ser Asp Gln Leu Ser Asp Tyr Tyr Glu Lys Phe Ile Ala
            995                1000                1005

Glu Ser Lys Arg Leu Ile Asp Leu Ser Ile Gln Asn Tyr His Thr Phe
           1010                1015                1020

Leu Ile Tyr Ile Thr Glu Leu Leu Lys Lys Leu Gln Ser Thr Thr Val
1025                1030                1035                1040

Met Asn Pro Tyr Met Lys Leu Ala Pro Gly Glu Leu Thr Ile Ile Leu
                   1045                1050                1055

(2) INFORMATION FOR SEQ ID NO:218:

(i) SEQUENCE CHARACTERISTICS:
        (A) LENGTH: 989 amino acids
        (B) TYPE: amino acid
        (C) STRANDEDNESS:
        (D) TOPOLOGY: linear (xi) SEQUENCE DESCRIPTION: SEQ ID NO:218:

Asn Ser Lys Gly Thr Arg Ser Ser Val Arg Leu Gln Gly Ala Ser Asn
1               5                  10                  15

Phe Ala Gly Ile Trp Asn Phe Glu Val Gly Glu Asn Phe Ala Gly Glu
            20                  25                  30

Ala Thr Leu Arg Arg Ile Tyr Gly Thr Trp Glu His Asn Met Ile Asn
            35                  40                  45

His Leu Gln Val Phe Ser Tyr Phe Asp Thr Lys Gly Lys Gln Thr Cys
    50                  55                  60

Arg Ala Thr Leu Glu Leu Ser Pro Trp Thr Met Ser Thr Leu Leu Gln
65                  70                  75                  80

Val His Val Ser Gln Pro Ser Pro Leu Phe Asp Leu His His Phe Asp
            85                  90                  95

Gln Glu Val Ile Leu Lys Ala Ser Thr Lys Asn Gln Lys Val Ser Trp
            100                 105                 110

Lys Ser Glu Val Gln Val Glu Ser Gln Val Leu Gln His Asn Ala His
            115                 120                 125

Phe Ser Asn Asp Gln Glu Glu Val Arg Leu Asp Ile Ala Gly Ser Leu
            130                 135                 140

Glu Gly Gln Leu Trp Asp Leu Glu Asn Phe Phe Leu Pro Ala Phe Gly
145                 150                 155                 160

Lys Ser Leu Arg Glu Leu Leu Gln Ile Asp Gly Lys Arg Gln Tyr Leu
            165                 170                 175

Gln Ala Ser Thr Ser Leu His Tyr Thr Lys Asn Pro Asn Gly Tyr Leu
            180                 185                 190

Leu Ser Leu Pro Val Gln Glu Leu Thr Asp Arg Phe Ile Ile Pro Gly
```

```
            195                 200                 205
Leu Lys Leu Asn Asp Phe Ser Gly Ile Lys Ile Tyr Lys Lys Leu Ser
        210                 215                 220

Thr Ser Pro Phe Ala Leu Asn Leu Thr Met Leu Pro Lys Val Lys Phe
225                 230                 235                 240

Pro Gly Val Asp Leu Leu Thr Gln Tyr Ser Lys Pro Glu Gly Ser Ser
                245                 250                 255

Val Pro Thr Phe Glu Thr Thr Ile Pro Glu Ile Gln Leu Thr Val Ser
                260                 265                 270

Gln Phe Thr Leu Pro Lys Ser Phe Pro Val Gly Asn Thr Val Phe Asp
            275                 280                 285

Leu Asn Lys Leu Thr Asn Leu Ile Ala Asp Val Asp Leu Pro Ser Ile
        290                 295                 300

Thr Leu Pro Glu Gln Thr Ile Glu Ile Pro Ser Leu Glu Phe Ser Val
305                 310                 315                 320

Pro Ala Gly Ile Phe Ile Pro Phe Phe Gly Glu Leu Thr Ala His Val
                325                 330                 335

Gly Met Ala Ser Pro Leu Tyr Asn Val Thr Trp Ser Thr Gly Trp Lys
                340                 345                 350

Asn Lys Ala Asp His Val Glu Thr Phe Leu Asp Ser Thr Cys Ser Ser
            355                 360                 365

Thr Leu Gln Phe Leu Glu Tyr Ala Leu Lys Val Val Gly Thr His Arg
        370                 375                 380

Ile Glu Asn Asp Lys Phe Ile Tyr Lys Ile Lys Gly Thr Leu Gln His
385                 390                 395                 400

Cys Asp Phe Asn Val Lys Tyr Asn Glu Asp Gly Ile Phe Glu Gly Leu
                405                 410                 415

Trp Asp Leu Glu Gly Glu Ala His Leu Asp Ile Thr Ser Pro Ala Leu
                420                 425                 430

Thr Asp Phe His Leu His Tyr Lys Glu Asp Lys Thr Ser Val Ser Ala
            435                 440                 445

Ser Ala Ala Ser Pro Ala Ile Gly Thr Val Ser Leu Asp Ala Ser Thr
        450                 455                 460

Asp Asp Gln Ser Val Arg Leu His Val Tyr Phe Arg Pro Gln Ser Pro
465                 470                 475                 480

Pro Asp Asn Lys Leu Ser Ile Phe Lys Met Glu Trp Arg Asp Lys Glu
                485                 490                 495

Ser Asp Gly Glu Thr Tyr Ile Lys Ile Asn Trp Glu Glu Ala Ala
                500                 505                 510

Phe Arg Leu Leu Asp Ser Leu Lys Ser Asn Val Pro Lys Ala Ser Glu
            515                 520                 525

Ala Val Tyr Asp Tyr Val Lys Lys Tyr His Leu Gly His Ala Ser Ser
        530                 535                 540

Glu Leu Arg Lys Ser Leu Gln Asn Asp Ala Glu His Ala Ile Arg Met
545                 550                 555                 560

Val Asp Glu Met Asn Val Asn Ala Gln Arg Val Thr Arg Asp Thr Tyr
                565                 570                 575

Gln Ser Leu Tyr Lys Lys Met Leu Ala Gln Glu Ser Gln Ser Ile Pro
            580                 585                 590

Glu Lys Leu Lys Lys Met Val Leu Gly Ser Leu Val Arg Ile Thr Gln
        595                 600                 605

Lys Tyr His Met Ala Val Thr Trp Leu Met Asp Ser Val Ile His Phe
610                 615                 620
```

```
Leu Lys Phe Asn Arg Val Gln Phe Pro Gly Asn Ala Gly Thr Tyr Thr
625                 630                 635                 640

Val Asp Glu Leu Tyr Thr Ile Ala Met Arg Glu Thr Lys Lys Leu Leu
            645                 650                 655

Ser Gln Leu Phe Asn Gly Leu Gly His Leu Phe Ser Tyr Val Gln Asp
            660                 665                 670

Gln Val Glu Lys Ser Arg Val Ile Asn Asp Ile Thr Phe Lys Cys Pro
            675                 680                 685

Phe Ser Pro Thr Pro Cys Lys Leu Lys Asp Val Leu Leu Ile Phe Arg
            690                 695                 700

Glu Asp Leu Asn Ile Leu Ser Asn Leu Gly Gln Gln Asp Ile Asn Phe
705                 710                 715                 720

Thr Thr Ile Leu Ser Asp Phe Gln Ser Phe Leu Glu Arg Leu Leu Asp
            725                 730                 735

Ile Ile Glu Glu Lys Ile Glu Cys Leu Lys Asn Asn Glu Ser Thr Cys
            740                 745                 750

Val Pro Asp His Ile Asn Met Phe Phe Lys Thr His Ile Pro Phe Ala
            755                 760                 765

Phe Lys Ser Leu Arg Glu Asn Ile Tyr Ser Val Phe Ser Glu Phe Asn
770                 775                 780

Asp Phe Val Gln Ser Ile Leu Gln Glu Gly Ser Tyr Lys Leu Gln Gln
785                 790                 795                 800

Val His Gln Tyr Met Lys Ala Phe Arg Glu Glu Tyr Phe Asp Pro Ser
            805                 810                 815

Val Val Gly Trp Thr Val Lys Tyr Tyr Glu Ile Glu Glu Lys Met Val
            820                 825                 830

Asp Leu Ile Lys Thr Leu Leu Ala Pro Leu Arg Asp Phe Tyr Ser Glu
            835                 840                 845

Tyr Ser Val Thr Ala Ala Asp Phe Ala Ser Lys Met Ser Thr Gln Val
            850                 855                 860

Glu Gln Phe Val Ser Arg Asp Ile Arg Glu Tyr Leu Ser Met Leu Ala
865                 870                 875                 880

Asp Ile Asn Gly Lys Gly Arg Glu Lys Val Ala Glu Leu Ser Ile Val
            885                 890                 895

Val Lys Glu Arg Ile Lys Ser Trp Ser Thr Ala Val Ala Glu Ile Thr
            900                 905                 910

Ser Asp Tyr Leu Arg Gln Leu His Ser Lys Leu Gln Asp Phe Ser Asp
            915                 920                 925

Gln Leu Ser Gly Tyr Tyr Glu Lys Phe Val Ala Glu Ser Thr Arg Leu
            930                 935                 940

Ile Asp Leu Ser Ile Gln Asn Tyr His Met Phe Leu Arg Tyr Ile Ala
945                 950                 955                 960

Glu Leu Leu Lys Lys Leu Gln Val Ala Thr Ala Asn Asn Val Ser Pro
            965                 970                 975

Tyr Leu Arg Phe Ala Gln Gly Glu Leu Ile Ile Thr Phe
            980                 985

(2) INFORMATION FOR SEQ ID NO:219:

(i) SEQUENCE CHARACTERISTICS:
        (A) LENGTH: 396 amino acids
        (B) TYPE: amino acid
        (C) STRANDEDNESS:
        (D) TOPOLOGY: linear
```

(xi) SEQUENCE DESCRIPTION: SEQ ID NO:219:

```
Lys Asp Asn Val Phe Asp Gly Leu Val Arg Val Thr Gln Lys Phe His
1               5                   10                  15

Met Lys Val Lys His Leu Ile Asp Ser Leu Ile Asp Phe Leu Asn Phe
            20                  25                  30

Pro Arg Phe Gln Phe Pro Gly Lys Pro Gly Ile Tyr Thr Arg Glu Glu
        35                  40                  45

Leu Cys Thr Met Phe Ile Arg Glu Val Gly Thr Val Leu Ser Gln Val
50                  55                  60

Tyr Ser Lys Val His Asn Gly Ser Glu Ile Leu Phe Ser Tyr Phe Gln
65                  70                  75                  80

Asp Leu Val Ile Thr Leu Pro Phe Glu Leu Arg Lys His Lys Leu Ile
                85                  90                  95

Asp Val Ile Ser Met Tyr Arg Glu Leu Leu Lys Asp Leu Ser Lys Glu
            100                 105                 110

Ala Gln Glu Val Phe Lys Ala Ile Gln Ser Leu Lys Thr Thr Glu Val
        115                 120                 125

Leu Arg Asn Leu Gln Asp Leu Leu Gln Phe Ile Phe Gln Leu Ile Glu
    130                 135                 140

Asp Asn Ile Lys Gln Leu Lys Glu Met Lys Phe Thr Tyr Leu Ile Asn
145                 150                 155                 160

Tyr Ile Gln Asp Glu Ile Asn Thr Ile Phe Asn Asp Tyr Ile Pro Tyr
                165                 170                 175

Val Phe Lys Leu Leu Lys Glu Asn Leu Cys Leu Asn Leu His Lys Phe
            180                 185                 190

Asn Glu Phe Ile Gln Asn Glu Leu Gln Glu Ala Ser Gln Glu Leu Gln
        195                 200                 205

Gln Ile His Gln Tyr Ile Met Ala Leu Arg Glu Glu Tyr Phe Asp Pro
    210                 215                 220

Ser Ile Val Gly Trp Thr Val Lys Tyr Tyr Glu Leu Glu Lys Ile
225                 230                 235                 240

Val Ser Leu Ile Lys Asn Leu Leu Val Ala Leu Lys Asp Phe His Ser
                245                 250                 255

Glu Tyr Ile Val Ser Ala Ser Asn Phe Thr Ser Gln Leu Ser Ser Gln
            260                 265                 270

Val Glu Gln Phe Leu His Arg Asn Ile Gln Glu Tyr Leu Ser Ile Leu
        275                 280                 285

Thr Asp Pro Asp Gly Lys Gly Lys Glu Lys Ile Ala Glu Leu Ser Ala
    290                 295                 300

Thr Ala Gln Glu Ile Ile Lys Ser Gln Ala Ile Ala Thr Lys Lys Ile
305                 310                 315                 320

Ile Ser Asp Tyr His Gln Gln Phe Arg Tyr Lys Leu Gln Asp Phe Ser
                325                 330                 335

Asp Gln Leu Ser Asp Tyr Tyr Glu Lys Phe Ile Ala Glu Ser Lys Arg
            340                 345                 350

Leu Ile Asp Leu Ser Ile Gln Asn Tyr His Thr Phe Leu Ile Tyr Ile
        355                 360                 365

Thr Glu Leu Leu Lys Lys Leu Gln Ser Thr Thr Val Met Asn Pro Tyr
    370                 375                 380

Met Lys Leu Ala Pro Gly Glu Leu Thr Ile Ile Leu
385                 390                 395
```

(2) INFORMATION FOR SEQ ID NO:220:

(i) SEQUENCE CHARACTERISTICS:
        (A) LENGTH: 433 amino acids
        (B) TYPE: amino acid
        (C) STRANDEDNESS:
        (D) TOPOLOGY: linear (xi) SEQUENCE DESCRIPTION: SEQ ID NO:220:

Ile Pro Gly Leu Ser Glu Lys Tyr Thr Gly Glu Glu Leu Tyr Leu Met
1               5                   10                  15

Thr Thr Glu Lys Ala Ala Lys Thr Ala Asp Ile Cys Leu Ser Lys Leu
                20                  25                  30

Gln Glu Tyr Phe Asp Ala Leu Ile Ala Ala Ile Ser Glu Leu Glu Val
            35                  40                  45

Arg Val Pro Ala Ser Glu Thr Ile Leu Arg Gly Arg Asn Val Leu Asp
50                  55                  60

Gln Ile Lys Glu Met Leu Lys His Leu Gln Glu Lys Ile Arg Gln Thr
65                  70                  75                  80

Phe Val Thr Leu Gln Glu Ala Asp Phe Ala Gly Lys Leu Asn Arg Leu
                85                  90                  95

Lys Gln Val Val Gln Lys Thr Phe Gln Lys Ala Gly Asn Met Val Arg
            100                 105                 110

Ser Leu Gln Ser Lys Asn Phe Glu Asp Ile Lys Val Gln Met Gln Gln
            115                 120                 125

Leu Tyr Lys Asp Ala Met Ala Ser Asp Tyr Ala His Lys Leu Arg Ser
130                 135                 140

Leu Ala Glu Asn Val Lys Lys Tyr Ile Ser Gln Ile Lys Asn Phe Ser
145                 150                 155                 160

Gln Lys Thr Leu Gln Lys Leu Ser Glu Asn Leu Gln Gln Leu Val Leu
                165                 170                 175

Tyr Ile Lys Ala Leu Arg Glu Glu Tyr Phe Asp Pro Thr Thr Leu Gly
            180                 185                 190

Trp Ser Val Lys Tyr Tyr Glu Val Glu Asp Lys Val Leu Gly Leu Leu
            195                 200                 205

Lys Asn Leu Met Asp Thr Leu Val Ile Trp Tyr Asn Glu Tyr Ala Lys
210                 215                 220

Asp Leu Ser Asp Leu Val Thr Arg Leu Thr Asp Gln Val Arg Glu Leu
225                 230                 235                 240

Val Glu Asn Tyr Arg Gln Glu Tyr Tyr Asp Leu Ile Thr Asp Val Glu
                245                 250                 255

Gly Lys Gly Arg Gln Lys Val Met Glu Leu Ser Ser Ala Ala Gln Glu
            260                 265                 270

Lys Ile Arg Tyr Trp Ser Ala Val Ala Lys Arg Lys Ile Asn Glu His
            275                 280                 285

Asn Arg Gln Val Lys Ala Lys Leu Gln Glu Ile Tyr Gly Gln Leu Ser
290                 295                 300

Asp Ser Gln Glu Lys Leu Ile Asn Val Ala Lys Met Leu Ile Asp Leu
305                 310                 315                 320

Thr Val Glu Lys Tyr Ser Thr Phe Met Lys Tyr Ile Phe Glu Leu Leu
                325                 330                 335

Arg Trp Phe Glu Gln Ala Thr Ala Asp Ser Ile Lys Pro Tyr Ile Ala
            340                 345                 350

Val Arg Glu Gly Glu Leu Arg Ile Asp Val Pro Phe Asp Trp Glu Tyr
            355                 360                 365

Ile Asn Gln Met Pro Gln Lys Ser Arg Glu Ala Leu Arg Asn Lys Val

-continued

```
                370                 375                 380
Glu Leu Thr Arg Ala Leu Ile Gln Gln Gly Val Gln Gly Thr Arg
385                 390                 395                 400

Lys Trp Glu Glu Met Gln Ala Phe Ile Asp Glu Gln Leu Ala Thr Glu
                405                 410                 415

Gln Leu Ser Phe Gln Gln Ile Val Glu Asn Ile Gln Lys Arg Met Lys
                420                 425                 430

Thr
```

(2) INFORMATION FOR SEQ ID NO:221:

(i) SEQUENCE CHARACTERISTICS:
        (A) LENGTH: 180 amino acids
        (B) TYPE: amino acid
        (C) STRANDEDNESS:
        (D) TOPOLOGY: linear (xi) SEQUENCE DESCRIPTION: SEQ ID NO:221:

```
Asp Met Thr Phe Ser Lys Gln Asn Ala Leu Leu Arg Ser Glu Tyr Gln
1               5                   10                  15

Ala Asp Tyr Glu Ser Leu Arg Phe Phe Ser Leu Leu Ser Gly Ser Leu
                20                  25                  30

Asn Ser His Gly Leu Glu Leu Asn Ala Asp Ile Leu Gly Thr Asp Lys
            35                  40                  45

Ile Asn Ser Gly Ala His Lys Ala Thr Leu Arg Ile Gly Gln Asp Gly
50                  55                  60

Ile Ser Thr Ser Ala Thr Thr Asn Leu Lys Cys Ser Leu Leu Val Leu
65                  70                  75                  80

Glu Asn Glu Leu Asn Ala Glu Leu Gly Leu Ser Gly Ala Ser Met Lys
                85                  90                  95

Leu Thr Thr Asn Gly Arg Phe Arg Glu His Asn Ala Lys Phe Ser Leu
                100                 105                 110

Asp Gly Lys Ala Ala Leu Thr Glu Leu Ser Leu Gly Ser Ala Tyr Gln
            115                 120                 125

Ala Met Ile Leu Gly Val Asp Ser Lys Asn Ile Phe Asn Phe Lys Val
            130                 135                 140

Ser Gln Glu Gly Leu Lys Leu Ser Asn Asp Met Met Gly Ser Tyr Ala
145                 150                 155                 160

Glu Met Lys Phe Asp His Thr Asn Ser Leu Asn Ile Ala Gly Leu Ser
                165                 170                 175

Leu Asp Phe Ser
            180
```

(2) INFORMATION FOR SEQ ID NO:222:

(i) SEQUENCE CHARACTERISTICS:
        (A) LENGTH: 142 amino acids
        (B) TYPE: amino acid
        (C) STRANDEDNESS:
        (D) TOPOLOGY: linear (xi) SEQUENCE DESCRIPTION: SEQ ID NO:222:

```
Asp Leu Thr Phe Ser Lys Gln Asn Ala Leu Leu Arg Ala Glu Tyr Gln
1               5                   10                  15

Ala Asp Tyr Lys Ser Leu Arg Phe Phe Thr Leu Leu Ser Gly Leu Leu
                20                  25                  30

Asn Thr His Gly Leu Glu Leu Asn Ala Asp Ile Leu Gly Thr Asp Lys
            35                  40                  45
```

```
Met Asn Thr Ala Ala His Lys Ala Thr Leu Arg Ile Gly Gln Asn Gly
    50                  55                  60

Val Ser Thr Ser Ala Thr Thr Ser Leu Arg Tyr Ser Pro Leu Met Leu
65                  70                  75                  80

Glu Asn Glu Leu Asn Ala Glu Leu Ala Leu Ser Gly Ala Ser Met Lys
                85                  90                  95

Leu Ala Thr Asn Gly Arg Phe Lys Glu His Asn Ala Lys Phe Ser Leu
                100                 105                 110

Asp Gly Lys Ala Thr Leu Thr Glu Leu Ser Leu Gly Ser Ala Tyr Gln
            115                 120                 125

Ala Met Ile Leu Gly Ala Asp Ser Lys Asn Ile Phe Asn Phe
130                 135                 140

(2) INFORMATION FOR SEQ ID NO:223:

(i) SEQUENCE CHARACTERISTICS:
        (A) LENGTH: 420 amino acids
        (B) TYPE: amino acid
        (C) STRANDEDNESS:
        (D) TOPOLOGY: linear (xi) SEQUENCE DESCRIPTION: SEQ ID NO:223:

His Ile Phe Ile Pro Ala Met Gly Asn Ile Thr Tyr Asp Phe Ser Phe
1               5                   10                  15

Lys Ser Ser Val Ile Thr Leu Asn Thr Asn Ala Glu Leu Phe Asn Gln
            20                  25                  30

Ser Asp Ile Val Ala His Leu Leu Ser Ser Ser Ser Val Ile Asp Asp
        35                  40                  45

Ala Leu Gln Tyr Lys Leu Glu Gly Thr Thr Arg Leu Thr Arg Lys Arg
    50                  55                  60

Gly Leu Lys Leu Ala Thr Ala Leu Ser Leu Ser Asn Lys Phe Val Glu
65                  70                  75                  80

Gly Ser His Asn Ser Thr Val Ser Leu Thr Thr Lys Asn Met Glu Val
                85                  90                  95

Ser Val Ala Lys Thr Thr Lys Ala Glu Ile Pro Ile Leu Arg Met Asn
                100                 105                 110

Phe Lys Gln Glu Leu Asn Gly Asn Thr Lys Ser Lys Pro Thr Val Ser
            115                 120                 125

Ser Ser Met Glu Phe Lys Tyr Asp Phe Asn Ser Ser Met Leu Tyr Ser
        130                 135                 140

Thr Ala Lys Gly Ala Val Asp His Lys Leu Ser Leu Glu Ser Leu Thr
145                 150                 155                 160

Ser Tyr Phe Ser Ile Glu Ser Ser Thr Lys Gly Asp Val Lys Gly Ser
                165                 170                 175

Val Leu Ser Arg Glu Tyr Ser Gly Thr Ile Ala Ser Glu Ala Asn Thr
            180                 185                 190

Tyr Leu Asn Ser Lys Ser Thr Arg Ser Ser Val Lys Leu Gln Gly Thr
        195                 200                 205

Ser Lys Ile Asp Asp Ile Trp Asn Leu Glu Val Lys Glu Asn Phe Ala
210                 215                 220

Gly Glu Ala Thr Leu Gln Arg Ile Tyr Ser Leu Trp Glu His Ser Thr
225                 230                 235                 240

Lys Asn His Leu Gln Leu Glu Gly Leu Phe Phe Thr Asn Gly Glu His
                245                 250                 255

Thr Ser Lys Ala Thr Leu Glu Leu Ser Pro Trp Gln Met Ser Ala Leu
```

-continued

```
              260                 265                 270
Val Gln Val His Ala Ser Gln Pro Ser Ser Phe His Asp Phe Pro Asp
            275                 280                 285
Leu Gly Gln Glu Val Ala Leu Asn Ala Asn Thr Lys Asn Gln Lys Ile
        290                 295                 300
Arg Trp Lys Asn Glu Val Arg Ile His Ser Gly Ser Phe Gln Ser Gln
305                 310                 315                 320
Val Glu Leu Ser Asn Asp Gln Glu Lys Ala His Leu Asp Ile Ala Gly
                325                 330                 335
Ser Leu Glu Gly His Leu Arg Phe Leu Lys Asn Ile Ile Leu Pro Val
            340                 345                 350
Tyr Asp Lys Ser Leu Trp Asp Phe Leu Lys Leu Asp Val Thr Thr Ser
            355                 360                 365
Ile Gly Arg Arg Gln His Leu Arg Val Ser Thr Ala Phe Val Tyr Thr
        370                 375                 380
Lys Asn Pro Asn Gly Tyr Ser Phe Ser Ile Pro Val Lys Val Leu Ala
385                 390                 395                 400
Asp Lys Phe Ile Thr Pro Gly Leu Lys Leu Asn Asp Leu Asn Ser Val
                405                 410                 415
Leu Val Met Pro
            420
```

(2) INFORMATION FOR SEQ ID NO:224:

(i) SEQUENCE CHARACTERISTICS:
        (A) LENGTH: 275 amino acids
        (B) TYPE: amino acid
        (C) STRANDEDNESS:
        (D) TOPOLOGY: linear (xi) SEQUENCE DESCRIPTION: SEQ ID NO:224:

```
Met Ala Ser Glu Lys Gly Pro Ser Asn Lys Asp Tyr Thr Leu Arg Arg
1               5                   10                  15
Arg Ile Glu Pro Trp Glu Phe Glu Val Phe Phe Asp Pro Gln Glu Leu
            20                  25                  30
Arg Lys Glu Ala Cys Leu Leu Tyr Glu Ile Lys Trp Gly Ala Ser Ser
        35                  40                  45
Lys Thr Trp Arg Ser Ser Gly Lys Asn Thr Thr Asn His Val Glu Val
    50                  55                  60
Asn Phe Leu Glu Lys Leu Thr Arg Lys Glu Ala Cys Leu Leu Tyr Glu
65                  70                  75                  80
Ile Lys Trp Gly Ala Ser Ser Lys Thr Trp Arg Ser Ser Gly Lys Asn
                85                  90                  95
Thr Thr Asn His Val Glu Val Asn Phe Leu Glu Lys Leu Thr Ser Glu
                100                 105                 110
Gly Arg Leu Gly Pro Ser Thr Cys Cys Ser Ile Thr Trp Phe Leu Ser
        115                 120                 125
Trp Ser Pro Cys Trp Glu Cys Ser Met Ala Ile Arg Glu Phe Leu Ser
        130                 135                 140
Gln His Pro Gly Val Thr Leu Ile Ile Phe Val Ala Arg Leu Phe Gln
145                 150                 155                 160
His Met Asp Arg Arg Asn Arg Gln Gly Leu Lys Asp Leu Val Thr Ser
                165                 170                 175
Gly Val Thr Val Arg Val Met Ser Val Ser Glu Tyr Cys Tyr Cys Trp
            180                 185                 190
```

```
Glu Asn Phe Val Asn Tyr Pro Pro Gly Lys Ala Ala Gln Trp Pro Arg
        195                 200                 205

Tyr Pro Pro Arg Trp Met Leu Met Tyr Ala Leu Glu Leu Tyr Cys Ile
    210                 215                 220

Ile Leu Gly Leu Pro Pro Cys Leu Lys Ile Ser Arg Arg His Gln Lys
225                 230                 235                 240

Gln Leu Thr Phe Phe Ser Leu Thr Pro Gln Tyr Cys His Tyr Lys Met
                245                 250                 255

Ile Pro Pro Tyr Ile Leu Leu Ala Thr Gly Leu Leu Gln Pro Ser Val
            260                 265                 270

Pro Trp Arg
        275

(2) INFORMATION FOR SEQ ID NO:225:

(i) SEQUENCE CHARACTERISTICS:
        (A) LENGTH: 589 base pairs
        (B) TYPE: nucleic acid
        (C) STRANDEDNESS: single
        (D) TOPOLOGY: linear (xi) SEQUENCE DESCRIPTION: SEQ ID NO:225:

GGATCTGACG GTTCACTAAA CCAGCTCTGC TTATATAGAC CTCCCACCGT ACACGCCTAC      60

CGCCCATTTG CGTCAATGGG GCGGAGTTGT TACGACATTT TGGAAAGTCC CGTTGATTTT     120

GGTGCCAAAA CAAACTCCAT TGACGTCAAT GGGGTGGAGA CTTGGAAATC CCCGTGAGTC     180

AAACCGCTAT CCACGCCCAT TGATGTACTG CCAAAACCGC ATCACCATGG TAATAGCGAT     240

GACTAATACG TAGATGTACT GCCAAGTAGG AAAGTCCCAT AAGGTCATGT ACTGGGCATA     300

ATGCCAGGCG GGCCATTTAC CGTCATTGAC GTCAATAGGG GGCGTACTTG GCATATGATA     360

CACTTGATGT ACTGCCAAGT GGGCAGTTTA CCGTAAATAC TCCACCCATT GACGTCAATG     420

GAAAGTCCCT ATTGGCGTTA CTATGGGAAC ATACGTCATT ATTGACGTCA ATGGGCGGGG     480

GTCGTTGGGC GGTCAGCCAG GCGGGCCATT TACCGTAAGT TATGTAACGC GGAACTCCAT     540

ATATGGGCTA TGAACTAATG ACCCCGTAAT TGATTACTAT TAATAACTA                 589

(2) INFORMATION FOR SEQ ID NO:226:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (xi) SEQUENCE DESCRIPTION: SEQ ID NO:226:

GATCCAAATC ACCCACTGCA ACTCCTCCCC CTGCG                                 35

(2) INFORMATION FOR SEQ ID NO:227:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:227:

GATCCATCCA ATTGGGCAAT CAGGAG                                           26

(2) INFORMATION FOR SEQ ID NO:228:

(i) SEQUENCE CHARACTERISTICS:
```

```
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:228:

GATCCGGTCT CCAATTGG                                              18

(2) INFORMATION FOR SEQ ID NO:229:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:229:

GATCCTCGGG AAAGGGAAAC CGAAACTGAA GCCG                            34
```